US008017602B2

(12) United States Patent
Bonnert et al.

(10) Patent No.: US 8,017,602 B2
(45) Date of Patent: Sep. 13, 2011

(54) N-(2-(2-(5-HYDROXY-3-OXO-3,4-DIHYDRO-2H-BENZO[B][1,4]OXAZIN-8-YL)ETHYL AMINO)ETHYL)-3-(PHENETHOXY)PRO PANAMIDE DERIVATIVES, PROCESSES FOR THEIR PREPARATION, PHARMACEUTICAL COMPOSITIONS CONTAINING THEM AND THEIR USE IN THERAPY

(75) Inventors: Roger Victor Bonnert, Loughborough (GB); Stephen Connolly, Loughborough (GB); Anthony Ronald Cook, Loughborough (GB); Richard Evans, Loughborough (GB); Piotr Raubo, Loughborough (GB)

(73) Assignee: AstraZeneca AB, Södertälje (SE)

( * ) Notice: Subject to any disclaimer, the term of this patent is extended or adjusted under 35 U.S.C. 154(b) by 117 days.

(21) Appl. No.: 12/486,854

(22) Filed: Jun. 18, 2009

(65) Prior Publication Data
US 2010/0105642 A1 Apr. 29, 2010

Related U.S. Application Data

(60) Provisional application No. 61/073,420, filed on Jun. 18, 2008.

(51) Int. Cl.
C07D 265/36 (2006.01)
A61K 31/536 (2006.01)
A61K 31/56 (2006.01)
(52) U.S. Cl. ..................... 514/230.5; 544/105
(58) Field of Classification Search .......... 544/105; 514/230.5
See application file for complete search history.

(56) References Cited

U.S. PATENT DOCUMENTS

| 2,653,977 | A | 9/1953 | Craig et al. |
| 3,775,477 | A | 11/1973 | Diana |
| 4,460,581 | A | 7/1984 | Schromm et al. |
| 5,648,370 | A | 7/1997 | Bonnert et al. |
| 6,686,353 | B1 | 2/2004 | Shiota et al. |
| 2002/0055651 | A1 | 5/2002 | Moran et al. |
| 2003/0229058 | A1 | 12/2003 | Moran et al. |

FOREIGN PATENT DOCUMENTS

| EP | 0162576 A1 | 11/1985 |
| EP | 0174811 A2 | 3/1986 |
| EP | 0175525 A1 | 3/1986 |
| EP | 0220878 A2 | 5/1987 |
| EP | 0303466 A2 | 2/1989 |
| EP | 0422889 A2 | 4/1991 |
| JP | 2005-187357 A | 7/2005 |
| WO | WO-92/08708 A1 | 5/1992 |
| WO | WO-93/23385 A1 | 11/1993 |
| WO | WO-93/24473 A1 | 12/1993 |
| WO | WO-97/10227 A1 | 3/1997 |
| WO | WO-97/23470 A1 | 7/1997 |
| WO | WO-97/44329 A1 | 11/1997 |
| WO | WO-98/38180 A1 | 9/1998 |
| WO | WO-98/45294 A1 | 10/1998 |
| WO | WO-99/36095 A1 | 7/1999 |
| WO | WO-99/64035 A1 | 12/1999 |
| WO | WO-00/75114 A1 | 12/2000 |
| WO | WO-01/11933 A2 | 2/2001 |
| WO | WO-01/12167 A2 | 2/2001 |
| WO | WO-01/12191 A2 | 2/2001 |
| WO | WO-01/12192 A2 | 2/2001 |
| WO | WO-01/42193 A1 | 6/2001 |
| WO | WO-02/06255 A2 | 1/2002 |
| WO | WO-02/076933 A1 | 10/2002 |
| WO | WO-03/024439 A1 | 3/2003 |
| WO | WO-2004/016578 A2 | 2/2004 |
| WO | WO-2004/016601 A1 | 2/2004 |
| WO | WO-2004/039766 A1 | 5/2004 |
| WO | WO-2004/071388 A2 | 8/2004 |
| WO | WO-2004/074276 A1 | 9/2004 |
| WO | WO-2004/089892 A2 | 10/2004 |
| WO | WO-2005/030678 A2 | 4/2005 |
| WO | WO-2005/040103 A1 | 5/2005 |
| WO | WO-2005/044787 A1 | 5/2005 |
| WO | WO-2005/070872 A1 | 8/2005 |
| WO | WO-2005/074924 A1 | 8/2005 |
| WO | WO-2005/092841 A1 | 10/2005 |
| WO | WO-2005/092861 A1 | 10/2005 |
| WO | WO-2005/092870 A1 | 10/2005 |

(Continued)

OTHER PUBLICATIONS

Otsuka Pharmaceutical Co., Ltd., Japan: 5-(1-Hydroxy-2-Aminoalkyl)-Carbostyril and 5-(1- Hydroxy-2-Aminoalkyl)-3,4-Dihydro-Carbostyril Derivatives, 1 page (1976).
Berge et al., "Pharmaceutical Salts", *Journal of Pharmaceutical Sciences*, vol. 66, No. 1, pp. 1-19 (1977).
Weinstock et al., "Synthesis and Evaluation of Non-Cathechol D-1 and D-2 Dopamine Receptor Agonists: Benzimidazol-2-One, Benzoxazol-2-One, and the Highly Potent Benzothiazol-2-One 7 Ethylamines", *J. Med. Chem.*, vol. 30, pp. 1166-1176 (1987).
Bonnert et al., "Dual $D_2$-Receptor and $\beta_2$-Adrenoceptor Agonists for the Treatment of Airway Diseases. 1. Discovery and Biological Evaluation of Some 7-(2-Aminoethyl)-4-Hydroxybenzothiazol-2(3H)-One Analogues", *J. Med. Chem.*, vol. 41, pp. 4915-4917 (1998).

(Continued)

*Primary Examiner* — Kahsay T Habte
(74) *Attorney, Agent, or Firm* — Connolly Bove Lodge & Hutz LLP

(57) ABSTRACT

The present invention provides a compound of formula (I)

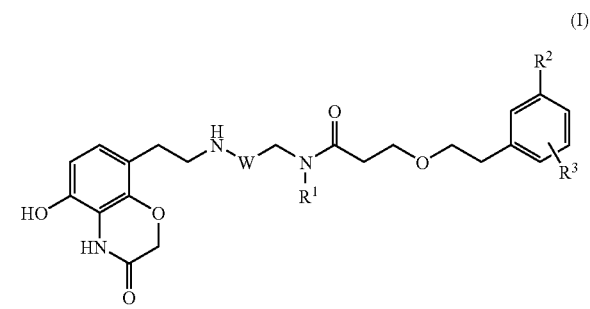

Figure 1:
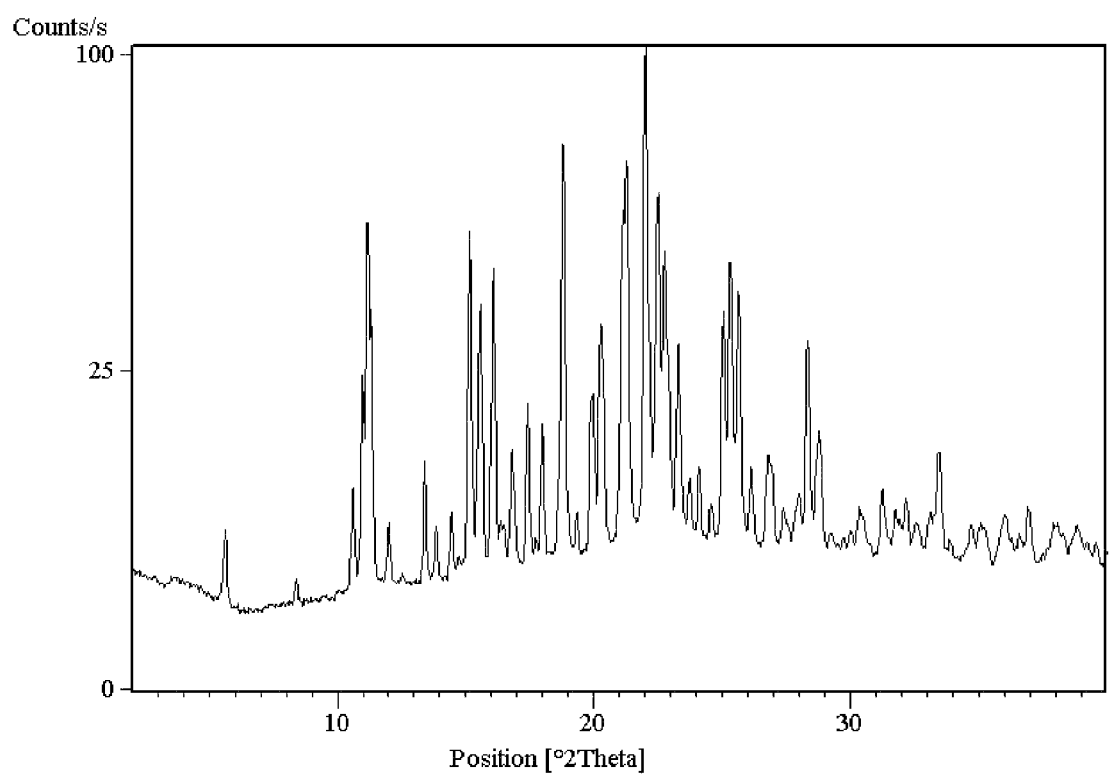

wherein W, $R^1$, $R^2$ and $R^3$ are as defined in the specification, processes for their preparation, pharmaceutical compositions containing them and their use in therapy.

12 Claims, 1 Drawing Sheet

FOREIGN PATENT DOCUMENTS

| | | |
|---|---|---|
| WO | WO-2005/110990 A1 | 11/2005 |
| WO | WO-2005/111002 A2 | 11/2005 |
| WO | WO-2005/111004 A1 | 11/2005 |
| WO | WO-2005/121065 A2 | 12/2005 |
| WO | WO-2006/014704 A1 | 2/2006 |
| WO | WO-2006/023457 A1 | 3/2006 |
| WO | WO-2006/023460 A2 | 3/2006 |
| WO | WO-2006/031556 A2 | 3/2006 |
| WO | WO-2006/056471 A1 | 6/2006 |
| WO | WO-2006/074897 A1 | 7/2006 |
| WO | WO-2006/128675 A1 | 12/2006 |
| WO | WO-2007/010356 A2 | 1/2007 |
| WO | WO-2007/018461 A1 | 2/2007 |
| WO | WO-2007/027133 A1 | 3/2007 |
| WO | WO-2007/027134 A1 | 3/2007 |
| WO | WO-2007/102771 A1 | 9/2007 |
| WO | WO-2007/106016 A1 | 9/2007 |
| WO | WO-2008/041914 A1 | 4/2008 |
| WO | WO-2008/075025 A1 | 6/2008 |
| WO | WO-2008/075026 A1 | 6/2008 |
| WO | WO-2008/096111 A1 | 8/2008 |
| WO | WO-2008/096112 A1 | 8/2008 |
| WO | WO-2008/096119 A1 | 8/2008 |
| WO | WO-2008/096121 A1 | 8/2008 |
| WO | WO-2008/104776 A1 | 9/2008 |
| WO | WO-2008/104790 A1 | 9/2008 |
| WO | WO-2009/037503 A2 | 3/2009 |
| WO | WO-2009/154557 A1 | 12/2009 |
| WO | WO-2009/154562 A1 | 12/2009 |

OTHER PUBLICATIONS

Wermuth et al., Handbook of Pharmaceutical Salts: Properties, Selection and Use; *Wiley-VCH Verlag*, pp. 1-7 (2002).

Dougall et al., "Dual Dopamine $D_2$-Receptor and $\beta_2$-Adrenoceptor Agonists for the Treatment of Chronic Obstructive Pulmonary Disease: the Pre-Clinical Rationale", *respiratoryMEDICINE*, vol. 97, (Supplemental A), pp. S3-S7 (2002).

Austin et al., "QSAR and the Rational Design of Long-Acting Dual $D_2$-Receptor/$\beta_2$-Adrenoceptor Agonists", J. Med. Chem., vol. 46, pp. 3210-3220 (2003).

Davies et al., "Indacaterol—Asthma Therapy, Treatment of COPD, $\beta_2$-Adrenoceptor Agonist", *Drugs of the Future*, vol. 30, No. 12, pp. 1219-1224 (2005).

N-(2-(2-(5-HYDROXY-3-OXO-3,4-DIHYDRO-2H-BENZO[B][1,4]OXAZIN-8-YL)ETHYLAMINO)ETHYL)-3-(PHENETHOXY)PROPANAMIDE DERIVATIVES, PROCESSES FOR THEIR PREPARATION, PHARMACEUTICAL COMPOSITIONS CONTAINING THEM AND THEIR USE IN THERAPY

This patent claims benefit under 35 USC §119(e) to U.S. Provisional Application No. 61/073,420 (filed 18 Jun. 2008). The entire text of U.S. Provisional Application No. 61/073,420 is incorporated by reference into this patent.

The present invention relates to benzoxazinone derivatives, processes for their preparation, pharmaceutical compositions containing them and their use in therapy.

Adrenoceptors are a group of G-protein coupled receptors divided into two major sub-families, α and β. These sub-families are further divided into sub-types of which the β sub-family has at least 3 members: β1, β2 and β3. β2 adrenoceptors (henceforth referred to as β2 receptors) are mainly expressed on smooth muscle cells.

Agonism of the β2 receptor on airway smooth muscle produces relaxation and therefore bronchodilatation. Through this mechanism, β2 agonists act as functional antagonists to all bronchoconstrictor substances such as the naturally-occurring histamine and acetylcholine as well as the experimental substances methacholine and carbachol. β2 agonists are widely used to treat airways diseases including asthma and chronic obstructive pulmonary disease (COPD), and this has been extensively reviewed in the literature and incorporated into national guidelines for the treatment of these diseases (British Guideline on the Management of Asthma, NICE guideline No. 12 on the Management of COPD).

β2 agonists are classed either as short-acting or long-acting. Short-acting β2 agonists (SABAs) such as salbutamol have a duration of action of 2-4 h. They are suitable for rescue medication during a period of acute bronchoconstriction but are not suitable for continuous medication because the beneficial effect of these drugs wears off during the night. Long-acting β2 agonists (LABAs) currently have a duration of action of about 12 h and are administered twice daily to provide continuous bronchodilatation. They are particularly effective when administered in combination with inhaled corticosteroids. This benefit is not seen when inhaled corticosteroids are combined with SABAs (Kips and Pauwels, *Am. J. Respir. Crit. Care Med.*, 2001, 164, 923-932). LABAs are recommended as add-on therapy to patients already receiving inhaled corticosteroids for asthma to reduce nocturnal awakening and reduce the incidence of exacerbations of the disease. Corticosteroids and LABAs are conveniently co-administered in a single inhaler to improve patient compliance.

There are shortcomings to existing LABAs and there is a need for a new drug in this class. Salmeterol, a commonly used LABA, has a narrow safety margin and side effects related to systemic agonism of β2 receptors (such as tremor, hypokalaemia, tachycardia and hypertension) are common. Salmeterol also has a long onset of action which precludes its use as both a rescue and a maintenance therapy. All current LABAs are administered twice daily and there is a medical need for once daily treatments to improve treatment and patient compliance. Such once daily compounds, co-administered with corticosteroids, will become the mainstay of asthma treatment (Barnes, *Nature Reviews*, 2004, 3, 831-844). The advantages of once-daily bronchodilator treatment in COPD has been demonstrated with tiotropium, a non-selective muscarinic antagonist (Koumis and Samuel, *Clin. Ther.* 2005, 27(4), 377-92). There is, however, a need for a once-daily LABA for the treatment of COPD to avoid the side effects of anti-muscarinics such as tiotropium.

In accordance with the present invention there is therefore provided a compound of formula (I):

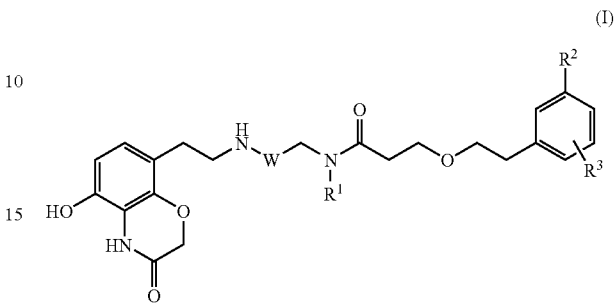

(I)

wherein:
W is $CH_2$ substituted by 0, 1 or 2 $CH_3$ groups;
$R^1$ is cyclopentyl, cyclohexyl, cycloheptyl or $CH(CH_3)(C_{1-6}$ alkyl);
$R^2$ is a 5-membered, nitrogen-containing heteroaryl that optionally has a ring oxygen atom, and $R^2$ is optionally substituted by $C_{1-6}$ alkyl (itself optionally substituted by $C_{1-6}$ alkoxy or $C_{3-6}$ cycloalkyl);
$R^3$ is hydrogen, halogen, $C_{1-4}$ alkyl, $CF_3$, $C_{1-4}$ alkoxy, $OCF_3$ or cyano;
or a pharmaceutically acceptable salt thereof FIG. 1 shows the XRPD spectra for the N-Cyclohexyl-N-(2-(2-(5-hydroxy-3-oxo-3,4-dihydro-2H-benzo[b][1,4]oxazin-8-yl)ethylamino)ethyl)-3-(3-(1-methyl-1H-pyrazol-4-yl)phenethoxy)propanamide Hemi-Fumaric Acid Salt discussed in Example 2a.

Alkyl, or the alkyl moiety of alkoxy, is linear or branched and is, for example, methyl, ethyl, n-propyl, iso-propyl, n-butyl, iso-butyl or tert-butyl.

The group $CH(CH_3)(C_{1-6}$ alkyl) is, for example, $CH(CH_3)_2$, $CH(CH_3)CH_2CH_3$, $CH(CH_3)(CH_2)_2CH_3$, $CH(CH_3)CH(CH_3)_2$, $CH(CH_3)(CH_2)_3CH_3$ or $CH(CH_3)C(CH_3)_3$.

Halogen is, for example, fluorine, chlorine or bromine

A 5-membered, nitrogen-containing heteroaryl that optionally has a ring oxygen atom is, for example, a 5-membered ring comprising two, three or four (such as two or three) ring-heteroatoms atoms. It is, for example, oxazolyl, oxadiazolyl, imidazolyl, pyrazolyl, 1,2,3-triazolyl, 1,2,4-triazolyl or tetrazolyl. In particular, all compounds of the invention are at least 10-fold more potent at the β2 receptor compared to the α1, β1, or dopamine (D2) receptors.

Certain compounds are also notable for having a fast onset of action, that is, the time interval between administration of a compound of the invention to a patient and the compound providing symptomatic relief Onset can be predicted in vitro using isolated trachea from guinea pig or human.

Certain compounds have been optimised to have appropriate duration in man. P Duration can be predicted from pharmokinetic half lives in mammalian systems, or a pharmacodynamic model in a mammalian system.

Certain compounds have reduced CYP (for example CYP3A4) inhibition.

Certain compounds of the invention are also characterised as having a high plasma protein binding, meaning that there is less free compound in the plasma leading to a reduction in systemic side-effects (for example tremor or hypokalemia).

In one particular aspect the present invention provides a compound of formula (I) wherein: W is $CH_2$ substituted by 0, 1 or 2 $CH_3$ groups; $R^1$ is cyclopentyl, cyclohexyl, cycloheptyl or $CH(CH_3)(C_{1-6}$ alkyl); $R^2$ is a 5-membered, nitrogen-containing heteroaryl that optionally has a ring oxygen atom, and $R^2$ is optionally substituted by $C_{1-6}$ alkyl; $R^3$ is hydrogen, halogen, $C_{1-4}$ alkyl, $CF_3$, $C_{1-4}$ alkoxy, $OCF_3$ or cyano; or a pharmaceutically acceptable salt thereof.

A compound of formula (I) can form a salt with a pharmaceutically acceptable acid the ionic nature of the salt ranging from full proton transfer (for example with a strong acid) to being a co-crystal (where the compound of formula (I) is associated with a weak acid). The present invention encompasses all such physical forms.

A suitable pharmaceutically acceptable salt is, for example, an acid addition salt such as a chloride (for example a monochloride or a dichloride), bromide (for example a monobromide or a dibromide), trifluoroacetate (for example a mono-trifluoroacetate or a di-trifluoroacetate), sulphate, phosphate, acetate, fumarate (for example a hemifumaric acid salt), maleate, tartrate (such as L-(+) tartrate), lactate, citrate, pyruvate, succinate, oxalate, methanesulphonate, p-toluenesulphonate, bisulphate, benzenesulphonate, ethanesulphonate, malonate, xinafoate, ascorbate, oleate, nicotinate, saccharinate, adipate, formate, glycolate, L-lactate, D-lactate, aspartate, malate, L-tartrate, D-tartrate, stearate, 2-furoate, 3-furoate, napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), isethionate (2-hydroxyethylsulfonate), 2-mesitylenesulphonate, 2-naphthalenesulphonate, D-(-)-mandelate, S-(+) or L-mandelate, 2,5-dichlorobenzenesulphonate, cinnamate, benzoate or 1-hydroxy-2-naphthenoate.

In another aspect a suitable pharmaceutically acceptable salt is, for example, an acid addition salt such as a chloride (for example a monochloride or a dichloride), bromide (for example a monobromide or a dibromide), trifluoroacetate (for example a mono-trifluoroacetate or a di-trifluoroacetate), sulphate, phosphate, acetate, fumarate, maleate, tartrate, lactate, citrate, pyruvate, succinate, oxalate, methanesulphonate, p-toluenesulphonate, bisulphate, benzenesulphonate, ethanesulphonate, malonate, xinafoate, ascorbate, oleate, nicotinate, saccharinate, adipate, formate, glycolate, L-lactate, D-lactate, aspartate, malate, L-tartrate, D-tartrate, stearate, 2-furoate, 3-furoate, napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), isethionate (2-hydroxyethylsulfonate), 2-mesitylenesulphonate, 2-naphthalenesulphonate, D-mandelate, L-mandelate, 2,5-dichlorobenzenesulphonate, cinnamate or benzoate.

Compounds of formula (I) are capable of existing in stereoisomeric forms. It will be understood that the invention encompasses the use of all geometric and optical isomers (including atropisomers) of the compounds of formula (I) and mixtures thereof including racemates. The use of tautomers and mixtures thereof also form an aspect of the present invention. Enantiomerically pure forms are particularly desired.

The compounds of formula (I), and their pharmaceutically acceptable salts, might exist as solvates (such as hydrates) and the present invention encompasses all such solvates in any proportion.

In one particular aspect the present invention provides a compound of formula (I) wherein $R^1$ is cyclohexyl.

In another aspect the present invention provides a compound of formula (I) wherein $R^1$ is $CH(CH_3)(C_{1-6}$ alkyl) (for example, $CH(CH_3)_2$, $CH(CH_3)CH_2CH_3$, $CH(CH_3)(CH_2)_2CH_3$, $CH(CH_3)CH(CH_3)_2$, $CH(CH_3)(CH_2)_3CH_3$ or $CH(CH_3)C(CH_3)_3$).

In yet another aspect the present invention provides a compound of formula (I) wherein $R^1$ is $CH(CH_3)CH(CH_3)_2$ or $CH(CH_3)(CH_2)_3CH_3$.

In a further aspect the present invention provides a compound of formula (I) wherein W is unsubstituted $CH_2$.

In a still further aspect the present invention provides a compound of formula (I) wherein $R^2$ is a 5-membered, nitrogen-containing heteroaryl optionally substituted by $C_{1-6}$ alkyl.

In another aspect the present invention provides a compound of formula (I) wherein $R^2$ is a C-linked, 5-membered, nitrogen-containing heteroaryl (for example comprising two, three or four (such as two or three) ring-nitrogen atoms) carrying a $C_{1-6}$ alkyl group on a ring-nitrogen. It is, for example, C-linked imidazolyl, pyrazolyl, 1,2,3-triazolyl, 1,2,4-triazolyl or tetrazolyl carrying a $C_{1-6}$ alkyl group (such as methyl or ethyl) on a ring-nitrogen. It is, for example 1-($C_{1-4}$ alkyl)pyrazol-4-yl. In a further aspect the alkyl group is methyl, ethyl, n-propyl or iso-propyl. In a still further aspect the alkyl group is methyl.

In a further aspect the present invention provides a compound of formula (I) wherein $R^2$ is C-linked pyrazolyl carrying a methyl on a ring nitrogen.

In yet another aspect the present invention provides a compound of formula (I) wherein $R^3$ is hydrogen.

In a further aspect the present invention provides each individual compound:

N-Cyclohexyl-N-(2-(2-(5-hydroxy-3-oxo-3,4-dihydro-2H-benzo[b][1,4]oxazin-8-yl)ethylamino)ethyl)-3-(3-(1-methyl-1H-pyrazol-4-yl)phenethoxy)propanamide Trifluoroacetic Acid Salt;

N-Cyclohexyl-N-(2-(2-(5-hydroxy-3-oxo-3,4-dihydro-2H-benzo[b][1,4]oxazin-8-yl)ethylamino)ethyl)-3-(3-(1-methyl-1H-pyrazol-4-yl)phenethoxy)propanamide Hemi-Fumaric Acid Salt;

N-Cyclohexyl-N-(2-(2-(5-hydroxy-3-oxo-3,4-dihydro-2H-benzo[b][1,4]oxazin-8-yl)ethylamino)ethyl)-3-(3-(1-methyl-1H-pyrazol-5-yl)phenethoxy)propanamide Trifluoroacetic Acid Salt;

N-Cyclohexyl-3-(3-(1-ethyl-1H-1,2,3-triazol-4-yl)phenethoxy)-N-(2-(2-(5-hydroxy-3-oxo-3,4-dihydro-2H-benzo[b][1,4]oxazin-8-yl)ethylamino)ethyl)propanamide Trifluoroacetic Acid Salt;

N-Cyclohexyl-N-(2-(2-(5-hydroxy-3-oxo-3,4-dihydro-2H-benzo[b][1,4]oxazin-8-yl)ethylamino)ethyl)-3-(3-(1-methyl-1H-1,2,3-triazol-4-yl)phenethoxy)propanamide Trifluoroacetic Acid Salt;

N-Cycloheptyl-N-(2-(2-(5-hydroxy-3-oxo-3,4-dihydro-2H-benzo[b][1,4]oxazin-8-yl)ethylamino)ethyl)-3-(3-(1-methyl-1H-1,2,3-triazol-4-yl)phenethoxy)propanamide Trifluoroacetic Acid Salt;

N-Cyclohexyl-N-(2-(2-(5-hydroxy-3-oxo-3,4-dihydro-2H-benzo[b][1,4]oxazin-8-yl)ethylamino)ethyl)-3-(3-(2-methyl-2H-tetrazol-5-yl)phenethoxy)propanamide Trifluoroacetic Acid Salt;

N-Cyclohexyl-N-(2-(2-(5-hydroxy-3-oxo-3,4-dihydro-2H-benzo[b][1,4]oxazin-8-yl)ethylamino)ethyl)-3-(3-(1-methyl-1H-tetrazol-5-yl)phenethoxy)propanamide Trifluoroacetic Acid Salt;

(R)—N-(2-(2-(5-Hydroxy-3-oxo-3,4-dihydro-2H-benzo[b][1,4]oxazin-8-yl)ethylamino)ethyl)-3-(3-(1-methyl-1H-pyrazol-4-yl)phenethoxy)-N-(3-methylbutan-2-yl)propanamide Trifluoroacetic Acid Salt;

N-Cyclohexyl-N-(2-(2-(5-hydroxy-3-oxo-3,4-dihydro-2H-benzo[b][1,4]oxazin-8-yl)ethylamino)ethyl)-3-(3-(oxazol-5-yl)phenethoxy)propanamide Trifluoroacetic Acid Salt;

3-(3-(1,2,4-Oxadiazol-3-yl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide Trifluoroacetic Acid Salt;

N-Cyclohexyl-N-(2-(2-(5-hydroxy-3-oxo-3,4-dihydro-2H-benzo[b][1,4]oxazin-8-yl)ethylamino)ethyl)-3-(3-(1-isopropyl-1H-1,2,3-triazol-4-yl)phenethoxy)propanamide Trifluoroacetic Acid Salt;

N-Cyclohexyl-3-(4-fluoro-3-(1-methyl-1H-pyrazol-4-yl)phenethoxy)-N-(2-(2-(5-hydroxy-3-oxo-3,4-dihydro-2H-benzo[b][1,4]oxazin-8-yl)ethylamino)ethyl)propanamide Trifluoroacetic Acid Salt;

3-(3-(1H-1,2,3-Triazol-4-yl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide Trifluoroacetic Acid Salt;

3-(3-(2H-Tetrazol-5-yl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide Trifluoroacetic Acid Salt;

N-Cyclohexyl-3-(2-fluoro-3-(1-methyl-1H-pyrazol-4-yl)phenethoxy)-N-(2-(2-(5-hydroxy-3-oxo-3,4-dihydro-2H-benzo[b][1,4]oxazin-8-yl)ethylamino)ethyl)propanamide Trifluoroacetic Acid Salt;

N-Cyclohexyl-3-(3-fluoro-5-(1-methyl-1H-pyrazol-4-yl)phenethoxy)-N-(2-(2-(5-hydroxy-3-oxo-3,4-dihydro-2H-benzo[b][1,4]oxazin-8-yl)ethylamino)ethyl)propanamide Trifluoroacetic Acid Salt;

N-Cyclopentyl-N-(2-(2-(5-hydroxy-3-oxo-3,4-dihydro-2H-benzo[b][1,4]oxazin-8-yl)ethylamino)ethyl)-3-(3-(1-propyl-1H-pyrazol-4-yl)phenethoxy)propanamide Trifluoroacetic Acid Salt;

N-Cyclopentyl-3-(3-(1-(cyclopropylmethyl)-1H-pyrazol-4-yl)phenethoxy)-N-(2-(2-(5-hydroxy-3-oxo-3,4-dihydro-2H-benzo[b][1,4]oxazin-8-yl)ethylamino)ethyl)propanamide Trifluoroacetic Acid Salt;

(R)—N-(2-(2-(5-Hydroxy-3-oxo-3,4-dihydro-2H-benzo[b][1,4]oxazin-8-yl)ethylamino)ethyl)-3-(3-(1-isopropyl-1H-pyrazol-4-yl)phenethoxy)-N-(3-methylbutan-2-yl)propanamide Trifluoroacetic Acid Salt;

(R)—N-(2-(2-(5-Hydroxy-3-oxo-3,4-dihydro-2H-benzo[b][1,4]oxazin-8-yl)ethylamino)ethyl)-3-(3-(1-isopropyl-1H-pyrazol-4-yl)phenethoxy)-N-(pentan-2-yl)propanamide Trifluoroacetic Acid Salt;

N-Cyclopentyl-N-(2-(2-(5-hydroxy-3-oxo-3,4-dihydro-2H-benzo[b][1,4]oxazin-8-yl)ethylamino)ethyl)-3-(3-(1-isopropyl-1H-pyrazol-4-yl)phenethoxy)propanamide Trifluoroacetic Acid Salt;

(R)-3-(3-(1-Ethyl-1H-pyrazol-4-yl)phenethoxy)-N-(2-(2-(5-hydroxy-3-oxo-3,4-dihydro-2H-benzo[b][1,4]oxazin-8-yl)ethylamino)ethyl)-N-(3-methylbutan-2-yl)propanamide Trifluoroacetic Acid Salt;

N-Cyclopentyl-3-(3-(1-ethyl-1H-pyrazol-4-yl)phenethoxy)-N-(2-(2-(5-hydroxy-3-oxo-3,4-dihydro-2H-benzo[b][1,4]oxazin-8-yl)ethylamino)ethyl)propanamide Trifluoroacetic Acid Salt;

(R)—N-(3,3-Dimethylbutan-2-yl)-3-(3-(1-ethyl-1H-pyrazol-4-yl)phenethoxy)-N-(2-(2-(5-hydroxy-3-oxo-3,4-dihydro-2H-benzo[b][1,4]oxazin-8-yl)ethylamino)ethyl)propanamide Trifluoroacetic Acid Salt;

(R)—N-(3,3-Dimethylbutan-2-yl)-N-(2-(2-(5-hydroxy-3-oxo-3,4-dihydro-2H-benzo[b][1,4]oxazin-8-yl)ethylamino)ethyl)-3-(3-(1-methyl-1H-pyrazol-4-yl)phenethoxy)propanamide Trifluoroacetic Acid Salt;

N-Cyclohexyl-N-(2-(2-(5-hydroxy-3-oxo-3,4-dihydro-2H-benzo[b][1,4]oxazin-8-yl)ethylamino)ethyl)-3-(3-(5-methyl-1,2,4-oxadiazol-3-yl)phenethoxy)propanamide Trifluoroacetic Acid Salt;

N-Cyclohexyl-3-(3-(1-ethyl-1H-imidazol-2-yl)phenethoxy)-N-(2-(2-(5-hydroxy-3-oxo-3,4-dihydro-2H-benzo[b][1,4]oxazin-8-yl)ethylamino)ethyl)propanamide Trifluoroacetic Acid Salt;

(R)—N-(Hexan-2-yl)-N-(2-(2-(5-hydroxy-3-oxo-3,4-dihydro-2H-benzo[b][1,4]oxazin-8-yl)ethylamino)ethyl)-3-(3-(1-methyl-1H-pyrazol-4-yl)phenethoxy)propanamide Trifluoroacetic Acid Salt;

N-Cycloheptyl-N-(2-(2-(5-hydroxy-3-oxo-3,4-dihydro-2H-benzo[b][1,4]oxazin-8-yl)ethylamino)ethyl)-3-(3-(1-methyl-1H-pyrazol-4-yl)phenethoxy)propanamide Trifluoroacetic Acid Salt;

N-Cyclohexyl-3-(3-(1,2-dimethyl-1H-imidazol-4-yl)phenethoxy)-N-(2-(2-(5-hydroxy-3-oxo-3,4-dihydro-2H-benzo[b][1,4]oxazin-8-yl)ethylamino)ethyl)propanamide Trifluoroacetic Acid Salt;

N-Cyclohexyl-N-(2-(2-(5-hydroxy-3-oxo-3,4-dihydro-2H-benzo[b][1,4]oxazin-8-yl)ethylamino)ethyl)-3-(3-(1-(2-methoxyethyl)-1H-pyrazol-4-yl)phenethoxy)propanamide Trifluoroacetic Acid Salt; or, N-Cyclohexyl-3-(3-(1,5-dimethyl-1H-pyrazol-4-yl)phenethoxy)-N-(2-(2-(5-hydroxy-3-oxo-3,4-dihydro-2H-benzo[b][1,4]oxazin-8-yl)ethylamino)ethyl)propanamide Trifluoroacetic Acid Salt.

In a still further aspect the present invention provides each individual compound:

N-Cyclohexyl-N-(2-(2-(5-hydroxy-3-oxo-3,4-dihydro-2H-benzo[b][1,4]oxazin-8-yl)ethylamino)ethyl)-3-(3-(1-methyl-1H-pyrazol-4-yl)phenethoxy)propanamide;

N-Cyclohexyl-N-(2-(2-(5-hydroxy-3-oxo-3,4-dihydro-2H-benzo[b][1,4]oxazin-8-yl)ethylamino)ethyl)-3-(3-(1-methyl-1H-pyrazol-5-yl)phenethoxy)propanamide;

N-Cyclohexyl-3-(3-(1-ethyl-1H-1,2,3-triazol-4-yl)phenethoxy)-N-(2-(2-(5-hydroxy-3-oxo-3,4-dihydro-2H-benzo[b][1,4]oxazin-8-yl)ethylamino)ethyl)propanamide;

N-Cyclohexyl-N-(2-(2-(5-hydroxy-3-oxo-3,4-dihydro-2H-benzo[b][1,4]oxazin-8-yl)ethylamino)ethyl)-3-(3-(1-methyl-1H-1,2,3-triazol-4-yl)phenethoxy)propanamide;

N-Cycloheptyl-N-(2-(2-(5-hydroxy-3-oxo-3,4-dihydro-2H-benzo[b][1,4]oxazin-8-yl)ethylamino)ethyl)-3-(3-(1-methyl-1H-1,2,3-triazol-4-yl)phenethoxy)propanamide;

N-Cyclohexyl-N-(2-(2-(5-hydroxy-3-oxo-3,4-dihydro-2H-benzo[b][1,4]oxazin-8-yl)ethylamino)ethyl)-3-(3-(2-methyl-2H-tetrazol-5-yl)phenethoxy)propanamide;

N-Cyclohexyl-N-(2-(2-(5-hydroxy-3-oxo-3,4-dihydro-2H-benzo[b][1,4]oxazin-8-yl)ethylamino)ethyl)-3-(3-(1-methyl-1H-tetrazol-5-yl)phenethoxy)propanamide;

(R)—N-(2-(2-(5-Hydroxy-3-oxo-3,4-dihydro-2H-benzo[b][1,4]oxazin-8-yl)ethylamino)ethyl)-3-(3-(1-methyl-1H-pyrazol-4-yl)phenethoxy)-N-(3-methylbutan-2-yl)propanamide;

N-Cyclohexyl-N-(2-(2-(5-hydroxy-3-oxo-3,4-dihydro-2H-benzo[b][1,4]oxazin-8-yl)ethylamino)ethyl)-3-(3-(oxazol-5-yl)phenethoxy)propanamide;

3-(3-(1,2,4-Oxadiazol-3-yl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide;

N-Cyclohexyl-N-(2-(2-(5-hydroxy-3-oxo-3,4-dihydro-2H-benzo[b][1,4]oxazin-8-yl)ethylamino)ethyl)-3-(3-(1-isopropyl-1H-1,2,3-triazol-4-yl)phenethoxy)propanamide;

N-Cyclohexyl-3-(4-fluoro-3-(1-methyl-1H-pyrazol-4-yl)
   phenethoxy)-N-(2-(2-(5-hydroxy-3-oxo-3,4-dihydro-2H-
   benzo[b][1,4]oxazin-8-yl)ethylamino)ethyl)propana-
   mide;
3-(3-(1H-1,2,3-Triazol-4-yl)phenethoxy)-N-cyclohexyl-N-
   (2-(2-(5-hydroxy-3-oxo-3,4-dihydro-2H-benzo[b][1,4]
   oxazin-8-yl)ethylamino)ethyl)propanamide;
3-(3-(2H-Tetrazol-5-yl)phenethoxy)-N-cyclohexyl-N-(2-(2-
   (5-hydroxy-3-oxo-3,4-dihydro-2H-benzo[b][1,4]oxazin-
   8-yl)ethylamino)ethyl)propanamide;
N-Cyclohexyl-3-(2-fluoro-3-(1-methyl-1H-pyrazol-4-yl)
   phenethoxy)-N-(2-(2-(5-hydroxy-3-oxo-3,4-dihydro-2H-
   benzo[b][1,4]oxazin-8-yl)ethylamino)ethyl)propana-
   mide;
N-Cyclohexyl-3-(3-fluoro-5-(1-methyl-1H-pyrazol-4-yl)
   phenethoxy)-N-(2-(2-(5-hydroxy-3-oxo-3,4-dihydro-2H-
   benzo[b][1,4]oxazin-8-yl)ethylamino)ethyl)propana-
   mide;
N-Cyclopentyl-N-(2-(2-(5-hydroxy-3-oxo-3,4-dihydro-2H-
   benzo[b][1,4]oxazin-8-yl)ethylamino)ethyl)-3-(3-(1-pro-
   pyl-1H-pyrazol-4-yl)phenethoxy)propanamide;
N-Cyclopentyl-3-(3-(1-(cyclopropylmethyl)-1H-pyrazol-4-
   yl)phenethoxy)-N-(2-(2-(5-hydroxy-3-oxo-3,4-dihydro-
   2H-benzo[b][1,4]oxazin-8-yl)ethylamino)ethyl)propana-
   mide;
(R)- N-(2-(2-(5-Hydroxy-3-oxo-3,4-dihydro-2H-benzo[b]
   [1,4]oxazin-8-yl)ethylamino)ethyl)-3-(3-(1-isopropyl-
   1H-pyrazol-4-yl)phenethoxy)-N-(3-methylbutan-2-yl)
   propanamide;
(R)- N-(2-(2-(5-Hydroxy-3-oxo-3,4-dihydro-2H-benzo[b]
   [1,4]oxazin-8-yl)ethylamino)ethyl)-3-(3-(1-isopropyl-
   1H-pyrazol-4-yl)phenethoxy)-N-(pentan-2-yl)propana-
   mide;
N-Cyclopentyl-N-(2-(2-(5-hydroxy-3-oxo-3,4-dihydro-2H-
   benzo[b][1,4]oxazin-8-yl)ethylamino)ethyl)-3-(3-(1-iso-
   propyl-1H-pyrazol-4-yl)phenethoxy)propanamide;
(R)-3-(3-(1-Ethyl-1H-pyrazol-4-yl)phenethoxy)-N-(2-(2-
   (5-hydroxy-3-oxo-3,4-dihydro-2H-benzo[b][1,4]oxazin-
   8-yl)ethylamino)ethyl)-N-(3-methylbutan-2-yl)propana-
   mide;
N-Cyclopentyl-3-(3-(1-ethyl-1H-pyrazol-4-yl)phenethoxy)-
   N-(2-(2-(5-hydroxy-3-oxo-3,4-dihydro-2H-benzo[b][1,4]
   oxazin-8-yl)ethylamino)ethyl)propanamide;
(R)- N-(3,3-Dimethylbutan-2-yl)-3-(3-(1-ethyl-1H-pyrazol-
   4-yl)phenethoxy)-N-(2-(2-(5-hydroxy-3-oxo-3,4-dihy-
   dro-2H-benzo[b][1,4]oxazin-8-yl)ethylamino)ethyl)pro-
   panamide;
(R)- N-(3,3-Dimethylbutan-2-yl)-N-(2-(2-(5-hydroxy-3-
   oxo-3,4-dihydro-2H-benzo[b][1,4]oxazin-8-yl)ethy-
   lamino)ethyl)-3-(3-(1-methyl-1H-pyrazol-4-yl)pheneth-
   oxy)propanamide;
N-Cyclohexyl-N-(2-(2-(5-hydroxy-3-oxo-3,4-dihydro-2H-
   benzo[b][1,4]oxazin-8-yl)ethylamino)ethyl)-3-(3-(5-me-
   thyl-1,2,4-oxadiazol-3-yl)phenethoxy)propanamide;
N-Cyclohexyl-3-(3-(1-ethyl-1H-pyrazol-4-yl)phenethoxy)-
   N-(2-(2-(5-hydroxy-3-oxo-3,4-dihydro-2H-benzo[b][1,4]
   oxazin-8-yl)ethylamino)ethyl)propanamide;
N-Cyclohexyl-3-(3-(1-ethyl-1H-imidazol-2-yl)pheneth-
   oxy)-N-(2-(2-(5-hydroxy-3-oxo-3,4-dihydro-2H-benzo
   [b][1,4]oxazin-8-yl)ethylamino)ethyl)propanamide;
(R)- N-(Hexan-2-yl)-N-(2-(2-(5-hydroxy-3-oxo-3,4-dihy-
   dro-2H-benzo[b][1,4]oxazin-8-yl)ethylamino)ethyl)-3-
   (3-(1-methyl-1H-pyrazol-4-yl)phenethoxy)propanamide;
N-Cycloheptyl-N-(2-(2-(5-hydroxy-3-oxo-3,4-dihydro-2H-
   benzo[b][1,4]oxazin-8-yl)ethylamino)ethyl)-3-(3-(1-me-
   thyl-1H-pyrazol-4-yl)phenethoxy)propanamide;
N-Cyclohexyl-3-(3-(4,5-dimethyl-1H-imidazol-2-yl)
   phenethoxy)-N-(2-(2-(5-hydroxy-3-oxo-3,4-dihydro-2H-
   benzo[b][1,4]oxazin-8-yl)ethylamino)ethyl)propana-
   mide;
N-Cyclohexyl-N-(2-(2-(5-hydroxy-3-oxo-3,4-dihydro-2H-
   benzo[b][1,4]oxazin-8-yl)ethylamino)ethyl)-3-(3-(1-me-
   thyl-1H-imidazol-2-yl)phenethoxy)propanamide;
N-Cyclohexyl-3-(3-(1,2-dimethyl-1H-imidazol-4-yl)
   phenethoxy)-N-(2-(2-(5-hydroxy-3-oxo-3,4-dihydro-2H-
   benzo[b][1,4]oxazin-8-yl)ethylamino)ethyl)propana-
   mide;
N-Cyclohexyl-3-(3-(1,2-dimethyl-1H-imidazol-4-yl)
   phenethoxy)-N-(2-(2-(5-hydroxy-3-oxo-3,4-dihydro-2H-
   benzo[b][1,4]oxazin-8-yl)ethylamino)ethyl)propana-
   mide;
N-Cyclohexyl-N-(2-(2-(5-hydroxy-3-oxo-3,4-dihydro-2H-
   benzo[b][1,4]oxazin-8-yl)ethylamino)ethyl)-3-(3-(1-(2-
   methoxyethyl)-1H-pyrazol-4-yl)phenethoxy)propana-
   mide; or,
N-Cyclohexyl-3-(3-(1,5-dimethyl-1H-pyrazol-4-yl)
   phenethoxy)-N-(2-(2-(5-hydroxy-3-oxo-3,4-dihydro-2H-
   benzo[b][1,4]oxazin-8-yl)ethylamino)ethyl)propana-
   mide;
or a pharmaceutically acceptable salt thereof In another aspect the present invention provides N-Cyclohexyl-N-(2-(2-(5-hydroxy-3-oxo-3,4-dihydro-2H-benzo[b][1,4]oxazin-8-yl)ethylamino)ethyl)-3-(3-(1-methyl-1H-pyrazol-4-yl)phenethoxy)propanamide or a pharmaceutically acceptable salt thereof (for example a Hemi-Fumaric Acid Salt).

The present invention further provides a process for the preparation of a compound of formula (I) or a pharmaceutically acceptable salt thereof as defined above. A compound of formula (I) can be prepared by adaptation of synthetic methods known in the literature, by using or adapting the synthetic methods described hereinbelow, or by using (when W in formula (I) is $CH_2$) or adapting the methods presented in Routes A, B, C and D below in which the following abbreviations are used:

SCX: Solid phase extraction with a sulfonic acid sorbent
HPLC: High performance liquid chromatography
THF: Tetrahydrofuran
DMF Dimethylformamide
NMP N-Methyl-2-Pyrrolidone
Triton B Benzyltrimethylammonium Hydroxide
DCM Dichloromethane
TFA Trifluoroacetic Acid
DIPEA Diisopropylethylamine
TEA Triethylamine
T3P 2-Propanephosphonic Acid Anhydride
Pd(Ph$_3$P)$_4$ Tetrakis(triphenylphosphine)palladium (0)
BOC anhydride Di-tert-butyldicarbonate
Pd-118 1,1'-Bis(di-t-butylphosphino)ferrocene palladium (II) dichloride
DAST Diethylaminosulfur trifluoride
HATU (2-(7-Aza-1H-benzotriazole-1-yl)-1,1,3,3-tetramethyluronium hexafluorophosphate)

Compounds of formula (I) can be converted into further compounds of formula (I) using standard procedures.

It will be appreciated by those skilled in the art that in the processes of the present invention certain functional groups such as hydroxyl or amino groups in the reagents may need to be protected by protecting groups. Thus, the preparation of the compounds of formula (I) may involve, at an appropriate stage, the removal of one or more protecting groups (for example by literature methods or by adapting techniques used in the Examples below).

The protection and deprotection of functional groups is described in 'Protective Groups in Organic Chemistry', edited by J. W. F. McOmie, Plenum Press (1973) and 'Protective Groups in Organic Synthesis', $3^{rd}$ edition, T. W. Greene and P. G. M. Wuts, Wiley-Interscience (1999).

A compound of formula (I) above can be converted to a pharmaceutically acceptable salt thereof by use or adaptation of methods used in the Examples or of methods described in the art.

The compounds of formula (I) and their pharmaceutically acceptable salts can be used in the treatment of:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) or adenovirus; or eosinophilic esophagitis;

2. bone and joints: arthritides associated with or including osteoarthritis/osteoarthrosis, both primary and secondary to, for example, congenital hip dysplasia; cervical and lumbar spondylitis, and low back and neck pain; osteoporosis; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;

3. pain and connective tissue remodelling of musculoskeletal disorders due to injury [for example sports injury] or disease: arthitides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritits, scleroderma, mixed connective tissue disorder, spondyloarthropathies or periodontal disease (such as periodontitis);

4. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

5. eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

6. gastrointestinal tract: glossitis, gingivitis, periodontitis; oesophagitis, including reflux; eosinophilic gastro-enteritis, mastocytosis, Crohn's disease, colitis (including ulcerative colitis, microscopic colitis and indeterminant colitis) proctitis, pruritis ani, coeliac disease, irritable bowel disorder, irritable bowel syndrome, non-inflammatory diarrhoea, and food-related allergies which may have effects remote from the gut (for example migraine, rhinitis or eczema);

7. abdominal: hepatitis, including autoimmune, alcoholic and viral; fibrosis and cirrhosis of the liver; cholecystitis; pancreatitis, both acute and chronic;

8. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

9. allograft rejection: acute and chronic following, for example, transplantation of kidney, heart, liver, lung, bone marrow, skin or cornea or following blood transfusion; or chronic graft versus host disease;

10. CNS: Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes;

11. other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome;
12. other disorders with an inflammatory or immunological component; including acquired immune deficiency syndrome (AIDS), leprosy, Sezary syndrome, and paraneoplastic syndromes;
13. cardiovascular: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins; and,
14. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes.

Thus, the present invention provides a compound of formula (I) or a pharmaceutically-acceptable salt thereof as hereinbefore defined for use in therapy.

In a further aspect, the present invention provides the use of a compound of formula (I) or a pharmaceutically acceptable salt thereof as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

The invention still further provides a method of treating, or reducing the risk of, an inflammatory disease or condition (including a reversible obstructive airways disease or condition) which comprises administering to a patient in need thereof a therapeutically effective amount of a compound of formula (I) or a pharmaceutically acceptable salt thereof as hereinbefore defined.

In particular, the compounds of this invention may be used in the treatment of adult respiratory distress syndrome (ARDS), pulmonary emphysema, bronchitis, bronchiectasis, chronic obstructive pulmonary disease (COPD), asthma and rhinitis.

For the above-mentioned therapeutic uses the dosage administered will, of course, vary with the compound employed, the mode of administration, the treatment desired and the disorder indicated. For example, the daily dosage of the compound of the invention, if inhaled, may be in the range from 0.05 micrograms per kilogram body weight (μg/kg) to 100 micrograms per kilogram body weight (μg/kg). Alternatively, if the compound is administered orally, then the daily dosage of the compound of the invention may be in the range from 0.01 micrograms per kilogram body weight (μg/kg) to 100 milligrams per kilogram body weight (mg/kg).

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I) or a pharmaceutically acceptable salt thereof as hereinbefore defined, in association with a pharmaceutically acceptable adjuvant, diluent or carrier.

The invention further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

The pharmaceutical compositions may be administered topically (e.g. to the skin or to the lung and/or airways) in the form, e.g., of creams, solutions, suspensions, heptafluoroalkane (HFA) aerosols and dry powder formulations, for example, formulations in the inhaler device known as the Turbuhaler®; or systemically, e.g. by oral administration in the form of tablets, capsules, syrups, powders or granules; or by parenteral administration in the form of solutions or suspensions; or by subcutaneous administration; or by rectal administration in the form of suppositories; or transdermally.

Dry powder formulations and pressurized HFA aerosols of the compounds of the invention may be administered by oral or nasal inhalation. For inhalation, the compound is desirably finely divided. The finely divided compound preferably has a mass median diameter of less than 10 μm, and may be suspended in a propellant mixture with the assistance of a dispersant, such as a $C_8$-$C_{20}$ fatty acid or salt thereof, (for example, oleic acid), a bile salt, a phospholipid, an alkyl saccharide, a perfluorinated or polyethoxylated surfactant, or other pharmaceutically acceptable dispersant.

The compounds of the invention may also be administered by means of a dry powder inhaler. The inhaler may be a single or a multi dose inhaler, and may be a breath actuated dry powder inhaler.

One possibility is to mix the finely divided compound of the invention with a carrier substance, for example, a mono-, di- or polysaccharide, a sugar alcohol, or another polyol. Suitable carriers are sugars, for example, lactose, glucose, raffinose, melezitose, lactitol, maltitol, trehalose, sucrose, mannitol; and starch. Alternatively the finely divided compound may be coated by another substance. The powder mixture may also be dispensed into hard gelatine capsules, each containing the desired dose of the active compound.

Another possibility is to process the finely divided powder into spheres which break up during the inhalation procedure. This spheronized powder may be filled into the drug reservoir of a multidose inhaler, for example, that known as the Turbuhaler® in which a dosing unit meters the desired dose which is then inhaled by the patient. With this system the active ingredient, with or without a carrier substance, is delivered to the patient.

For oral administration the compound of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compound of the invention may be admixed with, for example, a vegetable oil or polyethylene glycol. Hard gelatine capsules may contain granules of the compound using either the abovementioned excipients for tablets. Also liquid or semisolid formulations of the compound of the invention may be filled into hard gelatine capsules.

Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, saccharine and/or carboxymethylcellulose as a thickening agent or other excipients known to those skilled in art.

The compounds of the invention may also be administered in conjunction with other compounds used for the treatment of the above conditions.

The invention therefore further relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for the treatment of one or more of the conditions listed.

In particular, for the treatment of the inflammatory diseases such as (but not restricted to) rheumatoid arthritis, osteoarthritis, asthma, allergic rhinitis, chronic obstructive pulmonary disease (COPD), psoriasis, and inflammatory bowel disease, the compounds of the invention may be combined with the following agents: non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine The present invention still further relates to the combination of a compound of the invention, or a pharmaceutically acceptable salt thereof, together with a cytokine or agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 17, and interleukin antagonists or inhibitors such as anakinra; tumour necrosis factor alpha (TNF-α) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline.

In addition the invention relates to a combination of a compound of the invention, or a pharmaceutically acceptable salt thereof, with a monoclonal antibody targeting B-Lymphocytes (such as CD20 (rituximab), MRA-aIL16R) or T-Lymphocytes (CTLA4-Ig, HuMax Il-15).

The present invention still further relates to the combination of a compound of the invention, or a pharmaceutically acceptable salt thereof, with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the C—$X_3$—C family.

The present invention further relates to the combination of a compound of the invention, or a pharmaceutically acceptable salt thereof, with an inhibitor of matrix metalloprotease (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a compound of the invention, or a pharmaceutically acceptable salt thereof, and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739, 010; a 2-cyanoquinoline compound such as L-746,530; or an indole or quinoline compound such as MK-591, MK-886, and BAY×1005.

The present invention further relates to the combination of a compound of the invention, or a pharmaceutically acceptable salt thereof, and a receptor antagonist for leukotrienes (LT) B4, LTC4, LTD4, and LTE4. selected from the group consisting of the phenothiazin-3-1s such as L-651,392; amidino compounds such as CGS-25019c; benzoxalamines such as ontazolast; benzenecarboximidamides such as BILL 284/260; and compounds such as zafirlukast, ablukast, montelukast, pranlukast, verlukast (MK-679), RG-12525, Ro-245913, iralukast (CGP 45715A), and BAY×7195.

The present invention still further relates to the combination of a compound of the invention, or a pharmaceutically acceptable salt thereof, and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention, or a pharmaceutically acceptable salt thereof, and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention, or a pharmaceutically acceptable salt thereof, and a proton pump inhibitor (such as omeprazole) or a gastroprotective histamine type 2 receptor antagonist.

The present invention further relates to the combination of a compound of the invention, or a pharmaceutically acceptable salt thereof, and an antagonist of the histamine type 4 receptor.

The present invention still further relates to the combination of a compound of the invention, or a pharmaceutically acceptable salt thereof, and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention, or a pharmaceutically acceptable salt thereof, and an anticholinergic agents including muscarinic receptor (M1, M2, and M3) antagonist such as atropine, hyoscine, glycopyrrrolate, ipratropium bromide, tiotropium bromide, oxitropium bromide, pirenzepine or telenzepine.

The present invention further relates to the combination of a compound of the invention, or a pharmaceutically acceptable salt thereof, and a chromone, such as sodium cromoglycate or nedocromil sodium.

The present invention still further relates to the combination of a compound of the invention, or a pharmaceutically acceptable salt thereof, with a glucocorticoid, such as flunisolide, triamcinolone acetonide, beclomethasone dipropionate, budesonide, fluticasone propionate, ciclesonide or mometasone furoate.

The present invention further relates to the combination of a compound of the invention, or a pharmaceutically acceptable salt thereof, with an agent that modulates a nuclear hormone receptor such as PPARs.

The present invention still further relates to the combination of a compound of the invention, or a pharmaceutically acceptable salt thereof, together with an immunoglobulin (Ig) or Ig preparation or an antagonist or antibody modulating Ig function such as anti-IgE (for example omalizumab).

The present invention further relates to the combination of a compound of the invention, or a pharmaceutically acceptable salt thereof, and another systemic or topically-applied anti-inflammatory agent, such as thalidomide or a derivative thereof, a retinoid, dithranol or calcipotriol.

The present invention still further relates to the combination of a compound of the invention, or a pharmaceutically acceptable salt thereof, and combinations of aminosalicylates and sulfapyridine such as sulfasalazine, mesalazine, balsalazide, and olsalazine; and immunomodulatory agents such as the thiopurines, and corticosteroids such as budesonide.

The present invention further relates to the combination of a compound of the invention, or a pharmaceutically acceptable salt thereof, together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention, or a pharmaceutically acceptable salt thereof, and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The present invention further relates to the combination of a compound of the invention, or a pharmaceutically acceptable salt thereof, and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention, or a pharmaceutically acceptable salt thereof, and an agent for the treatment of acute or chronic pain, such as a centrally or peripherally-acting analgesic (for example an opioid or derivative thereof), carbamazepine, phenyloin, sodium valproate, amitryptiline or other anti-depressant agent-s, paracetamol, or a non-steroidal anti-inflammatory agent.

The present invention further relates to the combination of a compound of the invention, or a pharmaceutically acceptable salt thereof, together with a parenterally or topically-applied (including inhaled) local anaesthetic agent such as lignocaine or a derivative thereof.

A compound of the present invention, or a pharmaceutically acceptable salt thereof, can also be used in combination with an anti-osteoporosis agent including a hormonal agent such as raloxifene, or a biphosphonate such as alendronate.

The present invention still further relates to the combination of a compound of the invention, or a pharmaceutically acceptable salt thereof, together with a: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Gefitinib or Imatinib mesylate), a serine/threonine kinase (such as an inhibitor of a MAP kinase such as p38, JNK, protein kinase A, B or C, or IKK), or a kinase involved in cell cycle regulation (such as a cylin dependent kinase); (viii) glucose-6 phosphate dehydrogenase inhibitor; (ix) kinin-B.sub1.- or B.sub2.-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin NK.sub1. or NK.sub3. receptor antagonist such as NKP-608C, SB-233412 (talnetant) or D-4418; (xx) elastase inhibitor such as UT-77 or ZD-0892; (xxi) TNF-alpha converting enzyme inhibitor (TACE); (xxii) induced nitric oxide synthase (iNOS) inhibitor; (xxiii) chemoattractant receptorhomologous molecule expressed on TH2 cells, (such as a CRTH2 antagonist); (xxiv) inhibitor of P38; (xxv) agent modulating the function of Toll-like receptors (TLR), (xxvi) agent modulating the activity of purinergic receptors such as P2x7; (xxvii) inhibitor of transcription factor activation such as NFkB, API or STATS; or (xxviii) a glucocorticoid receptor (GR-receptor) agonist.

In a further aspect the present invention provides a combination (for example for the treatment of COPD, asthma or allergic rhinitis) of a compound of formula (I) and one or more agents selected from the list comprising:

a non-steroidal glucocorticoid receptor (GR-receptor) agonist;
a PDE4 inhibitor including an inhibitor of the isoform PDE4D;
a muscarinic receptor antagonist (for example a M1, M2 or M3 antagonist, such as a selective M3 antagonist) such as ipratropium bromide, tiotropium bromide, oxitropium bromide, pirenzepine or telenzepine;
a modulator of chemokine receptor function (such as a CCR1 receptor antagonist);
a steroid (such as budesonide); or,
an inhibitor of a kinase function (for example IKK2 or p38).

In a still further aspect, the invention provides a kit comprising a preparation of a first active ingredient which is a compound of formula (I) or a pharmaceutically acceptable salt thereof as hereinbefore defined, and a preparation of a second active ingredient which is:

a non-steroidal glucocorticoid receptor (GR-receptor) agonist;
a PDE4 inhibitor including an inhibitor of the isoform PDE4D;
a muscarinic receptor antagonist (for example a M1, M2 or M3 antagonist, such as a selective M3 antagonist) such as ipratropium bromide, tiotropium bromide, oxitropium bromide, pirenzepine or telenzepine;
a modulator of chemokine receptor function (such as a CCR1 receptor antagonist);
a steroid (such as budesonide); or,
an inhibitor of a kinase function (for example IKK2 or p38).

and instructions for the simultaneous or separate administration of the preparations to a patient in need thereof.

A compound of the invention, or a pharmaceutically acceptable salt thereof, can also be used in combination with an existing therapeutic agent for the treatment of cancer, for example suitable agents include:

(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);

(ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride;

(iii) an agent which inhibits cancer cell invasion (for example a metalloproteinase inhibitor like marimastat or an inhibitor of urokinase plasminogen activator receptor function);

(iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy)quinazolin-4-amine (CI 1033)), an inhibitor of the platelet-derived growth factor family, or an inhibitor of the hepatocyte growth factor family;

(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin);

(vi) a vascular damaging agent such as combretastatin A4, or a compound disclosed in WO 99/02166, WO 00/40529, WO 00/41669, WO 01/92224, WO 02/04434 or WO 02/08213;

(vii) an agent used in antisense therapy, for example one directed to one of the targets listed above, such as ISIS 2503, an anti-ras antisense;

(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

The present invention will now be further explained by reference to the following illustrative Examples.

General Methods $^1$H NMR spectra were recorded on a Varian UnityInova instrument. Either the central peaks of chloroform-d (CDCl$_3$; $\delta_H$ 7.27 ppm), dimethylsulfoxide-d$_6$ (d$_6$-DMSO; $\delta_H$ 2.50 ppm) or methanol-d$_4$ (CD$_3$OD; $\delta_H$ 3.31 ppm), or an internal standard of tetramethylsilane (TMS; $\delta_H$ 0.00 ppm) were used as references.

Mass spectra were recorded on a Agilent MSD (+ve and −ve APCI and EI) or a Waters ZMD (+ve and −ve EI) following analytical HPLC on an Agilent 1100.

Flash chromatography was carried out on silica causing Biotage FLASH™ or equivalent, for example Biotage Flashmaster™ or Isolute columns. Unless stated otherwise, starting materials were commercially available. All solvents and commercial reagents were of laboratory grade and were used as received.

Preparative HPLC was carried out using either a Phenomenex Gemini C18 5 μm, a Waters Xterra C8 5 μm or a Waters Xbridge C8 5 μm using aceonitrile in either aqueous ammonia or aqueous trifluoroacetic acid; or a Waters Sunfire C18 5 μm using acetonitrile in aqueous trifluoroacetic acid.

XRPD was carried out on PANalytical CubiX PRO machine in Ø-Ø configuration over the scan range 2° to 40° 2Ø with 100-second exposure per 0.02° increment. The X-rays were generated by a copper long-fine focus tube operated at 45 kV and 40 mA. The wavelength of the copper X-rays was 1.5418 Å. The Data was collected on zero background holders on which ~2 mg of the compound was placed. The holder was made from a single crystal of silicon, which had been cut along a non-diffracting plane and then polished on an optically flat finish. The X-rays incident upon this surface were negated by Bragg extinction.

DSC thermograms were measured using a TA Q1000 Differential Scanning Calorimeter, with aluminium pans and pierced lids. The sample weights varied between 0.3 to 5 mg. The procedure was carried out under a flow of nitrogen gas (50 ml/min) and the temperature studied from 25 to 300° C. at a constant rate of temperature increase of 10° C. per minute.

The abbreviations or terms used in the Preparations and Examples have the following meanings:
SCX: Solid phase extraction with a sulfonic acid sorbent
HPLC: High performance liquid chromatography
THF: Tetrahydrofuran
DMF Dimethylformamide
NMP N-Methyl-2-Pyrrolidone
Triton B Benzyltrimethylammonium Hydroxide
DCM Dichloromethane
TFA Trifluoroacetic Acid
DIPEA Diisopropylethylamine
TEA Triethylamine
T3P 2-Propanephosphonic Acid Anhydride
Pd(Ph$_3$P)$_4$ Tetrakis(triphenylphosphine)palladium (0)
BOC anhydride Di-tert-butyldicarbonate
Pd-118 1,1'-Bis(di-t-butylphosphino)ferrocene palladium (II) dichloride
DAST Diethylaminosulfur trifluoride
HATU (2-(7-Aza-1H-benzotriazole-1-yl)-1,1,3,3-tetramethyluronium hexafluorophosphate)

Preparation 1 8-(2-Aminoethyl)-5-hydroxy-2H-benzo[b][1,4]oxazin-3(4H)-one hydrochloride

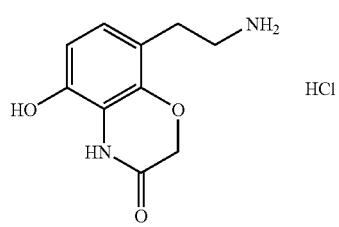

Step i) 1-(2,4-Dihydroxy-3-nitrophenyl)ethanone

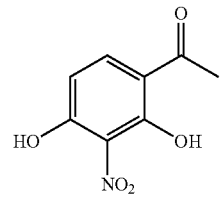

2-Nitrobenzene-1,3-diol (24.5 g) was added portionwise over 15 min to a vigorously stirred solution of aluminium chloride (46.3 g) in nitrobenzene (325 mL). Acetic anhydride (15.65 mL) was then added dropwise to the mixture over a further 15 min and the mixture then heated at 100° C. for 5 h. The reaction was cooled to ambient temperature and carefully quenched with ice cold 2M hydrochloric acid (300 mL). The mixture was extracted with ether (2×500 mL) and the combined ether extracts then extracted with 2M aqueous sodium hydroxide (2×400 mL). The combined basic extracts were washed with ether (4×500 mL) and then acidified to pH 1 with 2M hydrochloric acid (700 mL). The resulting precipitate was filtered off, washed with water, and dried under vacuum at 40° C. to afford the subtitled compound as a yellow/brown solid (29.5 g). $^1$H NMR (400 MHz, DMSO-d6) δ 13.32 (s, 1H), 12.31 (s, 1H), 7.98 (d, J=9.2 Hz, 1H), 6.63 (d, J=28.2 Hz, 1H), 2.59 (s, 3H).

Step ii) 1-(4-(Benzyloxy)-2-hydroxy-3-nitrophenyl)ethanone

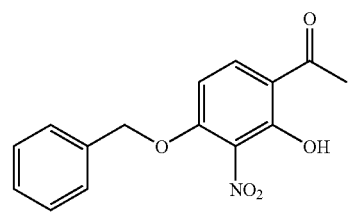

Lithium tert-butoxide (4.06 g) was added to a stirred solution of 1-(2,4-dihydroxy-3-nitrophenyl)ethanone (10 g) in DMF (100 mL), under nitrogen, whilst maintaining the internal temperature below 30° C. After stirring for a further 10 min at ambient temperature, benzyl bromide (6.03 mL) was added and the mixture stirred for a further 20 h. Further benzyl bromide (3 mL) was added and the mixture stirred for 24 h. The reaction was quenched with water (300 mL), 1M aqueous sodium hydroxide (50 mL) was added and the mixture was washed with ether (2×300 mL), filtering through Celite to aid separation. The basic solution was cooled in ice/water, acidified with ice cold 2M hydrochloric acid (200 mL) and the resulting precipitate filtered off, washed with water and dried to afford a light brown solid. The solid was slurried with ethanol (100 mL) for 1 h and the solid filtered off, washed with cold ethanol (20 mL), and dried under vacuum at 40° C. to afford the subtitled compound as a light brown solid (6.8 g).

¹H NMR (400 MHz, DMSO-d6) δ 13.04 (s, 1H), 8.14 (d, J=9.2 Hz, 1H), 7.45-7.32 (m, 5H), 7.01 (d, J=9.2 Hz, 1H), 5.42 (s, 2H), 2.64 (s, 3H).

Step iii) 1-(3-Amino-4-(benzyloxy)-2-hydroxyphenyl)ethanone

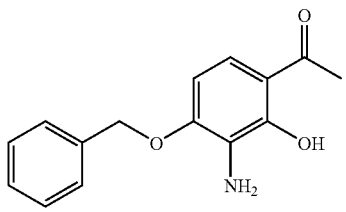

Zinc dust (5.5 g) was added portionwise to a suspension of 1-(4-(benzyloxy)-2-hydroxy-3-nitrophenyl)ethanone (5.5 g) in acetic acid (55 mL) over 15 min, whilst maintaining the internal temperature below 40° C. with an ice bath. The mixture was allowed to attain ambient temperature and stirred for a further 2 h. The mixture was filtered through Celite (caution gets hot, do not allow to dry), washed with acetic acid, and the filtrate poured onto ice/water (500 mL). The resulting precipitate was filtered off, washed with water, and dried under vacuum at 40° C. to afford the subtitled compound as a light brown solid (4.8 g). ¹H NMR (300 MHz, DMSO-d6) δ 7.53 (m, 2H), 7.48-7.33 (m, 3H), 7.28 (d, J=9.0 Hz, 1H), 6.72 (d, J=9.0 Hz, 1H), 5.29 (s, 2H), 2.59 (s, 3H).

Step iv) 8-Acetyl-5-(benzyloxy)-2H-benzo[b][1,4]oxazin-3(4H)-one

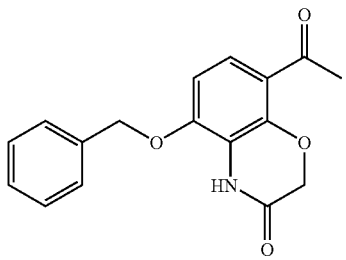

2-Chloroacetyl chloride (1.77 mL) was added dropwise to a stirred mixture of 1-(3-amino-4-(benzyloxy)-2-hydroxyphenyl)ethanone (5.2 g) and sodium hydrogen carbonate (3.74 g) in DMF (30 mL) and then stirred for a further 2 h. Cesium carbonate (7.90 g) was added and heated at 100° C. for 20 h. The mixture was cooled to ambient temperature, quenched with water (500 mL), extracted with ethyl acetate (2×200 mL), washed with water (3×300 mL) and brine, dried over anhydrous sodium sulfate, filtered and evaporated under vacuum. The solid residue was treated with ether, filtered and dried to afford the subtitled compound as a beige solid (5.7 g). ¹H NMR (400 MHz, DMSO-d6) δ 10.33 (s, 1H), 7.55 (m, 2H), 7.39 (m, 2H), 7.34 (d, J=8.8 Hz, 1H), 7.33 (m, 1H), 6.89 (d, J=9.2 Hz, 1H), 5.27 (s, 2H), 4.67 (s, 2H), 3.32 (s, 3H).

Step v) 5-(Benzyloxy)-8-(2-chloroacetyl)-2H-benzo[b][1,4]oxazin-3(4H)-one

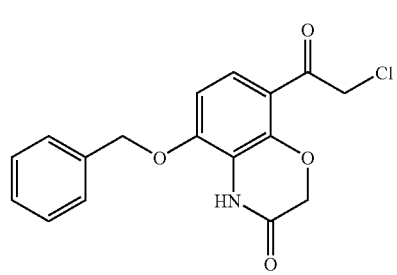

Benzyltrimethylammonium dichloroiodate (14.17 g) was added to a stirred solution of 8-acetyl-5-(benzyloxy)-2H-benzo[b][1,4]oxazin-3(4H)-one (5.5 g) in a mixture of dichloromethane (100 mL), acetic acid (33 mL) and water (5.5 mL) and the reaction mixture stirred at 65° C. for 20 h. The reaction was cooled to ambient temperature, treated with aqueous sodium bisulphite (5.78 g in 100 mL) and stirred for a further 30 min. The mixture was diluted with diethyl ether (200 mL) and the resulting solid filtered off, washed with water and further diethyl ether, and dried under vacuum at 40° C. to afford the subtitled compound as a light brown solid (5.6 g). ¹H NMR (300 MHz, DMSO-d6) δ 10.41 (s, 1H), 7.55 (m, 2H), 7.44 (d, J=9.4 Hz, 1H), 7.39 (m, 2H), 7.32 (m, 1H), 6.95 (d, J=9.4 Hz, 1H), 5.30 (s, 2H), 4.96 (s, 2H), 4.69 (s, 2H).

Step vi) 8-(2-Azidoacetyl)-5-(benzyloxy)-2H-benzo[b][1,4]oxazin-3(4H)-one

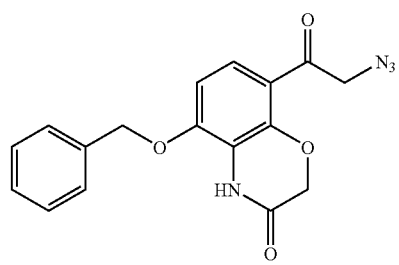

Sodium azide (1.18 g) was added to a suspension of 5-(benzyloxy)-8-(2-chloroacetyl)-2H-benzo[b][1,4]oxazin-3(4H)-one (4.8 g) in DMF (50 mL) and stirred for 2 h. The mixture was poured onto ice/water and the resulting solid filtered off, washed with water and dried under vacuum at 40° C. to afford the subtitled compound as a light brown solid (4.6 g). ¹H NMR (300 MHz, DMSO-d$_6$) δ 10.42 (s, 1H), 7.55 (m, 2H), 7.48 (m, 1H), 7.43-7.29 (m, 3H), 6.97 (m, 1H), 5.31 (s, 2H), 4.69 (s, 2H), 4.63 (s, 2H).

Step vii) 8-(2-Aminoethyl)-5-hydroxy-2H-benzo[b] [1,4]oxazin-3(4H)-one hydrochloride

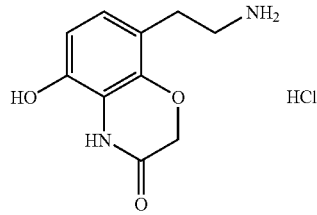

Procedure A

A slurry of 10% palladium on carbon (1 g) in acetic acid (20 mL) was added to a partial solution of 8-(2-azidoacetyl)-5-(benzyloxy)-2H-benzo[b][1,4]oxazin-3(4H)-one (5.65 g) in acetic acid (280 mL). Concentrated hydrochloric acid (14.34 mL) was then added, and the mixture hydrogenated at 5 bar for 6 h. Water (50 mL) was added to dissolve any solid, followed by further 10% palladium on carbon (1 g) and the mixture hydrogenated at 5 bar for a further 20 h. Further 10% palladium on carbon (1 g) was added and the mixture hydrogenated for a further 20 h. The mixture was filtered through Celite and the filtrate evaporated under vacuum, and azeotroped with acetonitrile. The solid residue was treated with ether, isolated by filtration and dried to afford the subtitled compound as a white solid (2.2 g).

Procedure B

Acetic acid (45 mL), concentrated hydrochloric acid (10.2 mL) and water (45 mL) were added to a hydrogenation vessel containing 8-(2-azidoacetyl)-5-(benzyloxy)-2H-benzo[b][1, 4]oxazin-3(4H)-one (5 g) and 10% palladium on carbon (2.5 g) to give a slurry. The mixture was hydrogenated at 4.7 bar and 25° C. for 2 h 20 min to give a partial solution. The solution was then warmed to 40° C. and hydrogenated at 4.7 bar for 68 h. The mixture was filtered through GF/F filter paper and the filtrate evaporated to 50 mL. 1-Butanol (50 mL) was added and the solution re-evaporated to 50 mL. 1-Butanol (50 mL) was added to give a suspension and this re-evaporated to 50 mL to give a suspension which was stirred at ambient temperature for 2 h then filtered, washed with 1-butanol (2.5 mL) and dried in a vacuum oven at 55° C. overnight to afford the sub-titled compound as a white solid (3.2 g). $^1$H NMR (300 MHz, DMSO-d6) δ 9.94 (s, 1H), 9.87 (s, 1H), 7.99-7.82 (m, 3H), 6.66 (d, J=8.0 Hz, 1H), 6.49 (d, J=8.0 Hz, 1H), 4.54 (s, 2H), 2.91 (m, 2H), 2.76 (m, 2H).

Preparation 2 Alternate preparative methodology for 8-(2-Aminoethyl)-5-hydroxy-2H-benzo[b][1,4]oxazin-3(4H)-one hydrochloride (also made in Preparation 1, above)

Step i) 1-(2,4-Dihydroxy-3-nitrophenyl)ethanone

The extraction solvent can be changed from diethyl ether to di-isopropyl ether. For example: Nitrobenzene (87.5 mL) was added to aluminium trichloride (46.33 g). 2-nitroresorcinol (25 g), in nitrobenzene (112.5 mL) was added. The mixture was cooled to 5° C. and acetic acid anhydride (15.68 mL) added maintaining the internal temperature below 20° C. The mixture was heated to 100° C. for 2 h then cooled to 5° C. Cold (3° C.) 3M aqueous hydrogen chloride (200 mL) was charged. The mixture was heated to 20° C. then di-isopropylether (200 mL) charged. The aqueous phase was removed and the organic phase extracted with 2 M aqueous sodium hydroxide (200 mL). The aqueous phase was washed with di-isopropylether (200 mL). The aqueous phase was removed and heated to 50° C. 3 M aqueous hydrogen chloride (467.5 mL) was charged and the mixture cooled to 20° C. The suspension was filtered, washed with water (50 mL) and dried under vacuum to yield the title compound (31.14 g).

In order to improve the final filtration, the following modification may be used: after the di-isopropylether wash, the aqueous phase may added to an identical quantity of preheated (50° C.) 3 M aqueous hydrogen chloride. On cooling to 20° C. the suspension may be filtered to yield the sub-titled compound.

Step ii) 1-(4-(Benzyloxy)-2-hydroxy-3-nitrophenyl) ethanone

The base can be changed from lithium tert-butoxide in DMF at RT, to sodium bicarbonate in acetonitrile at reflux, where reaction takes 6-8 h to go to completion instead of 2 days. With this procedure the product precipitates on addition of water. For example: Acetonitrile (700 mL) was added to the product of Preparation 2 Step i) (100 g) and sodium bicarbonate (49.0 g). The mixture was heated to 60° C. and benzyl bromide (75.62 mL) added. The mixture was heated to reflux. After 6.5 h the mixture was cooled to 60° C. and water (450 mL) added. The mixture was cooled to below 45° C. and methyl tert-butyl ether (450 mL) added. The mixture was cooled to 20° C. and stirred for at least 1.5 hours. The suspension was filtered and washed with water (250 mL) then ethanol (250 mL) to yield the title compound as a damp solid, 155.65 g. Alternatively the material can be dried under vacuum.

Step iii) 1-(3-Amino-4-(benzyloxy)-2-hydroxyphenyl)ethanone

The reduction conditions can be changed from using zinc dust in acetic acid to a catalytic hydrogenation in tetrahydrofuran using platinum-on-charcoal catalyst. For example: Tetrahydrofuran (1000 mL) and triethylamine (9.70 mL) were added to the product of Preparation 2 Step ii) (100 g) and platinum on carbon (1%; Johnson-Matthey Type 18MA) (6 g). The mixture was hydrogenated at 50° C. and 4 barg until complete then cooled to 20° C. and filtered. The mixture was concentrated under vacuum to approximately half the initial volume then methyl isobutyl ketone (500 mL) was charged. The mixture was concentrated under vacuum to half the initial volume then methyl isobutyl ketone (500 mL) was charged. The resulting mixture can be directly used in the next step or evaporated to dryness to afford the sub-titled compound as a brown solid.

Step iv) 8-Acetyl-5-(benzyloxy)-2H-benzo[b][1,4] oxazin-3(4H)-one

The base can be changed from using cesium carbonate and sodium bicarbonate to only potassium bicarbonate. With this procedure the solvent is changed from dimethylformamide to 2-methyl pentan-4-one/water leading to the product precipitating directly rather then needing an extractive work-up. For example:

To the product of Preparation 2 Step iii) (62.69 g, prepared as in Step iii), in methyl iso-butyl ketone 414 mL) was charged methyl isobutyl ketone (150 mL). Potassium bicarbonate was charged and the mixture heated to 50° C. then chloro-acetyl chloride (21.30 mL) in methyl isobutyl ketone (62.69 mL) was charged. After 30 min, further chloro-acetyl chloride (3.87 mL) was charged. After a further 30 min chloro-acetyl chloride (3.87 mL) was charged. After 15 min potassium bicarbonate (60.98 g) in water (344.79 mL) was added. The mixture was heated at reflux for 2 h then cooled to 19° C. The suspension was filtered and the residue washed with water (94.04 mL), then ethanol (94.04 mL) and then dried under vacuum to yield the sub-titled compound (58.4 g).

Step v) 5-(Benzyloxy)-8-(2-chloroacetyl)-2H-benzo[b][1,4]oxazin-3(4H)-one

The solvent can be changed from dichloromethane, acetic acid and water to ethanol/water leading to the product precipitating directly rather then needing an extractive work-up. With this procedure there is no need to use an aqueous sodium bisulfate wash. For example: To the product from Preparation 2 Step iv) (23 g) and benzyltrimethylammonium dichloroiodate (53.85 g) was added ethanol (230 mL). The mixture was heated at reflux for 1 h then cooled to 50° C. and water (230 mL) added. The mixture was cooled to 20° C. and stirred for at least 1 h. The suspension was filtered, washed with water (46 mL) and then ethanol (69 mL). To the damp solid was added ethyl acetate (460 mL). The mixture was heated at reflux for 1 h then cooled to 20° C. and stirred for at least 1 h. The suspension was filtered and the residue was washed with ethyl acetate (115 mL) and dried under vacuum to yield the sub-titled compound (61.0 g).

Step vi) 8-(2-Azidoacetyl)-5-(benzyloxy)-2H-benzo[b][1,4]oxazin-3(4H)-one

The solvent can be changed from DMF to NMP. For example: To the product from Preparation 2 Step v) (101.0 g) was added N-methylpyrrolidone (303 mL). To the mixture was added sodium azide (29.69 g). The mixture was stirred at 20° C. for 3 h then added into water (1820 mL). A line wash of N-methylpyrroldione (10.10 mL) was added and the mixture stirred for at least 30 min. The suspension was filtered, washed with water (505 mL), isopropyl alcohol (202 mL) and then dried to afford the sub-titled compound (96.064 g).

Step vii) 8-(2-Aminoethyl)-5-hydroxy-2H-benzo[b][1,4]oxazin-3(4H)-one hydrochloride The ratio of acetic acid to water can be changed from 6:1 to 2:1 or 1:1. With this procedure the water is added at the start and the catalyst is charged in one portion. The product can be crystallised from n-butane/water. For example: To the product from Preparation 2 Step vi) (5 g), palladium on carbon (60% moisture, Johnson-Matthey 10R39) (2.5 g) was added acetic acid (45.0 mL), 36 wt % aqueous hydrogen chloride (10.21 mL) and water (45.0 mL). The mixture was hydrogenated at 22-25° C., 4.7 barg until 1 mole of hydrogen had been consumed. The reaction was then hydrogenated at 45° C., 4.7 barg until complete then cooled to 22° C. and filtered. The solution was concentrated under vacuum by removal of approximately two-thirds of the solvent. 1-butanol (50 mL) was charged and the solution concentrated under vacuum by removal of approximately half the solvent. 1-butanol (50 mL) was charged and the mixture concentrated under vacuum by removal of approximately half the solvent. The mixture was cooled to 20° C. and stirred for at least 3 h. The suspension was filtered and the residue washed with 1-butanol (2.5 mL) and dried to yield the sub-titled compound (2.90 g).

Preparation 3 3-(3-Bromophenethoxy)-N-cyclohexyl-N-(2,2-dimethoxyethyl)propanamide

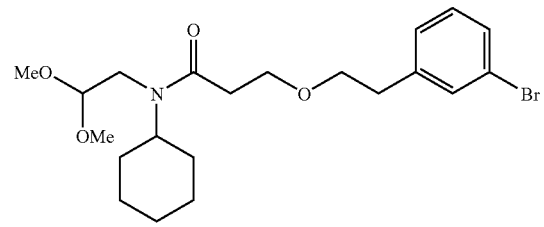

Step i) tert-Butyl 3-(3-bromophenethoxy)propanoate

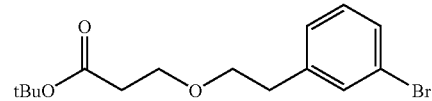

Procedure A

A solution of 2-(3-bromophenyl)ethanol (98.9 g) and tert-butyl acrylate (88.9 mL) in toluene (197.8 mL) was warmed to 50° C. Triton B (as a 40% solution in water, 96.3 mL) was added over 4 h at 50° C. and then the mixture stirred overnight at 20° C. The mixture was diluted with toluene (395.6 mL) and washed with 3M hydrochloric acid (395.6 mL) and the layers separated. The organic layer was used directly in the next Step.

Procedure B

A solution of 2-(3-bromophenyl)ethanol (5 g) was stirred in toluene (30 mL) followed by the addition of Triton-B in methanol (0.57 mL). The volatiles were removed until ~10 mL remained. To this solution was added tert-butyl acrylate (3.94 mL) and the mixture was left to stir for 24 h. The solvent was evaporated and the residue was purified on silica eluting with isohexane-10% ethyl acetate/isohexane. The solvent was evaporated to afford the sub-titled compound as a colourless oil (6.7 g). $^1$H NMR (300 MHz, CDCl$_3$) δ 7.39-7.30 (m, 2H), 7.17-7.12 (m, 2H), 3.68 (t, J=6.5 Hz, 2H), 3.64 (t, J=6.9 Hz, 2H), 2.84 (t, J=6.9 Hz, 2H), 2.48 (t, J=6.5 Hz, 2H), 1.44 (t, 9H)

Step ii) 3-(3-Bromophenethoxy)propanoic acid

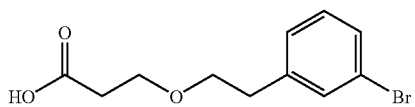

Procedure A p-Toluenesulfonic acid acid monohydrate (9.2 g) was added to the solution of tert-butyl 3-(3-bromophenethoxy)propanoate (132 g, prepared as in Preparation 3, Step I), Procedure A) in toluene (~590 mL) from the previous Step. The solution was heated to reflux and at reflux for 1.5 h then allowed to cool to 20° C. 2-Methyltetrahydrofuran (197.8 mL) was added and the solution extracted with water (194.4 mL) and 1M sodium hydroxide (725.3 mL). The separated aqueous layer was diluted with 2-methyltetrahydrofuran (593.4 mL), extracted with 3M hydrochloric acid (483.5 mL) and the layers separated. The separated organic layer can be evaporated to dryness to afford the sub-titled compound as a colourless oil (99.6 g) or the solution used directly in the next Step.

Procedure B

To tert-butyl 3-(3-bromophenethoxy)propanoate (6.7 g, prepared as in Preparation 3, Step i), Procedure B) in DCM (10 mL) was added TFA (10 mL). The mixture was stirred overnight before the solvent was evaporated under vacuum. The residue was azeotroped twice with toluene to afford a colourless oil (5.63 g). This material was used in the next step directly. $^1$H NMR (300 MHz, DMSO-d6) δ 7.46 (s, 1H), 7.39 (m, 1H), 7.24 (m, 2H), 3.60 (t, 2H), 3.58 (t, 2H), 2.79 (t, 2H), 2.42 (t, 2H)

Step iii) 3-(3-Bromophenethoxy)-N-cyclohexyl-N-(2,2-dimethoxyethyl)propanamide

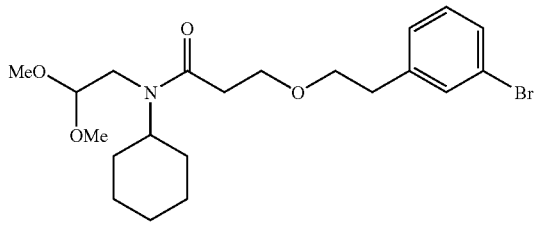

To a stirred solution of 3-(3-bromophenethoxy)propanoic acid (3.3 g, prepared as in Preparation 3, Step ii), Procedure B) in acetonitrile (60 mL) was added TEA (20.21 mL) and N-(2,2-dimethoxyethyl)cyclohexanamine (2.26 g). T3P (1.56M in THF, 15.39 mL) was then added portionwise. The reaction was stirred overnight, and then worked up by the addition of saturated sodium hydrogen carbonate, which was extracted twice with ethyl acetate. The pooled organics were washed once with water, once with brine, dried over sodium sulphate, filtered and the solvent removed to afford a brown oil, which was purified on silica (5% Ethyl acetate/isohexane to 20% Ethyl acetate/isohexane). The solvent was evaporated to afford an orange oil (4.5 g). MS [M+H-MeOH]+=410/412 (MultiMode+) $^1$H NMR (400 MHz, CD$_3$OD) δ 7.40-7.35 (m, 1H), 7.33-7.29 (m, 1H), 7.20-7.12 (m, 2H), 4.54 (t, J=5.0 Hz, 0.5H), 4.39 (t, J=5.4 Hz, 0.5H), 4.08-3.98 (m, 1H), 3.73-3.59 (m, 4H), 3.39-3.36 (m, 2H), 3.37 (s, 3H), 3.34 (s, 3H), 2.83-2.78 (m, 2H), 2.67-2.61 (m, 2H), 1.82-1.74 (m, 2H), 1.70-1.55 (m, 3H), 1.55-1.42 (m, 2H), 1.38-1.26 (m, 2H), 1.19-1.04 (m, 1H), a ~1:1 mixture of rotamers is observed.

Preparation 4 (R)—N-(2,2-Dimethoxyethyl)-3-methylbutan-2-amine

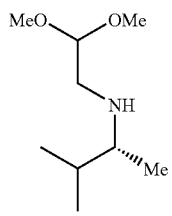

A solution of (R)-3-methylbutan-2-amine (10.50 g) and 2,2-dimethoxyacetaldehyde (18.18 mL) in methanol (50 mL) was added to palladium on carbon (3 g) in water (3.0 mL) at 25° C. The mixture was hydrogenated under 5 bar at 25° C. for 24 h. The reaction mixture was filtered through Celite and concentrated under vacuum to afford (R)—N-(2,2-dimethoxyethyl)-3-methylbutan-2-amine as a colourless liquid (16.40 g). $^1$H NMR (300 MHz, CDCl$_3$) δ 4.47 (t, J=5.6 Hz, 1H), 3.39 (s, 6H), 2.77 (dd, J=11.9, 5.4 Hz, 1H), 2.66 (dd, J=11.9, 6.0 Hz, 1H), 2.44 (qd, J=6.4, 5.1 Hz, 1H), 1.75-1.63 (m, 1H), 0.96 (d, J=6.3 Hz, 3H), 0.90 (d, J=6.9 Hz, 3H), 0.86 (d, J=6.9 Hz, 3H).

Preparation 5
N-(2,2-Dimethoxyethyl)cyclohexanamine

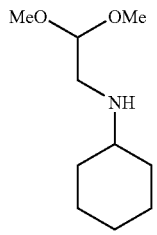

2-Chloro-1,1-dimethoxyethane (206 mL) was treated with cyclohexanamine (575 mL) and the mixture was heated at 120° C. for 24 h under an atmosphere of nitrogen before being cooled to room temperature. A solution of sodium hydroxide (100 g) in 400 mL water was added, the mixture was stirred at room temperature for 10 min and then the layers were separated. The organic fraction was purified by distillation under reduced pressure (b.p. 105-107° C., 13 mm Hg) to give the title compound as a colourless oil (280 g). $^1$H NMR (400

MHz, CDCl₃) δ 4.46 (t, J=5.5 Hz, 1H), 3.38 (s, 6H), 2.75 (d, J=5.6 Hz, 2H), 2.45-2.35 (m, 1H), 1.92-1.57 (m, 5H), 1.31-1.00 (m, 6H).

Preparation 6
N-(2,2-Dimethoxyethyl)cycloheptanamine

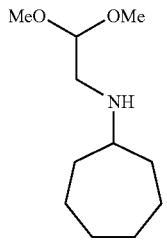

To a stirred solution of cycloheptanamine (8.62 g) in methanol (20 mL) was added 2,2-dimethoxyacetaldehyde (11.49 mL) and the mixture stirred at room temperature for 5 h. Palladium on carbon 10% (1 g) was added and the mixture hydrogenated at 5 bar for 16 h. It was filtered and concentrated under vacuum to give N-(2,2-dimethoxyethyl)cycloheptanamine as an oil (15.26 g). ¹H NMR (300 MHz, CDCl₃) δ 4.47 (t, J=5.6 Hz, 1H), 3.39 (s, 6H), 2.73 (d, J=5.6 Hz, 2H), 2.67-2.55 (m, 1H), 1.90-1.25 (m, 12H).

Preparation 7
N-(2,2-Diethoxyethyl)-2,2-dimethylpropan-1-amine

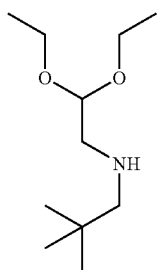

Sodium triacetoxyborohydride (5.30 g) was added to a cooled at 0° C. solution of aminoacetaldehyde diethyl acetal (2.91 mL) and pivalaldehyde (2.21 mL) in dichloromethane (50 mL). The reaction was stirred for 16 h, allowing the temperature to warm to ambient conditions. Water (50 mL) was added, followed by portionwise addition of sodium bicarbonate (8.40 g), causing effervescence. The mixture was stirred vigorously for 1 h, then allowed to partition. The phases were then separated and the aqueous phase extracted with further dichloromethane (20 mL). The combined organic extracts were dried over sodium sulfate, filtered and concentrated in vacuo to afford N-(2,2-diethoxyethyl)-2,2-dimethylpropan-1-amine (3.79 g) as an oil. ¹H NMR (400 MHz, CDCl₃) δ 4.63 (t, J=5.6 Hz, 1H), 3.71 (dq, J=9.5, 7.1 Hz, 2H), 3.55 (dq, J=9.4, 7.1 Hz, 2H), 2.73 (d, J=5.6 Hz, 2H), 2.37 (s, 2H), 1.22 (t, J=7.1 Hz, 6H), 0.91 (s, 9H)

Preparation 8 (R)—N-(2,2-Dimethoxyethyl)-3,3-dimethylbutan-2-amine

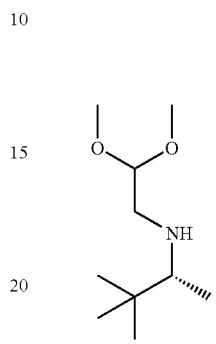

2,2-Dimethoxyacetaldehyde (7.54 mL) was added to a solution of (R)-3,3-dimethylbutan-2-amine (5.06 g) in methanol (20 mL) and the mixture stirred for 2 h. A slurry of palladium on carbon (10%, 200 mg) in methanol (5 mL) was added and the mixture hydrogenated at 5 bar for 66 h. The mixture was then filtered and concentrated in vacuo to afford (R)- N-(2,2-dimethoxyethyl)-3,3-dimethylbutan-2-amine (8.78 g) as an oil. ¹H NMR (400 MHz, CDCl₃) δ 4.47 (t, J=5.6 Hz, 1H), 3.38 (s, 3H), 3.37 (s, 3H), 2.86 (dd, J=12.2, 5.5 Hz, 1H), 2.58 (dd, J=12.1, 5.9 Hz, 1H), 2.23 (q, J=6.4 Hz, 1H), 0.97 (d, J=6.4 Hz, 3H), 0.89 (s, 9H)

Preparation 9
N-(2,2-Dimethoxyethyl)cyclopentanamine

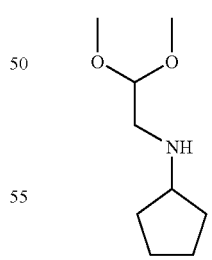

To a stirred solution of cyclopentanamine (5 g) in methanol (20 mL) was added 2,2-dimethoxyacetaldehyde 60% in water (8.86 mL) and the mixture stirred at ambient temperature for 5 h. A slurry of palladium on carbon (10%, 200 mg) in methanol (5 mL) was added and the mixture hydrogenated at 5 bar for 16 h. It was filtered and concentrated in vacuo to afford N-(2,2-dimethoxyethyl)cyclopentanamine (9.44 g) as a oil. ¹H NMR (400 MHz, CDCl₃) δ 4.47 (t, J=5.6 Hz, 1H), 3.39 (s, 6H), 3.05 (quintet, J=6.8 Hz, 1H), 2.72 (d, J=5.4 Hz, 2H), 1.89-1.80 (m, 2H), 1.73-1.62 (m, 2H), 1.58-1.48 (m, 2H), 1.36-1.27 (m, 2H)

Preparation 10
(R)—N-(2,2-Dimethoxyethyl)pentan-2-amine

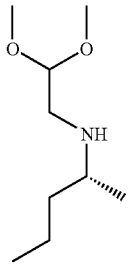

2,2-Dimethoxyacetaldehyde (0.59 mL) was added to a solution of (R)-pentan-2-amine hydrochloride (0.48 g) and triethylamine (0.54 mL) in methanol (4 mL) and the mixture stirred for 2 h. A slurry of palladium on carbon (10%, 20 mg) in methanol (1 mL) was added and the mixture hydrogenated at 5 bar for 20 h. The mixture was then filtered and in vacuo. The resulting residue was triturated with diethyl ether (5 mL) and the resulting white solid extracted with further diethyl ether (2×5 mL). The combined ether fractions were concentrated in vacuo to afford (R)—N-(2,2-dimethoxyethyl)pentan-2-amine (0.745 g) as an oil. $^1$H NMR (400 MHz, CDCl$_3$) δ 4.92 (t, J=5.4 Hz, 1H), 3.47 (s, 3H), 3.47 (s, 3H), 3.25-3.15 (m, 1H), 2.99 (ddd, J=27.9, 12.7, 5.5 Hz, 2H), 1.86-1.77 (m, 1H), 1.64-1.54 (m, 1H), 1.49-1.32 (m, 5H), 0.95 (t, J=7.3 Hz, 3H)

Preparation 11
N-(2,2-Dimethoxyethyl)-3-methylbutan-1-amine

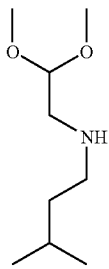

A solution of 3-methylbutan-1-amine (1.33 mL) and 2,2-dimethoxyacetaldehyde (1.73 mL) in MeOH (10 mL) was added to palladium on carbon (0.366 g) in water (0.5 mL) at 25° C. The mixture of was hydrogenated under 5 bar at 25° C. for 3 h. The reaction mixture was filtered and concentrated in vacuo to afford N-(2,2-dimethoxyethyl)-3-methylbutan-1-amine (1.8 g) as a liquid. $^1$H NMR (300 MHz, CDCl$_3$) δ 4.47 (t, J=5.5 Hz, 1H), 3.39 (s, 6H), 2.74 (d, J=5.6 Hz, 2H), 2.65-2.59 (m, 2H), 1.62 (septet, J=6.7 Hz, 1H), 1.44-1.33 (m, 2H), 0.90 (d, J=6.7 Hz, 6H)

Preparation 12
N-(2,2-Dimethoxyethyl)-3,3-dimethylbutan-1-amine

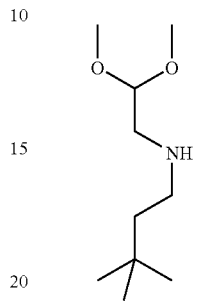

A solution of 3,3-dimethylbutan-1-amine (1.33 mL) and 2,2-dimethoxyacetaldehyde (1.5 mL) in MeOH (10 mL) was added to palladium on carbon (0.316 g) in water (0.5 mL) at 25° C. The mixture of was hydrogenated under 5 bar at 25° C. for 3 h. The reaction mixture was filtered and concentrated in vacuo to afford N-(2,2-dimethoxyethyl)-3,3-dimethylbutan-1-amine (1.85 g) as a liquid. $^1$H NMR (300 MHz, CDCl$_3$) δ 4.47 (t, J=5.6 Hz, 1H), 3.40 (s, 6H), 2.75 (d, J=5.8 Hz, 2H), 2.65-2.57 (m, 2H), 1.45-1.35 (m, 2H), 0.90 (s, 9H)

Preparation 13
(R)—N-(2,2-Dimethoxyethyl)hexan-2-amine

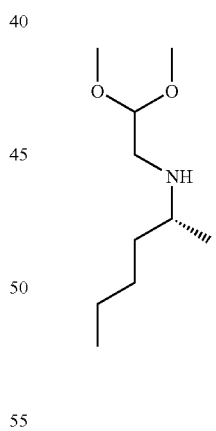

2,2-Dimethoxyacetaldehyde (7.54 mL) was added to a solution of (R)-hexan-2-amine (5.06 g) in methanol (20 mL) and the mixture stirred at ambient temperature for 5 h. A slurry of 10% palladium on carbon (200 mg) in methanol (5 mL) was added and the mixture hydrogenated at 5 bar for 16 h, then filtered and concentrated in vacuo to afford the sub-titled compound as a colourless liquid (9.22 g). $^1$H NMR (400 MHz, CDCl$_3$) δ 4.46 (t, J=5.5 Hz, 1H), 3.39 (s, 6H), 2.72 (ddd, J=31.1, 11.9, 5.6 Hz, 2H), 2.60 (sextet, J=6.0 Hz, 1H), 1.36-1.24 (m, 6H), 1.04 (d, J=6.2 Hz, 3H), 0.90 (t, J=6.9 Hz, 3H)

Example 1

N-Cyclohexyl-N-(2-(2-(5-hydroxy-3-oxo-3,4-dihydro-2H-benzo[b][1,4]oxazin-8-yl)ethylamino)ethyl)-3-(3-(1-methyl-1H-pyrazol-4-yl)phenethoxy)propanamide Trifluoroacetic Acid Salt

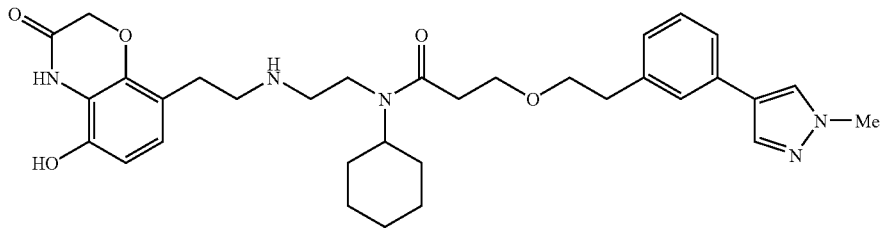

Step i) N-Cyclohexyl-N-(2,2-dimethoxyethyl)-3-(3-(1-methyl-1H-pyrazol-4-yl)phenethoxy)propanamide

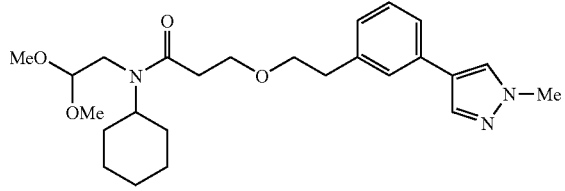

To 3-(3-bromophenethoxy)-N-cyclohexyl-N-(2,2-dimethoxyethyl)propanamide (1.4 g), prepared as in Preparation 3 Step iii), within a 35 mL microwave tube with stirrer were added 1-methyl-4-(4,4,5,5-tetramethyl-1,3,2-dioxaborolan-2-yl)-1H-pyrazole (0.92 g), potassium carbonate (0.88 g) and Pd(Ph$_3$P)$_4$ (0.18 g) followed by methanol (8 mL). The vial was sealed and heated within a CEM Discover microwave at 100° C. for 15 min. The mixture was diluted with DCM and washed once with water, once with brine, dried over sodium sulphate and the solvent evaporated to afford crude material as an orange oil. This was purified on silica using ethyl acetate as the eluent to afford the product (1.52 g). MS [M+H-MeOH]+=412 (MultiMode+) $^1$H NMR (400 MHz, CD$_3$OD) δ 7.92 (s, 1H), 7.78 and 7.77 (2×s, 1H), 7.40-7.32 (m, 2H), 7.23 and 7.22 (2×t, J=7.6 Hz, 1H), 7.07-7.03 (m, 1H), 4.52 and 4.36 (2×t, J=5.3 Hz, 1H), 4.05-3.95 and 3.69-3.60 (2×m, 1H), 3.901 and 3.898 (2×s, 3H), 3.75-3.64 (m, 4H), 3.34 (s, 3H), 3.32 (s, 3H), 3.34 and 3.25 (2×d, J=5.1 Hz, 2H), 2.84 and 2.83 (2×t, J=6.6 Hz, 2H), 2.65 and 2.63 (2×t, J=6.1 Hz, 2H), 1.79-1.04 (m, 10H); a ~1:1 mixture of rotamers is observed.

Step ii) N-Cyclohexyl-3-(3-(1-methyl-1H-pyrazol-4-yl)phenethoxy)-N-(2-oxoethyl)propanamide

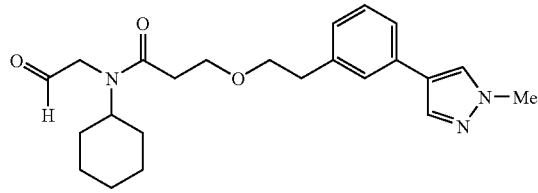

N-Cyclohexyl-N-(2,2-dimethoxyethyl)-3-(3-(1-methyl-1H-pyrazol-4-yl)phenethoxy)propanamide (0.5 g) was stirred in DCM (10 mL) followed by the addition of p-toluenesulfonic acid monohydrate (0.43 g). The mixture was stirred for 1 h. Ethyl acetate was added followed by sodium hydrogen carbonate solution. The aqueous phase was removed and the remaining organic phase washed once with water, once with brine, dried over sodium sulphate, filtered and the solvent removed to afford the desired material as an oil (0.48 g). This material was used in the next step directly. MS [M+H]+=398 (MultiMode+)

Step iii) N-Cyclohexyl-N-(2-(2-(5-hydroxy-3-oxo-3,4-dihydro-2H-benzo[b][1,4]oxazin-8-yl)ethylamino)ethyl)-3-(3-(1-methyl-1H-pyrazol-4-yl)phenethoxy)propanamide Trifluoroacetic Acid Salt

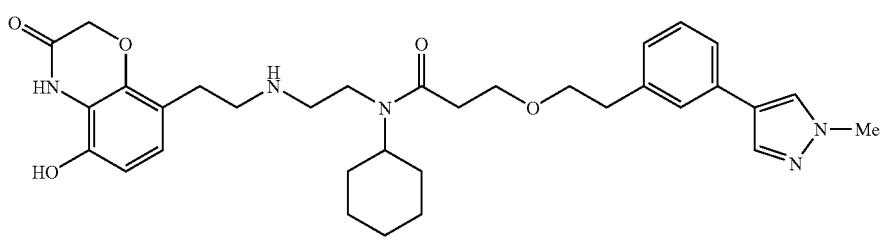

To a stirred solution of N-cyclohexyl-3-(3-(1-methyl-1H-pyrazol-4-yl)phenethoxy)-N-(2-oxoethyl)propanamide (448 mg) in NMP (10 mL) and water (0.5 mL) was added 8-(2-aminoethyl)-5-hydroxy-2H-benzo[b][1,4]oxazin-3(4H)-one hydrochloride (303 mg) and sodium bicarbonate (104 mg). The mixture was stirred for 5 min before the addition of sodium triacetoxyborohydride (358 mg). The reaction was stirred overnight before the addition of sodium hydrogen carbonate solution, which was extracted three times with DCM. The solvents were removed under vacuum from the pooled organics followed by the addition of ethyl acetate (100 mL), water (50 mL), sodium bicarbonate followed by BOC anhydride. The reaction was stirred overnight before the layers were separated and the aqueous layer extracted once more with ethyl acetate. The pooled organics were washed once with water, once with brine, dried over sodium sulphate, filtered and the solvent removed to afford crude product, which was purified on silica twice using ethyl acetate. The solvent was removed to afford 200 mg of a mixture of mono-protected and di-protected material. The mixture was taken up in diethyl ether (20 mL) followed by the addition of 4M Hydrochloric acid in dioxane (2 mL), which caused a white solid to form instantly. Diethyl ether (50 mL) was added and the mixture stirred overnight. The solvent was removed, the residue taken up in DCM (20 mL) followed by the addition of 4M Hydrochloric acid in dioxane (4 mL) and stirred overnight. The solvent was removed under vacuum to afford the titled compound (180 mg). This material was basified with sodium hydrogen carbonate solution, which was extracted three times with DCM. The pooled organics were acidified with 0.5 mL of TFA and volatiles removed to afford the TFA salt. This material was purified by reverse phase prep HPLC (Gemini column using 0.2% TFA/acetonitrile as the eluent) to afford the titled compound as a TFA salt. MS [M+H]+=590 (MultiMode+) $^1$H NMR (400 MHz, CD$_3$OD) δ 7.89 (s, 1H), 7.77-7.75 (m, 1H), 7.39-7.37 (m, 1H), 7.35-7.31 (m, 1H), 7.22 (t, J=7.6 Hz, 1H), 7.06-7.03 (m, 1H), 6.69 (d, J=8.2 Hz, 1H), 6.47 (d, J=8.5 Hz, 1H), 4.60 (s, 2H), 3.89 (s, 3H), 3.74-3.67 (m, 5H), 3.51-3.45 (m, 2H), 3.12-3.07 (m, 2H), 3.04-2.99 (m, 2H), 2.88-2.82 (m, 4H), 2.63 (t, J=6.0 Hz, 2H), 1.81-1.74 (m, 2H), 1.70-1.59 (m, 3H), 1.46-1.26 (m, 4H), 1.17-1.04 (m, 1H)

Example 2

N-Cyclohexyl-N-(2-(2-(5-hydroxy-3-oxo-3,4-dihydro-2H-benzo[b][1,4]oxazin-8-yl)ethylamino)ethyl)-3-(3-(1-methyl-1H-pyrazol-4-yl)phenethoxy)propanamide Trifluoroacetic Acid Salt

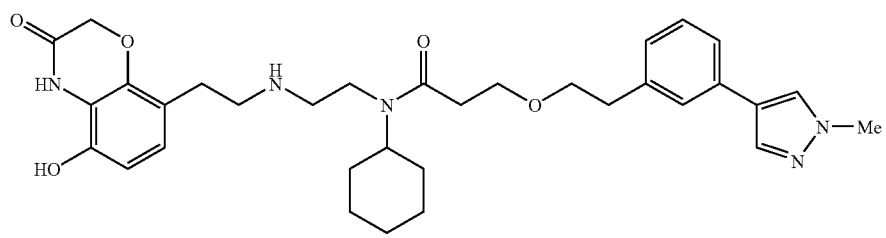

Step i) 3-(3-Bromophenethoxy)-N-cyclohexyl-N-(2-oxoethyl)propanamide

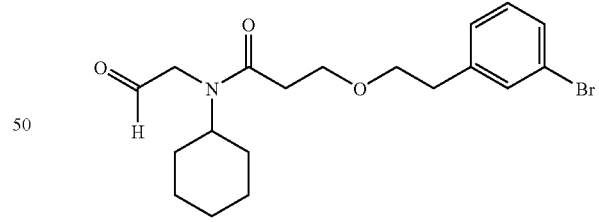

To a stirred solution of 3-(3-bromophenethoxy)-N-cyclohexyl-N-(2,2-dimethoxyethyl)propanamide (1.5 g) in acetone (30 mL) was added 2M hydrochloric acid (15 mL). The mixture was stirred for 2 h before the solvent was removed under vacuum, followed by the addition of water. The aqueous phase was extracted three times with DCM and the pooled DCM was washed once with brine, dried over sodium sulphate, filtered and the solvent removed to afford the desired material (1.5 g). This material was used in the next step directly.

Step ii) tert-Butyl 2-(3-(3-bromophenethoxy)-N-cyclohexylpropanamido)ethyl(2-(5-hydroxy-3-oxo-3,4-dihydro-2H-benzo[b][1,4]oxazin-8-yl)ethyl)carbamate To tert-butyl 2-(3-(3-bromophenethoxy)-N-cyclohexylpropanamido)ethyl(2-(5-hydroxy-3-oxo-3,4-dihydro-2H-benzo[b][1,4]oxazin-8-yl)ethyl)carbamate (500 mg) in a 35 mL microwave vial was added 1-methyl-4-(4,4,5,5-tetramethyl-

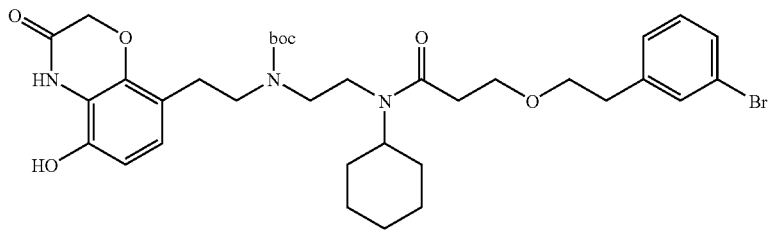

To a stirred solution of 3-(3-bromophenethoxy)-N-cyclohexyl-N-(2-oxoethyl)propanamide (1.5 g) in NMP (10 mL) and water (0.5 mL) was added 8-(2-aminoethyl)-5-hydroxy-2H-benzo[b][1,4]oxazin-3(4H)-one hydrochloride (1.02 g) and sodium bicarbonate (0.35 g). The mixture was stirred for 5 min before the addition of sodium triacetoxyborohydride (1.20 g). The reaction was stirred overnight before the addition of sodium hydrogen carbonate solution, which was then extracted three times with DCM. The mixture was evaporated to afford the product in NMP, which was diluted with 50 mL of DCM followed by the addition of BOC anhydride (0.88 mL) and triethylamine (0.53 mL). The reaction was stirred overnight before the addition of water, which was extracted once with DCM. The DCM phase was washed twice with water, twice with brine, dried over sodium sulphate, filtered and the solvent removed to afford product contaminated with NMP. Ethyl acetate was added which was subsequently washed twice with water, twice with brine, dried over sodium sulphate, filtered and the solvent removed. The crude product was purified on silica using 40% Ethyl acetate/isohexane to afford a pale brown/yellow oil (700 mg), which consisted of a mixture of mono and di-protected material. This material was used in the next step without further purification.

Step iii) N-Cyclohexyl-N-(2-(2-(5-hydroxy-3-oxo-3,4-dihydro-2H-benzo[b][1,4]oxazin-8-yl)ethylamino)ethyl)-3-(3-(1-methyl-1H-pyrazol-4-yl)phenethoxy)propanamide Trifluoroacetic Acid Salt 1,3,2-dioxaborolan-2-yl)-1H-pyrazole (181 mg), potassium carbonate (201 mg) and Pd(Ph$_3$P)$_4$ (42 mg) in ethanol (10 mL). The vial was sealed and heated at 110° C. within a Discover microwave for 40 min with stirring. The reaction was cooled followed by the addition of ethyl acetate, which was washed once with water, once with brine, dried over sodium sulphate and the solvent removed. The residue was purified on silica using neat ethyl acetate to afford the protected product (250 mg). This material was taken up in DCM followed by the addition of 4M hydrochloric acid in dioxane and stirred overnight. The solvent was removed under vacuum to afford of crude material (330 mg). This was basified with sodium hydrogen carbonate solution, which was extracted three times with DCM. The pooled organics were acidified with 0.5 mL of TFA and the solvent removed to afford the titled compound as a TFA salt. MS [M+H]+=590 (MultiMode+) $^1$H NMR (400 MHz, CD$_3$OD) δ 7.89 (s, 1H), 7.77-7.75 (m, 1H), 7.39-7.37 (m, 1H), 7.35-7.31 (m, 1H), 7.22 (t, J=7.6 Hz, 1H), 7.06-7.03 (m, 1H), 6.69 (d, J=8.2 Hz, 1H), 6.47 (d, J=8.5 Hz, 1H), 4.60 (s, 2H), 3.89 (s, 3H), 3.74-3.67 (m, 5H), 3.51-3.45 (m, 2H), 3.12-3.07 (m, 2H), 3.04-2.99 (m, 2H), 2.88-2.82 (m, 4H), 2.63 (t, J=6.0 Hz, 2H), 1.81-1.74 (m, 2H), 1.70-1.59 (m, 3H), 1.46-1.26 (m, 4H), 1.17-1.04 (m, 1H)

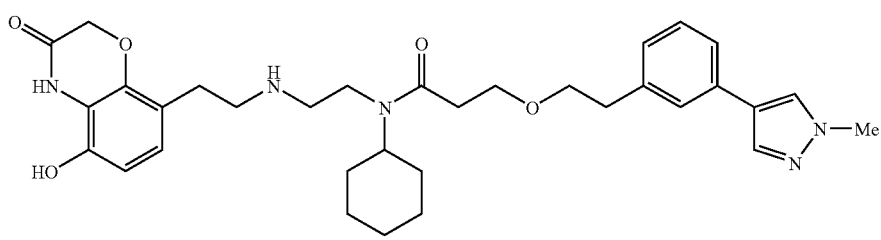

Example 2a

N-Cyclohexyl-N-(2-(2-(5-hydroxy-3-oxo-3,4-dihydro-2H-benzo[b][1,4]oxazin-8-yl)ethylamino)ethyl)-3-(3-(1-methyl-1H-pyrazol-4-yl)phenethoxy)propanamide Hemi-Fumaric Acid Salt

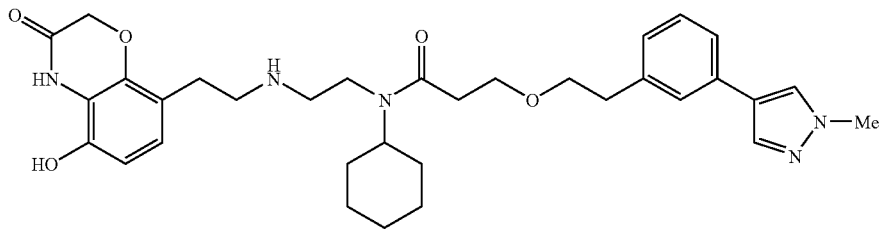

Step i) 3-(3-(1-Methyl-1H-pyrazol-4-yl)phenethoxy)propanoic acid

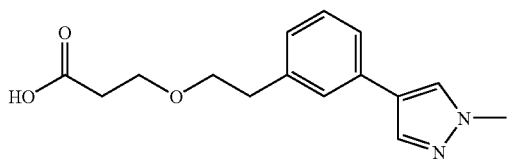

2-Methyltetrahydrofuran (142.1 mL) was added to Pd-118 (4.52 g) to give a red solution. To this solution was added a solution of sodium hydroxide (41.6 g) in water (473.5 mL), followed by a solution of 1-methyl-4-(4,4,5,5-tetramethyl-1,3,2-dioxaborolan-2-yl)-1H-pyrazole (81.81 g) in 2-methyltetrahydrofuran (142.1 mL), followed by the solution of 3-(3-bromophenethoxy)propanoic acid (94.7 g, prepared as in Preparation 3, Step (ii)) in 2-methyltetrahydrofuran (585 mL solution volume). The mixture was then heated to reflux and at reflux for 30 min then allowed to cool to 20° C. The mixture was filtered through GF/F filter paper then the layers separated. 20% w/w Citric acid (568.2 mL) was added to the separated aqueous layer, followed by 2-methyltetrahydrofuran (568.2 mL). After mixing, the layers were separated, the organic layer diluted with 2-methyltetrahydrofuran (to make the solution up to 950 mL) and filtered to give a small sample of the subtitled compound as an off-white solid (5.63 g). 800 mL of the filtrate (total volume 930 mL) was passed through a cartridge filter containing charcoal. The solution was partially evaporated under vacuum to give a solution measuring 490 mL and split into 2 portions. Firstly half of the solution was cooled to 20° C. and added to dibutyl ether (400 mL) at 20° C. to give a precipitate which was stirred at 20° C. for 2 h. The suspension was filtered, washed with dibutyl ether (100 mL) and dried at 50° C. under vacuum to afford the sub-titled compound (34.1 g). The second half of the solution was added to dibutyl ether (400 mL) at 65° C. to give a precipitate which was maintained at 65° C. for 10 min then cooled to 15° C. and stirred for 1 h. The suspension was filtered, washed with dibutyl ether (100 mL) and dried at 50° C. under vacuum to afford the subtitled compound as a white solid (30.5 g). MS [M+H]+=275.2 (MultiMode+) $^1$H NMR (400 MHz, DMSO-d6) δ 12.15 (s, 1H), 8.09 (s, 1H), 7.83 (s, 1H), 7.43 (s 1H), 7.37 (d, 1H), 7.24 (t, 1H), 7.05 (d, 1H), 3.86 (s, 3H), 3.62 (t, 2H), 3.61 (t, 2H), 2.80 (t, 2H), 2.45 (t, 2H).

Step ii) N-Cyclohexyl-N-(2,2-dimethoxyethyl)-3-(3-(1-methyl-1H-pyrazol-4-yl)phenethoxy)propanamide

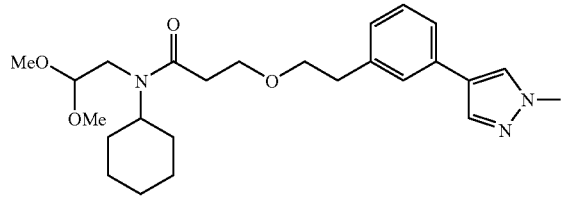

A solution of N-(2,2-dimethoxyethyl)cyclohexanamine (21.5 g) in tetrahydrofuran (30 mL) was added to a solution of 3-(3-(1-methyl-1H-pyrazol-4-yl)phenethoxy)propanoic acid in tetrahydrofuran (105 mL) at 20° C. Tetrahydrofuran (15 mL) was added, followed by triethylamine (51.8 mL), followed by a solution of T3P in tetrahydrofuran (121.9 mL of a 1.62M solution). The solution was stirred at 20° C. for 1 h then cooled to 10° C. Pre-chilled (10° C.) 0.5M sodium bicarbonate solution (225 mL) was added, followed by iso-propyl acetate (150 mL). After mixing the layers were separated and the organic layer washed with 20% w/w sodium chloride solution (150 mL), then evaporated to dryness to afford the subtitled compound as a brown oil (48.6 g). MS [M+H-MeOH]+=412.20 (100%) (MultiMode+) [M+H]+=444.20 (MultiMode+) $^1$H NMR (300 MHz, CDCl$_3$) δ 7.75 (s, 1H), 7.62 (s, 1H), 7.33-7.23 (m, 3H), 7.10-7.03 (m, 1H), 4.61 (t, 0.7H), 4.36 (t, 0.3H), 3.94 (s, 3H), 3.79 (q, 2H), 3.69 (q, 2H), 3.62-3.43 (m, 1.5H), 3.40 (s, 3H), 3.38 (s, 3H), 3.30 (d, 1.5H), 2.89 (q, 2H), 2.69 (quintet, 2H), 1.86-0.99 (m, 10H); approx: 2:1 ratio of rotamers Step iii) N-Cyclohexyl-3-(3-(1-methyl-1H-pyrazol-4-yl)phenethoxy)-N-(2-oxoethyl)propanamide

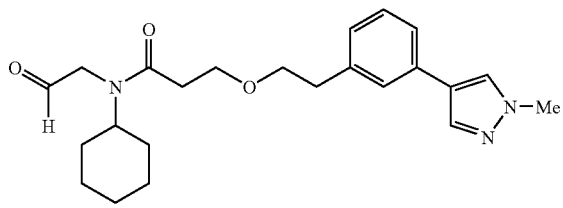

A solution of N-cyclohexyl-N-(2,2-dimethoxyethyl)-3-(3-(1-methyl-1H-pyrazol-4-yl)phenethoxy)propanamide (50.3 g) in tetrahydrofuran (150.9 mL) was added to a solution of p-toluenesulfonic acid monohydrate (86.3 g) in tetrahydrofuran (100.1 mL) at 20° C. to give a solution. A line wash of tetrahydrofuran (50.3 mL) was then added and the solution stirred at ambient temperature for 1 h before being added to a solution of sodium hydroxide (19.6 g) and sodium chloride (100.6 g) in water (502.9 mL) at 5° C. A line wash of tetrahydrofuran (25.1 mL) was then added and the solution warmed to 20° C. 1-Butanol (100.6 mL) was added and the layers separated. The separated organic layer can be evaporated to dryness to afford the sub-titled compound as an orange/brown oil or the solution used directly in the next Step. MS [M+H]+= 398.2 (MultiMode+)

Step iv) N-Cyclohexyl-N-(2-(2-(5-hydroxy-3-oxo-3,4-dihydro-2H-benzo[b][1,4]oxazin-8-yl)ethylamino)ethyl)-3-(3-(1-methyl-1H-pyrazol-4-yl)phenethoxy)propanamide Hemi-Fumaric Acid Salt

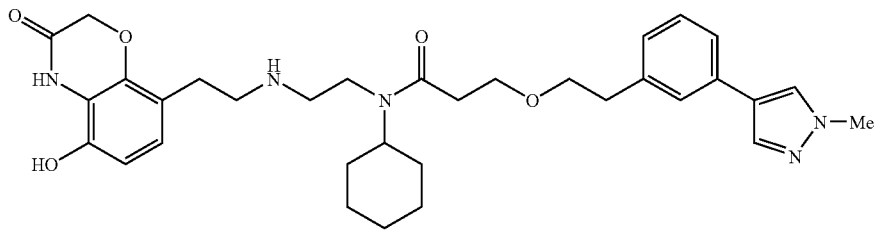

A solution of N-cyclohexyl-3-(3-(1-methyl-1H-pyrazol-4-yl)phenethoxy)-N-(2-oxoethyl)propanamide (assume 45.1 g) in tetrahydrofuran/1-butanol (~480 mL) was added to 8-(2-aminoethyl)-5-hydroxy-2H-benzo[b][1,4]oxazin-3(4H)-one hydrochloride (25.0 g), washing in with tetrahydrofuran (25.1 mL). Water (221.3 mL) was added, followed by palladium hydroxide on carbon (10.1 g of 20% w/w palladium on carbon). The mixture was hydrogenated at 2 bar of hydrogen and 20° C. for 26.5 h then filtered to remove the catalyst. Methyl isobutyl ketone (251.4 mL) was added and the layers separated. The separated organic layer was washed 3 times with 10% w/w aqueous potassium bicarbonate (3×251.4 mL) and then twice with water (2×251.4 mL) before being filtered through a 1 μm filter. A solution of fumaric acid (3.7 g) in isopropanol/water (111 mL of a 10 vol % solution of isopropanol in water) was then added at 20° C., the resulting solution seeded with N-cyclohexyl-N-(2-(2-(5-hydroxy-3-oxo-3,4-dihydro-2H-benzo[b][1,4]oxazin-8-yl)ethylamino)ethyl)-3-(3-(1-methyl-1H-pyrazol-4-yl)phenethoxy)propanamide hemi-fumaric acid salt (25 mg) and stirred at ambient temperature for 21.5 h to give a precipitate which was filtered, washing with tetrahydrofuran (251.4 mL) and dried at 50° C. under vacuum to afford the subtitled compound as a white solid (32.6 g). MS [M+H]+=590.20 (MultiMode+) $^1$H NMR (400 MHz, CD$_{30}$D) δ 7.89 (s, 1H), 7.78 (s, 1H), 7.38 (s, 1H), 7.33 (d, 1H), 7.23 (t, 1H), 7.05 (d, 1H), 6.70 (m, 2H, includes 2H of fumaric acid,), 6.47 (d, 1H), 4.60 (s, 2H), 3.88 (s, 3H), 3.76-3.64 (m, 5H), 3.48 (t, 2H), 3.08 (t, 2H), 3.00 (t, 2H), 2.88-2.82 (m, 4H), 2.63 (t, 2H), 1.82-1.58 (m, 4H), 1.48-1.24 (m, 5H), 1.18-1.05 (m, 1H); approx:5.2:1 ratio of rotamers Solid State Data for Example 2a N-Cyclohexyl-N-(2-(2-(5-hydroxy-3-oxo-3,4-dihydro-2H-benzo[b][1,4]oxazin-8-yl)ethylamino)ethyl)-3-(3-(1-methyl-1H-pyrazol-4-yl)phenethoxy)propanamide Hemi-Fumaric Acid Salt (XRPD—see FIG. 1)

| XRPD data | | | |
|---|---|---|---|
| 2Ø (°) | d space (Å) | rel. int. (%) | DSC data |
| 5.6 | 15.686 | 5 | melting onset: 174° C. |
| 10.6 | 8.334 | 8 | Accuracy: +/−2° C. |
| 11.0 | 8.051 | 19 | |
| 11.2 | 7.919 | 53 | |
| 12.0 | 7.367 | 4 | |
| 13.4 | 6.599 | 10 | |
| 13.9 | 6.387 | 3 | |
| 14.5 | 6.128 | 5 | |
| 15.1 | 5.851 | 50 | |
| 15.6 | 5.690 | 33 | |
| 16.1 | 5.515 | 41 | |
| 16.8 | 5.280 | 11 | |
| 17.4 | 5.094 | 16 | |
| 18.0 | 4.932 | 13 | |
| 18.8 | 4.720 | 72 | |
| 19.3 | 4.591 | 3 | |
| 19.9 | 4.460 | 18 | |
| 20.3 | 4.385 | 30 | |
| 21.3 | 4.173 | 63 | |
| 22.0 | 4.040 | 100 | |
| 22.5 | 3.953 | 58 | |

-continued

| XRPD data | | | DSC data |
|---|---|---|---|
| 2Ø (°) | d space (Å) | rel. int. (%) | |
| 22.8 | 3.908 | 44 | |
| 23.3 | 3.820 | 25 | |
| 23.7 | 3.749 | 6 | |
| 24.1 | 3.691 | 7 | |
| 24.5 | 3.627 | 3 | |
| 25.0 | 3.559 | 31 | |
| 25.3 | 3.520 | 42 | |
| 25.6 | 3.476 | 35 | |
| 26.1 | 3.412 | 7 | |
| 26.8 | 3.332 | 8 | |
| 26.9 | 3.309 | 7 | |
| 28.0 | 3.188 | 4 | |
| 28.3 | 3.151 | 26 | |
| 28.8 | 3.101 | 11 | |
| 30.3 | 2.947 | 3 | |
| 31.2 | 2.864 | 5 | |
| 31.7 | 2.820 | 3 | |
| 32.2 | 2.782 | 5 | |
| 33.1 | 2.707 | 3 | |
| 33.4 | 2.679 | 10 | |
| 36.0 | 2.493 | 4 | |
| 36.9 | 2.436 | 4 | |

Accuracy - +/−0.1° 2Ø

Example 2b

N-Cyclohexyl-N-(2-(2-(5-hydroxy-3-oxo-3,4-dihydro-2H-benzo[b][1,4]oxazin-8-yl)ethylamino)ethyl)-3-(3-(1-methyl-1H-pyrazol-4-yl)phenethoxy)propanamide: benzenesulfonic acid salt, hydrochloric acid salt, hydrobromic acid salt, methanesulfonic acid salt, benzensulfonic acid salt, p-toluenesulfonic acid salt, maleic acid salt, citric acid salt, 1-hydroxy-2-naphthoic acid salt, benzoic acid salt, (R)-(−)-mandelic acid salt or L-(+)-tartaric acid salt p-Toluenesulfonic acid monohydrate (5.31 g) was added in one portion to N-cyclohexyl-N-(2,2-dimethoxyethyl)-3-(3-(1-methyl-1H-pyrazol-4-yl)phenethoxy)propanamide (7.74 g, prepared as in Example 2a, Step ii)) in tetrahydrofuran (60 mL). The resulting solution was stirred at 20° C. for 30 min. This solution was added to a stirred mixture of 8-(2-aminoethyl)-5-hydroxy-2H-benzo[b][1,4]oxazin-3(4H)-one hydrochloride (4.27 g), sodium bicarbonate (4.40 g), water (6 mL) and NMP (60 mL). The mixture was stirred for 10 min. and sodium triacetoxyborohydride (9.25 g) and acetic acid (1 mL) were added. The mixture was stirred for 3 h. The reaction mixture was neutralised with saturated sodium hydrogen carbonate (100 mL) and extracted into ethyl actate (5×100 mL). Methanol (50 mL) was added and the organic was washed with a 1:1 mixture of water and saturated brine (2×70 mL). The organic was dried over magnesium sulfate, filtered and evaporated to afford crude product. The crude product was purified by flash silica chromatography, elution gradient 50 to 100% isohexane in ethyl acetate, then elution gradient 2 to 10% methanol in dichloromethane to afford N-cyclohexyl-N-(2-(2-(5-hydroxy-3-oxo-3,4-dihydro-2H-benzo[b][1,4]oxazin-8-yl)ethylamino)ethyl)-3-(3-(1-methyl-1H-pyrazol-4-yl)phenethoxy)propanamide (5.38 g) as a gum.

A solution of N-cyclohexyl-N-(2-(2-(5-hydroxy-3-oxo-3,4-dihydro-2H-benzo[b][1,4]oxazin-8-yl)ethylamino)ethyl)-3-(3-(1-methyl-1H-pyrazol-4-yl)phenethoxy)propanamide (0.160 g) in ethanol (8 mL) was mixed with corresponding acid (1 eq for benzenesulfonic acid, p-toluenesulfonic acid monohydrate, methanesulfonic acid, 1-hydroxy-2-naphthoic acid, benzoic acid, (R)-(−)-mandelic acid; 0.5 eq. for L-(+)-tartaric acid, maleic acid or 0.33 eq. for citric acid). The solution was divided into 8 aliquotes (1 mL) each into separate vials and the solvent allowed to evaporate under a nitrogen stream at 55° C.

A solution of N-cyclohexyl-N-(2-(2-(5-hydroxy-3-oxo-3,4-dihydro-2H-benzo[b][1,4]oxazin-8-yl)ethylamino)ethyl)-3-(3-(1-methyl-1H-pyrazol-4-yl)phenethoxy)propanamide (0.160 g) in ethanol (8 mL) was mixed with hydrochloric acid (0.3 mL) or hydrobromic acid (0.2 mL). The mixtures were concentrated in vacuo. Ethanol (8 mL) was added to each salt and the solution was divided into 8 alequotes (1 ml) each into separate vials and the solvent allowed to evaporate under the nitrogen stream at 55° C.

Solvents (ethanol, acetonitrile, tetrahydrofuran, dichloromethane, 2-propanol, nitromethane, ethyl acetate, 1,4-dioxane; 1 mL each) were then added to these residues and the mixtures were slurried for 7 days to form corresponding salts. If formed, solids were filtered using micro-filtration cartridges by centrifuge and dried under vacuum.

Example 3

N-Cyclohexyl-N-(2-(2-(5-hydroxy-3-oxo-3,4-dihydro-2H-benzo[b][1,4]oxazin-8-yl)ethylamino)ethyl)-3-(3-(1-methyl-1H-pyrazol-5-yl)phenethoxy)propanamide Trifluoroacetic Acid Salt

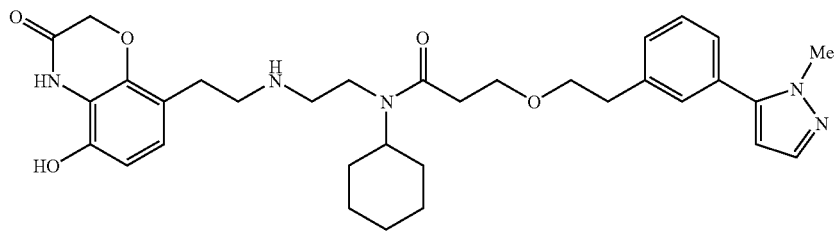

To tert-butyl 2-(3-(3-bromophenethoxy)-N-cyclohexylpropanamido)ethyl(2-(5-hydroxy-3-oxo-3,4-dihydro-2H-benzo[b][1,4]oxazin-8-yl)ethyl)carbamate (200 mg) [Example 2, Step ii], potassium carbonate (80 mg), 1-methyl-5-(4,4,5,5-tetramethyl-1,3,2-dioxaborolan-2-yl)-1H-pyrazole (91 mg) and Pd(Ph$_3$P)$_4$ (30 mg) was added ethanol (3 mL) and the mixture was heated within a microwave to 100° C. for 30 min. The reaction was filtered, concentrated and purified on silica eluting with ethyl acetate. The solvent was removed afford 130 mg of material. This material was taken up in 5 mL of DCM followed by the addition of TFA (3 mL). The reaction was stirred for 2 h before the solvent was removed, and azeotroped once with toluene to afford crude product, which was dissolved in methanol and purified via reverse phase prep HPLC (Gemini column, acetonitrile/0.2% TFA mobile

Example 4

N-Cyclohexyl-3-(3-(1-ethyl-1H-1,2,3-triazol-4-yl)phenethoxy)-N-(2-(2-(5-hydroxy-3-oxo-3,4-dihydro-2H-benzo[b][1,4]oxazin-8-yl)ethylamino)ethyl)propanamide Trifluoroacetic Acid Salt

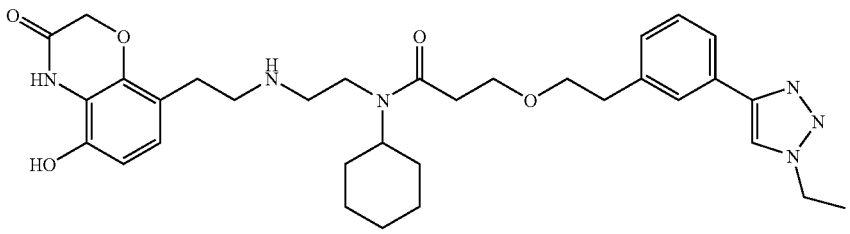

phase). The solvent was removed and the residue dried under high vacuum. A small quantity of ether was added which was removed under high vacuum to give the titled compound (46 mg) salt as a white foam. MS [M+H]+=590.3 (MultiMode+). $^1$H NMR (400 MHz, CD$_3$OD) δ 7.47 (d, J=2.1 Hz, 1H), 7.41-7.36 (m, 1H), 7.34-7.27 (m, 3H), 6.70 (d, J=8.5 Hz, 1H), 6.47 (d, J=8.5 Hz, 1H), 6.33 (d, J=2.1 Hz, 1H), 4.60 (s, 2H), 3.84 (s, 3H), 3.74-3.68 (m, 5H), 3.51-3.46 (m, 2H), 3.16-3.10 (m, 2H), 3.06-3.02 (m, 2H), 2.93-2.85 (m, 4H), 2.66-2.61 (m, 2H), 1.82-1.75 (m, 2H), 1.71-1.59 (m, 3H), 1.47-1.26 (m, 4H), 1.18-1.05 (m, 1H).

Step i) tert-Butyl 3-(3-((trimethylsilyl)ethynyl)phenethoxy)propanoate

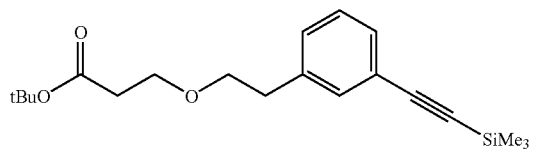

tert-Butyl 3-(3-bromophenethoxy)propanoate (1.5 g), triethylamine (6 mL), trimethylsilylacetylene (1.92 mL), Pd(Ph$_3$P)$_4$ (0.26 g) and copper (I) iodide (0.04 g) was sealed into a microwave tube. The reaction was heated to 100° C. over a period of 5 min in the microwave reactor. The reaction mixture was diluted with ethyl acetate and filtered through a pad of Celite and evaporated to afford crude product. The crude product was purified by flash silica chromatography, elution gradient 0-10% ethyl acetate in isohexane to afford tert-butyl 3-(3-((trimethylsilyl)ethynyl)phenethoxy)propanoate as a yellow liquid (1.56 g). $^1$H NMR (300 MHz, CDCl$_3$) δ 7.41-7.12 (m, 4H), 3.67 (t, J=6.3 Hz, 2H), 3.63 (t, J=7.1 Hz, 2H), 2.83 (t, J=7.1 Hz, 2H), 2.47 (t, J=6.5 Hz, 2H), 1.44 (s, 9H), 0.24 (s, 9H).

Step ii) tert-Butyl 3-(3-ethynylphenethoxy)propanoate

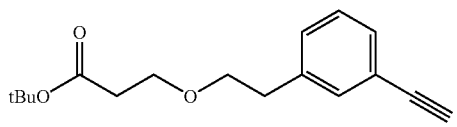

Potassium carbonate (1.20 g) was added in one portion to tert-butyl 3-(3-((trimethylsilyl)ethynyl)phenethoxy)propanoate [Example 4, Step i)] (2.09 g) in DCM (20 mL) and methanol (20 mL) at 25° C. under nitrogen. The resulting mixture was stirred at 25° C. for 1 h. The reaction mixture was diluted with water and extracted with dichloromethane. The organic layer was dried over magnesium sulfate, filtered and evaporated to afford tert-butyl 3-(3-ethynylphenethoxy)propanoate (1.65 g). $^1$H NMR (300 MHz, CDCl$_3$) δ 7.38-7.30 (m, 2H), 7.25-7.18 (m, 2H), 3.68 (t, J=6.5 Hz, 2H), 3.64 (t, J=7.0 Hz, 2H), 3.05 (s, 1H), 2.85 (t, J=7.2 Hz, 2H), 2.48 (t, J=6.4 Hz, 2H), 1.44 (s, 9H).

Step iii) tert-Butyl 3-(3-(1-ethyl-1H-1,2,3-triazol-4-yl)phenethoxy)propanoate

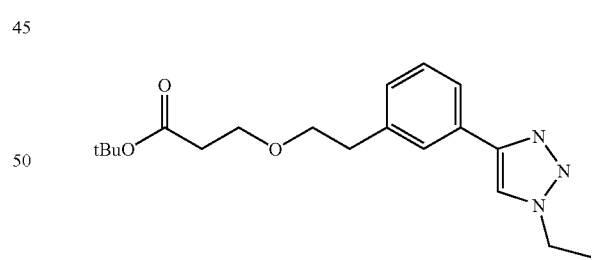

Ethyl iodide (0.216 mL) was added in one portion to a mixture of tert-butyl 3-(3-ethynylphenethoxy)propanoate [Example 4, Step ii)] (564 mg), sodium azide (160 mg) tert-butanol (0.25 mL), water (1 mL) and copper (I) iodide (39 mg) and sealed into a microwave tube. The reaction was heated to 70° C., over a period of 6 h in a microwave reactor. The reaction mixture was diluted with ethyl acetate and 35% ammonia was added. The mixture was stirred for 30 min and separated. The organic layer was dried over magnesium sulfate, filtered and evaporated to afford crude product. The crude product was purified by flash silica chromatography, elution gradient 20-100% ethyl acetate in isohexane, then elution gradient 0-10% methanol in ethyl acetate to afford the subtitled compound (396 mg) ¹H NMR (300 MHz, CDCl₃) δ 7.79 (s, 1H), 7.70 (s, 1H), 7.66 (d, J=7.7 Hz, 1H), 7.33 (t, J=7.7 Hz, 1H), 4.47 (q, J=7.3 Hz, 2H), 3.73-3.66 (m, 4H), 2.92 (t, J=7.2 Hz, 2H), 2.49 (t, J=6.5 Hz, 2H), 1.61 (t, J=7.3 Hz, 3H), 1.43 (s, 9H).

Step iv) 3-(3-(1-Ethyl-1H-1,2,3-triazol-4-yl)phenethoxy)propanoic acid

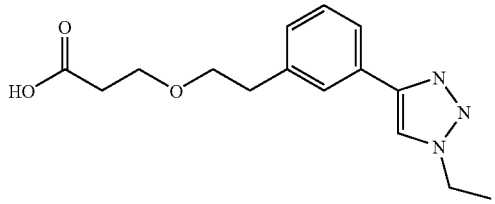

A mixture of tert-butyl 3-(3-(1-ethyl-1H-1,2,3-triazol-4-yl)phenethoxy)propanoate [Example 4, Step iii)] (382 mg), DCM (5 mL) and TFA (5 mL) was stirred at 25° C. for 30 min and concentrated under vacuum to give the subtitled compound as a gum (625 mg). ¹H NMR (300 MHz, CDCl₃) δ 7.92 (s, 1H), 7.75 (s, 1H), 7.48 (d, J=7.6 Hz, 1H), 7.37 (t, J=7.6 Hz, 1H), 7.24 (s, 1H), 4.53 (q, J=7.4 Hz, 2H), 3.76 (t, J=5.9 Hz, 2H), 3.76 (t, J=6.0 Hz, 2H), 2.93 (t, J=6.0 Hz, 2H), 2.63 (t, J=5.9 Hz, 2H), 1.67 (t, J=7.4 Hz, 3H).

Step v) N-Cyclohexyl-N-(2,2-dimethoxyethyl)-3-(3-(1-ethyl-1H-1,2,3-triazol-4-yl)phenethoxy)propanamide

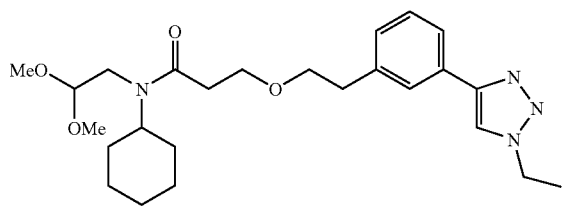

A solution of T3P (1.41 mL) dissolved in THF (1.57M) was added in one portion to a stirred solution of N-(2,2-dimethoxyethyl)cyclohexanamine (0.24 mL), 3-(3-(1-ethyl-1H-1,2,3-triazol-4-yl)phenethoxy)propanoic acid [Example 4, Step iv)] (0.45 g), and triethylamine (1.86 mL) in acetonitrile (5 mL) at 25° C. The resulting solution was stirred at 25° C. for 15 min. The reaction mixture was diluted with ethyl acetate (50 mL), and washed with saturated sodium hydrogen carbonate (20 mL). The organic layer was dried over magnesium sulfate, filtered and evaporated to afford crude product. The crude product was purified by flash silica chromatography, elution gradient 0-70% ethyl acetate in isohexane to afford the subtitled compound (0.46 g). ¹H NMR (400 MHz, CD₃OD) δ 8.32 and 8.31 (2×s, 1H), 7.68 and 7.66 (2×s, 1H), 7.65-7.61 (m, 1H), 7.32 and 7.32 (2×t, J=7.5 Hz, 1H), 7.22-7.18 (m, 1H), 4.52 and 4.36 (2×t, J=5.3 Hz, 1H), 4.47 (q, J=7.3 Hz, 2H), 4.04-3.94 (m, 1H), 3.76-3.61 (m, 4H), 3.34 (s, 3H), 3.32 (s, 3H), 3.25 (d, J=5.1 Hz, 2H), 2.91-2.85 (m, 2H), 2.68-2.62 (m, 2H), 1.79-1.03 (m, 10H), 1.56 (t, J=7.4 Hz, 3H), a ~1:1 mixture of rotamers is observed.

Step vi) tert-Butyl 2-(5-(tert-butoxycarbonyloxy)-3-oxo-3,4-dihydro-2H-benzo[b][1,4]oxazin-8-yl)ethyl (2-(N-cyclohexyl-3-(3-(1-ethyl-1H-1,2,3-triazol-4-yl)phenethoxy)propanamido)ethyl)carbamate

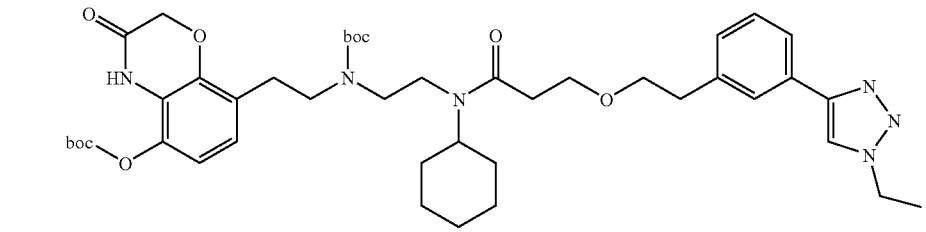

p-Toluenesulfonic acid monohydrate (377 mg) was added in one portion to N-cyclohexyl-N-(2,2-dimethoxyethyl)-3-(3-(1-ethyl-1H-1,2,3-triazol-4-yl)phenethoxy)propanamide [Example 4, Step v)] (455 mg) in DCM (5 mL) at 25° C. The resulting mixture was stirred at 25° C. for 30 min and this solution was added to a prepared solution of 8-(2-aminoethyl)-5-hydroxy-2H-benzo[b][1,4]oxazin-3(4H)-one hydrochloride (267 mg) and DIPEA (0.551 mL) in NMP (5.0 mL). The mixture stirred for 5 min, sodium triacetoxyborohydride (526 mg) was added in one portion and the resulting slurry was stirred at 25° C. for 4 h. The reaction mixture was neutralised with saturated sodium hydrogen carbonate and extracted into DCM. The organics were concentrated and the residue was treated with ethyl acetate (10 mL) and saturated sodium hydrogen carbonate (10 mL). A solution of BOC anhydride (0.36 mL) in ethyl acetate (5 mL) was added. The resulting mixture was stirred at 25° C. for 4 h. The reaction mixture was diluted with ethyl acetate (50 mL), and washed 3 times with water (50 mL). The organic layer was dried over magnesium sulfate filtered and evaporated to afford crude product. The crude product was purified by flash silica chromatography, elution gradient 50-100% ethyl acetate in isohexane to afford the subtitled compound (245 mg) as a solid. The solid was used directly in the next Step.

Step vii) N-Cyclohexyl-3-(3-(1-ethyl-1H-1,2,3-triazol-4-yl)phenethoxy)-N-(2-(2-(5-hydroxy-3-oxo-3,4-dihydro-2H-benzo[b][1,4]oxazin-8-yl)ethylamino)ethyl)propanamide Trifluoroacetic Acid Salt

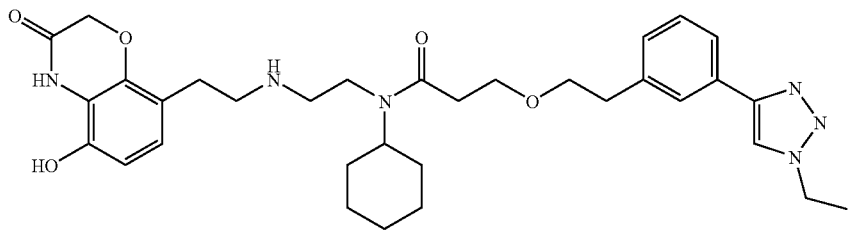

A mixture of tert-butyl 2-(5-(tert-butoxycarbonyloxy)-3-oxo-3,4-dihydro-2H-benzo[b][1,4]oxazin-8-yl)ethyl(2-(N-cyclohexyl-3-(3-(1-ethyl-1H-1,2,3-triazol-4-yl)phenethoxy)propanamido)ethyl)carbamate [Example 4, Step vi)] (245 mg), DCM (5 mL) and TFA (2.5 mL) was stirred at 25° C. for 30 min. The reaction mixture was evaporated to afford crude product. The crude product was purified by preparative HPLC on a Phenomenex Gemini column using a 15-60% gradient of aqueous 0.1% trifluoroacetic acid in acetonitrile as eluent to afford the titled compound as a white solid (62.3 mg). MS [M+H]+=605.3 (calc=605.3451) (MultiMode+) $^1$H NMR (400 MHz, CD$_3$OD) δ 8.28 (s, 1H), 7.70 (s, 1H), 7.59 (d, J=7.7 Hz, 1H), 7.32 (t, J=7.8 Hz, 1H), 7.19 (d, J=7.6 Hz, 1H), 6.69 (d, J=8.2 Hz, 1H), 6.47 (d, J=8.5 Hz, 1H), 4.60 (s, 2H), 4.46 (q, J=7.3 Hz, 2H), 3.76-3.62 (m, 5H), 3.48 (t, J=5.7 Hz, 2H), 3.12 (t, J=7.2 Hz, 2H), 3.02 (t, J=5.5 Hz, 2H), 2.92-2.83 (m, 4H), 2.62 (t, J=6.0 Hz, 2H), 1.80-1.56 (m, 4H), 1.55 (t, J=7.3 Hz, 3H), 1.44-1.24 (m, 5H), 1.17-1.02 (m, 1H).

Example 5

N-Cyclohexyl-N-(2-(2-(5-hydroxy-3-oxo-3,4-dihydro-2H-benzo[b][1,4]oxazin-8-yl)ethylamino)ethyl)-3-(3-(1-methyl-1H-1,2,3-triazol-4-yl)phenethoxy)propanamide Trifluoroacetic Acid Salt Step i) tert-Butyl 3-(3-(1-methyl-1H-1,2,3-triazol-4-yl)phenethoxy)propanoate

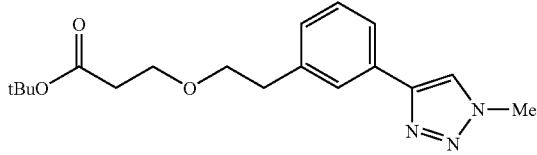

Methyl iodide (0.20 mL) was added in one portion to a mixture of tert-butyl 3-(3-ethynylphenethoxy)propanoate [Example 4, Step ii)] (682 mg), sodium azide (194 mg), tert-butanol (0.750 mL), water (3 mL) and copper (I) iodide (47 mg) and sealed into a microwave tube. The reaction was heated to 70° C., over a period of 2 h in the microwave reactor. The reaction mixture was diluted with ethyl acetate and 35% ammonia was added. The mixture was stirred for 30 min and separated. The organic layer was dried over magnesium sulfate, filtered and evaporated to afford crude product. The crude product was purified by flash silica chromatography,

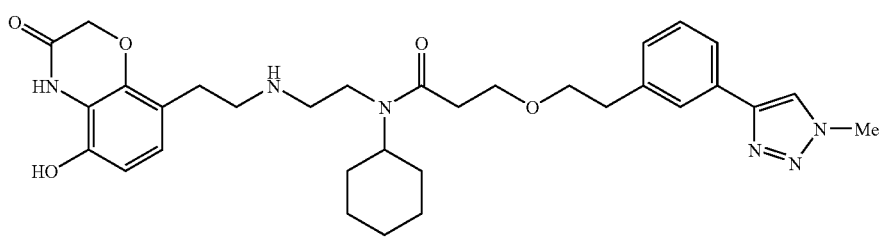

elution gradient 20-100% ethyl acetate in isohexane then elution gradient 0-10% methanol in ethyl acetate to afford the subtitled compound (500 mg). ¹H NMR (300 MHz, CDCl₃) δ 7.77 (s, 1H), 7.70 (s, 1H), 7.65 (d, J=7.9 Hz, 1H), 7.33 (t, J=7.7 Hz, 1H), 7.19 (d, J=7.7 Hz, 1H), 4.15 (s, 3H), 3.73-3.66 (m, 4H), 2.92 (t, J=7.0 Hz, 2H), 2.49 (t, J=6.4 Hz, 2H), 1.43 (s, 9H).

Step ii) 3-(3-(1-Methyl-1H-1,2,3-triazol-4-yl)phenethoxy)propanoic acid

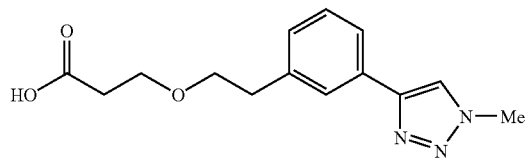

A mixture of tert-butyl 3-(3-(1-methyl-1H-1,2,3-triazol-4-yl)phenethoxy)propanoate [Example 5, Step i)] (880 mg), DCM (5 mL) and TFA (5 mL) was stirred at 25° C. for 30 min and concentrated under vacuum to the subtitled compound as a gum (1315 mg). ¹H NMR (300 MHz, CDCl₃) δ 7.85 (s, 1H), 7.77 (s, 1H), 7.49-7.44 (m, 1H), 7.36 (t, J=7.6 Hz, 1H), 7.27-7.21 (m, 1H), 4.21 (s, 3H), 3.77 (t, J=5.8 Hz, 2H), 3.76 (t, J=6.0 Hz, 2H), 2.94 (t, J=6.1 Hz, 2H), 2.63 (t, J=5.9 Hz, 2H).

Step iii) N-Cyclohexyl-N-(2,2-dimethoxyethyl)-3-(3-(1-methyl-1H-1,2,3-triazol-4-yl)phenethoxy)propanamide

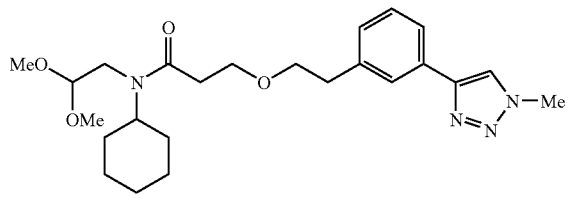

A solution of T3P (1.656 mL) dissolved in THF (1.57M) was added in one portion to a stirred solution of N-(2,2-dimethoxyethyl)cyclohexanamine (0.28 mL), 3-(3-(1-methyl-1H-1,2,3-triazol-4-yl)phenethoxy)propanoic acid [Example 5, Step ii)] (0.51 g) and triethylamine (2.17 mL) in acetonitrile (5 mL) at 25° C. The resulting solution was stirred at 25° C. for 15 min. The reaction mixture was diluted with ethyl acetate (50 mL) and washed with saturated sodium hydrogen carbonate (20 mL). The organic was dried over magnesium sulfate, filtered and evaporated to afford crude product. The crude product was purified by flash silica chromatography, elution gradient 20 to 100% ethyl acetate in isohexane then elution gradient 0-10% methanol in ethyl acetate to afford the subtitled compound (0.59 g). ¹H NMR (300 MHz, CD₃OD) δ 8.29 (s, 1H), 7.74-7.62 (m, 2H), 7.36 (t, J=7.6 Hz, 1H), 7.24 (d, J=7.5 Hz, 1H), 4.56 and 4.41 (2×t, J=5.4 Hz, 1H), 4.18 (s, 3H), 4.11-3.96 (m, 1H), 3.83-3.62 (m, 4H), 3.38 and 3.36 (2×s, 6H), 3.36-3.23 (m, 2H), 2.97-2.87 (m, 2H), 2.74-2.64 (m, 2H), 1.85-1.03 (m, 10H), a ~1:1 mixture of rotamers is observed.

Step iv) tert-Butyl 2-(5-(tert-butoxycarbonyloxy)-3-oxo-3,4-dihydro-2H-benzo[b][1,4]oxazin-8-yl)ethyl (2-(N-cyclohexyl-3-(3-(1-methyl-1H-1,2,3-triazol-4-yl)phenethoxy)propanamido)ethyl)carbamate

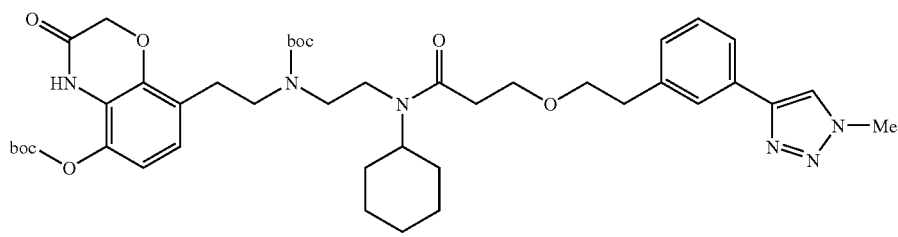

p-Toluenesulfonic acid monohydrate (504 mg) was added in one portion to N-cyclohexyl-N-(2,2-dimethoxyethyl)-3-(3-(1-methyl-1H-1,2,3-triazol-4-yl)phenethoxy)propanamide [Example 5, Step iii)] (59 mg) in DCM (8 mL) at 25° C. The resulting mixture was stirred at 25° C. for 45 min. A solution of 8-(2-aminoethyl)-5-hydroxy-2H-benzo[b][1,4]oxazin-3(4H)-one hydrochloride (357 mg) and DIPEA (0.74 mL) in NMP (3.0 mL) was added and the mixture stirred for 5 min. Sodium triacetoxyborohydride (702 mg) was added in one portion and the resulting slurry was stirred at 25° C. for 4 h. The reaction mixture was neutralised with saturated sodium hydrogen carbonate and extracted into DCM. The solvent was evaporated and the residue was treated with ethyl acetate (10 mL) and saturated sodium hydrogen carbonate (10 mL). A solution of BOC anhydride (0.34 mL) in ethyl acetate (2 mL) was added. The resulting mixture was stirred at 25° C. for 24 h. The reaction mixture was diluted with ethyl acetate (50 mL) and washed 3 times with water (50 mL). The organic layer was dried over magnesium sulfate, filtered and evaporated to afford crude product. The crude product was purified by flash silica chromatography, elution gradient 50-100% ethyl acetate in isohexane to afford the subtitled compound as a solid (290 mg). ¹H NMR (400 MHz, CD₃OD) δ 8.26-8.16 (m, 1H), 7.70-7.55 (m, 2H), 7.36-7.13 (m, 2H), 6.82-6.66 (m, 2H), 4.62-4.50 (m, 2H), 4.15-4.06 (m, 3H), 3.77-3.59 (m, 5H), 3.44-3.01 (m, 6H), 2.93-2.45 (m, 6H), 1.80-0.98 (m, 28H).

Step v) N-Cyclohexyl-N-(2-(2-(5-hydroxy-3-oxo-3, 4-dihydro-2H-benzo[b][1,4]oxazin-8-yl)ethylamino) ethyl)-3-(3-(1-methyl-1H-1,2,3-triazol-4-yl)phenethoxy)propanamide Trifluoroacetic Acid Salt

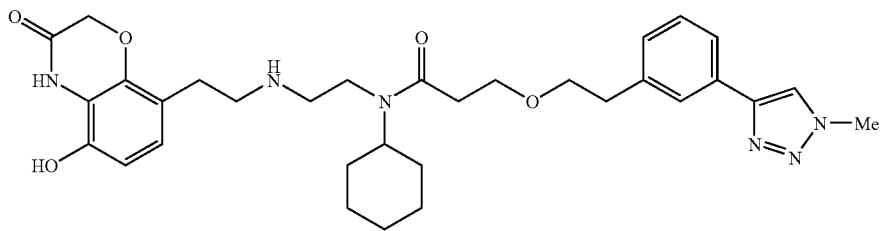

A mixture of tert-butyl 2-(5-(tert-butoxycarbonyloxy)-3-oxo-3,4-dihydro-2H-benzo[b][1,4]oxazin-8-yl)ethyl(2-(N-cyclohexyl-3-(3-(1-methyl-1H-1,2,3-triazol-4-yl)phenethoxy)propanamido)ethyl)carbamate [Example 5, Step iv)] (290 mg), DCM (5 mL) and TFA (2.5 mL) was stirred at 25° C. for 30 min. The reaction mixture was evaporated to afford crude product. The crude product was purified by preparative HPLC on a Phenomenex Gemini column using a 15-60% gradient of aqueous 0.1% trifluoroacetic acid in acetonitrile as eluent to afford the titled compound as a white solid (94 mg). MS [M+H]+=591.3 (calc=591.3295) (MultiMode+) $^1$H NMR (400 MHz, CD$_3$OD) δ 8.21 (s, 1H), 7.69 (s, 1H), 7.57 (dt, J=1.6 and 8.0 Hz, 1H), 7.32 (t, J=7.6 Hz, 1H), 7.19 (d, J=7.6 Hz, 1H), 6.69 (d, J=8.2 Hz, 1H), 6.47 (d, J=8.5 Hz, 1H), 4.60 (s, 2H), 4.12 (s, 3H), 3.75-3.64 (m, 5H), 3.52-3.44 (m, 2H), 3.12 (t, J=7.3 Hz, 2H), 3.02 (t, J=5.6 Hz, 2H), 2.88 (t, J=6.7 Hz, 2H), 2.86 (t, J=7.0 Hz, 2H), 2.63 (t, J=5.9 Hz, 2H), 1.80-1.72 (m, 2H), 1.69-1.58 (m, 2H), 1.46-1.24 (m, 5H), 1.15-1.03 (m, 1H).

Example 6

N-Cycloheptyl-N-(2-(2-(5-hydroxy-3-oxo-3,4-dihydro-2H-benzo[b][1,4]oxazin-8-yl)ethylamino)ethyl)-3-(3-(1-methyl-1H-1,2,3-triazol-4-yl)phenethoxy) propanamide Trifluoroacetic Acid Salt Step i) N-Cycloheptyl-N-(2,2-dimethoxyethyl)-3-(3-(1-methyl-1H-1,2,3-triazol-4-yl)phenethoxy)propanamide

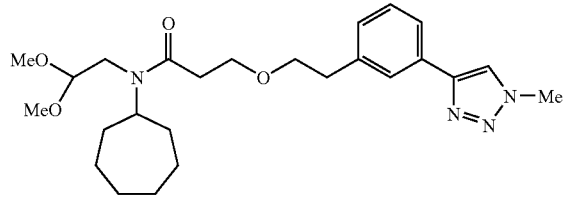

A solution of T3P (1.656 mL) dissolved in THF (1.57M) was added in one portion to a stirred solution of N-(2,2-dimethoxyethyl)cycloheptanamine (0.30 mL), 3-(3-(1-methyl-1H-1,2,3-triazol-4-yl)phenethoxy)propanoic acid [Example 5, Step ii)] (0.51 g) and triethylamine (2.17 mL) in acetonitrile (5 mL) at 25° C. The resulting solution was stirred at 25° C. for 15 min. The reaction mixture was diluted with ethyl acetate (100 mL), and washed with saturated sodium hydrogen carbonate (50 mL). The organic layer was dried over magnesium sulfate, filtered and evaporated to afford crude product. The crude product was purified by flash silica chromatography, elution gradient 0-70% ethyl acetate in iso-

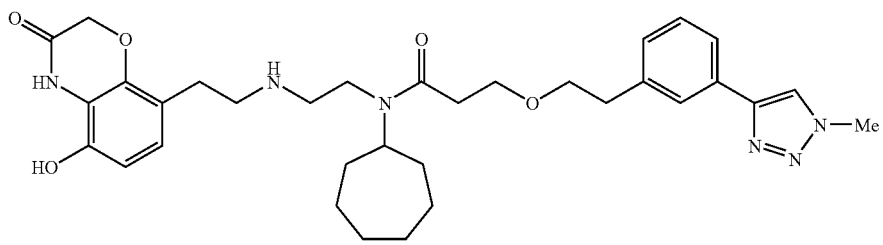

hexane to afford the subtitled compound (0.51 g). $^1$H NMR (400 MHz, CD$_3$OD) δ 8.25 and 8.24 (2×s, 1H), 7.68-7.65 (m, 1H), 7.62 (d, J=7.9 Hz, 1H), 7.32 and 7.31 (2×t, J=7.6 Hz, 1H), 7.20 (d, J=7.3 Hz, 1H), 4.56 and 4.39 (2×t, J=5.1 Hz, 1H), 4.13 (s, 3H), 3.85-3.66 (m, 5H), 3.36-3.32 (m, 2H), 3.34 (s, 3H), 3.32 (s, 3H), 3.22 (d, J=5.0 Hz, 2H), 2.92-2.85 (m, 2H), 2.63 and 2.60 (2×t, J=6.0 Hz, 2H), 1.83-1.32 (m, 10H), a ~1:1 mixture of rotamers is observed.

Step ii) tert-Butyl 2-(5-(tert-butoxycarbonyloxy)-3-oxo-3,4-dihydro-2H-benzo[b][1,4]oxazin-8-yl)ethyl (2-(N-cycloheptyl-3-(3-(1-methyl-1H-1,2,3-triazol-4-yl)phenethoxy)propanamido)ethyl)carbamate

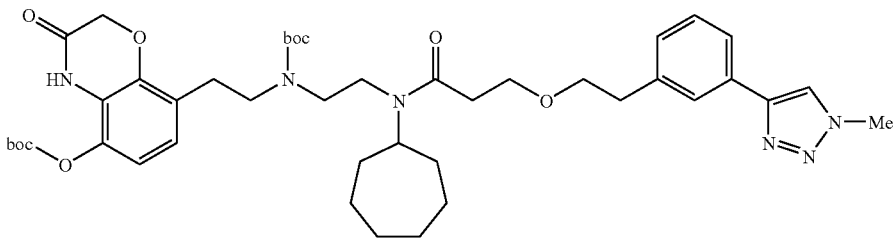

p-Toluenesulfonic acid monohydrate (415 mg) was added in one portion to N-cycloheptyl-N-(2,2-dimethoxyethyl)-3-(3-(1-methyl-1H-1,2,3-triazol-4-yl)phenethoxy)propanamide [Example 6, Step i)] (500 mg) in DCM (5 mL) at 25° C. The resulting mixture was stirred at 25° C. for 45 min. A solution of 8-(2-aminoethyl)-5-hydroxy-2H-benzo[b][1,4]oxazin-3 (4H)-one hydrochloride (293 mg) and DIPEA (0.61 mL) in NMP (5.0 mL) was added and the mixture stirred for 5 min. Sodium triacetoxyborohydride (578 mg) was added in one portion and the resulting slurry was stirred at 25° C. for 20 h. The reaction mixture was neutralised with saturated sodium hydrogen carbonate and extracted into DCM. The solvent was evaporated and the residue was treated with ethyl acetate (10 mL) and saturated sodium hydrogen carbonate (10 mL). A solution of BOC anhydride (0.25 mL) in ethyl acetate (5 mL) was added and the resulting mixture was stirred at 25° C. for 4 h. The reaction mixture was diluted with ethyl acetate (50 mL), and washed 3 times with water (50 mL), The organic layer was dried over magnesium sulfate, filtered and evaporated to afford crude product. The crude product was purified by flash silica chromatography, elution gradient 50-100% ethyl acetate in isohexane to afford the subtitled compound (300 mg). This material was carried onto the next step directly.

Step iii) N-Cycloheptyl-N-(2-(2-(5-hydroxy-3-oxo-3,4-dihydro-2H-benzo[b][1,4]oxazin-8-yl)ethylamino)ethyl)-3-(3-(1-methyl-1H-1,2,3-triazol-4-yl)phenethoxy)propanamide Trifluoroacetic Acid Salt

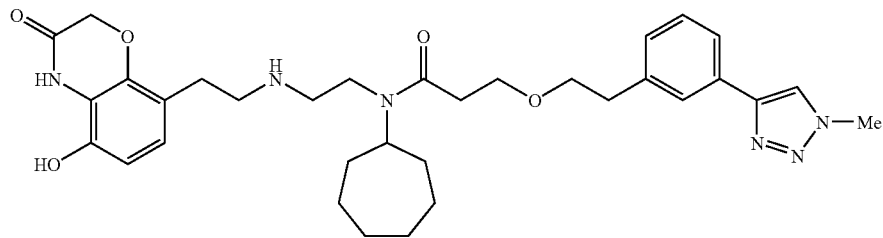

A mixture of tert-butyl 2-(5-(tert-butoxycarbonyloxy)-3-oxo-3,4-dihydro-2H-benzo[b][1,4]oxazin-8-yl)ethyl(2-(N-cycloheptyl-3-(3-(1-methyl-1H-1,2,3-triazol-4-yl)phenethoxy)propanamido)ethyl)carbamate (280 mg), DCM (5 mL) and TFA (2.50 mL) was stirred at 25° C. for 30 min. The reaction mixture was evaporated to afford crude product. The crude product was purified by preparative HPLC on a Phenomenex Gemini column using a 15-60% gradient of aqueous 0.1% trifluoroacetic acid in acetonitrile as eluent to afford the titled compound as a white solid (84 mg). MS [M+H]+ =605.3 (calc=605.3451) (MultiMode+) $^1$H NMR (400 MHz, CD$_3$OD) δ 8.21 (s, 1H), 7.69 (s, 1H), 7.57 (d, J=7.6 Hz, 1H), 7.32 (t, J=7.7 Hz, 1H), 7.19 (d, J=7.6 Hz, 1H), 6.69 (d, J=8.2 Hz, 1H), 6.47 (d, J=8.5 Hz, 1H), 4.60 (s, 2H), 4.12 (s, 3H), 3.88-3.78 (m, 1H), 3.72 (t, J=6.7 Hz, 2H), 3.71 (t, J=6.0 Hz, 2H), 3.48-3.42 (m, 2H), 3.12 (t, J=7.3 Hz, 2H), 3.05 (t, J=5.5 Hz, 2H), 2.88 (t, J=6.6 Hz, 2H), 2.86 (t, J=6.9 Hz, 2H), 2.62 (t, J=5.9 Hz, 2H), 1.78-1.38 (m, 12H).

Example 7

N-Cyclohexyl-N-(2-(2-(5-hydroxy-3-oxo-3,4-dihydro-2H-benzo[b][1,4]oxazin-8-yl)ethylamino)ethyl)-3-(3-(2-methyl-2H-tetrazol-5-yl)phenethoxy)propanamide Trifluoroacetic Acid Salt

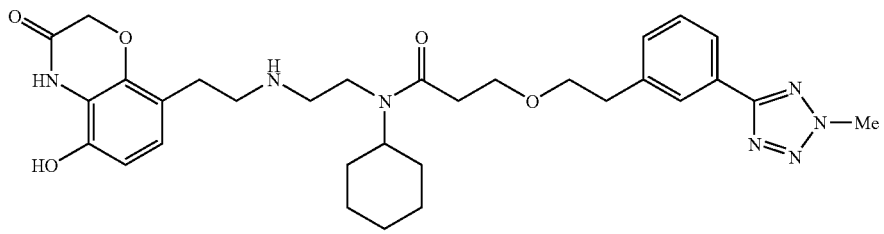

Step i) tert-Butyl 3-(3-cyanophenethoxy)propanoate

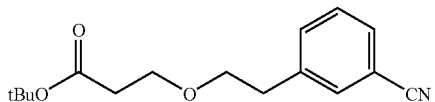

Pd(Ph₃P)₄ (0.53 g) was added in one portion to tert-butyl 3-(3-bromophenethoxy)propanoate [Preparation 3, Step i)] (3.00 g), and zinc cyanide (1.68 g) in DMF (35 mL) under nitrogen. The resulting mixture was stirred at 130° C. for 30 min. The reaction mixture was diluted with ethyl acetate (100 mL) and filtered through Celite. Isohexane (100 mL) was added and the mixture was washed with water (4×20 mL). The organic layer was dried over magnesium sulfate, filtered and evaporated to afford crude product. The crude product was purified by flash silica chromatography, elution gradient 0-20% ethyl acetate in isohexane to afford the subtitled compound (2.30 g). ¹H NMR (300 MHz, CDCl₃) δ 7.54-7.43 (m, 3H), 7.41-7.34 (m, 1H), 3.67 (t, J=6.3 Hz, 2H), 3.66 (t, J=6.6 Hz, 2H), 2.89 (t, J=6.5 Hz, 2H), 2.47 (t, J=6.3 Hz, 2H), 1.43 (s, 9H).

Step ii) tert-Butyl 3-(3-(2H-tetrazol-5-yl)phenethoxy)propanoate

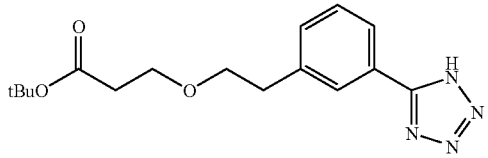

Triethylamine hydrochloride (2.09 g) was added in one portion to a mixture of tert-butyl 3-(3-cyanophenethoxy)propanoate [Example 7, Step i)] (1.74 g), sodium azide (0.99 g) and tert-butanol (12.64 mL), and sealed into a microwave tube. The reaction was heated to 140° C., over a period of 2 h in the microwave reactor. The reaction mixture was diluted with water and acidified with 2M hydrochloric acid (5 mL). The mixture was extracted with DCM and the organic layer was dried over magnesium sulfate, filtered and evaporated to afford crude product. The crude product was purified by flash silica chromatography, elution gradient 20-100% ethyl acetate in isohexane, then elution gradient 0-10% methanol in DCM to afford the subtitled compound (1.77 g). ¹H NMR (300 MHz, CDCl₃) δ 8.11 (d, J=7.8 Hz, 1H), 8.06 (s, 1H), 7.44 (t, J=7.7 Hz, 1H), 7.31 (d, J=7.7 Hz, 1H), 3.79 (t, J=5.3 Hz, 2H), 3.75 (t, J=5.6 Hz, 2H), 2.96 (t, J=5.2 Hz, 2H), 2.63 (t, J=5.3 Hz, 2H), 1.48 (s, 9H).

Step iii) tert-Butyl 3-(3-(2-methyl-2H-tetrazol-5-yl)phenethoxy)propanoate and tert-Butyl 3-(3-(1-methyl-1H-tetrazol-5-yl)phenethoxy)propanoate

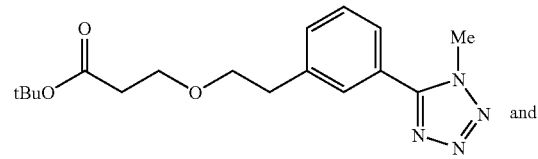

and

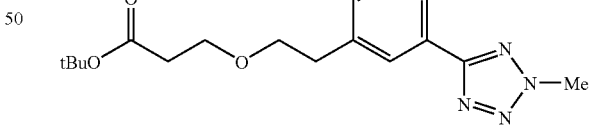

Trimethylsilyldiazomethane (4.5 mL) in diethyl ether was added to an ice-bath cooled solution of tert-butyl 3-(3-(2H-tetrazol-5-yl)phenethoxy)propanoate [Example 7, Step ii)] (0.72 g) in DCM (5 mL) and methanol (5 mL). The mixture was stirred for 15 min and concentrated under vacuum. The crude product was purified by flash silica chromatography, elution gradient 10-100% ethyl acetate in isohexane to afford the subtitled compound as a gum (0.51 g, ¹H NMR (300 MHz, CDCl₃) δ 8.01-7.95 (m, 2H), 7.44-7.31 (m, 2H), 4.40 (s, 3H), 3.71 (t, J=7.0 Hz, 2H), 3.70 (t, J=6.6 Hz, 2H), 2.96 (t, J=7.0 Hz, 2H), 2.49 (t, J=6.4 Hz, 2H), 1.43 (s, 9H)); and tert-butyl 3-(3-(1-methyl-1H-3.71 (t, J=6.7 Hz, 2H), 3.69 (t, J=6.4 Hz, 2H), 2.96 (t, J=6.5 Hz, 2H), 2.46 (t, J=6.4 Hz, 2H), 1.41 (s, 9H)).

Step iv) 3-(3-(2-Methyl-2H-tetrazol-5-yl)phenethoxy)propanoic acid

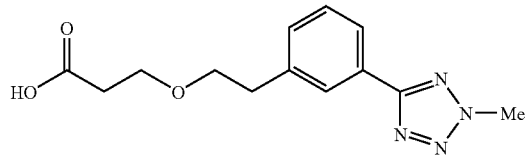

A mixture of tert-butyl 3-(3-(2-methyl-2H-tetrazol-5-yl) phenethoxy)propanoate [Example 7, Step iii)] (500 mg), DCM (4 mL) and TFA (4 mL) was stirred at 25° C. for 30 min and concentrated under vacuum to give the subtitled compound as a gum (612 mg). $^1$H NMR (300 MHz, CDCl$_3$) δ 8.05 (s, 1H), 7.93 (dt, J=7.8, 1.4 Hz, 1H), 7.41 (t, J=7.6 Hz, 1H), 7.31 (dt, J=1.4 and 7.7 Hz, 1H), 4.42 (s, 3H), 3.78 (t, J=5.9 Hz, 2H), 3.77 (t, J=6.3 Hz, 2H), 2.97 (t, J=6.3 Hz, 2H), 2.64 (t, J=6.1 Hz, 2H).

Step iv) N-Cyclohexyl-N-(2,2-dimethoxyethyl)-3-(3-(2-methyl-2H-tetrazol-5-yl)phenethoxy)propanamide

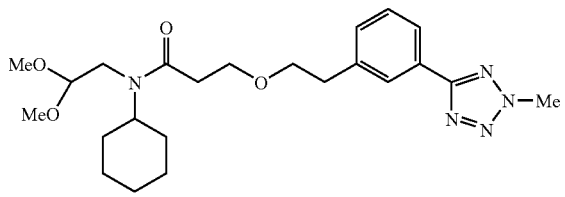

A solution of T3P (1.91 mL) dissolved in THF (1.57M) was added in one portion to a stirred solution of N-(2,2-dimethoxyethyl)cyclohexanamine (0.33 mL), 3-(3-(2-methyl-2H-tetrazol-5-yl)phenethoxy)propanoic acid [Example 7, Step iii)] (0.41 g) and triethylamine (2.51 mL) in acetonitrile (5 mL) at 25° C. The resulting solution was stirred at 25° C. for 15 min. The reaction mixture was diluted with ethyl acetate (50 mL), and washed with saturated sodium hydrogen carbonate (20 mL). The organic layer was dried over magnesium sulfate, filtered and evaporated to afford crude product. The crude product was purified by flash silica chromatography, elution gradient 20-100% ethyl acetate in isohexane, then elution gradient 0-10% methanol in ethyl acetate to afford the subtitled compound (0.66 g). $^1$H NMR (400 MHz, CD$_3$OD) δ 7.97-7.93 (m, 1H), 7.92-7.89 (m, 1H), 7.43-7.33 (m, 2H), 4.52 and 4.36 (2×t, J=5.3 Hz, 1H), 4.40 and 4.39 (2×s, 3H), 4.04-3.95 and 3.69-3.60 (2×m, 1H), 3.75-3.66 (m, 4H), 3.33 (s, 6H), 3.25 (d, J=4.9 Hz, 2H), 2.94-2.88 (m, 2H), 2.67-2.61 (m, 2H), 1.79-1.00 (m, 10H), a ~1:1 mixture of rotamers is observed.

Step v) N-Cyclohexyl-N-(2-(2-(5-hydroxy-3-oxo-3,4-dihydro-2H-benzo[b][1,4]oxazin-8-yl)ethylamino)ethyl)-3-(3-(2-methyl-2H-tetrazol-5-yl)phenethoxy)propanamide Trifluoroacetic Acid Salt

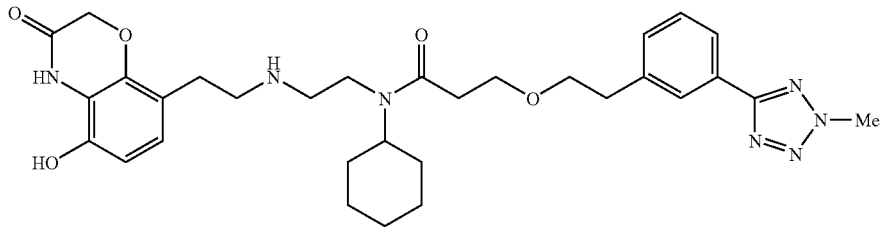

p-Toluenesulfonic acid monohydrate (565 mg) was added in one portion to N-cyclohexyl-N-(2,2-dimethoxyethyl)-3-(3-(2-methyl-2H-tetrazol-5-yl)phenethoxy)propanamide [Example 7, Step iv)] (662 mg) in DCM (5 mL) at 25° C. The resulting mixture was stirred at 25° C. for 15 min. This solution was added to a solution of 8-(2-aminoethyl)-5-hydroxy-2H-benzo[b][1,4]oxazin-3(4H)-one hydrochloride (473 mg) and DIPEA (0.88 mL) in NMP (5 mL) and the mixture stirred for 5 min. Sodium triacetoxyborohydride (787 mg) was added in one portion and the resulting slurry was stirred at 25° C. for 1 h. Acetic acid (0.1 mL) was added and the mixture was stirred overnight. An additional portion of sodium triacetoxyborohydride (310 mg) was added and the mixture was stirred at 40° C. for a further 3 h. Then the reaction mixture was neutralised with saturated sodium hydrogen carbonate and extracted into DCM. The solvent was evaporated and the residue was treated with ethyl acetate (5 mL) and saturated sodium hydrogen carbonate (10 mL). A solution of BOC anhydride (0.53 mL, 2.29 mmol) in ethyl acetate (5 mL) was added. The resulting mixture was stirred at 25° C. for 1 h. The reaction mixture was diluted with ethyl acetate (50 mL), and washed 3 times with water (50 mL). The organic layer was dried over magnesium sulfate, filtered and evaporated to afford crude product. The crude product was purified by flash silica chromatography, elution gradient 20-100% ethyl acetate in isohexane and pure fractions were evaporated to dryness. The residue was treated with DCM (5 mL) and TFA (2 mL) and the mixture was stirred for 30 min, and then concentrated. The crude product was purified by preparative HPLC on a Phenomenex Gemini column using a gradient of aqueous 0.1% trifluoroacetic acid in acetonitrile as eluent to afford the titled compound as a white solid (36.9 mg). MS [M+H]+=592.3 (calc=592.3247)(MultiMode+) $^1$H NMR (400 MHz, CD$_3$OD) δ 7.96 (s, 1H), 7.89 (dt, J=1.5 and 7.6 Hz, 1H), 7.40 (t, J=7.6 Hz, 1H), 7.35 (dt, J=1.6 and 7.9 Hz, 1H), 6.69 (d, J=8.5 Hz, 1H), 6.47 (d, J=8.5 Hz, 1H), 4.61 (s, 2H), 4.38 (s, 3H), 3.77-3.64 (m, 5H), 3.49 (t, J=5.7 Hz, 2H), 3.12 (t, J=6.9 Hz, 2H), 3.03 (t, J=5.2 Hz, 2H), 2.92 (t, J=6.2 Hz, 2H), 2.86 (t, J=7.3 Hz, 2H), 2.63 (t, J=6.1 Hz, 2H), 1.81-1.58 (m, 5H), 1.46-1.24 (m, 4H), 1.18-1.04 (m, 1H).

Example 8

N-Cyclohexyl-N-(2-(2-(5-hydroxy-3-oxo-3,4-dihydro-2H-benzo[b][1,4]oxazin-8-yl)ethylamino)ethyl)-3-(3-(1-methyl-1H-tetrazol-5-yl)phenethoxy)propanamide Trifluoroacetic Acid Salt

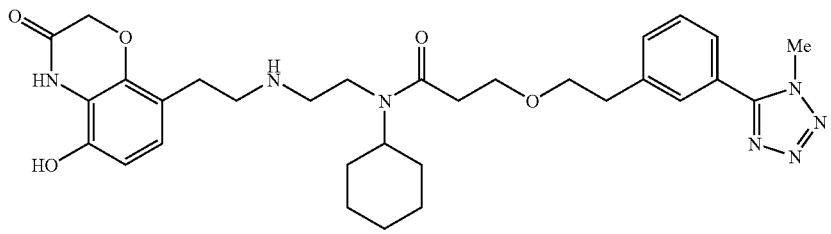

Step i) 3-(3-(1-Methyl-1H-tetrazol-5-yl)phenethoxy)propanoic acid

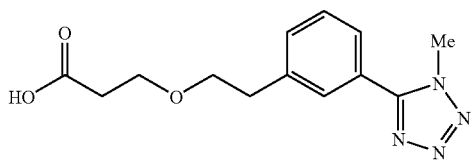

A mixture of tert-butyl 3-(3-(1-methyl-1H-tetrazol-5-yl)phenethoxy)propanoate [Example 7, Step iii] (135 mg), DCM (4 mL) and TFA (4 mL) was stirred at 25° C. for 30 min and concentrated under vacuum to afford the subtitled compound as a gum. $^1$H NMR (400 MHz, CDCl$_3$) δ 7.72 (s, 1H), 7.53-7.41 (m, 3H), 4.18 (s, 3H), 3.78-3.72 (m, 4H), 2.96 (t, J=5.9 Hz, 2H), 2.59 (t, J=5.9 Hz, 2H).

Step ii) N-Cyclohexyl-N-(2,2-dimethoxyethyl)-3-(3-(1-methyl-1H-tetrazol-5-yl)phenethoxy)propanamide

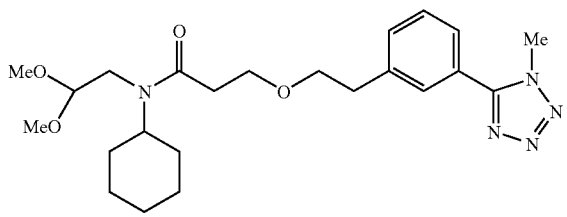

A solution of T3P (0.52 mL) dissolved in THF (1.57M) was added in one portion to a stirred solution of N-(2,2-dimethoxyethyl)cyclohexanamine (0.09 mL), 3-(3-(1-methyl-1H-tetrazol-5-yl)phenethoxy)propanoic acid [Example 8, Step i)] (0.11 g) and triethylamine (0.69 mL) in acetonitrile (2 mL) at 25° C. The resulting solution was stirred at 25° C. for 15 min. The reaction mixture was diluted with ethyl acetate (50 mL), and washed with saturated sodium hydrogen carbonate (20 mL). The organic was dried over magnesium sulfate, filtered and evaporated to afford crude product. The crude product was purified by flash silica chromatography, elution gradient 20-100% ethyl acetate in isohexane to afford the subtitled compound (0.10 g). $^1$H NMR (400 MHz, CD$_3$OD) δ 7.68 (s, 1H), 7.65-7.60 (m, 1H), 7.54-7.48 (m, 2H), 4.52 and 4.37 (2×t, J=5.3 Hz, 1H), 4.18 and 4.18 (2×s, 3H), 4.05-3.95 and 3.68-3.61 (2×m, 1H), 3.76-3.67 (m, 4H), 3.35 and 3.33 (2×s, 6H), 3.25 (d, J=5.1 Hz, 2H), 2.96 and 2.95 (2×t, J=6.3 Hz, 2H), 2.66 and 2.64 (2×t, J=6.6 Hz, 2H), 1.82-1.04 (m, 10H), a ~1:1 mixture of rotamers is observed.

Step iii) N-Cyclohexyl-N-(2-(2-(5-hydroxy-3-oxo-3,4-dihydro-2H-benzo[b][1,4]oxazin-8-yl)ethylamino)ethyl)-3-(3-(1-methyl-1H-tetrazol-5-yl)phenethoxy)propanamide Trifluoroacetic Acid Salt

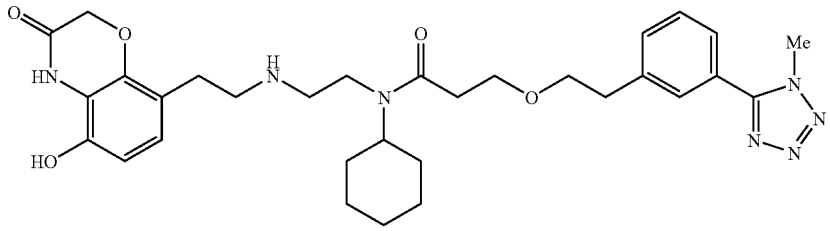

p-Toluenesulfonic acid monohydrate (0.09 g) was added in one portion to N-cyclohexyl-N-(2,2-dimethoxyethyl)-3-(3-(1-methyl-1H-tetrazol-5-yl)phenethoxy)propanamide [Example 8, Step ii)] (0.1 g) in DCM (2 mL) at 25° C. The resulting mixture was stirred at 25° C. for 15 min and the solution was added to a stirred solution of 8-(2-aminoethyl)-5-hydroxy-2H-benzo[b][1,4]oxazin-3(4H)-one hydrochloride (0.07 g) and DIPEA (0.13 mL) in NMP (2 mL). The mixture stirred for 5 min. Sodium triacetoxyborohydride (0.15 g) was added in one portion and the resulting slurry was stirred at 25° C. for 2 h. Acetic acid (0.05 mL) was added and the mixture was stirred overnight An additional portion of sodium triacetoxyborohydride (135 mg) was added and the mixture was stirred for a further 24 h. Then the reaction mixture was neutralised with saturated sodium hydrogen carbonate and extracted into DCM. The solvent was evaporated and the residue was treated with Ethyl acetate (2 mL) and saturated sodium hydrogen carbonate (10 mL). A solution of BOC anhydride (0.14 mL) in ethyl acetate (3 mL) was added. The resulting mixture was stirred at 25° C. for 30 min. The reaction mixture was diluted with ethyl acetate (50 mL), and washed 3 times with water (50 mL). The organic was dried over magnesium sulfate, filtered and evaporated to afford crude product. The crude product was purified by flash silica chromatography, elution gradient 20-100% ethyl acetate in isohexane. Pure fractions were evaporated to dryness. The residue was treated with DCM (2 mL) and TFA (1 mL) and the mixture was stirred for 30 min, then concentrated. The crude product was purified by preparative HPLC on a Phenomenex Gemini column using a gradient of aqueous 0.1% trifluoroacetic acid in acetonitrile as eluent to afford the titled compound as a white solid (14 mg). MS [M+H]+=592.3 (calc=592.3247) (MultiMode+) $^1$H NMR (400 MHz, CD$_3$OD) δ 7.67 (s, 1H), 7.60 (dt, J=2.0 and 7.0 Hz, 1H), 7.54-7.47 (m, 2H), 6.70 (d, J=8.3 Hz, 1H), 6.46 (d, J=8.3 Hz, 1H), 4.60 (s, 2H), 4.16 (s, 3H), 3.73 (t, J=6.4 Hz, 2H), 3.71 (t, J=5.9 Hz, 2H), 3.72-3.64 (m, 1H), 3.48 (t, J=5.6 Hz, 2H), 3.15 (t, J=7.1 Hz, 2H), 3.05 (t, J=5.7 Hz, 2H), 2.95 (t, J=6.3 Hz, 2H), 2.88 (t, J=7.0 Hz, 2H), 2.63 (t, J=6.2 Hz, 2H), 1.82-1.73 (m, 2H), 1.70-1.59 (m, 3H), 1.46-1.25 (m, 4H), 1.18-1.06 (m, 1H)

Example 9

(R)—N-(2-(2-(5-Hydroxy-3-oxo-3,4-dihydro-2H-benzo[b][1,4]oxazin-8-yl)ethylamino)ethyl)-3-(3-(1-methyl-1H-pyrazol-4-yl)phenethoxy)-N-(3-methylbutan-2-yl)propanamide Trifluoroacetic Acid Salt

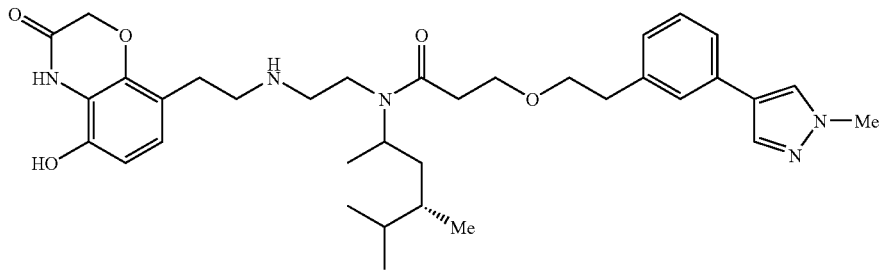

Step i) (R)—N-(2,2-Dimethoxyethyl)-3-(3-(1-methyl-1H-pyrazol-4-yl)phenethoxy)-N-(3-methylbutan-2-yl)propanamide

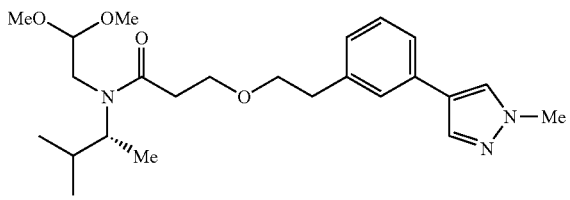

A solution of T3P (1.86 mL) dissolved in THF (1.57M) was added in one portion to a stirred solution of 3-(3-(1-methyl-1H-pyrazol-4-yl)phenethoxy)propanoic acid [Example 2a, Step i)] (567 mg), (R)—N-(2,2-dimethoxyethyl)-3-methylbutan-2-amine [Preparation 4] (307 mg), and triethylamine (2.44 mL) in acetonitrile (6 mL) at 25° C. The resulting solution was stirred at 25° C. for 15 min. The reaction mixture was diluted with ethyl acetate (50 mL), and washed with saturated sodium hydrogen carbonate (20 mL). The organic layer was dried over magnesium sulfate, filtered and evaporated to afford crude product. The crude product was purified by flash silica chromatography, elution gradient 0-100% ethyl acetate in isohexane, then elution gradient 5-10% methanol in ethyl acetate to afford the subtitled compound as a gum (210 mg). $^1$H NMR (400 MHz, CD$_3$OD) δ 7.92 and 7.91 (2×s, 1H), 7.77 (s, 1H), 7.40-7.37 (m, 1H), 7.36-7.32 (m, 1H), 7.23 and 7.22 (2×t, J=7.7 Hz, 1H), 7.05 (d, J=7.6 Hz, 1H), 4.59 and 4.43 (2×t, J=5.4 Hz, 1H), 3.90 (s, 3H), 3.75-3.45 (m, 5H), 3.36 (d, J=1.5 Hz, 2H), 3.35, 3.34, 3.33, 3.32 (4×s, 6H), 2.84 and 2.84 (2×t, J=7.0 Hz, 2H), 2.76-2.61 (m, 2H), 1.98-1.86 and 1.79-1.66 (2×m, 1H), 1.16 and 1.14 (2×d, J=7.0 Hz, 3H), 0.90 and 0.88 (2×d, J=6.8 Hz, 3H), 0.79 and 0.75 (2×d, J=6.8 Hz, 3H), a ~1:1 mixture of rotamers is observed.

Step ii) (R)—N-(2-(2-(5-Hydroxy-3-oxo-3,4-dihydro-2H-benzo[b][1,4]oxazin-8-yl)ethylamino)ethyl)-3-(3-(1-methyl-1H-pyrazol-4-yl)phenethoxy)-N-(3-methylbutan-2-yl)propanamide Trifluoroacetic Acid Salt

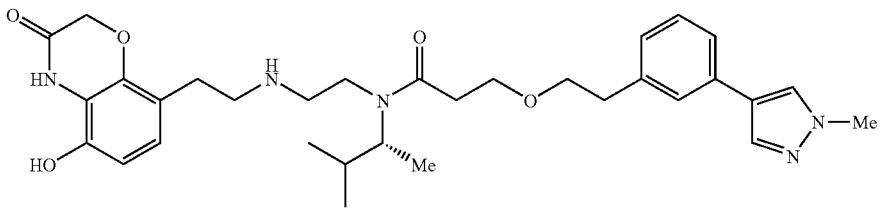

p-Toluenesulfonic acid monohydrate (181 mg) was added in one portion to (R)—N-(2,2-dimethoxyethyl)-3-(3-(1-methyl-1H-pyrazol-4-yl)phenethoxy)-N-(3-methylbutan-2-yl)propanamide [Example 9, Step i)] (205 mg) in DCM (2 mL) at 25° C. The resulting mixture was stirred at 25° C. for 5 min and the solution was added to a prepared solution of 8-(2-aminoethyl)-5-hydroxy-2H-benzo[b][1,4]oxazin-3(4H)-one hydrochloride (138 mg) and DIPEA (0.27 mL) in NMP (2.0 mL). The mixture stirred for 5 min and the sodium triacetoxyborohydride (252 mg) was added in one portion and the resulting slurry was stirred at 25° C. for 4 h. The reaction mixture was neutralised with saturated sodium hydrogen carbonate and extracted into DCM. The solvent was evaporated and the residue was treated with ethyl acetate (1 mL) and saturated sodium hydrogen carbonate (3 mL). A solution of BOC anhydride (0.303 mL) in ethyl acetate (3 mL) was added and the resulting mixture was stirred at 25° C. for 30 min. The reaction mixture was diluted with ethyl acetate (50 mL), and washed 3 times with water (50 mL). The organic was dried over magnesium sulfate, filtered and evaporated to afford crude product. The crude product was purified by flash silica chromatography, elution gradient 50-100% ethyl acetate in isohexane, then 0-10% methanol in ethyl acetate. Pure fractions were evaporated to dryness and DCM (4 mL) was added followed by TFA (2 mL). The mixture was stirred for 30 min and evaporated to afford crude product. The crude product was purified by preparative HPLC on a Phenomenex Gemini column using a gradient of aqueous 0.1% trifluoroacetic acid in acetonitrile as eluent to afford the titled compound as a white solid (45.9 mg). MS [M+H]+=578.3 (calc=578.3342) (MultiMode+) ¹H NMR (400 MHz, CD₃OD) δ 7.88 (s, 1H), 7.76 (s, 1H), 7.39 (s, 1H), 7.33 (d, J=7.9 Hz, 1H), 7.22 (t, J=7.6 Hz, 1H), 7.05 (d, J=7.4 Hz, 1H), 6.70 (d, J=8.3 Hz, 1H), 6.48 (d, J=8.3 Hz, 1H), 4.60 (s, 2H), 3.89 (s, 3H), 3.74-3.67 (m, 4H), 3.62-3.51 (m, 1H), 3.35-3.26 (m, 2H), 3.17-2.96 (m, 4H), 2.86 (t, J=6.7 Hz, 2H), 2.85 (t, J=6.3 Hz, 2H), 2.70 (dt, J=6.6 and 16.1 Hz, 1H), 2.54 (dt, J=5.7 and 16.2 Hz, 1H), 1.75-1.63 (m, 1H), 1.15 (d, J=6.6 Hz, 3H), 0.94 (d, J=6.4 Hz, 3H), 0.80 (d, J=6.9 Hz, 3H).

Example 10

N-Cyclohexyl-N-(2-(2-(5-hydroxy-3-oxo-3,4-dihydro-2H-benzo[b][1,4]oxazin-8-yl)ethylamino)ethyl)-3-(3-(oxazol-5-yl)phenethoxy)propanamide Trifluoroacetic Acid Salt

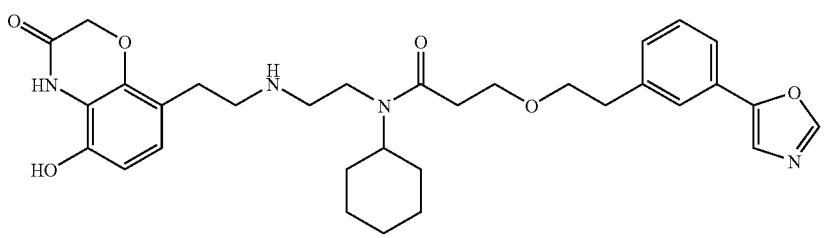

Step i) 3-(3-Cyanophenethoxy)-N-cyclohexyl-N-(2,2-dimethoxyethyl)propanamide

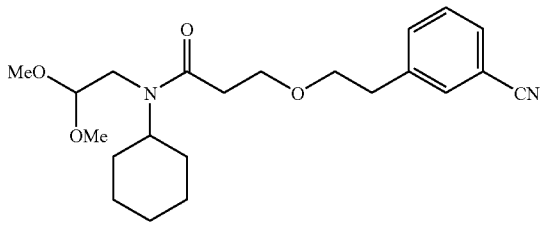

To 3-(3-bromophenethoxy)-N-cyclohexyl-N-(2,2-dimethoxyethyl)propanamide (4 g) [Preparation 3] in DMF (30 mL) was added zinc cyanide (1.59 g) and Pd(Ph₃P)₄ (0.52 g). The reaction flask was flushed with nitrogen then heated to 130° C. with stirring under nitrogen for 1 h. The reaction was worked up by the addition of ethyl acetate, which was washed three times with water, twice with brine, dried over sodium sulphate, filtered and the solvent removed to afford crude product as a yellow oil/gum. Further purification on silica eluting with 10-40% ethyl acetate/isohexane afforded the sub-titled compound as a pale yellow oil (3.44 g). MS [M+H-MeOH]+=357 (MultiMode+)

Step ii) N-Cyclohexyl-N-(2,2-dimethoxyethyl)-3-(3-formylphenethoxy)propanamide

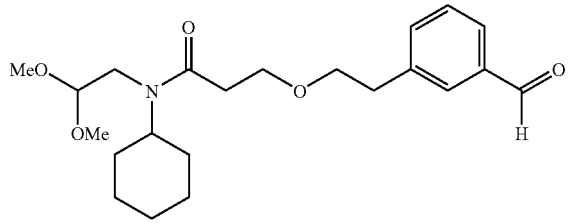

To 3-(3-cyanophenethoxy)-N-cyclohexyl-N-(2,2-dimethoxyethyl)propanamide [Example 10, Step i)] (600 mg) in acetic acid (6 mL), pyridine (9 mL) and water (6 mL) was added sodium hypophosphite monohydrate (1964 mg) and Raney (R) nickel (397 mg). The reaction was heated to 45° C. under nitrogen for 2 h, then cooled to room temperature, filtered and washed with water/ethyl acetate. The filtrate was diluted with ethyl acetate, which was washed with water then dried over brine, filtered and the solvent removed. The residue was azeotroped once with ethanol to afford a light yellow oil (600 mg). MS [M+H-MeOH]+=360 (Multi-Mode+)

Step iii) N-Cyclohexyl-N-(2,2-dimethoxyethyl)-3-(3-(oxazol-5-yl)phenethoxy)propanamide

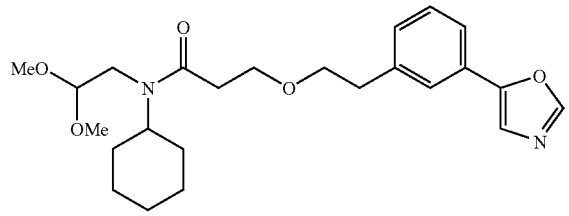

To N-cyclohexyl-N-(2,2-dimethoxyethyl)-3-(3-formylphenethoxy)propanamide [Example 10, Step ii)] (600 mg) in a 10 ml microwave vial was added toluenesulfonylmethyl isocyanide (329 mg), potassium carbonate (233 mg) and methanol (2 mL). The vial was sealed and heated at 80° C. for 40 min within a microwave before cooling to room temperature. The solvents were evaporated under vacuum followed by the addition of water, which was extracted once with ethyl acetate. The organic phase was washed once with water, dried over sodium sulphate, filtered and the solvent removed to afford desired material, which was carried onto the next step directly. MS [M+H-MeOH]+=399 (MultiMode+)

Step iv) N-Cyclohexyl-3-(3-(oxazol-5-yl)phenethoxy)-N-(2-oxoethyl)propanamide

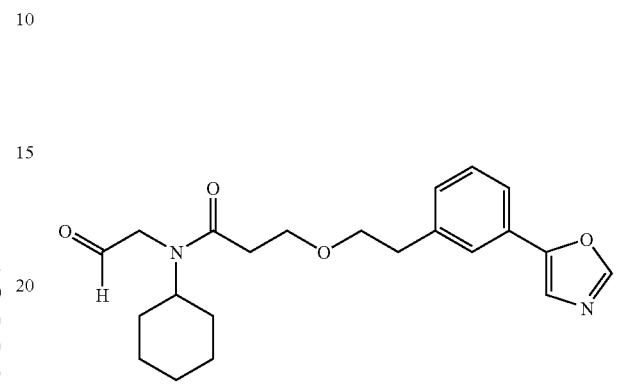

To a stirred solution of N-cyclohexyl-N-(2,2-dimethoxyethyl)-3-(3-(oxazol-5-yl)phenethoxy)propanamide [Example 10, Step iii)] (660 mg) in acetone (30 mL) was added 2M hydrochloric acid (10 mL). The mixture was stirred for 6 h before the solvents were removed followed by the addition of saturated sodium hydrogen carbonate until basic. The mixture was extracted three times with ethyl acetate, and the pooled organic fractions were washed once with brine, dried over sodium sulphate, filtered and evaporated to afford the sub-titled compound (525 mg). This material was used in the next step directly.

Step v) N-Cyclohexyl-N-(2-(2-(5-hydroxy-3-oxo-3,4-dihydro-2H-benzo[b][1,4]oxazin-8-yl)ethylamino)ethyl)-3-(3-(oxazol-5-yl)phenethoxy)propanamide Trifluoroacetic Acid Salt

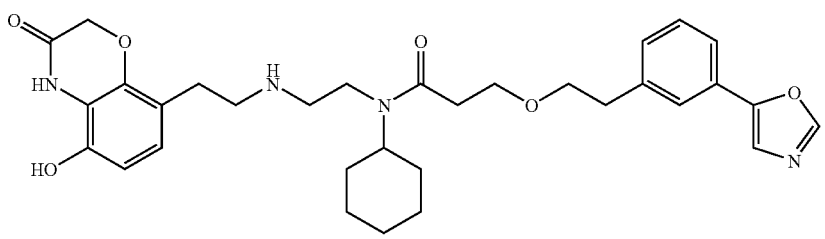

To a stirred solution of 8-(2-aminoethyl)-5-hydroxy-2H-benzo[b][1,4]oxazin-3(4H)-one hydrochloride (200 mg) in NMP (5 mL) and water (0.5 mL) was added sodium bicarbonate (68.7 mg). The mixture was stirred for 5 min before the addition of N-cyclohexyl-3-(3-(oxazol-5-yl)phenethoxy)-N-(2-oxoethyl)propanamide [Example 10, Step iv)] (346 mg) and stirred for 15 min before the addition of sodium triacetoxyborohydride (346 mg). The reaction was stirred for 2 h before the addition of saturated sodium hydrogen carbonate solution, which was extracted three times with DCM. The pooled organic fractions were concentrated and purified via reverse phase prep HPLC using TFA/acetonitrile as eluent. The solvent was removed, followed by the addition of diethylether, which was evaporated to afford the titled compound (14 mg). MS [M+H]+=577 (MultiMode+) $^1$H NMR (400 MHz, CD$_3$OD) δ 8.21 (s, 1H), 7.60-7.57 (m, 1H), 7.56-7.51 (m, 1H), 7.48 (s, 1H), 7.37-7.32 (m, 1H), 7.25-7.21 (m, 1H), 6.70 (d, J=7.1 Hz, 1H), 6.47 (d, J=8.3 Hz, 1H), 4.60 (s, 2H), 3.74-3.66 (m, 5H), 3.51-3.45 (m, 2H), 3.15-3.09 (m, 2H), 3.05-3.00 (m, 2H), 2.91-2.84 (m, 4H), 2.65-2.60 (m, 2H), 1.81-1.74 (m, 2H), 1.70-1.58 (m, 3H), 1.46-1.26 (m, 4H), 1.17-1.07 (m, 1H)

Example 11

3-(3-(1,2,4-Oxadiazol-3-yl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide Trifluoroacetic Acid Salt

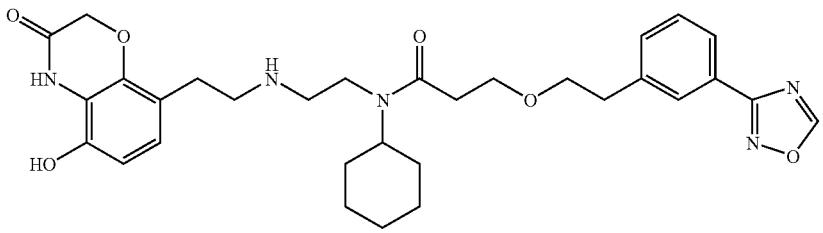

Step i) N-Cyclohexyl-N-(2,2-dimethoxyethyl)-3-(3-(N-hydroxycarbamimidoyl)phenethoxy)propanamide

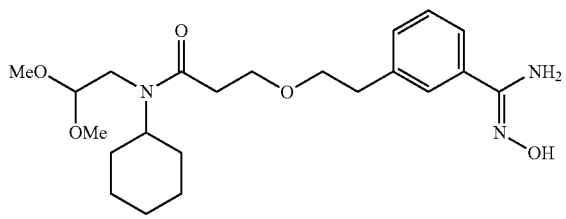

To 3-(3-cyanophenethoxy)-N-cyclohexyl-N-(2,2-dimethoxyethyl)propanamide [Example 10, Step i)] (1.5 g) within a 35 mL microwave vial was added potassium carbonate (0.80 g), hydroxylamine hydrochloride (0.402 g), water (2.5 mL) and ethanol (10 mL). The vial was sealed and stirred for 3 days before being heated at 90° C. for a total of 3 h. The reaction was diluted with water, extracted twice with ethyl acetate, which were pooled and washed twice with water, twice with brine, dried over sodium sulphate, filtered and the solvent removed to afford a colourless gum (1.7 g). This material was used in the next step directly.

Step ii) 3-(3-(1,2,4-Oxadiazol-3-yl)phenethoxy)-N-cyclohexyl-N-(2,2-dimethoxyethyl)propanamide

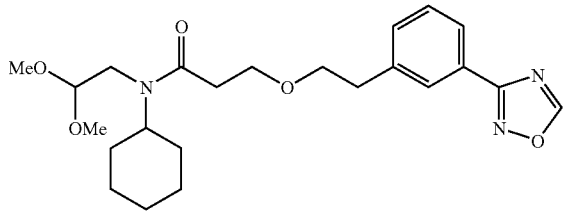

To N-cyclohexyl-N-(2,2-dimethoxyethyl)-3-(3-(N-hydroxycarbamimidoyl)phenethoxy)propanamide [Example 11, Step i)] (530 mg) in a 10 mL microwave vial was added trimethyl orthoformate (1 mL), sealed and heated at 100° C. for 20 min. The vial was then heated to 120° C. for 3 h before the addition of p-toluenesulfonic acid (3 mg) and then heated to 120° C. for a further 60 min. Ethanol was added (30 mL) and the solvent was evaporated to afford the sub-titled compound (500 mg). MS [M+H-MeOH]+=400 (MultiMode+)

Step iii) 3-(3-(1,2,4-Oxadiazol-3-yl)phenethoxy)-N-cyclohexyl-N-(2-oxoethyl)propanamide

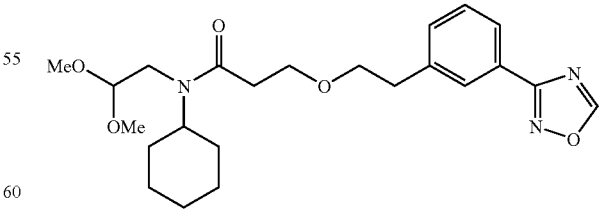

To 3-(3-(1,2,4-oxadiazol-3-yl)phenethoxy)-N-cyclohexyl-N-(2,2-dimethoxyethyl)propanamide [Example 11, Step ii)] (500 mg) in NMP (4 mL) was added p-toluenesulfonic acid (441 mg) and the mixture stirred for 8 h. After work-up the material was used in the next step directly.

Step iv) 3-(3-(1,2,4-Oxadiazol-3-yl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide Trifluoroacetic Acid Salt

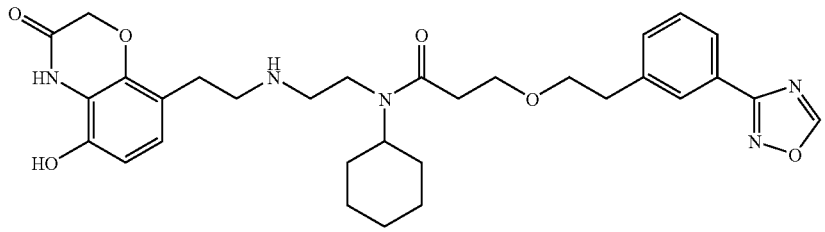

To a stirred solution of 8-(2-aminoethyl)-5-hydroxy-2H-benzo[b][1,4]oxazin-3(4H)-one hydrochloride (284 mg) in water (0.5 mL) and NMP (5 mL) was added sodium bicarbonate (292 mg) and 3-(3-(1,2,4-oxadiazol-3-yl)phenethoxy)-N-cyclohexyl-N-(2-oxoethyl)propanamide [Example 11, Step iii] (447 mg). The mixture was stirred for 20 min before the addition of sodium triacetoxyborohydride (492 mg). The reaction was stirred overnight before the addition of saturated sodium hydrogen carbonate solution, which was extracted three times with DCM. The solvent was removed and the residue was purified via reverse phase prep HPLC using TFA/acetonitrile as eluent. The solvent was removed, followed by the addition of diethyl ether, which was evaporated to afford the titled compound (110 mg). MS [M+H]+= 578 (MultiMode+) $^1$H NMR (400 MHz, CD$_3$OD) δ 9.24 (s, 1H), 7.95 (s, 1H), 7.93-7.87 (m, 1H), 7.45-7.38 (m, 2H), 6.70 (d, J=8.6 Hz, 1H), 6.47 (d, J=8.0 Hz, 1H), 4.61 (s, 2H), 3.78-3.63 (m, 5H), 3.49 (t, J=5.5 Hz, 2H), 3.15-3.10 (m, 2H), 3.05-3.00 (m, 2H), 2.95-2.84 (m, 4H), 2.63 (t, J=6.0 Hz, 2H), 1.81-1.73 (m, 2H), 1.70-1.58 (m, 3H), 1.46-1.25 (m, 4H), 1.17-1.04 (m, 1H)

Example 12

N-Cyclohexyl-N-(2-(2-(5-hydroxy-3-oxo-3,4-dihydro-2H-benzo[b][1,4]oxazin-8-yl)ethylamino)ethyl)-3-(3-(1-isopropyl-1H-1,2,3-triazol-4-yl)phenethoxy)propanamide Trifluoroacetic Acid Salt Step i) tert-Butyl 3-(3-(1-isopropyl-1H-1,2,3-triazol-4-yl)phenethoxy)propanoate

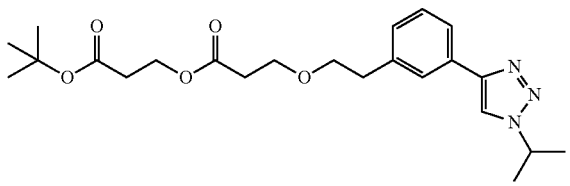

2-Iodopropane (0.168 mL) was added in one portion to a mixture tert-butyl 3-(3-ethynylphenethoxy)propanoate [Example 4, Step ii] (383 mg), sodium azide (109 mg), tert-butanol (0.75 mL), water (3 mL) and copper(I) iodide (26.6 mg) and sealed into a microwave tube. The reaction was heated to 80° C., over a period of 3 h in the microwave reactor. The reaction mixture was diluted with ethyl acetate and 35% ammonia (1 mL) and ethyl acetate (2 mL) were added. The mixture was stirred for 30 min. and extracted into ethyl acetate. The organic was evaporated to afford crude product. The crude product was purified by flash silica chromatography, elution gradient 20 to 100% ethyl acetate in isohexane to afford the titled compound (291 mg) as an oil. $^1$H NMR (300 MHz, CDCl$_3$) δ 7.79 (s, 1H), 7.72-7.64 (m, 2H), 7.33 (t, J=7.6 Hz, 1H), 7.18 (d, J=7.5 Hz, 1H), 4.89 (septet, J=6.6 Hz, 1H),

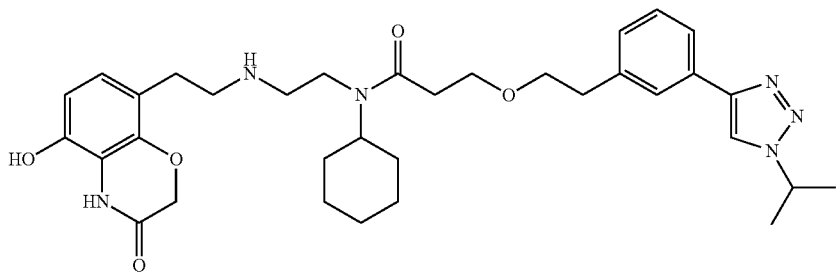

3.70 (t, J=6.4 Hz, 2H), 3.697 (t, J=7.3 Hz, 2H), 2.92 (t, J=7.1 Hz, 2H), 2.49 (t, J=6.4 Hz, 2H), 1.63 (d, J=6.7 Hz, 6H), 1.43 (s, 9H)

Step ii) 3-(3-(1-Isopropyl-1H-1,2,3-triazol-4-yl)phenethoxy)propanoic acid

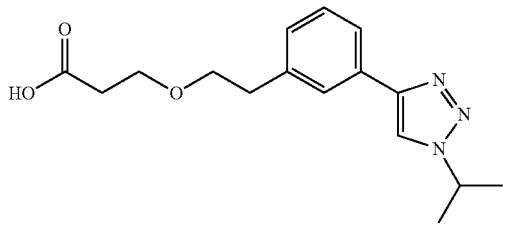

The subtitled compound (777 mg) was prepared from tert-butyl 3-(3-(1-isopropyl-1H-1,2,3-triazol-4-yl)phenethoxy)propanoate [Example 12, Step i)] using a similar method to that described in Example 4, Step iv). MS [M+H]+=304 (MultiMode+) ¹H NMR (400 MHz, CDCl₃) δ 7.91 (s, 1H), 7.79 (s, 1H), 7.48 (d, J=7.7 Hz, 1H), 7.36 (t, J=7.7 Hz, 1H), 7.23 (d, J=7.7 Hz, 1H), 4.92 (septet, J=6.6 Hz, 1H), 3.77 (t, J=5.8 Hz, 2H), 3.76 (t, J=5.8 Hz, 2H), 2.93 (t, J=6.0 Hz, 2H), 2.62 (t, J=5.9 Hz, 2H), 1.68 (d, J=6.7 Hz, 6H)

Step iii) N-Cyclohexyl-N-(2,2-dimethoxyethyl)-3-(3-(1-isopropyl-1H-1,2,3-triazol-4-yl)phenethoxy)propanamide

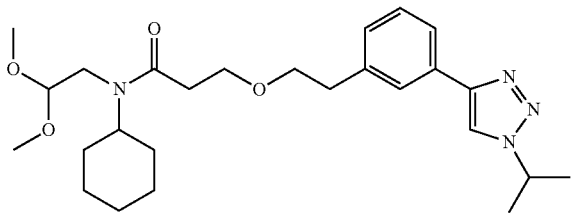

The subtitled compound (230 mg) was prepared from 3-(3-(1-isopropyl-1H-1,2,3-triazol-4-yl)phenethoxy)propanoic acid [Example 12, Step ii)] and N-(2,2-dimethoxyethyl)cyclohexanamine using a similar method to that described in Example 4, Step v) and the elution gradient to 0 to 100% ethyl acetate in isohexane. MS [M+H-MeOH]+=441 (MultiMode+) ¹H NMR (400 MHz, CD₃OD) δ 8.36 (s, 1H), 7.71-7.61 (m, 2H), 7.32 and 7.31 (2×t, J=7.7 Hz, 1H), 7.19 (d, J=8.0 Hz, 1H), 4.87 (septet, J=6.7 Hz, 1H), 4.51 and 4.36 (2×t, J=5.4 Hz, 1H), 4.03-3.94 and 3.69-3.60 (2×m, 1H), 3.76-3.66 (m, 4H), 3.34 and 3.25 (2×d, J=5.3 Hz, 2H), 3.34 (s, 3H), 3.31 (s, 3H), 2.91-2.85 (m, 2H), 2.68-2.61 (m, 2H), 1.79-1.01 (m, 10H), 1.61 (d, J=6.8 Hz, 6H), a ~1:1 mixture of rotamers is observed.

Step iv) N-Cyclohexyl-N-(2-(2-(5-hydroxy-3-oxo-3,4-dihydro-2H-benzo[b][1,4]oxazin-8-yl)ethylamino)ethyl)-3-(3-(1-isopropyl-1H-1,2,3-triazol-4-yl)phenethoxy)propanamide Trifluoroacetic Acid Salt

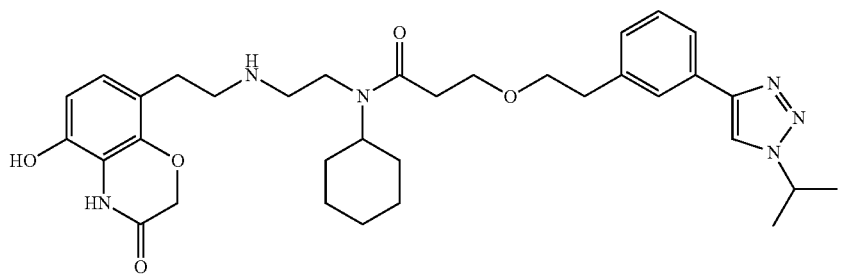

p-Toluenesulfonic acid monohydrate (156 mg) was added in one portion to N-cyclohexyl-N-(2,2-dimethoxyethyl)-3-(3-(1-isopropyl-1H-1,2,3-triazol-4-yl)phenethoxy)propanamide [Example 12, Step iii)] (242 mg) in tetrahydrofuran (3 mL). The resulting solution was stirred at 20° C. for 40 min. This solution was added to a stirred mixture of 8-(2-aminoethyl)-5-hydroxy-2H-benzo[b][1,4]oxazin-3(4H)-one hydrochloride (146 mg), sodium bicarbonate (129 mg), water (0.3 mL) and NMP (3 mL). The mixture was stirred for 10 min and sodium triacetoxyborohydride (271 mg) and acetic acid (0.03 mL) were added. The mixture was stirred for 2 h. The reaction mixture was neutralised with saturated sodium hydrogen carbonate (20 ml) and extracted into ethyl acetate/MeOH (10%, 3×50 ml). The organic was washed with a 1:1 mixture of water and saturated brine (2×10 ml). The organic was dried over magnesium sulfate, filtered and evaporated to afford crude product. The crude product was purified by flash silica chromatography, elution gradient 0 to 10% methanol in dichloromethane and repurified by preparative HPLC on a Phenomenex Gemini column using aqueous 0.1% trifluoroacetic acid in acetonitrile as eluent to afford the titled compound (175 mg). MS [M+H]+=619.4 (calc=619.3608) (MultiMode+) ¹H NMR (400 MHz, CD₃OD) δ 8.34 (s, 1H), 7.71 (s, 1H), 7.60 (d, J=8.3 Hz, 1H), 7.32 (t, J=7.7 Hz, 1H), 7.19 (d, J=7.9 Hz, 1H), 6.69 (d, J=8.6 Hz, 1H), 6.47 (d, J=8.1 Hz, 1H), 4.86 (septet, J=6.4 Hz, 1H), 4.60 (s, 2H), 3.76-3.64 (m, 5H), 3.50-3.44 (m, 2H), 3.13 (t, J=7.2 Hz, 2H), 3.03 (t, J=5.6 Hz, 2H), 2.89 (t, J=6.4 Hz, 2H), 2.87 (t, J=7.3 Hz, 2H), 2.62 (t, J=6.1 Hz, 2H), 1.79-1.57 (m, 5H), 1.60 (d, J=6.7 Hz, 6H), 1.45-1.24 (m, 4H), 1.18-1.04 (m, 1H).

Example 13

N-Cyclohexyl-3-(4-fluoro-3-(1-methyl-1H-pyrazol-4-yl)phenethoxy)-N-(2-(2-(5-hydroxy-3-oxo-3,4-dihydro-2H-benzo[b][1,4]oxazin-8-yl)ethylamino)ethyl)propanamide Trifluoroacetic Acid Salt

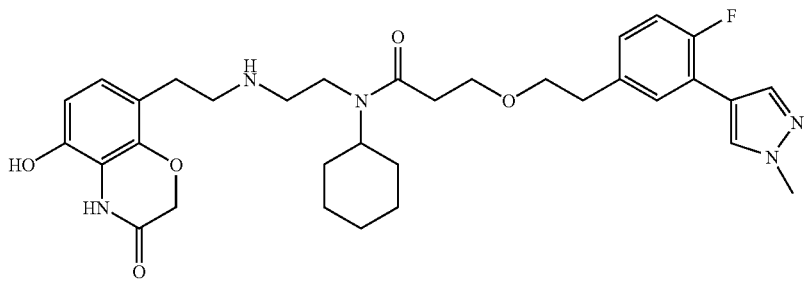

Step i) Methyl 2-(3-bromo-4-fluorophenyl)acetate

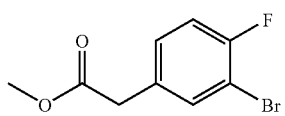

A solution of (diazomethyl)trimethylsilane (12.87 mL) in diethyl ether was added to an ice-batch cooled solution of 2-(3-bromo-4-fluorophenyl)acetic acid (3 g) in dichloromethane (20 mL) and methanol (5 mL). The mixture was stirred for 10 min. and concentrated in vacuo to give methyl 2-(3-bromo-4-fluorophenyl)acetate (3.20 g) that was

Step ii) Methyl 2-(4-fluoro-3-(1-methyl-1H-pyrazol-4-yl)phenyl)acetate

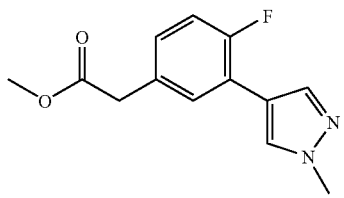

Pd-118 (0.201 g) was dissolved in acetonitrile (20 mL) and stirred for 5 min before addition of potassium carbonate (5.34 g), water (20 mL) and 1-methyl-4-(4,4,5,5-tetramethyl-1,3,2-dioxaborolan-2-yl)-1H-pyrazole (2.95 g). The mixture was stirred for a further 5 min then methyl 2-(3-bromo-4-fluorophenyl)acetate [Example 13, Step i)] (3.18 g) in MeCN (2 mL) added and the reaction was heated at the heating block (80° C.) for 25 min. The mixture was cooled and extracted into DCM (100 mL). Organic was separated, dried over magnesium sulfate. Solvents were evaporated to give a brown oil. The crude product was purified by flash silica chromatography, elution gradient 0 to 60% ethyl acetate in isohexane to afford the subtitled compound (3.36 g) as a gum. $^1$H NMR (300 MHz, CDCl$_3$) δ 7.84 (s, 1H), 7.77 (d, J=2.3 Hz, 1H), 7.44 (dd, J=7.3, 1.5 Hz, 1H), 7.12-7.02 (m, 2H), 3.96 (s, 3H), 3.71 (s, 3H), 3.62 (s, 2H)

Step iii) 2-(4-Fluoro-3-(1-methyl-1H-pyrazol-4-yl)phenyl)ethanol

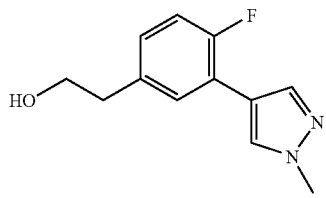

A solution of diisobutylaluminium hydride in dichloromethane (1M, 35 mL) was added dropwise to a stirred solution of methyl 2-(4-fluoro-3-(1-methyl-1H-pyrazol-4-yl)phenyl)acetate [Example 13, Step ii)] (3.36 g) in dichloromethane (15 mL) keeping temp of reaction mixture at gentle reflux. The mixture was stirred for 15 min. and carefully quenched by dropwise addition of MeOH (3 mL). The mixture was poured onto 2M HCl (100 mL) and extracted with a mixture DCM/MeOH (9:1, 5×50 mL). The organic was dried over magnesium sulfate, filtered and evaporated to afford 2-(4-fluoro-3-(1-methyl-1H-pyrazol-4-yl)phenyl)ethanol (2.2 g) that was used in the next step without purification. $^1$H NMR (300 MHz, CDCl$_3$) δ 7.86 (s, 1H), 7.78 (s, 1H), 7.39 (d, J=7.3 Hz, 1H), 7.09-7.02 (m, 2H), 3.97 (s, 3H), 3.88 (t, J=6.5 Hz, 2H), 2.87 (t, J=6.4 Hz, 2H)

Step iv) tert-Butyl 3-(4-fluoro-3-(1-methyl-1H-pyrazol-4-yl)phenethoxy)propanoate

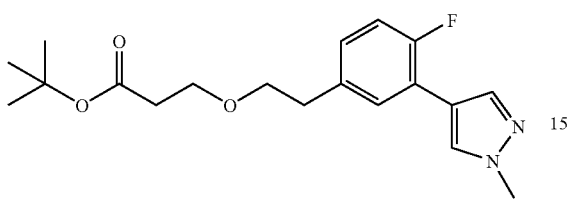

Triton-B (0.4 ml, 0.88 mmol) was added to a stirred mixture of 2-(4-fluoro-3-(1-methyl-1H-pyrazol-4-yl)phenyl)ethanol [Example 13, Step iii)] (1.7 g) and tert-butyl acrylate (8 mL). The mixture was stirred at room temperature over 1 h. The crude product was purified by flash silica chromatography, elution gradient 0 to 100% ethyl acetate in isohexane to afford tert-butyl 3-(4-fluoro-3-(1-methyl-1H-pyrazol-4-yl) phenethoxy)propanoate (2.65 g) as a colorless liquid. MS [M+H-C4H8]+=293 (MultiMode+) $^1$H NMR (300 MHz, CDCl$_3$) δ 7.84 (s, 1H), 7.77 (d, J=2.5 Hz, 1H), 7.40-7.35 (m, 1H), 7.05-6.98 (m, 2H), 3.96 (s, 3H), 3.69 (t, J=6.4 Hz, 2H), 3.66 (t, J=6.9 Hz, 2H), 2.86 (t, J=6.9 Hz, 2H), 2.48 (t, J=6.4 Hz, 2H), 1.43 (s, 9H).

Step v) 3-(4-Fluoro-3-(1-methyl-1H-pyrazol-4-yl) phenethoxy)propanoic acid

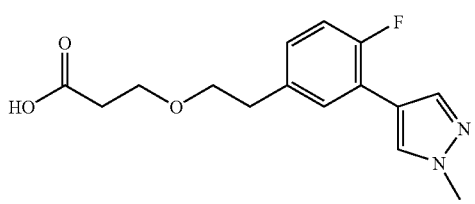

The subtitled compound (4.32 g) was prepared from tert-butyl 3-(4-fluoro-3-(1-methyl-1H-pyrazol-4-yl)phenethoxy) propanoate [Example 13, Step iv)] using a similar method to that described in Example 4, Step iv). MS [M−H]$^-$=291 (MultiMode-) $^1$H NMR (300 MHz, CDCl$_3$) δ 8.24 (s, 1H), 7.90 (d, J=2.1 Hz, 1H), 7.50 (dd, J=7.4, 2.0 Hz, 1H), 7.12-7.00 (m, 2H), 4.08 (s, 3H), 3.76 (t, J=5.9 Hz, 2H), 3.73 (t, J=6.3 Hz, 2H), 2.89 (t, J=6.1 Hz, 2H), 2.65 (t, J=5.7 Hz, 2H)

Step vi) N-Cyclohexyl-N-(2,2-dimethoxyethyl)-3-(4-fluoro-3-(1-methyl-1H-pyrazol-4-yl)phenethoxy) propanamide The subtitled compound (3.3 g) was prepared from 3-(4-fluoro-3-(1-methyl-1H-pyrazol-4-yl)phenethoxy)propanoic acid [Example 13, Step v)] and N-(2,2-dimethoxyethyl)cyclohexanamine using a similar method to that described in Example 12, Step iii). MS [M+H-MeOH]+=430 (MultiMode+) $^1$H NMR (400 MHz, CD$_3$OD) δ 7.99 and 7.98 (2×s, 1H), 7.86 (and 7.85 (2×s, 1H), 7.47 (m, 1H), 7.09-6.97 (m, 2H), 4.51 and 4.36 (2×t, J=5.4 Hz, 1H), 4.00 and 3.62 (tt, J=3.2 and 12.0 Hz, 1H), 3.920 and 3.918 (2×s, 3H), 3.75-3.63 (m, 4H), 3.34 (s, 3H), 3.33 (d, J=5.6 Hz, 1H), 3.32 (s, 3H), 3.25 (d, J=5.2 Hz, 1H), 2.86-2.79 (m, 2H), 2.65 and 2.63 (2×t, J=6.1 Hz, 2H), 1.79-1.01 (m, 10H); a ~1:1 mixture of rotamers is observed.

Step vii) N-Cyclohexyl-3-(4-fluoro-3-(1-methyl-1H-pyrazol-4-yl)phenethoxy)-N-(2-(2-(5-hydroxy-3-oxo-3,4-dihydro-2H-benzo[b][1,4]oxazin-8-yl)ethylamino)ethyl)propanamide Trifluoroacetic Acid Salt

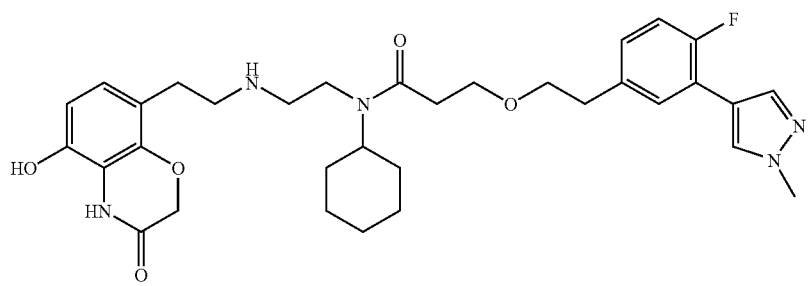

The titled compound (324 mg) was prepared from N-cyclohexyl-N-(2,2-dimethoxyethyl)-3-(4-fluoro-3-(1-methyl-1H-pyrazol-4-yl)phenethoxy)propanamide [Example 13, Step vi)] using a similar method to that described in Example 12, Step iv). MS [M+H]+=608.3 (calc=608.3248) (MultiMode+) $^1$H NMR (400 MHz, CD$_3$OD) δ 7.95 (d, J=2.5 Hz, 1H), 7.85 (s, 1H), 7.48 (dd, J=1.9 and 7.2 Hz, 1H), 7.08-6.98 (m, 2H), 6.69 (d, J=8.2 Hz, 1H), 6.47 (d, J=8.2 Hz, 1H), 4.60 (s, 2H), 3.90 (s, 3H), 3.71 (t, J=5.9 Hz, 2H), 3.69 (t, J=6.6 Hz, 2H), 3.72-3.63 (m, 1H), 3.48 (t, J=5.6 Hz, 2H), 3.11 (t, J=7.2 Hz, 2H), 3.02 (t, J=5.6 Hz, 2H), 2.86 (t, J=7.4 Hz, 2H), 2.84 (t, J=6.6 Hz, 2H), 2.63 (t, J=6.1 Hz, 2H), 1.82-1.73 (m, 2H), 1.70-1.59 (m, 3H), 1.47-1.25 (m, 4H), 1.18-1.03 (m, 1H)

Example 14

3-(3-(1H-1,2,3-Triazol-4-yl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide Trifluoroacetic Acid Salt Step i) tert-Butyl 3-(3-(1-allyl-1H-1,2,3-triazol-4-yl)phenethoxy)propanoate

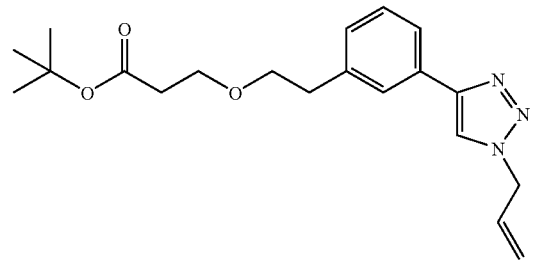

Cyclopropyl bromide (0.177 mL) was added in one portion to a mixture tert-butyl 3-(3-ethynylphenethoxy)propanoate [Example 4, Step ii)] (506 mg), sodium azide (144 mg), tert-butanol (0.5 mL), water (2 mL) and copper(I) iodide (35.1 mg) and sealed into a microwave tube. The reaction was

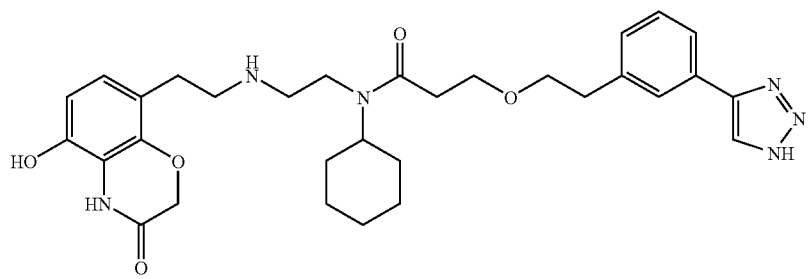

heated to 70° C., over a period of 3 h in the microwave reactor. The reaction mixture was diluted with ethyl acetate and 35% ammonia (1 mL) and ethyl acetate (2 mL) were added. The mixture was stirred for 30 min. and extracted into ethyl acetate. The organic was evaporated to afford crude product. The crude product was purified by flash silica chromatography, elution gradient 20 to 100% ethyl acetate in isohexane to afford the titled compound (470 mg) as an oil. $^1$H NMR (400 MHz, CDCl$_3$) δ 7.78 (s, 1H), 7.70 (s, 1H), 7.66 (d, J=7.9 Hz, 1H), 7.33 (t, J=7.7 Hz, 1H), 7.19 (d, J=7.7 Hz, 1H), 6.08 (ddt, J=5.9, 10.3 and 16.9 Hz, 1H), 5.41-5.32 (m, 2H), 5.03 (dt, J=6.2, 1.3 Hz, 2H), 3.70 (t, J=6.3 Hz, 2H), 3.69 (t, J=7.1 Hz, 2H), 2.92 (t, J=7.0 Hz, 2H), 2.48 (t, J=6.5 Hz, 2H), 1.43 (s, 9H)

Step ii) 3-(3-(1-Allyl-1H-1,2,3-triazol-4-yl)phenethoxy)propanoic acid

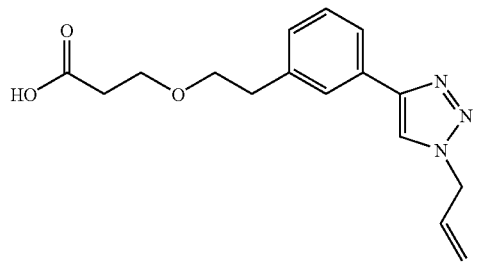

The subtitled compound (713 mg) was prepared from tert-butyl 3-(3-(1-allyl-1H-1,2,3-triazol-4-yl)phenethoxy)propanoate [Example 14, Step i)] using a similar method to that described in Example 4, Step iv). $^1$H NMR (400 MHz, CDCl$_3$) δ 7.91 (s, 1H), 7.78 (s, 1H), 7.48 (d, J=7.4 Hz, 1H), 7.35 (t, J=7.6 Hz, 1H), 7.23 (d, J=7.7 Hz, 1H), 6.08 (ddt, J=6.3, 10.2 and 16.8 Hz, 1H), 5.50-5.41 (m, 2H), 5.07 (d, J=6.4 Hz, 2H), 3.77 (t, J=5.7 Hz, 2H), 3.76 (t, J=5.8 Hz, 2H), 2.94 (t, J=6.2 Hz, 2H), 2.64 (t, J=5.8 Hz, 2H)

Step iii) 3-(3-(1-Allyl-1H-1,2,3-triazol-4-yl)phenethoxy)-N-cyclohexyl-N-(2,2-dimethoxyethyl)propanamide The subtitled compound (584 mg) was prepared from tert-butyl 3-(3-(1-allyl-1H-1,2,3-triazol-4-yl)phenethoxy)propanoate [Ex 4, Step iii)] and N-(2,2-dimethoxyethyl)cyclohexanamine using a similar method to that described in Example 12, Step iii) the elution gradient 20 to 100% ethyl acetate in isohexane. $^1$H NMR (400 MHz, CD$_3$OD) δ 8.29 (s, 1H), 7.69 and 7.67 (2 s, 1H), 7.64 (d, J=7.9 Hz, 1H), 7.322 and 7.318 (2×t, J=7.7 Hz, 1H), 7.20 (d, J=6.9 Hz, 1H), 6.17-6.06 (m, 1H), 5.36-5.27 (m, 2H), 5.06 (d, J=5.9 Hz, 2H), 4.52 and 4.36 (2×t, J=5.5 Hz, 1H), 3.99 and 3.65 (tt, J=5.3 and 11.7 Hz, 1H), 3.76-3.66 (m, 4H), 3.34 (s, 3H), 3.32 (s, 3H), 3.34 and 3.25 (2×d, J=4.9 Hz, 2H), 2.92-2.85 (m, 2H), 2.68-2.61 (m, 2H), 1.79-1.02 (m, 10H); a ~1:1 mixture of rotamers is observed.

Step iv) tert-Butyl 2-(3-(3-(1-allyl-1H-1,2,3-triazol-4-yl)phenethoxy)-N-cyclohexylpropanamido)ethyl (2-(5-(tert-butoxycarbonyloxy)-3-oxo-3,4-dihydro-2H-benzo[b][1,4]oxazin-8-yl)ethyl)carbamate

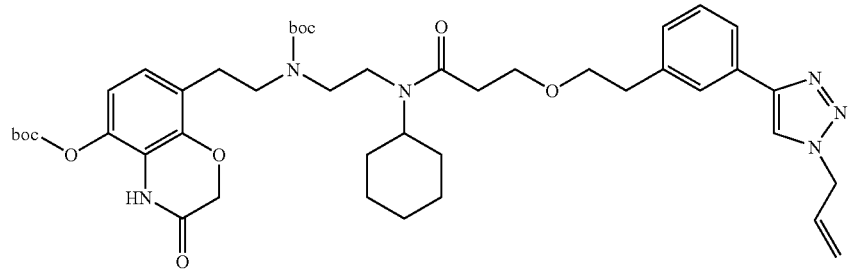

p-Toluenesulfonic acid monohydrate (236 mg) was added in one portion to 3-(3-(1-allyl-1H-1,2,3-triazol-4-yl)phenethoxy)-N-cyclohexyl-N-(2,2-dimethoxyethyl)propanamide [Example 14, Step iii)] (292 mg) in DCM (3 mL). The resulting solution was stirred at 25° C. for 15 min and this mixture was added to a stirred solution of 8-(2-aminoethyl)-5-hydroxy-2H-benzo[b][1,4]oxazin-3(4H)-one hydrochloride (152 mg) and acetic acid (0.05 mL) in NMP (3 mL). DIPEA (0.325 mL) was added and the mixture stirred for 5 min. Sodium triacetoxyborohydride (380 mg) was added in one portion and the resulting slurry was stirred at room temperature for 5 h. The reaction mixture was neutralised with saturated sodium hydrogen carbonate and extracted into DCM. The organics were concentrated. The residue was treated with methanol (5.0 mL) and potassium carbonate (171 mg). Di-tert-butyldicarbonate (296 mg) was added. The resulting mixture was stirred at 25° C. for 45 min. The reaction mixture was diluted with ethyl acetate (50 mL), and washed 3 times with water (20 mL). The organic was dried over sodium sulfate, filtered and evaporated to afford crude product. The crude product was purified by flash silica chromatography, elution gradient 20 to 100% ethyl acetate in isohexane to afford the subtitled compound (225 mg) as a white solid. $^1$H NMR (400 MHz, CD$_3$OD) δ 8.30-8.22 (m, 1H), 7.71-7.57 (m, 2H), 7.35-7.13 (m, 2H), 6.81-6.67 (m, 2H), 6.17-6.02 (m, 1H), 5.36-5.25 (m, 2H), 5.08-4.99 (m, 2H), 4.64-4.49 (m, 2H), 4.18-4.06 and 3.69-3.59 (m, 1H), 3.76-3.65 (m, 4H), 3.43-2.46 (m, 12H), 1.81-0.99 (m, 28H)

Step v) 3-(3-(1H-1,2,3-Triazol-4-yl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide Trifluoroacetic Acid Salt

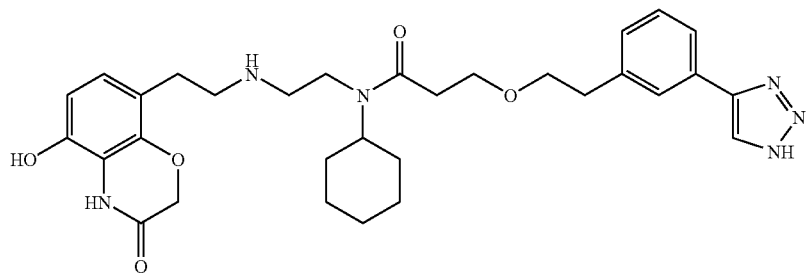

tert-Butyl 2-(3-(3-(1-allyl-1H-1,2,3-triazol-4-yl)phenethoxy)-N-cyclohexylpropanamido)ethyl(2-(5-(tert-butoxycarbonyloxy)-3-oxo-3,4-dihydro-2H-benzo[b][1,4]oxazin-8-yl)ethyl)carbamate [Example 14, Step iv)] (220 mg), 1,3-dimethylpyrimidine-2,4,6(1H,3H,5H)-trione (126 mg) and tetrakis(triphenylphosphine)palladium(0) (31 mg) were dissolved in DCM (2 mL) and sealed into a microwave tube. The reaction was heated to 100° C., over a period of 90 min in the microwave reactor. After cooling to room temperature, TFA (1 mL) was added and the mixture was stirred for 30 min, then concentrated. The crude product was purified by preparative HPLC on a Phenomenex Gemini column using a gradient of aqueous 0.1% trifluoroacetic acid in acetonitrile as eluent to afford the titled compound (63.5 mg) as a solid. MS [M+H]+= 577.3 (calc=577.3138) (MultiMode+) $^1$H NMR (400 MHz, CD$_3$OD) δ 8.12 (s, 1H), 7.71 (s, 1H), 7.63 (d, J=7.8 Hz, 1H), 7.33 (t, J=7.5 Hz, 1H), 7.21 (d, J=8.0 Hz, 1H), 6.69 (d, J=8.2 Hz, 1H), 6.47 (d, J=8.5 Hz, 1H), 4.61 (s, 2H), 3.72 (t, J=6.7 Hz, 2H), 3.72 (t, J=5.9 Hz, 2H), 3.71-3.63 (m, 1H), 3.47 (t, J=6.9 Hz, 2H), 3.11 (t, J=7.2 Hz, 2H), 3.02 (t, J=5.7 Hz, 2H), 2.89 (t, J=6.7 Hz, 2H), 2.87 (t, J=7.1 Hz, 2H), 2.62 (t, J=6.0 Hz, 2H), 1.80-1.72 (m, 2H), 1.69-1.58 (m, 3H), 1.46-1.24 (m, 4H), 1.16-1.05 (m, 1H).

Example 15

3-(3-(2H-Tetrazol-5-yl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide Trifluoroacetic Acid Salt

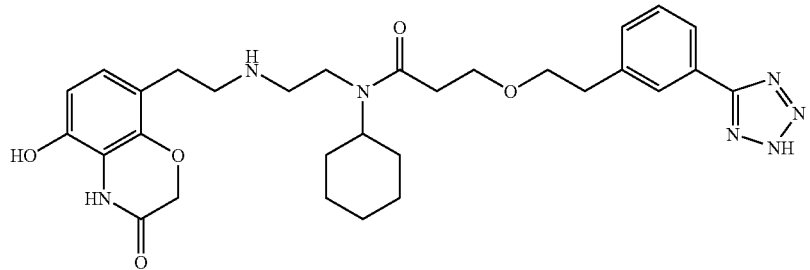

Step i) tert-Butyl 3-(3-(2-allyl-2H-tetrazol-5-yl)phenethoxy)propanoate and tert-butyl 3-(3-(1-allyl-1H-tetrazol-5-yl)phenethoxy)propanoate

Step ii) 3-(3-(2-Allyl-2H-tetrazol-5-yl)phenethoxy)propanoic acid

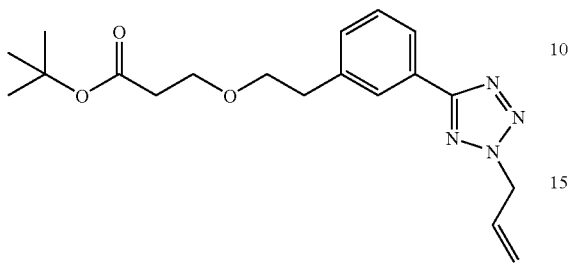

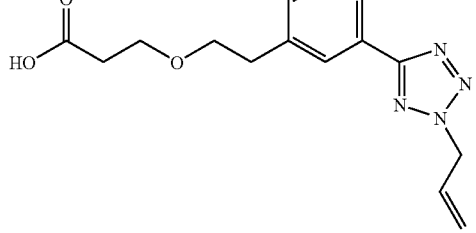

The subtitled compound (500 mg) was prepared from tert-butyl 3-(3-(2-allyl-2H-tetrazol-5-yl)phenethoxy)propanoate using a similar method to that described in Example 4, Step iv). MS [M−H]⁻=301 (MultiMode-) ¹H NMR (300 MHz, CDCl₃) δ 8.06 (s, 1H), 7.95 (dt, J=1.4 and 7.7 Hz, 1H), 7.40 (t, J=7.7 Hz, 1H), 7.31 (dt, J=1.3 and 7.6 Hz, 4H), 5.48-5.40 (m, 2H), 5.27 (dt, J=6.3, 1.3 Hz, 2H), 3.78 (t, J=6.0 Hz, 2H), 3.77 (t, J=6.4 Hz, 2H), 2.97 (t, J=6.2 Hz, 2H), 2.64 (t, J=6.0 Hz, 2H)

Step iii) 3-(3-(2-Allyl-2H-tetrazol-5-yl)phenethoxy)-N-cyclohexyl-N-(2,2-dimethoxyethyl)propanamide

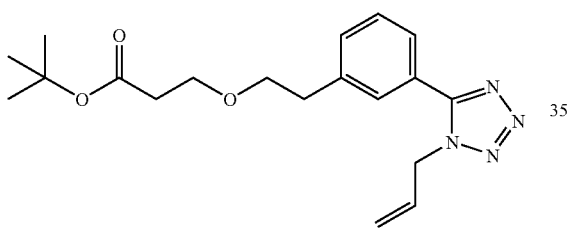

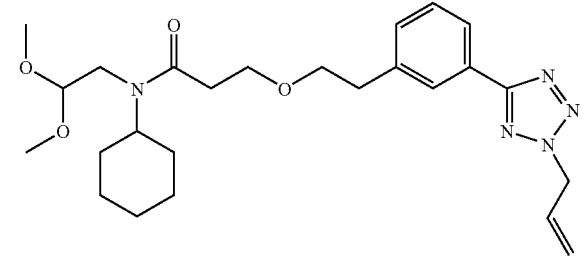

Allyl bromide (0.4 mL) was added in one portion to tert-butyl 3-(3-(2H-tetrazol-5-yl)phenethoxy)propanoate [Example 7, Step ii)] (1.05 g) and potassium carbonate (905 mg) in acetonitrile (10 mL). The resulting mixture was stirred at 65° C. for 1 h. After cooling to rt, the reaction mixture was diluted with ethyl acetate (50 mL) and washed with water (1×20 mL). The organic was dried over magnesium sulfate, filtered and evaporated to afford crude product. The crude product was purified by flash silica chromatography, elution gradient 0 to 80% ethyl acetate in isohexane to afford the subtitled compounds tert-butyl 3-(3-(2-allyl-2H-tetrazol-5-yl)phenethoxy)propanoate (427 mg) and tert-butyl 3-(3-(1-allyl-1H-tetrazol-5-yl)phenethoxy)propanoate (136 mg). Tert-butyl 3-(3-(2-allyl-2H-tetrazol-5-yl)phenethoxy)propanoate: ¹H NMR (300 MHz, CDCl₃) δ 8.02-7.96 (m, 2H), 7.44-7.30 (m, 2H), 6.12 (m, 1H), 5.45-5.37 (m, 2H), 5.26 (dt, J=6.2, 1.4 Hz, 2H), 3.70 (t, J=7.1 Hz, 2H), 3.70 (t, J=6.5 Hz, 2H), 2.95 (t, J=7.1 Hz, 2H), 2.49 (t, J=6.5 Hz, 2H), 1.43 (s, 9H). Tert-butyl 3-(3-(1-allyl-1H-tetrazol-5-yl)phenethoxy)propanoate: ¹H NMR (300 MHz, CDCl₃) δ 7.59 (s, 1H), 7.56-7.39 (m, 3H), 6.07 (ddt, J=5.5, 10.6 and 17.2 Hz, 1H), 5.39 (dt, J=1.5 and 10.4 Hz, 1H), 5.16 (dt, J=1.8 and 17.1 Hz, 1H), 5.06 (dt, J=1.6 and 5.5 Hz, 2H), 3.70 (t, J=6.7 Hz, 2H), 3.68 (t, J=6.4 Hz, 2H), 2.95 (t, J=6.8 Hz, 2H), 2.46 (t, J=6.4 Hz, 2H), 1.41 (s, 9H).

The subtitled compound (450 mg) was prepared from 3-(3-(2-allyl-2H-tetrazol-5-yl)phenethoxy)propanoic acid [Example 7, Step ii)] and N-(2,2-dimethoxyethyl)cyclohexanamine using a similar method to that described in Example 14, Step iii). ¹H NMR (300 MHz, CD₃OD) δ 8.04-7.92 (m, 2H), 7.49-7.36 (m, 2H), 6.29-6.11 (m, 1H), 5.47-5.30 (m, 4H), 4.56 and 4.39 (2×t, J=5.3 Hz, 1H), 4.09-3.94 (m, 1H), 3.81-3.67 (m, 4H), 3.372 and 3.368 (2×s, 6H), 3.34 and 3.29 (d, J=5.3 Hz, 2H), 3.00-2.91 (m, 2H), 2.72-2.64 (m, 2H), 1.84-1.02 (m, 10H); a ~1:1 mixture of rotamers is observed.

Step iv) tert-Butyl 2-(3-(3-(2-allyl-2H-tetrazol-5-yl) phenethoxy)-N-cyclohexylpropanamido)ethyl(2-(5-(tert-butoxycarbonyloxy)-3-oxo-3,4-dihydro-2H-benzo[b][1,4]oxazin-8-yl)ethyl)carbamate

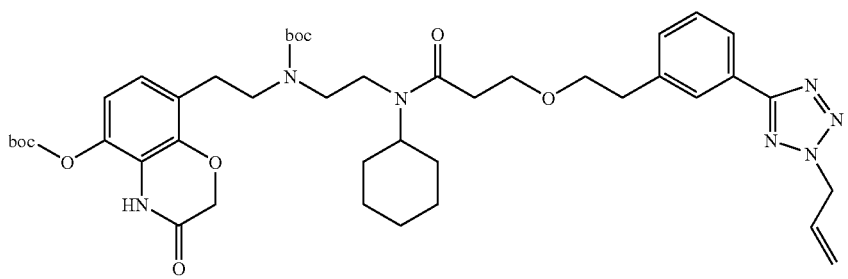

p-Toluenesulfonic acid monohydrate (179 mg) was added to a solution of 3-(3-(2-allyl-2H-tetrazol-5-yl)phenethoxy)-N-cyclohexyl-N-(2,2-dimethoxyethyl)propanamide [Example 15, Step iii)] (222 mg) in DCM (3 mL). The resulting mixture was stirred for 15 min and this solution was added to a stirred solution of 8-(2-aminoethyl)-5-hydroxy-2H-benzo[b][1,4]oxazin-3(4H)-one hydrochloride (120 mg) and acetic acid (0.05 mL) in NMP (3 mL). DIPEA (0.246 mL) was added. The mixture stirred for 5 min. Sodium triacetoxyborohydride (261 mg) was added in one portion and the resulting slurry was stirred at room temperature for 5 h. Then the reaction mixture was neutralised with saturated sodium hydrogen carbonate and extracted into DCM. The organics were concentrated. The residue was treated with MeOH (5 mL) and potassium carbonate (140 mg) followed by di-tert-butyldicarbonate (230 mg). The resulting mixture was stirred at 25° C. for 45 min. The reaction mixture was diluted with ethyl acetate (50 mL), and washed 3 times with water (20 mL). The organic was dried over sodium sulfate, filtered and evaporated to afford crude product. The crude product was purified by flash silica chromatography, elution gradient 20 to 100% ethyl acetate in isohexane to the titled compound (173 mg) as a gum. $^1$H NMR (400 MHz, CD$_3$OD) δ 8.00-7.85 (m, 2H), 7.45-7.30 (m, 2H), 6.81-6.66 (m, 2H), 6.23-6.05 (m, 1H), 5.41-5.24 (m, 4H), 4.66-4.51 (m, 2H), 3.77-3.59 (m, 5H), 3.48-2.44 (m, 12H), 1.80-1.00 (m, 28H)

Step iv) 3-(3-(2H-Tetrazol-5-yl)phenethoxy)-N-cyclohexyl-N-(2-(2-(5-hydroxy-3-oxo-3,4-dihydro-2H-benzo[b][1,4]oxazin-8-yl)ethylamino)ethyl)propanamide Trifluoroacetic Acid Salt tert-Butyl 2-(3-(3-(2-allyl-2H-tetrazol-5-yl)phenethoxy)-N-cyclohexylpropanamido)ethyl(2-(5-(tert-butoxycarbonyloxy)-3-oxo-3,4-dihydro-2H-benzo[b][1,4]oxazin-8-yl)ethyl)carbamate [Example 15, Step v)] (170 mg), 1,3-dimethylpyrimidine-2,4,6(1H,3H,5H)-trione (97 mg) and tetrakis(triphenylphosphine)palladium(0) (24 mg, 0.02 mmol) were dissolved in DCM (2 mL) and sealed into a microwave tube. The reaction was heated to 100° C., over a period of 30 min in the microwave reactor. After cooling to rt, TFA (1 mL) was added and the mixture stirred for 30 min. The mixture was concentrate in vacuo do give a crude product. The crude product was purified by preparative HPLC on a Phenomenex Gemini column using a gradient of aqueous 0.1% trifluoroacetic acid in acetonitrile as eluent to afford the titled compound (41.8 mg) as a solid. MS [M+H]+=578.3 (calc=578.3091) (MultiMode+) $^1$H NMR (400 MHz, CD$_3$OD) δ 7.92 (s, 1H), 7.80 (dt, J=1.6 and 7.4 Hz, 1H), 7.47 (t, J=7.5 Hz, 1H), 7.44 (dt, J=1.5 and 7.9 Hz, 1H), 6.70 (d, J=8.5 Hz, 1H), 6.46 (d, J=8.2 Hz, 1H), 4.61 (s, 2H), 3.74 (t, J=6.5 Hz, 2H), 3.72 (t, J=6.0 Hz, 2H), 3.71-3.63 (m, 1H), 3.48 (t, J=5.8 Hz, 2H), 3.14 (t, J=7.1 Hz, 2H), 3.04 (t, J=5.7 Hz, 2H), 2.94 (t, J=6.3 Hz, 2H), 2.87 (t, J=7.0 Hz, 2H), 2.63 (t, J=6.0 Hz, 2H), 1.79-1.71 (m, 2H), 1.68-1.57 (m, 3H), 1.44-1.23 (m, 4H), 1.16-1.03 (m, 1H)

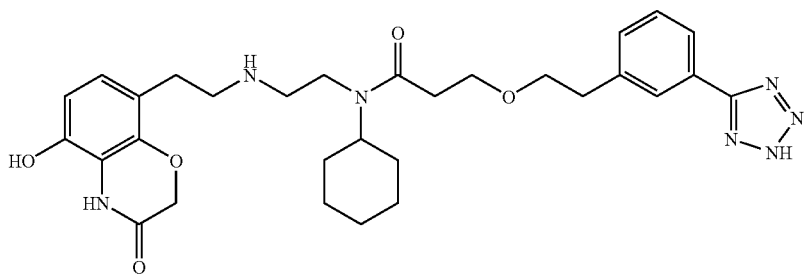

Example 16

N-Cyclohexyl-3-(2-fluoro-3-(1-methyl-1H-pyrazol-4-yl)phenethoxy)-N-(2-(2-(5-hydroxy-3-oxo-3,4-dihydro-2H-benzo[b][1,4]oxazin-8-yl)ethylamino)ethyl)propanamide Trifluoroacetic Acid Salt

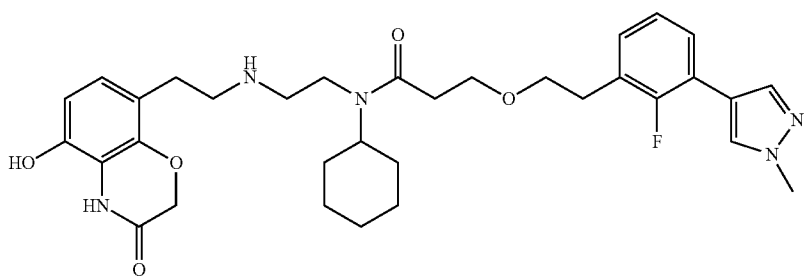

Step i) 1-Bromo-2-fluoro-3-(2-methoxyvinyl)benzene

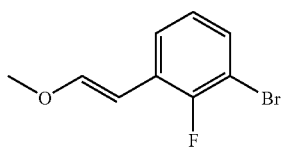

A solution of potassium bis(trimethylsilyl)amide (0.5 M in toluene, 31.5 mL) was added to an ice-bath cooled, stirred slurry of (methoxymethyl)triphenylphosphonium chloride (5.07 g) in tetrahydrofuran (50 mL) keeping the temperature of the reaction mixture below 10° C. The mixture was stirred for 30 min. A solution of 3-bromo-2-fluorobenzaldehyde (2 g) in THF (5+3 mL) was added dropwise and the cold bath was removed. The mixture was stirred at ambient temperature for 1.5 h. The mixture was quenched with saturated ammonium chloride solution and extracted into ethyl acetate (70 mL). The organic phase was washed with brine, dried over magnesium sulfate, filtered and evaporated to afford crude product. Ether (50 mL) was added and the mixture was left overnight in the fridge. The solid was filtered off and the filtrate was concentrated. The crude product was purified by flash silica chromatography, elution gradient 0 to 20% ethyl acetate in isohexane to afford the subtitled compound (1.84 g) as a liquid. (5:3 mixture of isomers). $^1$H NMR (300 MHz, CDCl$_3$) δ (a mixture of isomers) 7.98 (ddd, J=1.5, 7.1 and 8.4 Hz, 1H), 7.36-7.18 (m, 3H), 7.17 (d, J=13.1 Hz, 2H), 7.00-6.88 (m, 2H), 6.28 (d, J=7.1 Hz, 1H), 5.85 (d, J=13.1 Hz, 1H), 5.47 (d, J=7.1 Hz, 1H), 3.81 (d, J=6.5 Hz, 3H), 3.72 (d, J=6.5 Hz, 3H).

Step ii) 2-(3-Bromo-2-fluorophenyl)ethanol

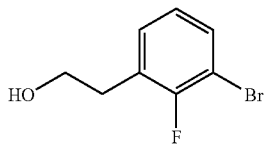

Methanesulfonic acid (0.4 mL) was added to a mixture of 1-bromo-2-fluoro-3-(2-methoxyvinyl)benzene [Example 16, Step i)] (1.8 g), tetrahydrofuran (15 mL) and water (1.5 mL) and sealed into a microwave tube. The reaction was heated to 80° C., over a period of 90 min in the microwave reactor. Sodium bicarbonate (654 mg) was added portionwise and the mixture was stirred for 10 min. Sodium borohydride (295 mg) was added portionwise (gas evolution) and the mixture was stirred for 30 min. The reaction mixture was poured into saturated sodium hydrogen carbonate solution and extracted with DCM (3×30 mL). The organic was dried over magnesium sulfate, filtered and evaporated to afford crude product. The crude product was purified by flash silica chromatography, elution gradient 0 to 30% ethyl acetate in isohexane to afford the subtitled compound (1.26 g) as a liquid. $^1$H NMR (300 MHz, CDCl$_3$) δ 7.47-7.40 (m, 1H), 7.23-7.16 (m, 1H), 6.97 (t, J=7.8 Hz, 1H), 3.88 (q, J=6.2 Hz, 2H), 2.95 (t, J=6.5 Hz, 2H), 1.43 (t, J=5.7 Hz, 1H).

Step iii) tert-Butyl 3-(3-bromo-2-fluorophenethoxy)propanoate

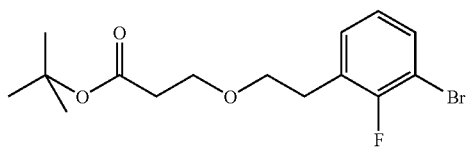

The subtitled compound (1.99 g) was prepared from 2-(3-bromo-2-fluorophenyl)ethanol [Example 16, Step ii)] using a similar method to that described in Example 13, Step iv) and elution gradient 0-10% ethyl acetate in isohexane. ¹H NMR (400 MHz, CDCl₃) δ 7.39 (d, J=16.1 Hz, 1H), 7.21-7.16 (m, 1H), 6.93 (t, J=7.6 Hz, 1H), 3.68 (t, J=6.4 Hz, 2H), 3.66 (t, J=6.8 Hz, 2H), 2.93 (td, J=6.8, 1.0 Hz, 2H), 2.46 (t, J=6.4 Hz, 2H), 1.43 (s, 9H).

Step iv) tert-Butyl 3-(2-fluoro-3-(1-methyl-1H-pyrazol-4-yl)phenethoxy)propanoate

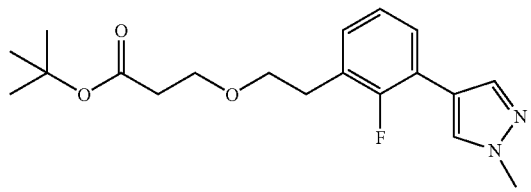

Pd-118 (104 mg) was dissolved in acetonitrile (10 mL) and stirred for 5 min before addition of potassium carbonate (2.364 g), water (10 mL) and 1-methyl-4-(4,4,5,5-tetramethyl-1,3,2-dioxaborolan-2-yl)-1H-pyrazole (1.305 g). The mixture was stirred for a further 5 min then tert-butyl 3-(3-bromo-2-fluorophenethoxy)propanoate [Example 16, Step iii)] (1.98 g) added and the reaction was heated at the heating block (80° C.) for 2 h. The mixture was cooled and extracted into ethyl acetate (150 mL). Organic was separated, dried (MgSO4) solvents evaporated to give a brown oil. The crude product was purified by flash silica chromatography, elution gradient 0 to 60% ethyl acetate in isohexane to afford the subtitled compound (1.480 g) as a gum. MS [M+H-C4H9]+= 293 (MultiMode+) ¹H NMR (300 MHz, CDCl₃) δ 7.83 (s, 1H), 7.75 (d, J=2.5 Hz, 1H), 7.39 (td, J=2.5 and 7.3 Hz, 1H), 7.13-7.01 (m, 2H), 3.96 (s, 3H), 3.74-3.64 (m, 4H), 2.96 (t, J=6.8 Hz, 2H), 2.49 (t, J=6.4 Hz, 2H), 1.44 (s, 9H).

Step v) 3-(2-Fluoro-3-(1-methyl-1H-pyrazol-4-yl)phenethoxy)propanoic acid

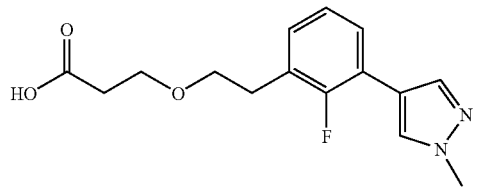

The subtitled compound (2.45 g) was prepared from tert-butyl 3-(2-fluoro-3-(1-methyl-1H-pyrazol-4-yl)phenethoxy)propanoate [Example 16, Step iv)] using a similar method to that described in Example 4, Step iv). ¹H NMR (300 MHz, CDCl₃) δ 8.01 (s, 1H), 7.83 (d, J=1.9 Hz, 1H), 7.38 (td, J=2.1 and 7.3 Hz, 1H), 7.19-7.06 (m, 2H), 4.06 (s, 3H), 3.76 (t, J=6.1 Hz, 2H), 3.74 (t, J=6.5 Hz, 2H), 2.98 (t, J=6.7 Hz, 2H), 2.65 (t, J=6.1 Hz, 2H).

Step vi) N-cyclohexyl-N-(2,2-dimethoxyethyl)-3-(2-fluoro-3-(1-methyl-1H-pyrazol-4-yl)phenethoxy)propanamide

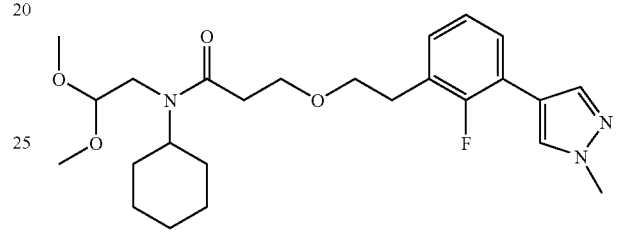

The subtitled compound (1.6 g) was prepared form 3-(2-fluoro-3-(1-methyl-1H-pyrazol-4-yl)phenethoxy)propanoic acid [Example 16, Step v)] and N-(2,2-dimethoxyethyl)cyclohexanamine using a similar method to that described in Example 12, Step iii). MS [M+H-MeOH]+=430 (MultiMode+) ¹H NMR (400 MHz, CD₃OD) δ 7.97 (s, 1H), 7.84 (d, J=2.3 Hz, 1H), 7.46 (td, J=2.0 and 7.6 Hz, 1H), 7.15-7.02 (m, 2H), 4.53 and 4.37 (2×t, J=5.4 Hz, 1H), 4.04-3.94 and 3.70-3.60 (2×m, 1H), 3.92 (s, 3H), 3.76-3.64 (m, 4H), 3.35 and 3.33 (2×s, 6H), 3.36-3.26 (m, 2H), 2.95-2.88 (m, 2H), 2.65 and 2.63 (2×t, J=6.3 Hz, 2H), 1.81-1.00 (m, 10H); a ~1:1 mixture of rotamers is observed.

Step vii) N-Cyclohexyl-3-(2-fluoro-3-(1-methyl-1H-pyrazol-4-yl)phenethoxy)-N-(2-(2-(5-hydroxy-3-oxo-3,4-dihydro-2H-benzo[b][1,4]oxazin-8-yl)ethylamino)ethyl)propanamide Trifluoroacetic Acid Salt

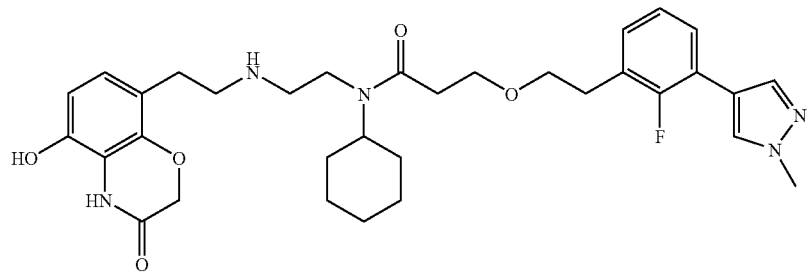

The titled compound (333 mg) was prepared from N-cyclohexyl-N-(2,2-dimethoxyethyl)-3-(2-fluoro-3-(1-methyl-1H-pyrazol-4-yl)phenethoxy)propanamide [Example 16, Step vi)] using a similar method to that described in Example 12, Step iv). MS [M+H]+=608.3 (calc=608.3248) (MultiMode+) ¹H NMR (400 MHz, CD₃OD) δ 7.95 (d, J=1.8 Hz, 1H), 7.82 (s, 1H), 7.46 (td, J=1.8, 7.5 Hz, 1H), 7.15-7.03 (m, 2H), 6.69 (d, J=8.5 Hz, 1H), 6.47 (d, J=8.2 Hz, 1H), 4.60 (s, 2H), 3.91 (s, 3H), 3.76-3.64 (m, 5H), 3.49 (t, J=5.6 Hz, 2H), 3.12 (t, J=7.2 Hz, 2H), 3.03 (t, J=5.9 Hz, 2H), 2.92 (t, J=6.7 Hz, 2H), 2.86 (t, J=7.2 Hz, 2H), 2.63 (t, J=5.8 Hz, 2H), 1.82-1.58 (m, 5H), 1.48-1.24 (m, 4H), 1.17-1.04 (m, 1H)

Example 17

N-Cyclohexyl-3-(3-fluoro-5-(1-methyl-1H-pyrazol-4-yl)phenethoxy)-N-(2-(2-(5-hydroxy-3-oxo-3,4-dihydro-2H-benzo[b][1,4]oxazin-8-yl)ethylamino)ethyl)propanamide Trifluoroacetic Acid Salt

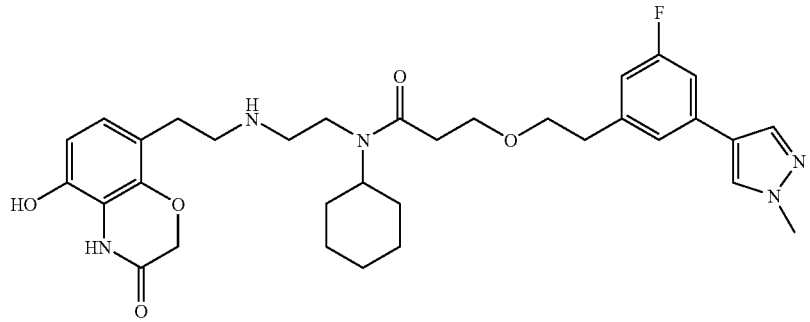

Step i) Methyl 2-(3-bromo-5-fluorophenyl)acetate

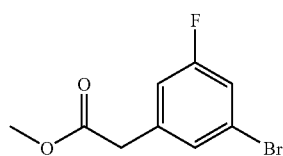

The subtitled compound (1.0 g) was prepared from 2-(3-bromo-5-fluorophenyl)acetic acid using a similar method to that described in Example 13 Step i). ¹H NMR (300 MHz, CDCl₃) δ 7.23 (s, 1H), 7.17 (dt, J=8.2, 2.0 Hz, 1H), 6.97 (dt, J=9.1, 1.9 Hz, 1H), 3.72 (s, 3H), 3.59 (s, 2H)

Step ii) Methyl 2-(3-fluoro-5-(1-methyl-1H-pyrazol-4-yl)phenyl)acetate

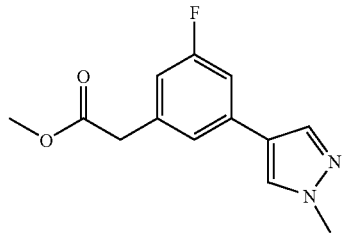

The subtitled compound (1.09 g) was prepared from methyl 2-(3-bromo-5-fluorophenyl)acetate [Example 17, Step i)] using a similar method to that described in Example 13 Step ii). ¹H NMR (300 MHz, CDCl₃) δ 7.73 (s, 1H), 7.61 (s, 1H), 7.15 (s, 1H), 7.06 (dt, J=9.8, 1.9 Hz, 1H), 6.86 (dt, J=9.3, 1.8 Hz, 1H), 3.94 (s, 3H), 3.72 (s, 3H), 3.63 (s, 2H)

Step iii) 2-(3-Fluoro-5-(1-methyl-1H-pyrazol-4-yl)phenyl)ethanol

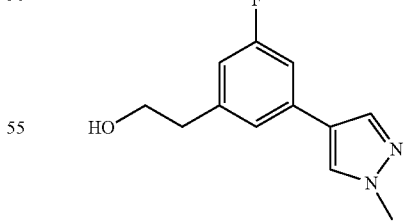

The subtitled compound (0.98 g) was prepared from methyl 2-(3-fluoro-5-(1-methyl-1H-pyrazol-4-yl)phenyl)acetate [Example 17, Step ii)] using a similar method to that described in Example 13 Step iii). ¹H NMR (300 MHz, CDCl₃) δ 7.76 (s, 1H), 7.62 (s, 1H), 7.12 (s, 1H), 7.03 (dd, J=9.8, 1.3 Hz, 1H), 6.82 (d, J=9.4 Hz, 1H), 3.97 (s, 3H), 3.91 (t, J=6.7 Hz, 2H), 2.89 (t, J=6.4 Hz, 2H)

Step iv) tert-Butyl 3-(3-fluoro-5-(1-methyl-1H-pyrazol-4-yl)phenethoxy)propanoate

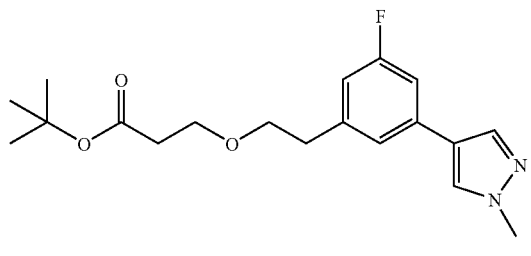

The subtitled compound (1.05 g) was prepared from 2-(3-fluoro-5-(1-methyl-1H-pyrazol-4-yl)phenyl)ethanol [Example 17, Step iii)] using a similar method to that described in Example 13 Step iv). $^1$H NMR (300 MHz, CDCl$_3$) δ 7.76 (s, 1H), 7.62 (s, 1H), 7.12 (s, 1H), 7.03 (dd, J=9.8, 1.3 Hz, 1H), 6.82 (d, J=9.4 Hz, 1H), 3.97 (s, 3H), 3.91 (t, J=6.7 Hz, 2H), 2.89 (t, J=6.4 Hz, 2H)

Step v) 3-(3-Fluoro-5-(1-methyl-1H-pyrazol-4-yl)phenethoxy)propanoic acid

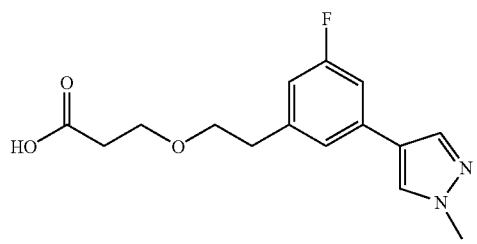

The subtitled compound (1.05 g) was prepared from tert-butyl 3-(3-fluoro-5-(1-methyl-1H-pyrazol-4-yl)phenethoxy)propanoate [Example 17, Step yl)] using a similar method to that described in Example 4, Step iv). MS [M+H]+=293 (MultiMode+) $^1$H NMR (300 MHz, CDCl$_3$) δ 8.06 (s, 1H), 7.70 (s, 1H), 7.20 (s, 1H), 6.99 (dt, J=9.5, 1.9 Hz, 1H), 6.85 (ddd, J=1.5, 2.3 and 9.5 Hz, 1H), 4.06 (s, 3H), 3.76 (t, J=5.7 Hz, 2H), 3.74 (t, J=6.3 Hz, 2H), 2.90 (t, J=6.3 Hz, 2H), 2.65 (t, J=5.8 Hz, 2H)

Step vi) N-Cyclohexyl-N-(2,2-dimethoxyethyl)-3-(3-fluoro-5-(1-methyl-1H-pyrazol-4-yl)phenethoxy)propanamide

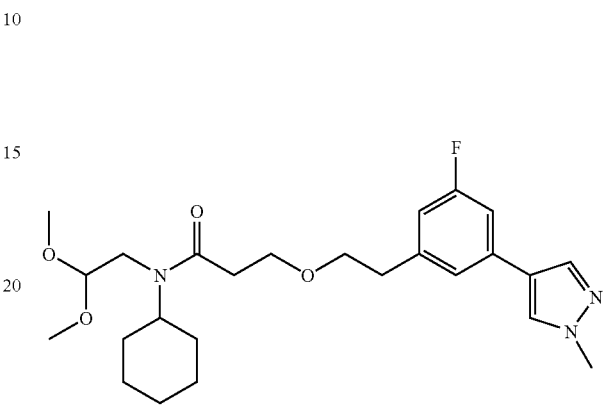

The subtitled compound (3.3 g) was prepared from 3-(3-fluoro-5-(1-methyl-1H-pyrazol-4-yl)phenethoxy)propanoic acid [Example 17, Step v)] and N-(2,2-dimethoxyethyl)cyclohexanamine using a similar method to that described in Example 12, Step iii). MS [M+H-MeOH]+=430 (MultiMode+) $^1$H NMR (400 MHz, CD$_3$OD) δ 7.97 (s, 1H), 7.81 and 7.80 (2×s, 1H), 7.19 (m, 1H), 7.09 (dt, J=10.0, 1.9 Hz, 1H), 6.80 (m, 1H), 4.52 and 4.36 (2×t, J=5.0 Hz, 1H), 4.00 and 3.64 (2×tt, J=3.6 and 11.7 Hz, 1H), 3.902 and 3.898 (2×s, 3H), 3.76-3.64 (m, 4H), 3.34 (s, 3H), 3.33 and 3.25 (2×d, J=5.1 Hz, 2H), 3.32 (s, 3H), 2.85 and 2.84 (2×t, J=6.2 Hz, 2H), 2.65 and 2.63 (2×t, J=6.1 Hz, 2H), 1.79-1.69 (m, 2H), 1.68-1.49 (m, 3H), 1.49-1.19 (m, 4H), 1.16-1.01 (m, 1H); a ~1:1 mixture of rotamers is observed.

Step vii) N-Cyclohexyl-3-(3-fluoro-5-(1-methyl-1H-pyrazol-4-yl)phenethoxy)-N-(2-(2-(5-hydroxy-3-oxo-3,4-dihydro-2H-benzo[b][1,4]oxazin-8-yl)ethylamino)ethyl)propanamide Trifluoroacetic Acid Salt

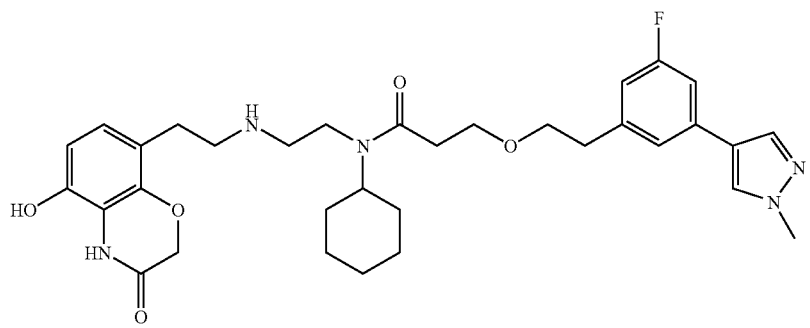

The titled compound (345 mg) was prepared from N-cyclohexyl-N-(2,2-dimethoxyethyl)-3-(3-fluoro-5-(1-methyl-1H-pyrazol-4-yl)phenethoxy)propanamide [Example 17, Step vi)] using a similar method to that described in Example 12, Step iv). MS [M+H]+=608.3 (calc=608.3248) (MultiMode+) $^1$H NMR (400 MHz, CD$_3$OD) δ 7.93 (s, 1H), 7.79 (s, 1H), 7.22 (s, 1H), 7.08 (dt, J=1.8 and 10.2 Hz, 1H), 6.81 (dt, J=1.8 and 9.7 Hz, 1H), 6.69 (d, J=8.2 Hz, 1H), 6.47 (d, J=8.2 Hz, 1H), 4.60 (s, 2H), 3.89 (s, 3H), 3.72 (t, J=6.0 Hz, 2H), 3.71 (t, J=6.4 Hz, 2H), 3.70 (m, 1H), 3.49 (t, J=5.7 Hz, 2H), 3.11 (t, J=7.1 Hz, 2H), 3.02 (t, J=5.7 Hz, 2H), 2.86 (t, J=7.2 Hz, 2H), 2.85 (t, J=6.5 Hz, 2H), 2.63 (t, J=6.1 Hz, 2H), 1.82-1.73 (m, 2H), 1.70-1.58 (m, 3H), 1.46-1.25 (m, 4H), 1.17-1.03 (m, 1H).

Example 18

N-Cyclopentyl-N-(2-(2-(5-hydroxy-3-oxo-3,4-dihydro-2H-benzo[b][1,4]oxazin-8-yl)ethylamino)ethyl)-3-(3-(1-propyl-1H-pyrazol-4-yl)phenethoxy)propanamide Trifluoroacetic Acid Salt

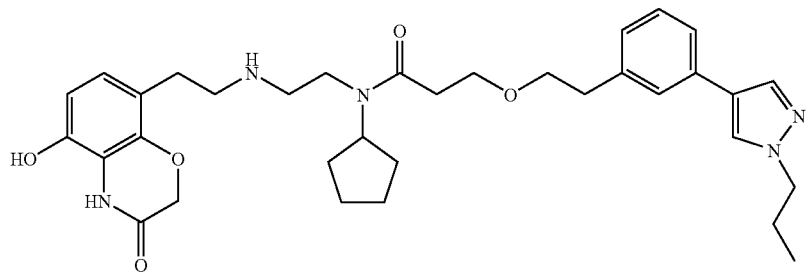

Step i) tert-Butyl 3-(3-(1-propyl-1H-pyrazol-4-yl)phenethoxy)propanoate

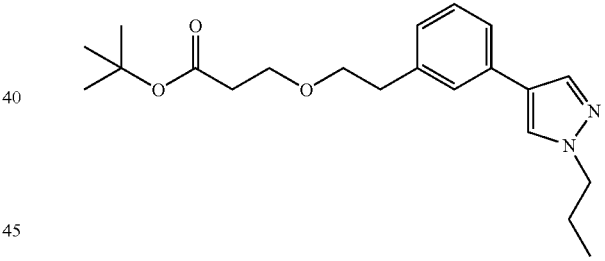

Pd-118 (51.7 mg) was dissolved in acetonitrile (8 mL) and stirred for 5 min before addition of potassium carbonate (1.1 g), water (8 mL) and a solution of 1-propyl-4-(4,4,5,5-tetramethyl-1,3,2-dioxaborolan-2-yl)-1H-pyrazole (750 mg) in MeCN (1 mL). The mixture was stirred for a further 5 min then a solution of tert-butyl 3-(3-bromophenethoxy)propanoate (870 mg, prepared as in Preparation 3, Step i)) was added and the reaction was heated at the heating block (80° C.) for 30 min. The mixture was cooled and extracted into DCM. Organic was separated using a phase separator cartridge, solvents evaporated to give a brown oil. The crude product was purified by flash silica chromatography using elution gradient 0 to 100% ethyl acetate in isohexane to afford the subtitled compound (1 g) as a gum. MS [M+H-C4H9]+= 303 (MultiMode+) $^1$H NMR (400 MHz, CDCl$_3$) δ 7.76 (s, 1H), 7.63 (s, 1H), 7.34-7.30 (m, 2H), 7.26 (t, J=8.0 Hz, 1H), 7.09-7.05 (m, 1H), 4.11 (t, J=7.2 Hz, 2H), 3.70 (t, J=6.5 Hz, 2H), 3.68 (t, J=7.2 Hz, 2H), 2.89 (t, J=7.2 Hz, 2H), 2.49 (t, J=6.4 Hz, 2H), 1.93 (sextet, J=7.2 Hz, 2H), 1.43 (s, 9H), 0.95 (t, J=7.3 Hz, 3H)

Step ii) 3-(3-(1-Propyl-1H-pyrazol-4-yl)phenethoxy)propanoic acid

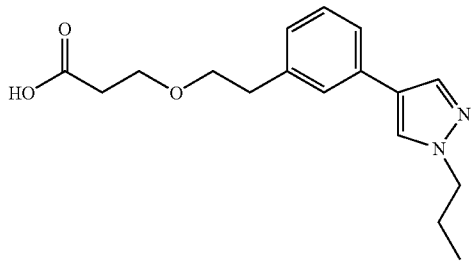

The subtitled compound (1.65 g) was prepared from tert-butyl 3-(3-(1-propyl-1H-pyrazol-4-yl)phenethoxy)propanoate [Example 18, Step i)] using a similar method to that described in Example 4, Step iv). ¹H NMR (300 MHz, CDCl₃) δ 8.21 (s, 1H), 7.76 (s, 1H), 7.46 (s, 1H), 7.34-7.29 (m, 2H), 7.18-7.11 (m, 1H), 4.29 (t, J=7.0 Hz, 2H), 3.80-3.73 (m, 4H), 2.93 (t, J=6.2 Hz, 2H), 2.66 (t, J=5.9 Hz, 2H), 1.97 (sextet, J=7.2 Hz, 2H), 0.98 (t, J=7.4 Hz, 3H)

Step iii) N-Cyclopentyl-N-(2,2-dimethoxyethyl)-3-(3-(1-propyl-1H-pyrazol-4-yl)phenethoxy)propanamide

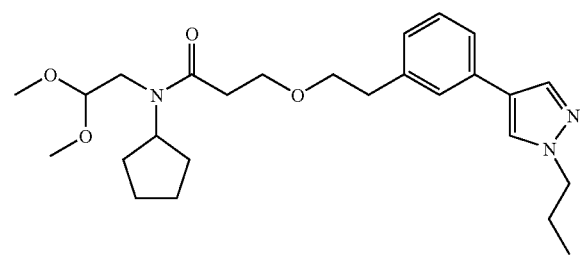

A solution of T3P (0.637 mL, 1.57M) dissolved in THF was added to a stirred solution of 3-(3-(1-propyl-1H-pyrazol-4-yl)phenethoxy)propanoic acid [Example 18, Step ii)] (151 mg), triethylamine (0.906 mL) and N-(2,2-dimethoxyethyl)cyclopentanamine [Preparation 9] (106 mg) in acetonitrile (2 mL) at 22° C. under air. The resulting solution was stirred at 22° C. for 30 min. The reaction mixture was neutralised with saturated sodium hydrogen carbonate and extracted with DCM. The organic was filtered through a phase separator cartridge and evaporated to afford crude product. The crude product was purified by flash silica chromatography using elution gradient 0 to 100% ethyl acetate in isohexane to the subtitled compound (150 mg) as an oil. MS [M+H-MeOH]+= 426 (MultiMode+) ¹H NMR (300 MHz, CD₃OD) δ 8.00 (s, 1H), 7.83 (s, 1H), 7.43 (s, 1H), 7.39 (d, J=7.9 Hz, 1H), 7.26 (t, J=7.6 Hz, 1H), 7.09 (d, J=7.5 Hz, 1H), 4.60 and 4.41 (2×t, J=5.2 Hz, 1H), 4.31-4.18 (m, 1H), 4.14 (t, J=7.0 Hz, 2H), 3.80-3.67 (m, 4H), 3.39 and 3.26 (2×d, J=5.3 Hz, 2H), 3.38 (s, 3H), 3.36 (s, 3H), 2.88 (t, J=6.6 Hz, 2H), 2.69 (t, J=6.2 Hz, 2H), 1.92 (sextet, J=7.2 Hz, 2H), 1.85-1.47 (m, 8H), 0.95 (t, J=7.4 Hz, 3H), a ~1:1 mixture of rotamers is observed.

Step iv) N-Cyclopentyl-N-(2-(2-(5-hydroxy-3-oxo-3,4-dihydro-2H-benzo[b][1,4]oxazin-8-yl)ethylamino)ethyl)-3-(3-(1-propyl-1H-pyrazol-4-yl)phenethoxy)propanamide Trifluoroacetic Acid Salt

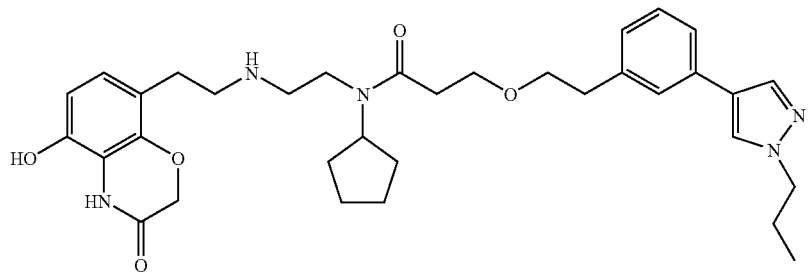

The titled compound (65 mg) was prepared from N-cyclopentyl-N-(2,2-dimethoxyethyl)-3-(3-(1-propyl-1H-pyrazol-4-yl)phenethoxy)propanamide [Example 18, Step iii)] using a similar method to that described in Example 12, Step iv). MS [M+H]+=604.3 (calc=604.3499) (MultiMode+) ¹H NMR (400 MHz, CD₃OD) δ 7.94 (s, 1H), 7.78 (s, 1H), 7.40 (s, 1H), 7.34 (d, J=7.7 Hz, 1H), 7.23 (t, J=7.6 Hz, 1H), 7.05 (d, J=7.7 Hz, 1H), 6.69 (d, J=8.5 Hz, 1H), 6.47 (d, J=8.5 Hz, 1H), 4.59 (s, 2H), 4.28-4.16 (m, 1H), 4.09 (t, J=6.9 Hz, 2H), 3.71 (t, J=6.0 Hz, 2H), 3.70 (t, J=6.6 Hz, 2H), 3.43 (t, J=5.7 Hz, 2H), 3.08 (t, J=7.2 Hz, 2H), 3.01 (t, J=5.8 Hz, 2H), 2.85 (t, J=6.8 Hz, 4H), 2.66 (d, J=5.9 Hz, 2H), 1.87 (sextet, J=7.1 Hz, 2H), 1.88-1.77 (m, 2H), 1.75-1.64 (m, 2H), 1.63-1.51 (m, 2H), 1.48-1.36 (m, 2H), 0.90 (t, J=7.4 Hz, 3H)

Example 19

N-Cyclopentyl-3-(3-(1-(cyclopropylmethyl)-1H-pyrazol-4-yl)phenethoxy)-N-(2-(2-(5-hydroxy-3-oxo-3,4-dihydro-2H-benzo[b][1,4]oxazin-8-yl)ethylamino)ethyl)propanamide Trifluoroacetic Acid Salt

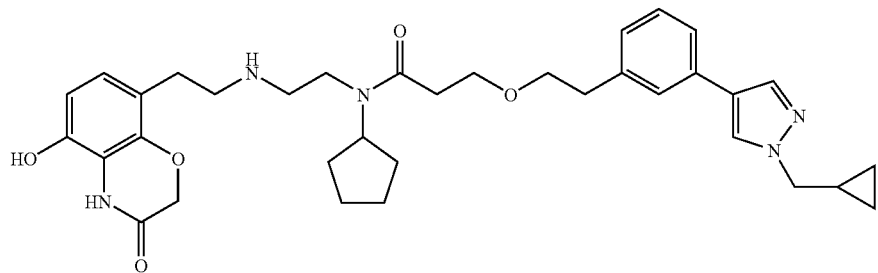

Step i) 1-(Cyclopropylmethyl)-4-(4,4,5,5-tetramethyl-1,3,2-dioxaborolan-2-yl)-1H-pyrazole

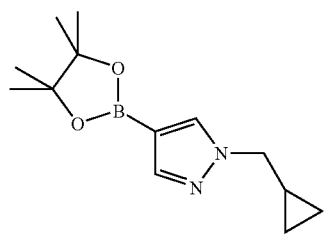

Sodium hydride (0.195 g) was washed with 2 ml of dry THF. DMF (4 mL) was added followed by portionwise addition of 4-(4,4,5,5-tetramethyl-1,3,2-dioxaborolan-2-yl)-1H-pyrazole (0.63 g). The mixture was stirred for 30 min and (bromomethyl)cyclopropane (0.313 mL) added. The mixture was stirred at 60° C. for 50 min and at rt for 16 h. The mixture was quenched with sat. ammonium chloride and ethyl acetate (70 mL). The mixture was washed with water (4×). The organic was dried over magnesium sulfate, filtered and evaporated to afford crude 1-(cyclopropylmethyl)-4-(4,4,5,5-tetramethyl-1,3,2-dioxaborolan-2-yl)-1H-pyrazole (717 mg) that was used in the next step without purification. MS [M+H]+=249 (MultiMode+) $^1$H NMR (400 MHz, CDCl$_3$) δ 7.81 (s, 1H), 7.79 (s, 1H), 3.99 (d, J=6.9 Hz, 2H), 1.32 (s, 12H), 1.31-1.23 (m, 1H), 0.70-0.61 (m, 2H), 0.42-0.33 (m, 2H)

Step ii) tert-Butyl 3-(3-(1-(cyclopropylmethyl)-1H-pyrazol-4-yl)phenethoxy)propanoate

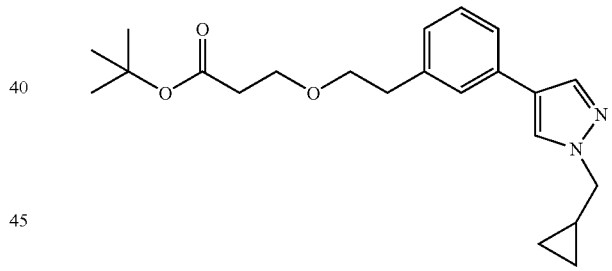

Pd-118 (28.6 mg) was dissolved in acetonitrile (6 mL) and stirred for 5 min before addition of potassium carbonate (606 mg), water (6 mL) and a solution of 1-(cyclopropylmethyl)-4-(4,4,5,5-tetramethyl-1,3,2-dioxaborolan-2-yl)-1H-pyrazole [Example 19, Step i)] (435 mg) in MeCN (1 mL). The mixture was stirred for a further 5 min then a solution of tert-butyl 3-(3-bromophenethoxy)propanoate (481 mg, prepared as in Preparation 3, Step i)) was added and the reaction was heated at the heating block (80° C.) for 60 min. The mixture was cooled and extracted into DCM. Organic was separated using a phase separator cartridge, solvents evaporated to give a brown oil. The crude product was purified by flash silica chromatography, elution gradient 0 to 100% ethyl acetate in isohexane to afford the subtitled compound (398 mg) as a gum. MS [M+H-C4H9]+=315 (MultiMode+) $^1$H NMR (300 MHz, CDCl$_3$) δ 7.77 (s, 1H), 7.75 (s, 1H), 7.36-7.24 (m, 3H), 7.08 (d, J=7.2 Hz, 1H), 4.02 (d, J=6.9 Hz, 2H), 3.71 (t, J=6.0 Hz, 2H), 3.68 (t, J=7.1 Hz, 2H), 2.90 (t, J=7.1 Hz, 2H), 2.49 (t, J=6.5 Hz, 2H), 1.44 (s, 9H), 1.42-1.24 (m, 1H), 0.73-0.64 (m, 2H), 0.46-0.38 (m, 2H)

Step iii) 3-(3-(1-(Cyclopropylmethyl)-1H-pyrazol-4-yl)phenethoxy)propanoic acid

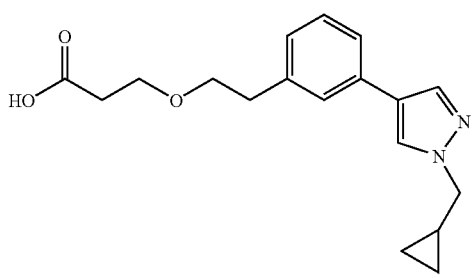

The subtitled compound (0.65 g) was prepared from tert-butyl 3-(3-(1-(cyclopropylmethyl)-1H-pyrazol-4-yl)phenethoxy)propanoate [Example 19, Step ii)] using a similar method to that described in Example 4, Step iv). MS[M+H]+=315 (MultiMode+) ¹H NMR (400 MHz, CDCl₃) δ 8.21 (s, 1H), 7.88 (s, 1H), 7.48 (s, 1H), 7.34-7.30 (m, 2H), 7.16-7.11 (m, 1H), 4.17 (d, J=7.2 Hz, 2H), 3.77 (t, J=5.8 Hz, 2H), 3.76 (t, J=6.3 Hz, 2H), 2.93 (t, J=6.4 Hz, 2H), 2.65 (t, J=5.8 Hz, 2H), 1.42-1.29 (m, 1H), 0.80-0.73 (m, 2H), 0.52-0.45 (m, 2H)

Step iv) N-Cyclopentyl-3-(3-(1-(cyclopropylmethyl)-1H-pyrazol-4-yl)phenethoxy)-N-(2,2-dimethoxy-ethyl)propanamide

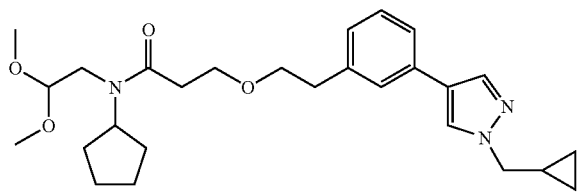

The subtitled compound (246 mg) was prepared from 3-(3-(1-(cyclopropylmethyl)-1H-pyrazol-4-yl)phenethoxy)propanoic acid [Example 19, Step iii)] and N-(2,2-dimethoxyethyl)cyclopentanamine, prepared as in Preparation 9 using a similar method to that described in Example 18, Step iii). MS [M+H-MeOH]+=438 (MultiMode+) ¹H NMR (400 MHz, CD₃OD) δ 8.01 (s, 1H), 7.79 (s, 1H), 7.40 (s, 1H), 7.36 (d, J=7.7 Hz, 1H), 7.23 (t, J=7.8 Hz, 1H), 6.96 (d, J=7.7 Hz, 1H), 4.56 and 4.37 (2×t, J=5.4 Hz, 1H), 4.26-4.15 (m, 1H), 4.00 (d, J=6.9 Hz, 2H), 3.76-3.65 (m, 4H), 3.35 and 3.22 (2×d, J=4.8 Hz, 2H), 3.34 (s, 3H), 3.32 (s, 3H), 2.85 (t, J=6.4 Hz, 2H), 2.65 (t, J=6.3 Hz, 2H), 1.82-1.44 (m, 8H), 1.38-1.23 (m, 1H), 0.65-0.57 (m, 2H), 0.44-0.33 (m, 2H), a ~1:1 mixture of rotamers is observed.

Step v) N-Cyclopentyl-3-(3-(1-(cyclopropylmethyl)-1H-pyrazol-4-yl)phenethoxy)-N-(2-(2-(5-hydroxy-3-oxo-3,4-dihydro-2H-benzo[b][1,4]oxazin-8-yl)ethylamino)ethyl)propanamide Trifluoroacetic Acid Salt

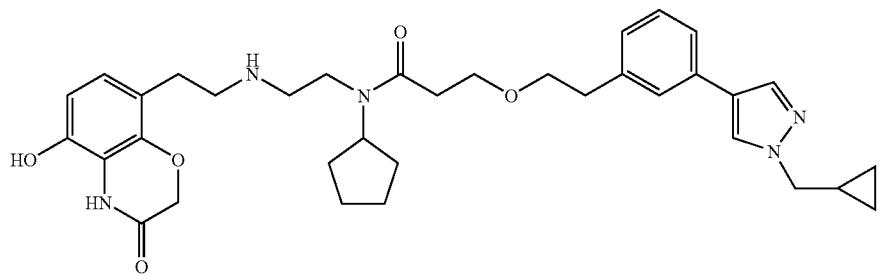

The titled compound (82 mg) was prepared from N-cyclopentyl-3-(3-(1-(cyclopropylmethyl)-1H-pyrazol-4-yl)phenethoxy)-N-(2,2-dimethoxyethyl)propanamide [Example 19, Step iv)] using a similar method to that described in Example 12, Step iv). MS [M+H]+=616.3 (calc=616.3499) (MultiMode+) ¹H NMR (400 MHz, CD₃OD) δ 8.00 (s, 1H), 7.79 (s, 1H), 7.41 (s, 1H), 7.36 (d, J=8.3 Hz, 1H), 7.24 (t, J=7.6 Hz, 1H), 7.06 (d, J=7.6 Hz, 1H), 6.70 (d, J=8.5 Hz, 1H), 6.48 (d, J=8.5 Hz, 1H), 4.61 (s, 2H), 4.22 (quintet, J=8.7 Hz, 1H), 3.99 (d, J=7.2 Hz, 2H), 3.721 (t, J=5.9 Hz, 2H), 3.715 (t, J=6.7 Hz, 2H), 3.45 (t, J=5.3 Hz, 2H), 3.11 (t, J=7.2 Hz, 2H), 3.05 (t, J=5.7 Hz, 2H), 2.77 (t, J=7.1 Hz, 2H), 2.76 (t, J=6.7 Hz, 2H), 2.66 (t, J=6.4 Hz, 2H), 1.89-1.78 (m, 2H), 1.76-1.64 (m, 2H), 1.62-1.50 (m, 2H), 1.49-1.36 (m, 2H), 1.36-1.24 (m, 1H), 0.65-0.56 (m, 2H), 0.45-0.34 (m, 2H)

Example 20

(R)—N-(2-(2-(5-Hydroxy-3-oxo-3,4-dihydro-2H-benzo[b][1,4]oxazin-8-yl)ethylamino)ethyl)-3-(3-(1-isopropyl-1H-pyrazol-4-yl)phenethoxy)-N-(3-methylbutan-2-yl)propanamide Trifluoroacetic Acid Salt

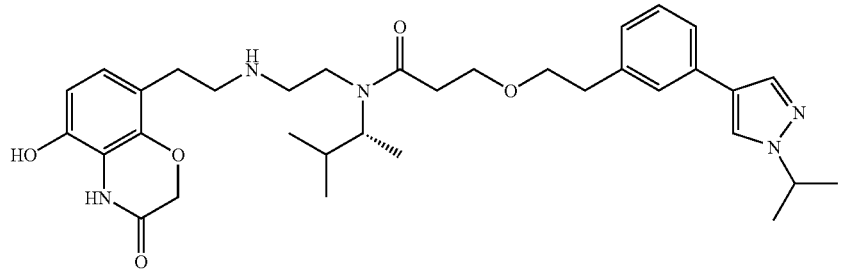

Step i) 1-Isopropyl-4-(4,4,5,5-tetramethyl-1,3,2-dioxaborolan-2-yl)-1H-pyrazole

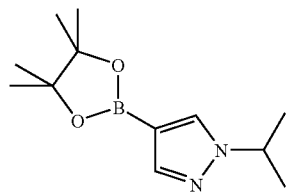

Sodium hydride (0.412 g, 60% in oil) was washed with 2 ml of dry THF. DMF (6 mL) was added followed by portionwise addition of 4-(4,4,5,5-tetramethyl-1,3,2-dioxaborolan-2-yl)-1H-pyrazole (1 g). The mixture was stirred for 30 min. and 2-iodopropane (1.546 mL) was added. The mixture was stirred at 60° C. for 50 min. and at 20° C. for 16 h. The mixture was quenched with sat. ammonium chloride and ethyl acetate (70 ml). The mixture was washed with water (4×). The organic was dried over magnesium sulfate, filtered and evaporated to afford crude product. The crude product was purified by flash silica chromatography, elution gradient 0 to 60% ethyl acetate in isohexane to afford the subtitled compound (840 mg) as a solid. MS [M+H]+=237 (MultiMode+) $^1$H NMR (400 MHz, CDCl$_3$) δ 7.79 (s, 1H), 7.74 (s, 1H), 4.52 (septet, J=6.7 Hz, 1H), 1.50 (d, J=6.7 Hz, 6H), 1.32 (s, 12H)

Step ii) tert-Butyl 3-(3-(1-isopropyl-1H-pyrazol-4-yl)phenethoxy)propanoate

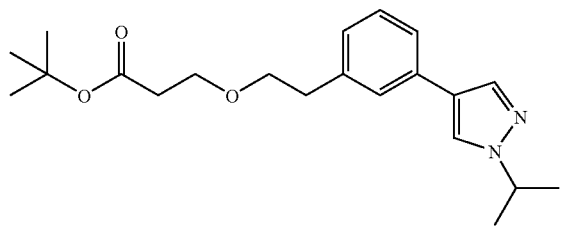

The subtitled compound (1.03 g) was prepared from tert-butyl 3-(3-bromophenethoxy)propanoate [Preparation 3, Step i)] and 1-isopropyl-4-(4,4,5,5-tetramethyl-1,3,2-dioxaborolan-2-yl)-1H-pyrazole [Example 20, Step i)] using a similar method to that described in Example 18, Step i). MS [M+H-C4H9]+=303 (MultiMode+) $^1$H NMR (400 MHz, CDCl$_3$) δ 7.76 (s, 1H), 7.67 (s, 1H), 7.36-7.23 (m, 3H), 7.07 (d, J=7.4 Hz, 1H), 4.53 (septet, J=6.7 Hz, 1H), 3.70 (t, J=6.5 Hz, 2H), 3.68 (t, J=7.3 Hz, 2H), 2.89 (t, J=7.1 Hz, 2H), 2.49 (t, J=6.5 Hz, 2H), 1.55 (d, J=6.7 Hz, 6H), 1.43 (s, 9H)

Step iii) 3-(3-(1-Isopropyl-1H-pyrazol-4-yl)phenethoxy)propanoic acid

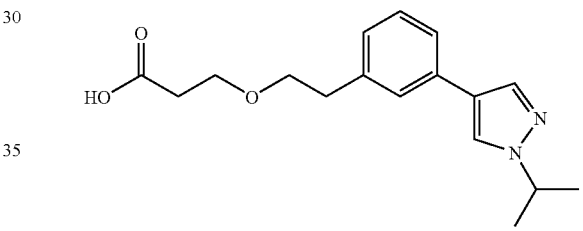

The subtitled compound (1.84 g) was prepared from tert-butyl 3-(3-(1-isopropyl-1H-pyrazol-4-yl)phenethoxy)propanoate [Example 20, Step ii)] using a similar method to that described in Example 4, Step iv). MS [M+H]+=303 (MultiMode+) $^1$H NMR (400 MHz, CDCl$_3$) δ 8.30 (s, 1H), 7.85 (s, 1H), 7.47 (s, 1H), 7.35-7.29 (m, 1H), 7.18-7.13 (m, 2H), 4.81 (septet, J=6.7 Hz, 1H), 3.775 (t, J=5.8 Hz, 2H), 3.767 (t, J=6.3 Hz, 2H), 2.93 (t, J=6.3 Hz, 2H), 2.66 (t, J=5.8 Hz, 2H), 1.64 (d, J=6.7 Hz, 6H)

Step iv) (R)—N-(2,2-Dimethoxyethyl)-3-(3-(1-isopropyl-1H-pyrazol-4-yl)phenethoxy)-N-(3-methylbutan-2-yl)propanamide

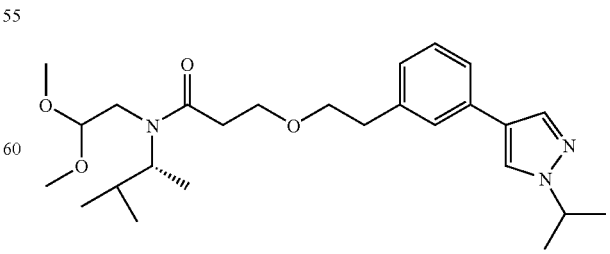

The subtitled compound (105 mg) was prepared from 3-(3-(1-isopropyl-1H-pyrazol-4-yl)phenethoxy)propanoic acid

[Example 20, Step iii)] and (R)—N-(2,2-dimethoxyethyl)-3-methylbutan-2-amine, prepared as in Preparation 4 using a similar method to that described in Example 18, Step iii). MS [M+H-MeOH]+=428 (MultiMode+) $^1$H NMR (400 MHz, CD$_3$OD) δ 8.01 and 8.00 (2×s, 1H), 7.78 (s, 1H), 7.42-7.33 (m, 2H), 7.23 and 7.22 (2×t, J=7.8 Hz, 1H), 7.05 (d, J=7.6 Hz, 1H), 4.59 and 4.43 (2×t, J=5.1 Hz, 1H), 4.53 (septet, J=7.0 Hz, 1H), 3.76-3.63 (m, 5H), 3.37-3.27 (m, 8H), 2.85 and 2.84 (2×t, J=6.8 Hz, 2H), 2.75-2.49 (m, 2H), 1.97-1.85 and 1.78-1.66 (2×m, 1H), 1.51 (d, J=6.9 Hz, 6H), 1.15 and 1.14 (2×d, J=6.9 Hz, 3H), 0.90 and 0.87 (2×d, J=6.8 Hz, 3H), 0.79 and 0.74 (2×d, J=6.3 Hz, 3H); a ~1:1 mixture of rotamers is observed.

Step v) (R)—N-(2-(2-(5-Hydroxy-3-oxo-3,4-dihydro-2H-benzo[b][1,4]oxazin-8-yl)ethylamino)ethyl)-3-(3-(1-isopropyl-1H-pyrazol-4-yl)phenethoxy)-N-(3-methylbutan-2-yl)propanamide Trifluoroacetic Acid Salt p-Toluenesulfonic acid monohydrate (69.5 mg) was added in one portion to (R)—N-(2,2-dimethoxyethyl)-3-(3-(1-isopropyl-1H-pyrazol-4-yl)phenethoxy)-N-(3-methylbutan-2-yl)propanamide [Example 20, Step iv)] (105 mg) in tetrahydrofuran (2 mL). The resulting solution was stirred at 20° C. for 30 min. This solution was added to a stirred mixture of 8-(2-aminoethyl)-5-hydroxy-2H-benzo[b][1,4]oxazin-3(4H)-one hydrochloride (64.3 mg), sodium bicarbonate (57.6 mg), water (0.2 mL) and NMP (2 mL). The mixture was stirred for 10 min and sodium triacetoxyborohydride (121 mg) and acetic acid (0.01 mL) were added. The mixture was stirred for 2 h. The reaction mixture was neutralised with saturated sodium hydrogen carbonate (8 mL) and extracted into ethyl acetate/MeOH (10%, 3×5 mL). The organic was washed with a 1:1 mixture of water and saturated brine (3 mL). The organic was dried over magnesium sulfate, filtered and evaporated to afford crude product. The crude product was purified by flash silica chromatography, elution gradient 0 to 15% methanol in dichloromethane and repurified by preparative HPLC on a Phenomenex Gemini column using aqueous 0.1% trifluoroacetic acid in methanol as eluent to afford the titled compound (40.4 mg) as a white solid. MS [M+H]+=606.3 (calc=606.3655) (MultiMode+) $^1$H NMR (400 MHz, CD$_3$OD) δ 7.98 (s, 1H), 7.78 (s, 1H), 7.40 (s, 1H), 7.35 (d, J=8.1 Hz, 1H), 7.23 (t, J=7.6 Hz, 1H), 7.05 (d, J=7.8 Hz, 1H), 6.70 (d, J=8.5 Hz, 1H), 6.48 (d, J=8.5 Hz, 1H), 4.603 and 4.601 (2×s, 2H), 4.52 (septet, J=6.7 Hz, 1H), 3.71 (t, J=6.1 Hz, 2H), 3.70 (t, J=6.7 Hz, 2H), 3.61-3.52 (m, 2H), 3.36-3.26 (m, 1H), 3.17-2.98 (m, 4H), 2.86 (q, J=6.8 Hz, 4H), 2.74-2.65

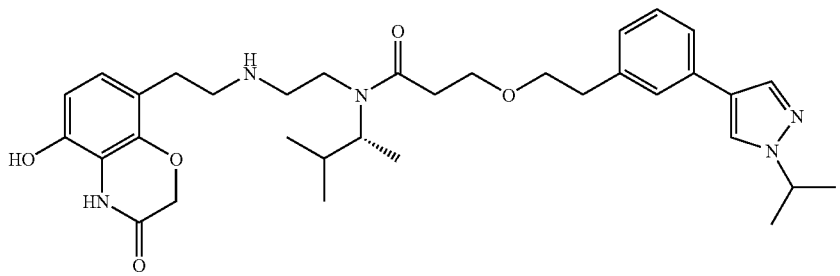

(m, 1H), 2.59-2.50 (m, 1H), 1.76-1.62 (m, 1H), 1.50 (d, J=6.7 Hz, 6H), 1.15 (d, J=6.7 Hz, 3H), 0.94 (d, J=6.4 Hz, 3H), 0.80 (d, J=6.7 Hz, 3H)

Example 21

(R)—N-(2-(2-(5-Hydroxy-3-oxo-3,4-dihydro-2H-benzo[b][1,4]oxazin-8-yl)ethylamino)ethyl)-3-(3-(1-isopropyl-1H-pyrazol-4-yl)phenethoxy)-N-(pentan-2-yl)propanamide Trifluoroacetic Acid Salt

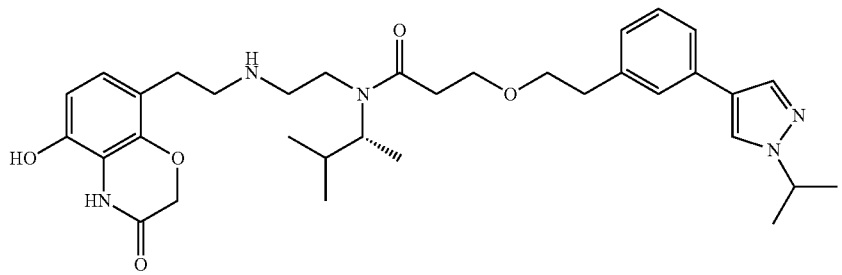

Step i) (R)—N-(2,2-Dimethoxyethyl)-3-(3-(1-isopropyl-1H-pyrazol-4-yl)phenethoxy)-N-(pentan-2-yl)propanamide

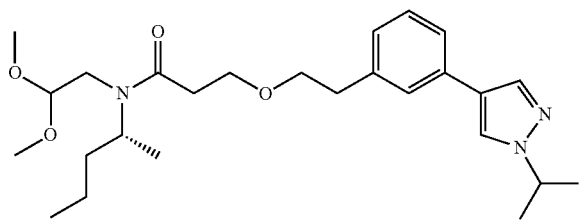

The subtitled compound (100 mg) was prepared from 3-(3-(1-isopropyl-1H-pyrazol-4-yl)phenethoxy)propanoic acid [Example 20 Step iii)] and ((R)—N-(2,2-dimethoxyethyl) pentan-2-amine [Preparation 10] using a similar method to that described in Example 18, Step iii). MS [M+H-MeOH]+= 428 (MultiMode+) ¹H NMR (400 MHz, CD₃OD) δ 8.01 and 8.00 (2×s, 1H), 7.79 (s, 1H), 7.42-7.34 (m, 2H), 7.23 (t, J=7.7 Hz, 1H), 7.05 (d, J=7.7 Hz, 1H), 4.56 and 4.40 (2×t, J=5.3 Hz, 1H), 4.53 (septet, J=6.7 Hz, 1H), 4.26-4.16 and 3.96-3.86 (2×m, 1H), 3.75-3.64 (m, 4H), 3.34 (s, 3H), 3.32 (s, 3H), 3.25-3.10 (m, 2H), 2.84 (t, J=6.5 Hz, 2H), 2.72-2.50 (m, 2H), 1.60-1.14 (m, 4H), 1.51 (d, J=6.9 Hz, 6H), 1.10 and 1.09 (2×d, J=6.7 Hz, 3H), 0.86 (t, J=7.3 Hz, 3H); a ~1:1 mixture of rotamers is observed.

Step ii) (R)—N-(2-(2-(5-Hydroxy-3-oxo-3,4-dihydro-2H-benzo[b][1,4]oxazin-8-yl)ethylamino)ethyl)-3-(3-(1-isopropyl-1H-pyrazol-4-yl)phenethoxy)-N-(pentan-2-yl)propanamide Trifluoroacetic Acid Salt

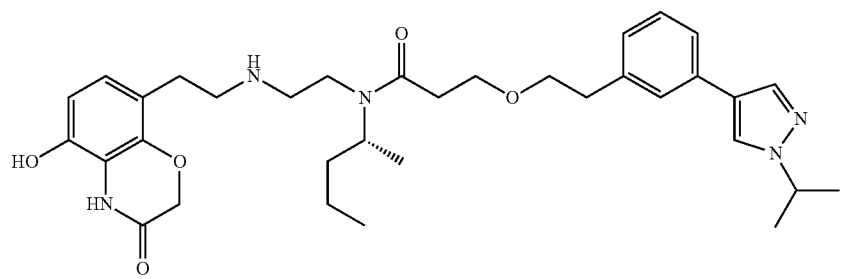

The titled compound (58 mg) was prepared from (R)—N-(2,2-dimethoxyethyl)-3-(3-(1-isopropyl-1H-pyrazol-4-yl)phenethoxy)-N-(pentan-2-yl)propanamide [Example 21, Step i)] using a similar method to that described in Example 20, Step v). MS [M+H]+=606.3 (calc=606.3655) (MultiMode+) ¹H NMR (400 MHz, CD₃OD) δ 7.99 (s, 1H), 7.78 (s, 1H), 7.41 (s, 1H), 7.35 (d, J=7.6 Hz, 1H), 7.23 (t, J=7.5 Hz, 1H), 7.05 (d, J=7.6 Hz, 1H), 6.70 (d, J=8.5 Hz, 1H), 6.48 (d, J=8.5 Hz, 1H), 4.60 (s, 2H), 4.52 (septet, J=6.7 Hz, 1H), 4.01-3.91 (m, 1H), 3.71 (t, J=6.0 Hz, 2H), 3.70 (t, J=6.6 Hz, 2H), 3.54-3.44 (m, 1H), 3.41-3.31 (m, 1H), 3.17-2.99 (m, 4H), 2.87 (t, J=6.8 Hz, 2H), 2.85 (t, J=6.6 Hz, 2H), 2.71-2.52 (m, 2H), 1.50 (d, J=6.7 Hz, 6H), 1.47-1.38 (m, 2H), 1.33-1.06 (m, 2H), 1.11 (d, J=6.7 Hz, 3H), 0.89 (t, J=7.3 Hz, 3H)

Example 22

N-Cyclopentyl-N-(2-(2-(5-hydroxy-3-oxo-3,4-dihydro-2H-benzo[b][1,4]oxazin-8-yl)ethylamino)ethyl)-3-(3-(1-isopropyl-1H-pyrazol-4-yl)phenethoxy)propanamide Trifluoroacetic Acid Salt

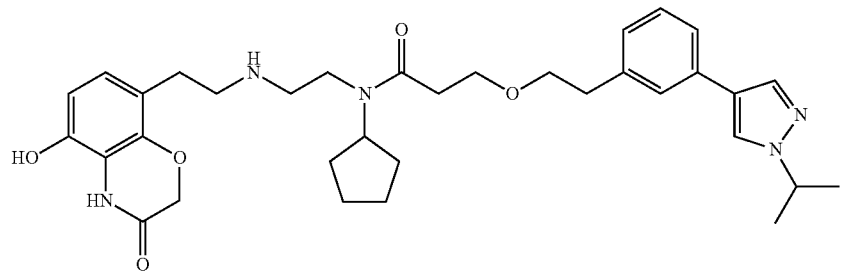

Step i) N-Cyclopentyl-N-(2,2-dimethoxyethyl)-3-(3-(1-isopropyl-1H-pyrazol-4-yl)phenethoxy)propanamide

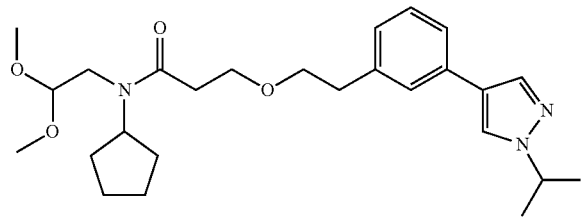

The subtitled compound (140 mg) was prepared from 3-(3-(1-isopropyl-1H-pyrazol-4-yl)phenethoxy)propanoic acid [Example 20 Step iii)] and N-(2,2-dimethoxyethyl)cyclopentanamine [Preparation 9] using a similar method to that described in Example 18, Step iii). MS [M+H-MeOH]+=426 (MultiMode+) ¹H NMR (400 MHz, CD₃OD) δ 8.01 and 8.00 (2×s, 1H), 7.79 (s, 1H), 7.40 (s, 1H), 7.36 (d, J=7.9 Hz, 1H), 7.23 (t, J=7.6 Hz, 1H), 7.05 (d, J=7.6 Hz, 1H), 4.56 and 4.37 (2×t, J=5.1 Hz, 1H), 4.53 (septet, J=6.8 Hz, 1H), 4.26-4.16 (m, 1H), 3.76-3.64 (m, 4H), 3.35 and 3.22 (2×d, J=5.1 Hz, 2H), 3.34 (s, 3H), 3.32 (s, 3H), 2.84 (t, J=6.7 Hz, 2H), 2.65 (t, J=6.2 Hz, 2H), 1.82-1.45 (m, 8H), 1.51 (d, J=6.8 Hz, 6H); a ~2:1 mixture of rotamers is observed.

Step ii) N-Cyclopentyl-N-(2-(2-(5-hydroxy-3-oxo-3,4-dihydro-2H-benzo[b][1,4]oxazin-8-yl)ethylamino)ethyl)-3-(3-(1-isopropyl-1H-pyrazol-4-yl)phenethoxy)propanamide Trifluoroacetic Acid Salt

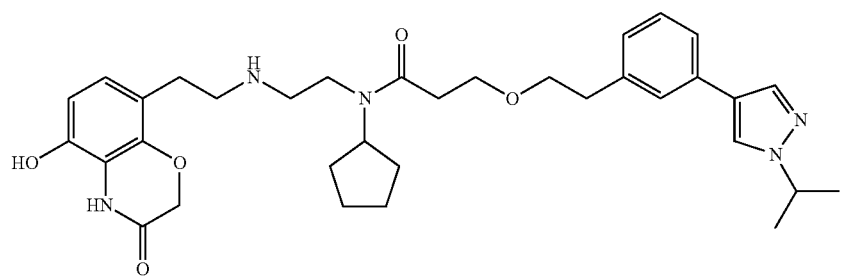

The titled compound (31 mg) was prepared from N-cyclopentyl-N-(2,2-dimethoxyethyl)-3-(3-(1-isopropyl-1H-pyrazol-4-yl)phenethoxy)propanamide [Example 22, Step i)] using a similar method to that described in Example 20, Step v). MS [M+H]+=604.3 (calc=604.3499) (MultiMode+) ¹H NMR (400 MHz, CD₃OD) δ 7.99 (s, 1H), 7.78 (s, 1H), 7.40 (s, 1H), 7.35 (d, J=8.0 Hz, 1H), 7.23 (t, J=7.6 Hz, 1H), 7.05 (d, J=7.5 Hz, 1H), 6.69 (d, J=8.5 Hz, 1H), 6.47 (d, J=8.5 Hz, 1H), 4.60 (s, 2H), 4.52 (septet, J=6.7 Hz, 1H), 4.27-4.16 (m, 1H), 3.71 (t, J=6.1 Hz, 2H), 3.71 (t, J=6.6 Hz, 2H), 3.48-3.42 (m, 2H), 3.11 (t, J=7.2 Hz, 2H), 3.05 (t, J=5.6 Hz, 2H), 2.86 (t, J=6.5 Hz, 2H), 2.85 (t, J=6.5 Hz, 2H), 2.65 (t, J=6.2 Hz, 2H), 1.89-1.34 (m, 8H), 1.50 (d, J=6.9 Hz, 6H)

Example 23

(R)-3-(3-(1-Ethyl-1H-pyrazol-4-yl)phenethoxy)-N-(2-(2-(5-hydroxy-3-oxo-3,4-dihydro-2H-benzo[b][1,4]oxazin-8-yl)ethylamino)ethyl)-N-(3-methylbutan-2-yl)propanamide Trifluoroacetic Acid Salt

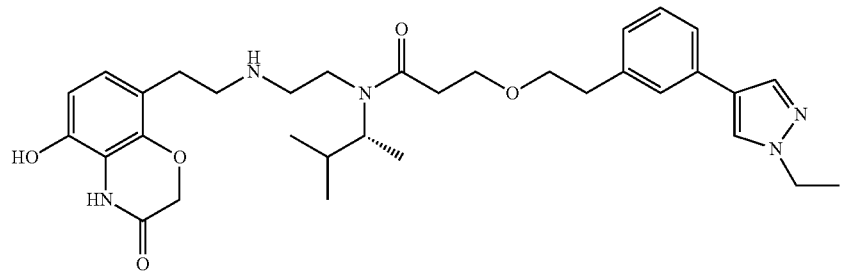

113

Step i) tert-Butyl 3-(3-(1-ethyl-1H-pyrazol-4-yl)phenethoxy)propanoate

114

Step iii) (R)—N-(2,2-Dimethoxyethyl)-3-(3-(1-ethyl-1H-pyrazol-4-yl)phenethoxy)-N-(3-methylbutan-2-yl)propanamide

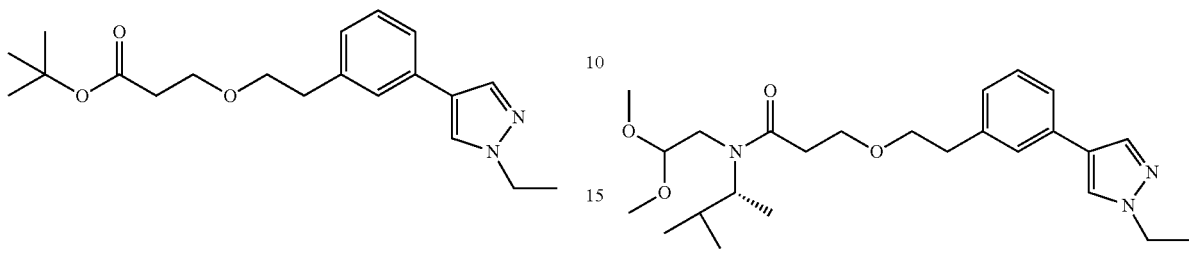

The subtitled compound (0.64 g) was prepared from tert-butyl 3-(3-bromophenethoxy)propanoate [Preparation 3, Step i)] and 1-ethyl-4-(4,4,5,5-tetramethyl-1,3,2-dioxaborolan-2-yl)-1H-pyrazole using a similar method to that described in Example 18, Step i). MS[M+H-C4H8]+=289 (MultiMode+) $^1$H NMR (300 MHz, CDCl$_3$) δ 7.76 (s, 1H), 7.65 (s, 1H), 7.35-7.23 (m, 3H), 7.07 (d, J=7.5 Hz, 1H), 4.21 (q, J=7.2 Hz, 2H), 3.70 (t, J=6.4 Hz, 2H), 3.68 (t, J=7.3 Hz, 2H), 2.89 (t, J=7.1 Hz, 2H), 2.49 (t, J=6.5 Hz, 2H), 1.53 (t, J=7.3 Hz, 3H), 1.43 (s, 9H)

Step ii) 3-(3-(1-Ethyl-1H-pyrazol-4-yl)phenethoxy)propanoic acid

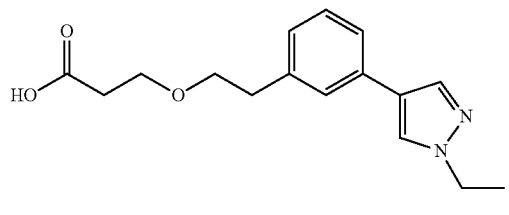

The subtitled compound (1.12 g) was prepared from tert-butyl 3-(3-(1-ethyl-1H-pyrazol-4-yl)phenethoxy)propanoate [Example 23, Step i)] using a similar method to that described in Example 4, Step iv). MS [M+H]+=289 (MultiMode+) $^1$H NMR (300 MHz, CDCl$_3$) δ 8.21 (s, 1H), 7.79 (s, 1H), 7.45 (s, 1H), 7.34-7.28 (m, 2H), 7.18-7.11 (m, 1H), 4.39 (q, J=7.3 Hz, 2H), 3.77 (t, J=5.8 Hz, 2H), 3.76 (t, J=6.3 Hz, 2H), 2.93 (t, J=6.3 Hz, 2H), 2.66 (t, J=5.9 Hz, 2H), 1.60 (t, J=7.4 Hz, 3H)

The subtitled compound (133 mg) was prepared from 3-(3-(1-ethyl-1H-pyrazol-4-yl)phenethoxy)propanoic acid [Example 23, Step ii)] and N-(2,2-dimethoxyethyl)cyclopentanamine [Preparation 4] using a similar method to that described in Example 18, Step iii) extending the reaction time to 2 h. MS [M+H-MeOH]+=414 (MultiMode+) $^1$H NMR (400 MHz, CD30D) δ 7.97 and 7.96 (2×s, 1H), 7.78 (s, 1H), 7.41-7.33 (m, 2H), 7.23 and 7.22 (2×t, J=7.7 Hz, 1H), 7.05 (d, J=7.9 Hz, 1H), 4.59 and 4.43 (2×t, J=5.3 Hz, 1H), 4.19 (q, J=7.3 Hz, 2H), 3.76-3.64 (m, 5H), 3.37-3.35 (m, 2H), 3.34 and 3.34 and 3.33 and 3.31 (4×s, 6H), 2.85 and 2.84 (2×t, J=6.8 Hz, 2H), 2.75-2.61 (m, 2H), 1.98-1.85 and 1.79-1.67 (2×m, 1H), 1.47 (t, J=7.4 Hz, 3H), 1.16 and 1.14 (2×d, J=6.1 Hz, 3H), 0.90 and 0.88 (2×d, J=6.6 Hz, 3H), 0.79 and 0.75 (2×d, J=6.7 Hz, 3H); a ~1:1 mixture of rotamers is observed.

Step iv) (R)-3-(3-(1-Ethyl-1H-pyrazol-4-yl)phenethoxy)-N-(2-(2-(5-hydroxy-3-oxo-3,4-dihydro-2H-benzo[b][1,4]oxazin-8-yl)ethylamino)ethyl)-N-(3-methylbutan-2-yl)propanamide Trifluoroacetic Acid Salt

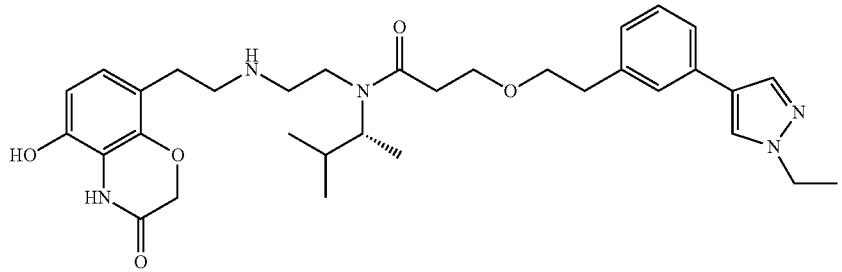

The titled compound (31 mg) was prepared from (R)—N-(2,2-dimethoxyethyl)-3-(3-(1-ethyl-1H-pyrazol-4-yl)phenethoxy)-N-(3-methylbutan-2-yl)propanamide [Example 23, Step iii)] using a similar method to that described in Example 20, Step v). MS[M+H]+=592.3 (calc=592.3499) (MultiMode+) $^1$H NMR (400 MHz, CD$_3$OD) δ 7.94 (s, 1H), 7.78 (s, 1H), 7.40 (s, 1H), 7.34 (d, J=7.9 Hz, 1H), 7.23 (t, J=7.7 Hz, 1H), 7.05 (d, J=8.0 Hz, 1H), 6.70 (d, J=8.5 Hz, 1H), 6.48 (d, J=8.5 Hz, 1H), 4.60 (s, 2H), 4.18 (q, J=7.3 Hz, 2H), 3.73-3.68 (m, 4H), 3.62-3.51 (m, 2H), 3.35-3.25 (m, 1H), 3.18-2.96 (m, 4H), 2.89-2.82 (m, 4H), 2.74-2.65 (m, 1H), 2.59-2.50 (m, 1H), 1.76-1.61 (m, 1H), 1.46 (t, J=7.3 Hz, 3H), 1.15 (d, J=6.7 Hz, 3H), 0.94 (d, J=6.7 Hz, 3H), 0.80 (d, J=6.4 Hz, 3H)

Example 24

N-Cyclopentyl-3-(3-(1-ethyl-1H-pyrazol-4-yl)phenethoxy)-N-(2-(2-(5-hydroxy-3-oxo-3,4-dihydro-2H-benzo[b][1,4]oxazin-8-yl)ethylamino)ethyl)propanamide Trifluoroacetic Acid Salt

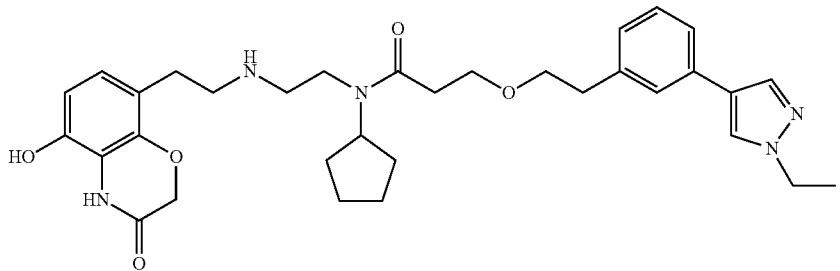

Step i) N-Cyclopentyl-N-(2,2-dimethoxyethyl)-3-(3-(1-ethyl-1H-pyrazol-4-yl)phenethoxy)propanamide The subtitled compound (138 mg) was prepared from 3-(3-(1-ethyl-1H-pyrazol-4-yl)phenethoxy)propanoic acid [Example 23 Step ii)] and N-(2,2-dimethoxyethyl)cyclopentanamine [Preparation 9] using a similar method to that described in Example 18, Step iii), extending the reaction time to 1 h. MS [M+H-MeOH]+=412 (MultiMode+) $^1$H NMR (400 MHz, CD$_3$OD) δ 7.97 (s, 1H), 7.79 (s, 1H), 7.40 (s, 1H), 7.35 (d, J=7.5 Hz, 1H), 7.23 (t, J=7.5 Hz, 1H), 7.05 (d, J=7.7 Hz, 1H), 4.56 and 4.37 (2×t, J=5.1 Hz, 1H), 4.26-4.16 (m, 1H), 4.19 (q, J=7.4 Hz, 2H), 3.75-3.64 (m, 4H), 3.35 and 3.22 (2×d, J=4.9 Hz, 2H), 3.34 (s, 3H), 3.32 (s, 3H), 2.84 (t, J=6.8 Hz, 2H), 2.65 (t, J=6.3 Hz, 2H), 1.82-1.44 (m, 8H), 1.47 (t, J=7.3 Hz, 3H); a ~1:1 mixture of rotamers is observed.

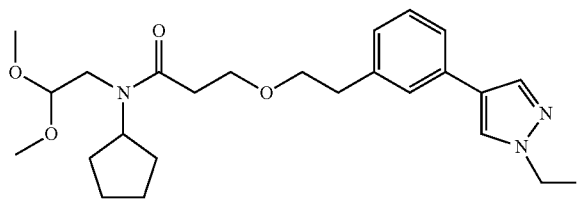

Step ii) N-Cyclopentyl-3-(3-(1-ethyl-1H-pyrazol-4-yl)phenethoxy)-N-(2-(2-(5-hydroxy-3-oxo-3,4-dihydro-2H-benzo[b][1,4]oxazin-8-yl)ethylamino)ethyl)propanamide Trifluoroacetic Acid Salt

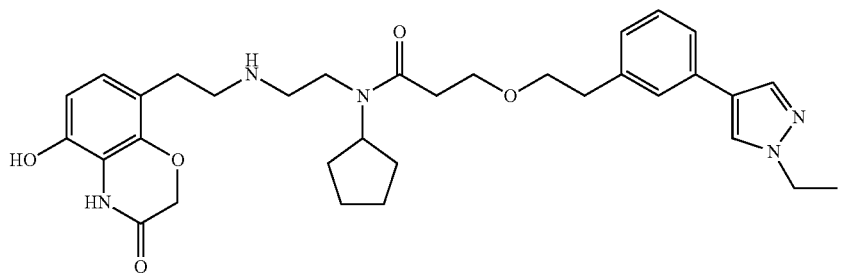

The titled compound (53 mg) was prepared from N-cyclopentyl-N-(2,2-dimethoxyethyl)-3-(3-(1-ethyl-1H-pyrazol-4-yl)phenethoxy)propanamide [Example 24, Step i)] using a similar method to that described in Example 20, Step v). MS [M+H]+=590.3 (calc=590.3342) (MultiMode+) ¹H NMR (400 MHz, CD₃OD) δ 7.95 (s, 1H), 7.78 (s, 1H), 7.40 (s, 1H), 7.34 (d, J=7.7 Hz, 1H), 7.23 (t, J=7.6 Hz, 1H), 7.05 (d, J=7.6 Hz, 1H), 6.69 (d, J=8.3 Hz, 1H), 6.47 (d, J=8.3 Hz, 1H), 4.60 (s, 2H), 4.27-4.14 (m, 1H), 4.18 (q, J=7.3 Hz, 2H), 3.71 (t, J=5.9 Hz, 2H), 3.70 (t, J=6.6 Hz, 2H), 3.45 (t, J=5.5 Hz, 2H), 3.11 (t, J=7.0 Hz, 2H), 3.05 (t, J=5.4 Hz, 2H), 2.90-2.81 (m, 4H), 2.65 (t, J=6.4 Hz, 2H), 1.89-1.77 (m, 2H), 1.75-1.63 (m, 2H), 1.63-1.51 (m, 2H), 1.46 (t, J=7.4 Hz, 3H), 1.48-1.36 (m, 2H)

Example 25

(R)—N-(3,3-Dimethylbutan-2-yl)-3-(3-(1-ethyl-1H-pyrazol-4-yl)phenethoxy)-N-(2-(2-(5-hydroxy-3-oxo-3,4-dihydro-2H-benzo[b][1,4]oxazin-8-yl)ethylamino)ethyl)propanamide Trifluoroacetic Acid Salt To a solution of 3-(3-(1-ethyl-1H-pyrazol-4-yl)phenethoxy)propanoic acid [Example 23, Step ii)] (115 mg) and DIPEA (0.349 mL) in DMF (3 mL) was added HATU (183 mg) and the mixture was stirred at ambient temperature for 10 min. To this solution was added (R)- N-(2,2-dimethoxyethyl)-3,3-dimethylbutan-2-amine (83 mg, Preparation 8) and the reaction mixture was stirred at ambient temperature for 4 h. HATU (144 mg) and (R)—N-(2,2-dimethoxyethyl)-3,3-dimethylbutan-2-amine (90 mg) were added and the mixture was stirred for 16 h. The reaction mixture was diluted with ethyl acetate (100 mL). The organics were washed well with water, then brine and dried over magnesium sulfate, filtered and evaporated. The crude product was purified by flash silica chromatography, elution gradient 25-30% ethyl acetate in isohexane to afford the titled compound (130 mg) as an oil. ¹H NMR (400 MHz, CD₃OD) δ 7.97 and 7.96 (2×s, 1H), 7.78 (s, 1H), 7.42-7.37 (m, 1H), 7.37-7.33 (m, 1H), 7.23 and 7.22 (2×t, J=7.5 Hz, 1H), 7.05 (d, J=7.8 Hz, 1H), 4.65 and 4.45

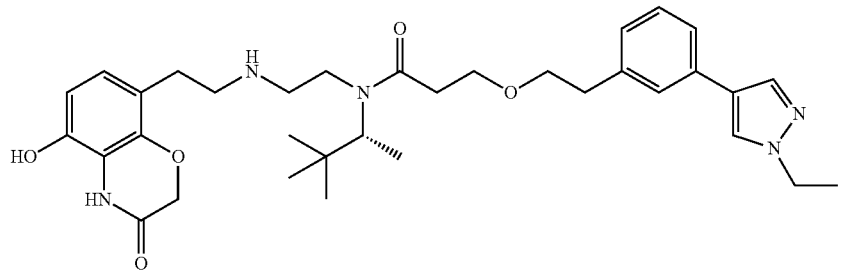

Step i) (R)—N-(2,2-Dimethoxyethyl)-N-(3,3-dimethylbutan-2-yl)-3-(3-(1-ethyl-1H-pyrazol-4-yl)phenethoxy)propanamide

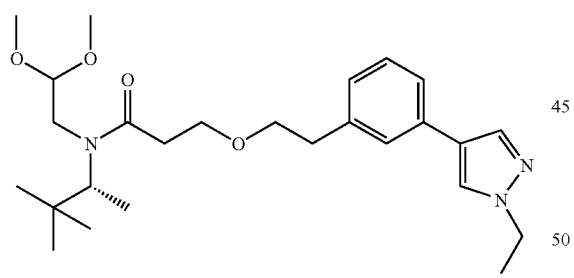

(2×t, J=5.4 Hz, 1H), 4.19 (q, J=7.3 Hz, 2H), 3.80 (q, J=6.9 Hz, 1H), 3.76-3.62 (m, 4H), 3.35 and 2.79 (2×s, 6H), 3.33 (d, J=2.9 Hz, 2H), 3.39-3.25 (m, 2H), 2.85 (t, J=6.8 Hz, 2H), 1.47 (t, J=7.3 Hz, 3H), 1.17 (d, J=6.7 Hz, 3H), 0.90 (s, 9H); a ~1:1 mixture of rotamers is observed.

Step ii) (R)—N-(3,3-Dimethylbutan-2-yl)-3-(3-(1-ethyl-1H-pyrazol-4-yl)phenethoxy)-N-(2-(2-(5-hydroxy-3-oxo-3,4-dihydro-2H-benzo[b][1,4]oxazin-8-yl)ethylamino)ethyl)propanamide Trifluoroacetic Acid Salt

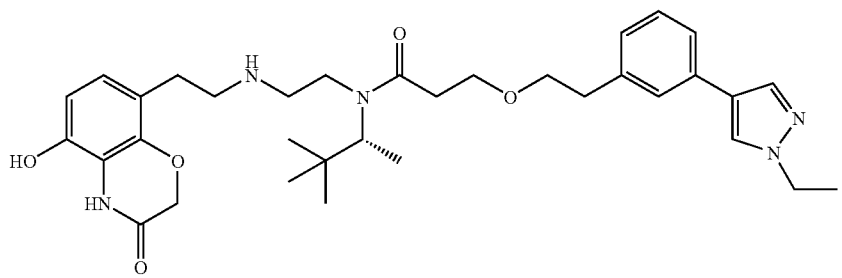

The titled compound (33 mg) was prepared from (R)—N-(2,2-dimethoxyethyl)-N-(3,3-dimethylbutan-2-yl)-3-(3-(1-ethyl-1H-pyrazol-4-yl)phenethoxy)propanamide [Example 25, Step i)] using a similar method to that described in Example 20, Step v). MS [M+H]+=606.3 (calc=606.3655) (MultiMode+) ¹H NMR (400 MHz, CD₃OD) δ 7.94 (s, 1H), 7.77 (s, 1H), 7.40-7.38 (m, 1H), 7.35-7.32 (m, 1H), 7.22 (t, J=7.7 Hz, 1H), 7.05 (d, J=7.7 Hz, 1H), 6.69 (d, J=8.6 Hz, 1H), 6.48 (d, J=8.4 Hz, 1H), 4.598 (s, 1H), 4.596 (s, 1H), 4.18 (q, J=7.2 Hz, 2H), 3.83 (q, J=6.9 Hz, 1H), 3.73-3.65 (m, 4H), 3.65-3.56 (m, 1H), 3.39-3.30 (m, 1H), 3.15-2.94 (m, 4H), 2.89-2.74 (m, 5H), 2.57-2.49 (m, 1H), 1.46 (t, J=7.3 Hz, 3H), 1.16 (d, J=6.9 Hz, 3H), 0.90 (s, 9H)

Example 26

(R)—N-(3,3-Dimethylbutan-2-yl)-N-(2-(2-(5-hydroxy-3-oxo-3,4-dihydro-2H-benzo[b][1,4]oxazin-8-yl)ethylamino)ethyl)-3-(3-(1-methyl-1H-pyrazol-4-yl)phenethoxy)propanamide Trifluoroacetic Acid Salt

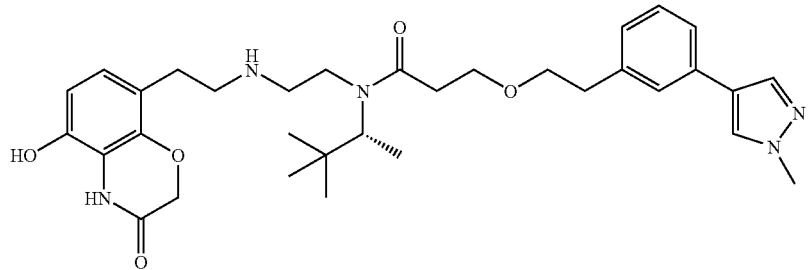

Step i) (R)—N-(2,2-Dimethoxyethyl)-N-(3,3-dimethylbutan-2-yl)-3-(3-(1-methyl-1H-pyrazol-4-yl)phenethoxy)propanamide

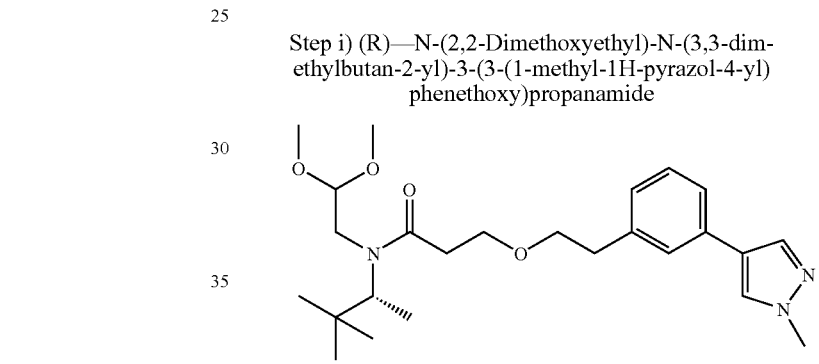

The titled compound (415 mg) was prepared from (3-(3-(1-methyl-1H-pyrazol-4-yl)phenethoxy)propanoic acid [Example 2a Step i] using a similar method to that described in Example 24, Step i). MS [M+H-MeOH]+=414 (MultiMode+) ¹H NMR (400 MHz, CD₃OD) δ 7.92 and 7.91 (2×s, 1H), 7.77 (s, 1H), 7.41-7.31 (m, 2H), 7.23 and 7.22 (2×t, J=7.7 Hz, 1H), 7.05 (d, J=8.1 Hz, 1H), 4.65 and 4.45 (2×t, J=4.9 Hz, 1H), 3.90 (s, 3H), 3.80 (q, J=6.9 Hz, 1H), 3.75-3.62 (m, 4H), 3.38-3.24 (m, 4H), 3.35 (s, 3H), 2.84 (t, J=6.8 Hz, 2H), 2.79 (s, 3H), 1.18 (d, J=7.1 Hz, 3H), 0.89 (s, 9H); a ~3:1 mixture of rotamers is observed.

Step ii) (R)—N-(3,3-Dimethylbutan-2-yl)-N-(2-(2-(5-hydroxy-3-oxo-3,4-dihydro-2H-benzo[b][1,4]oxazin-8-yl)ethylamino)ethyl)-3-(3-(1-methyl-1H-pyrazol-4-yl)phenethoxy)propanamide Trifluoroacetic Acid Salt

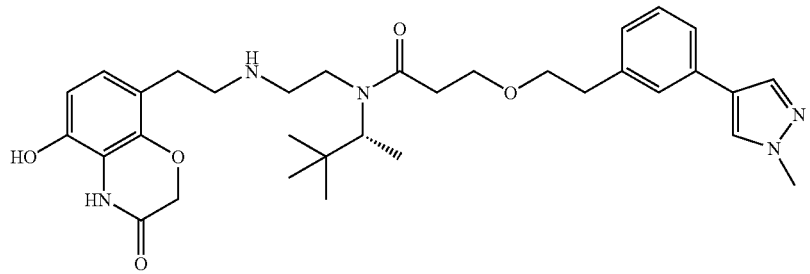

The titled compound (81 mg) was prepared from (R)—N-(2,2-dimethoxyethyl)-N-(3,3-dimethylbutan-2-yl)-3-(3-(1-methyl-1H-pyrazol-4-yl)phenethoxy)propanamide [Example 26, Step i)] using a similar method to that described in Example 20, Step v). MS [M+H]+=592.3 (calc=592.3499) (MultiMode+) ¹H NMR (400 MHz, CD₃OD) δ 7.88 (s, 1H), 7.76 (s, 1H), 7.38 (s, 1H), 7.34-7.30 (m, 1H), 7.22 (t, J=7.7 Hz, 1H), 7.05 (d, J=7.6 Hz, 1H), 6.69 (d, J=8.3 Hz, 1H), 6.48 (d, J=8.3 Hz, 1H), 4.60 (s, 2H), 4.595 (s, 2H), 3.89 (s, 3H), 3.84 (q, J=6.7 Hz, 1H), 3.73-3.56 (m, 5H), 3.40-3.29 (m, 1H), 3.15-2.93 (m, 4H), 2.89-2.74 (m, 5H), 2.58-2.49 (m, 1H), 1.16 (d, J=6.9 Hz, 3H), 0.91 (s, 9H)

Example 27

N-Cyclohexyl-N-(2-(2-(5-hydroxy-3-oxo-3,4-dihydro-2H-benzo[b][1,4]oxazin-8-yl)ethylamino)ethyl)-3-(3-(5-methyl-1,2,4-oxadiazol-3-yl)phenethoxy)propanamide Trifluoroacetic Acid Salt

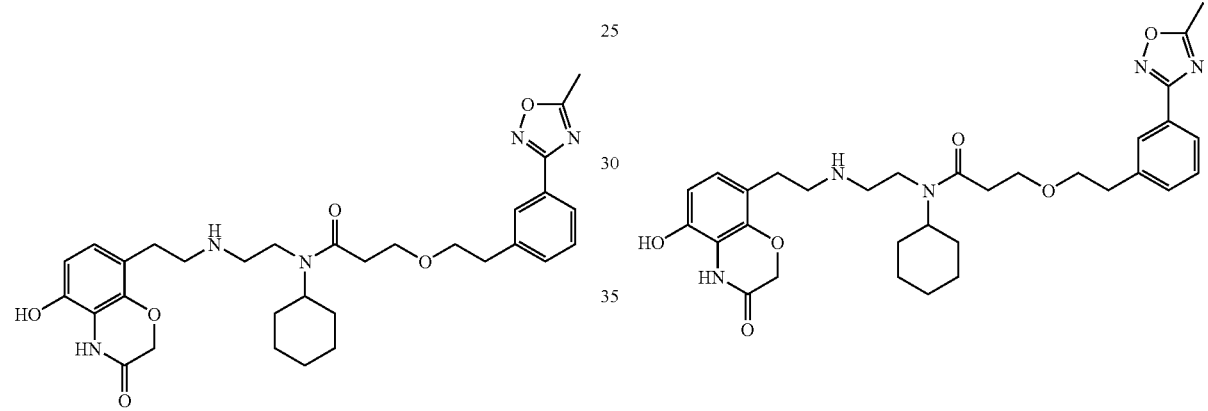

Step i) N-Cyclohexyl-N-(2,2-dimethoxyethyl)-3-(3-(5-methyl-1,2,4-oxadiazol-3-yl)phenethoxy)propanamide

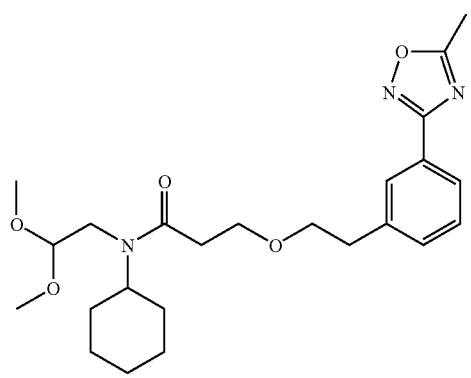

The subtitled compound (100 mg) was prepared using a similar method to that described in Example 11 Step ii) using 1,1,1-trimethoxyethane. After the addition of p-toluenesulfonic acid monohydrate (3 mg) the reaction was heated to 120° C. for 30 min. The crude product was purified by flash silica chromatography, eluting with 40% ethyl acetate in isohexane to afford the subtitled compound. MS [M+H-MeOH]+=414 (MultiMode+)

Step ii) N-Cyclohexyl-N-(2-(2-(5-hydroxy-3-oxo-3,4-dihydro-2H-benzo[b][1,4]oxazin-8-yl)ethylamino)ethyl)-3-(3-(5-methyl-1,2,4-oxadiazol-3-yl)phenethoxy)propanamide Trifluoroacetic Acid Salt p-Toluenesulfonic acid monohydrate (55.5 mg) was added to N-cyclohexyl-N-(2,2-dimethoxyethyl)-3-(3-(5-methyl-1,2,4-oxadiazol-3-yl)phenethoxy)propanamide [Example 27, Step i)] (100 mg) in THF (3 mL) and stirred for 20 min. 8-(2-Aminoethyl)-5-hydroxy-2H-benzo[b][1,4]oxazin-3(4H)-one hydrochloride (54.9 mg) was stirred in NMP (3 mL), water (0.3 mL) and sodium bicarbonate (47.1 mg) for 20 min. before being added to the THF solution. The combined solutions were stirred for 20 min. before the addition of sodium triacetoxyborohydride (95 mg). The mixture was stirred for 16 h before being diluted with sodium hydrogen carbonate solution and extracted three times with DCM. The organic was dried over sodium sulphate and the solvent was removed in vacuo. The residue was purified by preparative HPLC on a Phenomenex Gemini column using a gradient of aqueous 0.1% trifluoroacetic acid in acetonitrile as eluent to afford the titled compound (40 mg). MS [M+H]+=592.3 (calc=592.3135) (MultiMode+) ¹H NMR (400 MHz, CD₃OD) δ 7.90-7.88 (m, 1H), 7.86-7.82 (m, 1H), 7.41-7.37 (m, 2H), 6.69 (d, J=8.1 Hz, 1H), 6.47 (d, J=8.4 Hz, 1H), 4.61 (s, 2H), 3.74-3.68 (m, 5H), 3.51-3.45 (m, 2H), 3.14-3.09 (m, 2H), 3.05-3.01 (m, 2H), 2.93-2.84 (m, 4H), 2.65-2.60 (m, 2H), 2.62 (s, 3H), 1.81-1.74 (m, 2H), 1.70-1.58 (m, 3H), 1.47-1.24 (m, 4H), 1.17-1.06 (m, 1H)

Example 28

N-Cyclohexyl-3-(3-(1-ethyl-1H-pyrazol-4-yl)phenethoxy)-N-(2-(2-(5-hydroxy-3-oxo-3,4-dihydro-2H-benzo[b][1,4]oxazin-8-yl)ethylamino)ethyl)propanamide

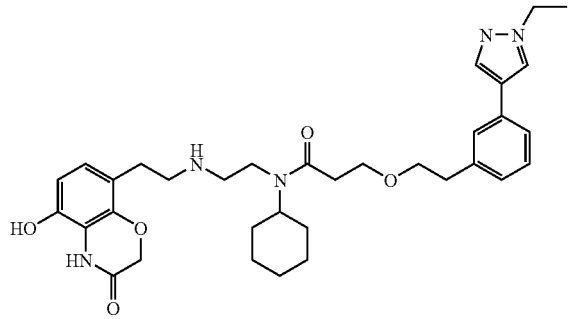

Step i) N-Cyclohexyl-N-(2,2-dimethoxyethyl)-3-(3-(1-ethyl-1H-pyrazol-4-yl)phenethoxy)propanamide

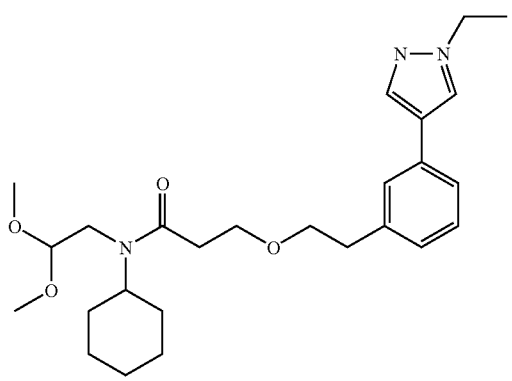

The subtitled compound (1.11 g) was prepared using a similar method to that described in Example 1 Step i) using 1-ethyl-4-(4,4,5,5-tetramethyl-1,3,2-dioxaborolan-2-yl)-1H-pyrazole. The reaction was heated to 100° C. for 25 min. The crude product was purified by flash silica chromatography, eluting with 60% ethyl acetate in isohexane. $^1$H NMR (400 MHz, DMSO-d6) δ 8.16 and 8.15 (2×s, 1H), 7.83 (s, 1H), 7.44-7.41 (m, 1H), 7.40-7.34 (m, 1H), 7.27-7.20 (m, 1H), 7.06-7.01 (m, 1H), 4.46 and 4.36 (2×t, J=5.3 Hz, 1H), 4.14 (q, J=7.3 Hz, 2H), 3.99-3.89 and 3.63-3.53 (2×m, 1H), 3.68-3.56 (m, 4H), 3.31 (s, 3H), 3.30 and 3.19 (2×d, J=5.1 Hz, 2H), 3.25 (s, 3H), 2.82-2.76 (m, 2H), 2.59 (t, J=6.7 Hz, 2H), 1.74-1.66 (m, 2H), 1.65-0.98 (m, 11H); a ~1:1 mixture of rotamers is observed.

Step ii) N-Cyclohexyl-3-(3-(1-ethyl-1H-pyrazol-4-yl)phenethoxy)-N-(2-(2-(5-hydroxy-3-oxo-3,4-dihydro-2H-benzo[b][1,4]oxazin-8-yl)ethylamino)ethyl)propanamide

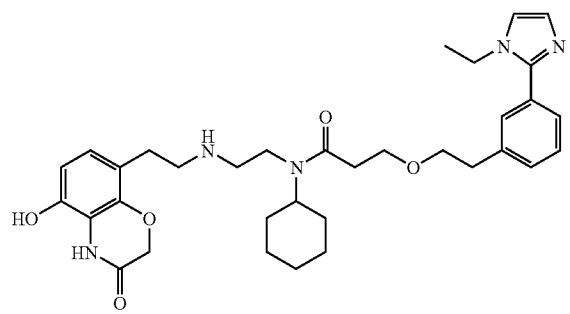

To N-cyclohexyl-N-(2,2-dimethoxyethyl)-3-(3-(1-ethyl-1H-pyrazol-4-yl)phenethoxy)propanamide [Example 28, Step i)] (374 mg) in THF (3 mL) was added p-toulenesulfonic acid monohydrate (202 mg) and the mixture was stirred for 20 min to form an aldehyde. 8-(2-Aminoethyl)-5-hydroxy-2H-benzo[b][1,4]oxazin-3(4H)-one hydrochloride (200 mg) was stirred in NMP (3.00 mL), water (0.3 mL) and sodium bicarbonate (172 mg) for 20 min before being added to an aldehyde solution and the resulting mixture was stirred for 20 min before the addition of sodium triacetoxyborohydride (346 mg). The reaction mixture was stirred for 2 h, then diluted with sodium hydrogen carbonate solution and extracted three times with DCM. The pooled organics were dried over sodium sulphate and solvent. The residue was purified by preparative HPLC on a Phenomenex Gemini column using a gradient of aqueous 0.1% trifluoroacetic acid in acetonitrile as eluent. The product was repurified on silica using 6% MeOH/DCM as eluent to afford the titled compound (150 mg). MS [M+H]+=604.2 (calc=604.3499) (MultiMode+) $^1$H NMR (400 MHz, CD$_3$OD) δ 7.95 (s, 1H), 7.78 (s, 1H), 7.41-7.32 (m, 2H), 7.23 (t, J=7.7 Hz, 1H), 7.07-7.03 (m, 1H), 6.69 (d, J=8.4 Hz, 1H), 6.48 (d, J=8.4 Hz, 1H), 4.60 (s, 2H), 4.18 (q, J=7.2 Hz, 2H), 3.74-3.64 (m, 5H), 3.51-3.45 (m, 2H), 3.13-3.07 (m, 2H), 3.04-2.98 (m, 2H), 2.88-2.82 (m, 4H), 2.63 (t, J=6.0 Hz, 2H), 1.81-1.74 (m, 2H), 1.70-1.57 (m, 3H), 1.46 (t, J=7.4 Hz, 3H), 1.46-1.25 (m, 4H), 1.17-1.04 (m, 1H).

Example 29

N-Cyclohexyl-3-(3-(1-ethyl-1H-imidazol-2-yl)phenethoxy)-N-(2-(2-(5-hydroxy-3-oxo-3,4-dihydro-2H-benzo[b][1,4]oxazin-8-yl)ethylamino)ethyl)propanamide Trifluoroacetic Acid Salt Step i) N-Cyclohexyl-N-(2,2-dimethoxyethyl)-3-(3-(1-ethyl-1H-imidazol-2-yl)phenethoxy)propanamide

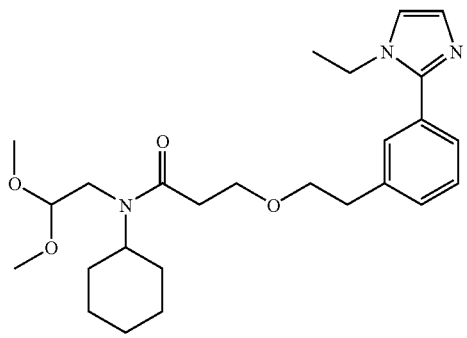

Ethylamine (70% in water, 0.526 mL), followed by oxalaldehyde (40% in water, 0.889 mL) and ammonium acetate (473 mg) were added to a stirred solution of N-cyclohexyl-N-(2,2-dimethoxyethyl)-3-(3-formylphenethoxy)propanamide [Example 10, Step ii)] (400 mg) in methanol (3 mL). The mixture was stirred for 36 h. DCM was added and the mixture was washed with water. The volatiles were removed under vacuum and the crude product was purified by flash silica chromatography, elution gradient 50%-100% ethyl acetate in isohexane to afford the subtitled compound (98 mg). $^1$H NMR (400 MHz, CD$_3$OD) δ 7.42-7.31 (m, 4H), 7.22 (d, J=1.5 Hz, 1H), 7.02 (d, J=1.3 Hz, 1H), 4.54 and 4.39 (2×t, J=5.5 Hz, 1H), 4.06-3.98 and 3.70-3.62 (2×m, 1H), 4.06 (q, J=7.3 Hz, 2H), 3.74-3.63 (m, 4H), 3.39-3.25 (m, 2H), 3.36 (s, 3H), 3.34 (s, 3H), 2.93-2.88 (m, 2H), 2.69-2.61 (m, 2H), 1.82-1.02 (m, 10H), 1.34 (t, J=6.8 Hz, 3H); a ~1:1 mixture of rotamers is observed.

Step ii) N-Cyclohexyl-3-(3-(1-ethyl-1H-imidazol-2-yl)phenethoxy)-N-(2-(2-(5-hydroxy-3-oxo-3,4-dihydro-2H-benzo[b][1,4]oxazin-8-yl)ethylamino)ethyl) propanamide Trifluoroacetic Acid Salt

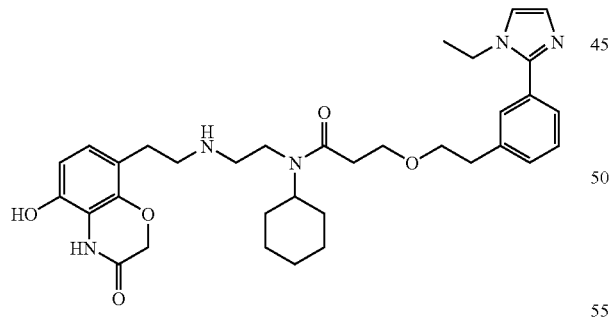

The titled compound (98 mg) was prepared from N-cyclohexyl-N-(2,2-dimethoxyethyl)-3-(3-(1-ethyl-1H-imidazol-2-yl)phenethoxy)propanamide [Example 29, Step i)] using a similar method to that described in Example 27 Step ii). The THF solution was stirred for 9 h before the NMP solution was added. The reaction mixture was stirred for 4 h after the addition of sodium triacetoxyborohydride. MS [M+H]+= 604.2 (calc=604.3499) (MultiMode+) $^1$H NMR (400 MHz, CD$_3$OD) δ 7.76 (d, J=2.4 Hz, 1H), 7.65 (d, J=2.2 Hz, 1H), 7.63-7.51 (m, 4H), 6.71 (d, J=8.4 Hz, 1H), 6.48 (d, J=8.4 Hz, 1H), 4.61 (s, 2H), 4.24 (q, J=7.3 Hz, 2H), 3.75-3.65 (m, 5H), 3.55-3.51 (m, 2H), 3.19-3.14 (m, 2H), 3.10-3.06 (m, 2H), 3.01-2.96 (m, 2H), 2.92-2.87 (m, 2H), 2.68-2.64 (m, 2H), 1.85-1.77 (m, 2H), 1.75-1.61 (m, 3H), 1.52-1.26 (m, 4H), 1.46 (t, J=7.6 Hz, 3H), 1.21-1.08 (m, 1H).

Example 30

(R)—N-(Hexan-2-yl)-N-(2-(2-(5-hydroxy-3-oxo-3,4-dihydro-2H-benzo[b][1,4]oxazin-8-yl)ethylamino)ethyl)-3-(3-(1-methyl-1H-pyrazol-4-yl)phenethoxy)propanamide Trifluoroacetic Acid Salt

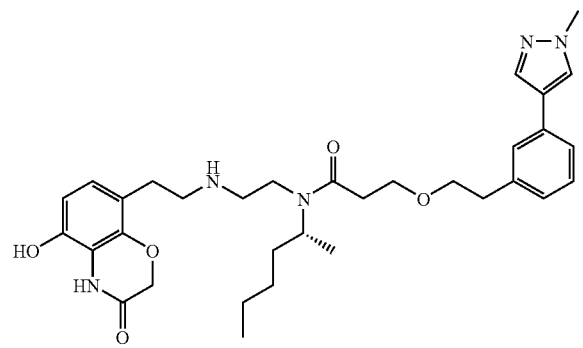

Step i) (R)—N-(2,2-Dimethoxyethyl)-N-(hexan-2-yl)-3-(3-(1-methyl-1H-pyrazol-4-yl)phenethoxy)propanamide

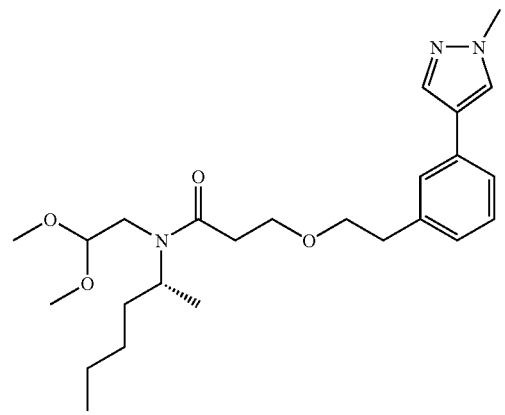

The subtitled compound (234 mg) was prepared using a similar method to that described in Preparation 3 Step iii) from 3-(3-(1-methyl-1H-pyrazol-4-yl)phenethoxy)propanoic acid [Example 2a, Step i)] and (R)—N-(2,2-dimethoxyethyl) hexan-2-amine [Preparation 13] and the reaction mixture was stirred for 2 h. The elution gradient used was 30-50% ethyl acetate in isohexane. $^1$H NMR (400 MHz, CDCl$_3$) δ 7.75 (s, 1H), 7.62 (s, 1H), 7.36-7.24 (m, 3H), 7.11-7.05 (m, 1H), 4.69-4.63 and 4.41-4.37 (m, 1H), 4.38-4.31 and 3.85-3.76 (m, 1H), 3.94 (s, 3H), 3.85-3.76 (m, 2H), 3.74-3.65 (m, 2H), 3.43-3.37 (m, 6H), 3.33-3.25 (m, 1H), 3.22-3.14 (m, 1H), 2.94-2.85 (m, 2H), 2.80-2.57 (m, 2H), 1.59-1.12 (m, 9H), 0.93-0.85 (m, 3H); a ~1:1 mixture of rotamers is observed.

Step iv) (R)—N-(Hexan-2-yl)-N-(2-(2-(5-hydroxy-3-oxo-3,4-dihydro-2H-benzo[b][1,4]oxazin-8-yl)ethylamino)ethyl)-3-(3-(1-methyl-1H-pyrazol-4-yl)phenethoxy)propanamide Trifluoroacetic Acid Salt

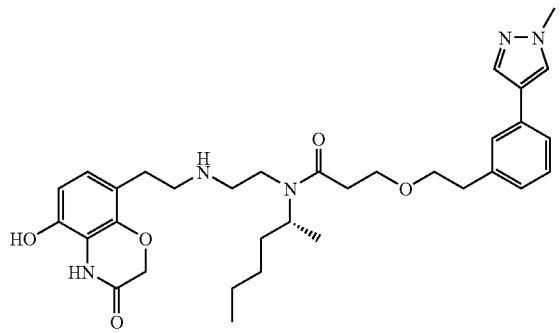

The titled compound (150 mg) was prepared from (R)—N-(2,2-dimethoxyethyl)-N-(hexan-2-yl)-3-(3-(1-methyl-1H-pyrazol-4-yl)phenethoxy)propanamide [Example 30, Step i)] using a similar method to that described in Example 27 Step ii). The THF solution was stirred for 2 h before the NMP solution was added. The mixture was stirred overnight after the addition of sodium triacetoxyborohydride, then diluted with water. MS [M+H]+=592.3 (calc=592.3499) (MultiMode+) $^1$H NMR (400 MHz, CD$_3$OD) δ 7.89 (s, 1H), 7.77 (s, 1H), 7.40-7.38 (m, 1H), 7.35-7.31 (m, 1H), 7.22 (t, J=7.7 Hz, 1H), 7.07-7.04 (m, 1H), 6.69 (d, J=8.4 Hz, 1H), 6.47 (d, J=8.4 Hz, 1H), 4.60 (s, 2H), 3.98-3.92 (m, 1H), 3.89 (s, 3H), 3.74-3.68 (m, 4H), 3.54-3.44 (m, 1H), 3.40-3.31 (m, 1H), 3.15-3.07 (m, 2H), 3.07-3.00 (m, 2H), 2.89-2.82 (m, 4H), 2.70-2.62 (m, 1H), 2.61-2.52 (m, 1H), 1.49-1.41 (m, 2H), 1.35-1.07 (m, 7H), 0.87 (t, J=7.2 Hz, 3H)

Example 31

N-Cycloheptyl-N-(2-(2-(5-hydroxy-3-oxo-3,4-dihydro-2H-benzo[b][1,4]oxazin-8-yl)ethylamino)ethyl)-3-(3-(1-methyl-1H-pyrazol-4-yl)phenethoxy)propanamide Trifluoroacetic Acid Salt

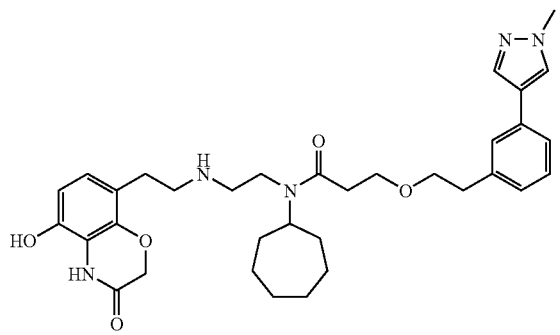

Step i) N-Cycloheptyl-N-(2,2-dimethoxyethyl)-3-(3-(1-methyl-1H-pyrazol-4-yl)phenethoxy)propanamide

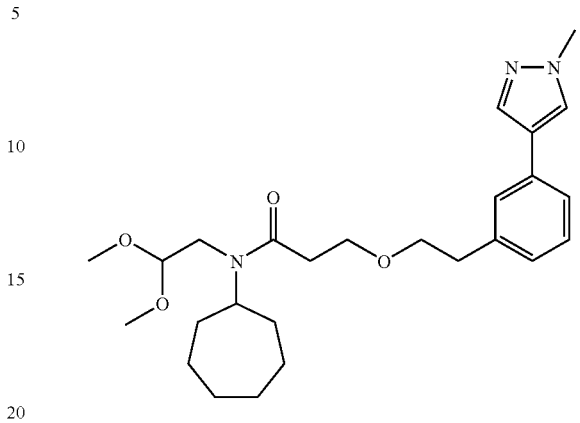

The subtitled compound (1.2 g) was prepared from 3-(3-(1-methyl-1H-pyrazol-4-yl)phenethoxy)propanoic acid [Example 2a, Step i)] and N-(2,2-dimethoxyethyl)cycloheptanamine [Preparation 6], using a similar method to that described in Preparation 3 Step iii) and the elution gradient used was 50-80% ethyl acetate in isohexane. $^1$H NMR (400 MHz, DMSO-d6) δ 8.10 and 8.09 (2×s, 1H), 7.82 (s, 1H), 7.44-7.40 (m, 1H), 7.37 (d, J=7.7 Hz, 1H), 7.26-7.21 (m, 1H), 7.06-7.02 (m, 1H), 4.51 and 4.39 (2×t, J=5.0 Hz, 1H), 3.85 (s, 3H), 3.86-3.66 (m, 1H), 3.68-3.56 (m, 4H), 3.31 (s, 3H), 3.30 and 3.16 (2×d, J=5.0 Hz, 2H), 3.25 (s, 3H), 2.81-2.76 (m, 2H), 2.61-2.51 (m, 2H), 1.79-1.23 (m, 12H); a ~1:1 mixture of rotamers is observed.

Step ii) N-Cycloheptyl-N-(2-(2-(5-hydroxy-3-oxo-3,4-dihydro-2H-benzo[b][1,4]oxazin-8-yl)ethylamino)ethyl)-3-(3-(1-methyl-1H-pyrazol-4-yl)phenethoxy)propanamide Trifluoroacetic Acid Salt

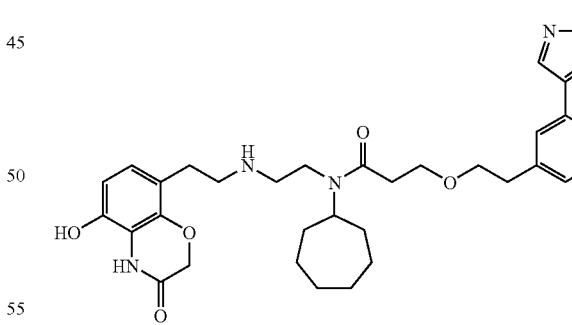

The titled compound (270 mg) was prepared from N-cycloheptyl-N-(2,2-dimethoxyethyl)-3-(3-(1-methyl-1H-pyrazol-4-yl)phenethoxy)propanamide [Example 31, Step i)] using a similar method to that described in Example 27 Step ii). The mixture was stirred for 2 h after the addition of sodium triacetoxyborohydride. MS [M+H]+=604.2 (calc=604.3499) (MultiMode+) $^1$H NMR (300 MHz, CD$_3$OD) δ 7.93 (s, 1H), 7.81 (s, 1H), 7.44-7.33 (m, 2H), 7.30-7.22 (m, 1H), 7.09 (d, J=7.5 Hz, 1H), 6.74 (d, J=8.3 Hz, 1H), 6.52 (d, J=8.3 Hz, 1H), 4.64 (s, 2H), 3.93 (s, 3H), 3.98-3.80 (m, 1H), 3.79-3.68 (m, 4H), 3.53-3.44 (m, 2H), 3.18-3.03 (m, 4H), 2.94-2.83 (m, 4H), 2.70-2.62 (m, 2H), 1.82-1.37 (m, 12H).

Example 32

N-Cyclohexyl-3-(3-(4,5-dimethyl-1H-imidazol-2-yl) phenethoxy)-N-(2-(2-(5-hydroxy-3-oxo-3,4-dihydro-2H-benzo[b][1,4]oxazin-8-yl)ethylamino)ethyl)propanamide

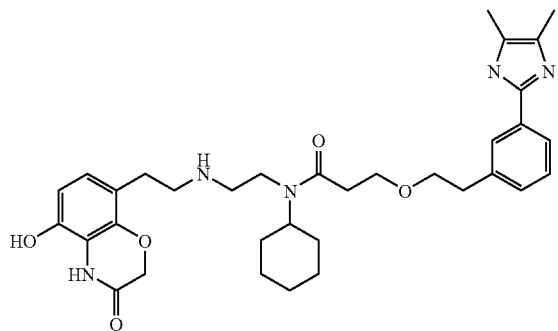

Step i) N-Cyclohexyl-N-(2,2-dimethoxyethyl)-3-(3-(4,5-dimethyl-1H-imidazol-2-yl)phenethoxy)propanamide

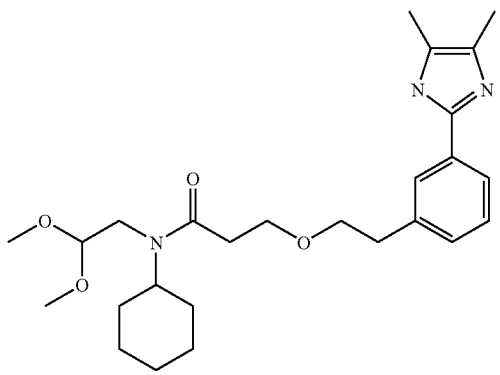

To N-cyclohexyl-N-(2,2-dimethoxyethyl)-3-(3-formylphenethoxy)propanamide [Example 10, Step ii)] (450 mg) in MeOH (3 mL) was added ammonium acetate (532 mg) and biacetyl (0.502 mL). Stirred overnight before reaction worked up by the addition of water which was extracted using DCM. Solvent removed form organics phase and purified on silica using 3% MeOH/DCM as eluent to afford subtitled compound (416 mg) as an oil. MS [M+H]+=458 (MultiMode+) $^1$H NMR (400 MHz, CDCl$_3$) δ 7.87 (t, J=8.5 Hz, 1H), 7.68 (d, J=44.0 Hz, 1H), 7.31-7.23 (m, 1H), 7.07 (t, J=7.7 Hz, 1H), 4.45 and 4.36 (2×t, J=5.3 Hz, 1H), 4.29-4.19 and 3.64-3.53 (2×m, 1H) 3.84 (t, J=5.8 Hz, 2H), 3.75 (t, J=5.8 Hz, 2H), 3.38 and 3.29 (2×d, J=5.7 Hz, 2H) 3.37 (s, 3H), 3.16 (s, 3H), 2.89 (t, J=5.6 Hz, 2H), 2.75 (t, J=5.5 Hz, 1H), 2.69 (t, J=5.9 Hz, 1H), 2.26 (s, 3H), 2.22 (s, 3H), 1.86-1.77 (m, 1H), 1.73-0.93 (m, 9H).

Step ii) N-Cyclohexyl-3-(3-(4,5-dimethyl-1H-imidazol-2-yl)phenethoxy)-N-(2-(2-(5-hydroxy-3-oxo-3,4-dihydro-2H-benzo[b][1,4]oxazin-8-yl)ethylamino)ethyl)propanamide

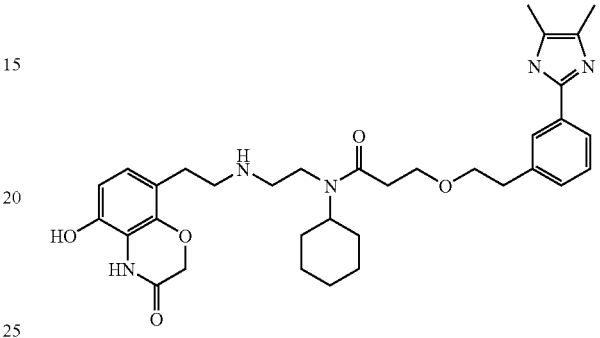

The titled compound (120 mg) was prepared from N-cyclohexyl-3-(2,2-difluoro-2-(3-(1-methyl-1H-pyrazol-4-yl)phenyl)ethoxy)-N-(2,2-dimethoxyethyl)propanamide [Example 32, Step i)] using a similar method to that described in Example 27 Step ii). and repurified by flash silica chromatography, using 5% MeOH/1% NH$_3$/DCM as eluent. MS [M+H]+=604.3 (calc=604.3499) (MultiMode+) $^1$H NMR (400 MHz, CD$_3$OD) δ 7.67-7.58 (m, 2H), 7.31-7.23 (m, 1H), 7.18-7.12 (m, 1H), 6.64 (t, J=7.9 Hz, 1H), 6.45-6.41 (m, 1H), 4.54 and 4.50 (s, 2H), 4.15-4.06 and 3.68-3.59 (2×m, 1H), 3.76-3.68 (m, 4H), 3.36-3.22 (m, 2H), 2.89-2.81 (m, 3H), 2.77-2.52 (m, 7H), 2.16 (s, 3H), 2.16 (s, 3H), 1.79-1.68 (m, 2H), 1.65-1.55 (m, 2H), 1.51-1.16 (m, 5H), 1.15-1.02 (m, 1H)

Example 33

N-Cyclohexyl-N-(2-(2-(5-hydroxy-3-oxo-3,4-dihydro-2H-benzo[b][1,4]oxazin-8-yl)ethylamino)ethyl)-3-(3-(1-methyl-1H-imidazol-2-yl)phenethoxy)propanamide

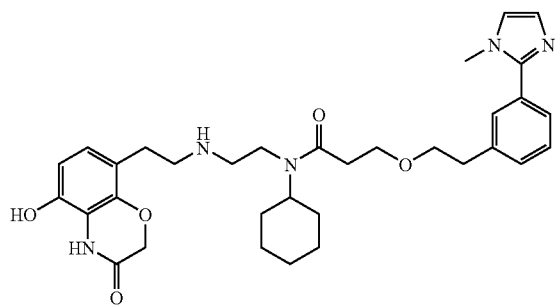

Step i) N-Cyclohexyl-N-(2,2-dimethoxyethyl)-3-(3-(1-methyl-1H-imidazol-2-yl)phenethoxy)propanamide

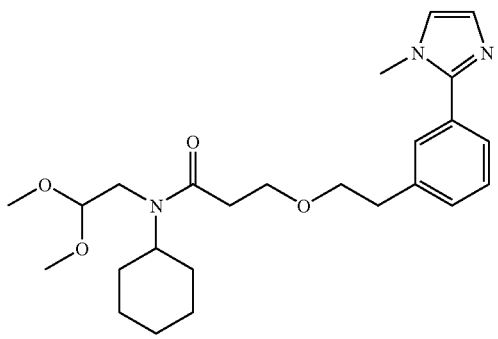

The titled compound (231 mg) was prepared methyl amine and N-cyclohexyl-N-(2,2-dimethoxyethyl)-3-(3-formylphenethoxy)propanamide [Example 10 Step ii] using a similar method to that described in Example 28 Step i). The crude product was purified on silica using ethyl acetate followed by 2.5% MeOH/DCM. MS [M+H-MeOH]+=412 (MultiMode+)

Step ii) N-Cyclohexyl-N-(2-(2-(5-hydroxy-3-oxo-3,4-dihydro-2H-benzo[b][1,4]oxazin-8-yl)ethylamino)ethyl)-3-(3-(1-methyl-1H-imidazol-2-yl)phenethoxy)propanamide

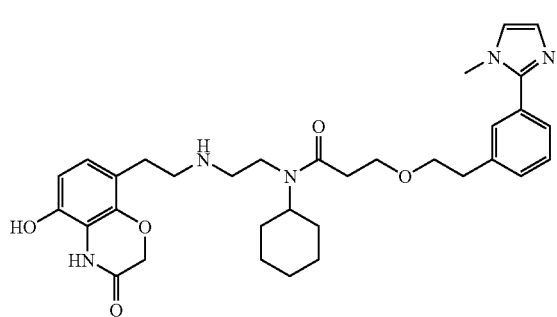

To N-cyclohexyl-N-(2,2-dimethoxyethyl)-3-(3-(1-methyl-1H-imidazol-2-yl)phenethoxy)propanamide [Example 33, Step i)] (231 mg) in DCM (3 mL) was added p-toulenesulfonic acid monohydrate (297 mg) and stirred for 1 h to form an aldehyde. 8-(2-Aminoethyl)-5-hydroxy-2H-benzo[b][1,4]oxazin-3(4H)-one hydrochloride (127 mg) and sodium bicarbonate (184 mg) in water (0.3 mL) and NMP (3 mL) was stirred for 20 min before the addition to the aldehyde solution and the resulting mixture was stirred for 20 min before the addition of sodium triacetoxyborohydride (221 mg). The reaction mixture was stirred for 16 h. Sat sodium hydrogen carbonate was added and the reaction mixture was extracted three times with DCM. Pooled organics were concentrated. The crude product was purified via reverse phase prep HPLC—Gemini column using a gradient of aqueous 0.1% trifluoroacetic acid in acetonitrile as eluent and repurified on silica using 6% MeOH/1% NH3/DCM to afford the titled compound (90 mg) as a solid. MS [M+H]+=590.3 (calc=590.3342) (MultiMode+) $^1$H NMR (400 MHz, CD$_3$OD) δ 7.47-7.43 (m, 1H), 7.43-7.28 (m, 3H), 7.14-7.12 (m, 1H), 6.99 (d, J=1.3 Hz, 1H), 6.67-6.62 (m, 1H), 6.45-6.40 (m, 1H), 4.54-4.48 (m, 2H), 3.75-3.61 (m, 8H), 3.34-3.24 (m, 1H), 2.93-2.86 (m, 2H), 2.82-2.64 (m, 6H), 2.62-2.53 (m, 2H), 1.81-1.72 (m, 2H), 1.67-1.57 (m, 3H), 1.57-1.22 (m, 4H), 1.18-1.03 (m, 1H).

Example 34

N-Cyclohexyl-3-(3-(1,2-dimethyl-1H-imidazol-4-yl)phenethoxy)-N-(2-(2-(5-hydroxy-3-oxo-3,4-dihydro-2H-benzo[b][1,4]oxazin-8-yl)ethylamino)ethyl)propanamide

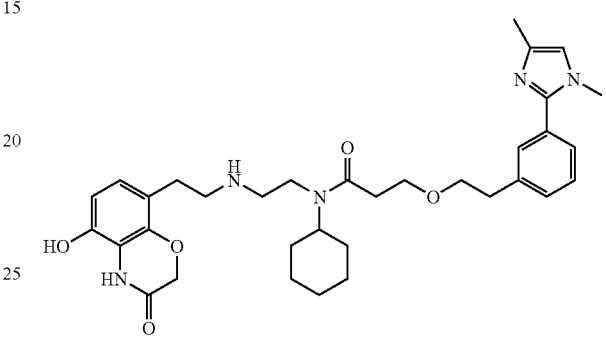

Step i) N-Cyclohexyl-N-(2,2-dimethoxyethyl)-3-(3-(4,4,5,5-tetramethyl-1,3,2-dioxaborolan-2-yl)phenethoxy)propanamide

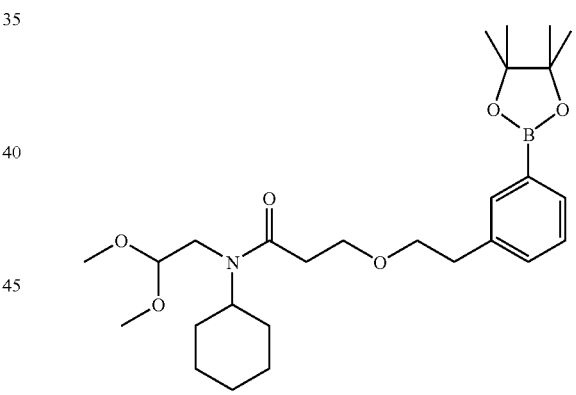

1,1'-Bis(diphenylphosphino)ferrocene (0.095 g) and 1,1'-bis(diphenylphosphino)ferrocene-palladium(II)dichloride dichloromethane complex (0.138 g) were stirred in dry dimethylsulfoxide (5.97 mL) under nitrogen for 10 min. Potassium acetate (0.998 g), 3-(3-bromophenethoxy)-N-cyclohexyl-N-(2,2-dimethoxyethyl)propanamide [Preparation 3] (1.5 g) dissolved in dry dimethylsulfoxide (5.97 mL) and 4,4,4',4',5,5,5',5'-octamethyl-2,2'-bi(1,3,2-dioxaborolane) (1.145 g) were added and the reaction mixture was heated at 80° C. for 15 h. Ethyl acetate was added to the cooled reaction mixture which was washed three times with water, twice with brine, dried over sulphate, filtered and solvent removed. The residue was purified on silica using 20%-100% ethyl acetate/isohexane gradient to afford the subtitled compound (1.489 g) as an oil. $^1$H NMR (300 MHz, CDCl$_3$) δ 7.68-7.61 (m, 2H), 7.35-7.24 (m, 2H), 4.62 and 4.37 (t, J=5.2 Hz, 1H), 4.27-4.12 and 3.63-3.49 (m, 1H), 3.82-3.73 (m, 2H), 3.72-3.62 (m, 2H), 3.41 (s, 3H), 3.39 (s, 3H), 3.38 and 3.30 (2×d, J=4.8 Hz, 2H), 2.93-2.84 (m, 2H), 2.74-2.63 (m, 2H), 1.87-1.74 (m, 2H), 1.74-1.59 (m, 3H), 1.54-1.00 (m, 5H), 1.34 (s, 6H), 1.26 (s, 3H), 1.24 (s, 3H)

Step ii) N-Cyclohexyl-N-(2,2-dimethoxyethyl)-3-(3-(1,4-dimethyl-1H-imidazol-2-yl)phenethoxy)propanamide

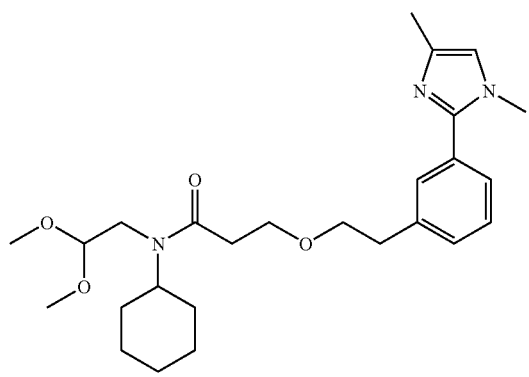

N-Cyclohexyl-N-(2,2-dimethoxyethyl)-3-(3-(4,4,5,5-tetramethyl-1,3,2-dioxaborolan-2-yl)phenethoxy)propanamide [Example 34, Step i)] (390 mg), potassium carbonate (220 mg), Pd(Ph₃P)₄ (46 mg) and 2-bromo-1,4-dimethyl-1H-imidazole (279 mg) in MeOH (3 mL) was loaded into a microwave vial, flushed with nitrogen and sealed. The vial was heated within a Discover microwave at 120° C. for 30 min. After cooling, the reaction and the filtrate washed with DCM. Volatiles were removed and the residue purified on silica using 20%-100% EtOAc/iso gradient to afford the subtitled compound (358 mg). MS [M+H]+=458 (MultiMode+) $^1$H NMR (400 MHz, CDCl$_3$) δ 7.51-7.47 (m, 1H), 7.43-7.40 (m, 1H), 7.37-7.30 (m, 1H), 7.27-7.22 (m, 1H), 6.67 (s, 1H), 4.61 and 4.37 (2×t, J=5.2 Hz, 1H), 4.25-4.16 and 3.61-3.51 (2×m, 1H), 3.81-3.74 (m, 2H), 3.73-3.65 (m, 2H), 3.68 (s, 3H), 3.41 (s, 3H), 3.39 (s, 3H), 3.37 and 3.29 (2×d, J=4.9 Hz, 2H), 2.96-2.89 (m, 2H), 2.73-2.65 (m, 2H), 2.26 (s, 3H), 1.85-1.74 (m, 2H), 1.73-1.05 (m, 8H); a ~2:1 mixture of rotamers is observed.

Step iii) N-Cyclohexyl-3-(3-(1,2-dimethyl-1H-imidazol-4-yl)phenethoxy)-N-(2-(2-(5-hydroxy-3-oxo-3,4-dihydro-2H-benzo[b][1,4]oxazin-8-yl)ethylamino)ethyl)propanamide

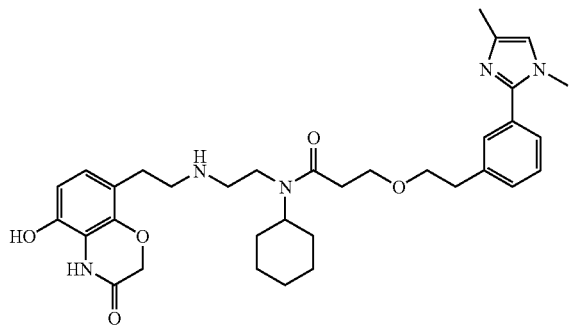

To N-cyclohexyl-N-(2,2-dimethoxyethyl)-3-(3-(1,4-dimethyl-1H-imidazol-2-yl)phenethoxy)propanamide [Example 34, Step i)] (358 mg) in DCM (3 mL) was added p-toluenesulfonic acid monohydrate (406 mg) and stirred for 1 h to form an aldehyde. 8-(2-Aminoethyl)-5-hydroxy-2H-benzo[b][1,4]oxazin-3(4H)-one hydrochloride (174 mg) was stirred in NMP (3 mL) and water (0.3 mL) with the addition of sodium bicarbonate (251 mg) and stirred for 60 min before being added to the aldehyde solution. The resulting mixture was stirred for 20 min before the addition of sodium triacetoxyborohydride (301 mg). The reaction mixture was stirred for 16 h. DCM was added and the mixture was washed with water and concentrated in vacuo. The residue was purified by reverse phase prep HPLC—Gemini column, 0.1% TFA aq/acetonitrile eluent and repurified on silica using 5% MeOH/DCM/1% NH3aq. to afford the titled compound (122 mg). MS [M+H]+=604.3 (calc=604.3499) (MultiMode+) $^1$H NMR (400 MHz, CD$_3$OD) δ 7.44-7.41 (m, 1H), 7.40-7.32 (m, 2H), 7.31-7.25 (m, 1H), 6.81 (s, 1H), 6.66-6.62 (m, 1H), 6.43-6.40 (m, 1H), 4.52 and 4.49 (s, 2H), 4.18-4.06 and 3.75-3.61 (m, 1H), 3.75-3.61 (m, 4H), 3.64 and 3.63 (2×s, 3H), 3.33-3.26 (m, 2H), 2.92-2.86 (m, 2H), 2.79-2.63 (m, 6H), 2.62-2.53 (m, 2H), 2.17 and 2.17 (s, 3H), 1.80-1.72 (m, 2H), 1.68-1.57 (m, 2H), 1.57-1.24 (m, 5H), 1.18-1.04 (m, 1H)

Example 35

N-Cyclohexyl-3-(3-(1,2-dimethyl-1H-imidazol-4-yl)phenethoxy)-N-(2-(2-(5-hydroxy-3-oxo-3,4-dihydro-2H-benzo[b][1,4]oxazin-8-yl)ethylamino)ethyl)propanamide Trifluoroacetic Acid Salt

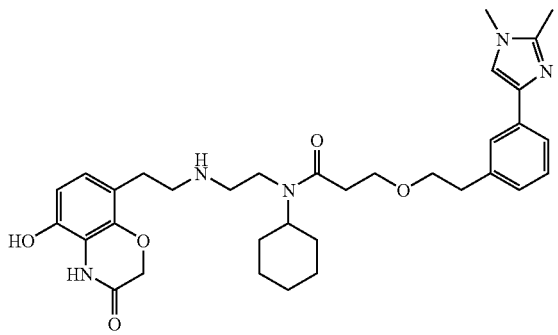

Step i) N-Cyclohexyl-N-(2,2-dimethoxyethyl)-3-(3-(1,2-dimethyl-1H-imidazol-4-yl)phenethoxy)propanamide

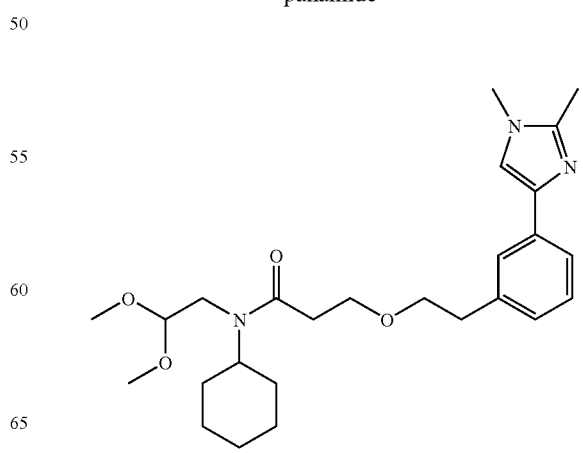

N-Cyclohexyl-N-(2,2-dimethoxyethyl)-3-(3-(4,4,5,5-tetramethyl-1,3,2-dioxaborolan-2-yl)phenethoxy)propanamide [Example 34 Step i)] (360 mg), potassium carbonate (203 mg), Pd(Ph₃P)₄ (42.5 mg) and 4-bromo-1,2-dimethyl-1H-imidazole (193 mg) in MeOH (3 mL) was loaded into a microwave vial, flushed with nitrogen and sealed. The reaction mixture was heated within a Discover microwave at 120° C. for 20 min. After cooling, the mixture was filtered and the filtrate was washed with DCM. Volatiles removed and the residue was purified on silica using 50%-100% EtOAc/iso hexane and then 5% MeOH/DCM to afford the subtitled compound (250 mg). MS [M+H-MeOH]+=426 (MultiMode+) ¹H NMR (400 MHz, CDCl₃) δ 7.61 and 7.59 (2×s, 1H), 7.53 (d, J=7.7 Hz, 1H), 7.28-7.21 (m, 1H), 7.10-7.03 (m, 2H), 4.62 and 4.37 (2×t, J=5.1 Hz, 1H), 4.26-4.17 and 3.62-3.52 (2×m, 1H), 3.82-3.74 (m, 2H), 3.73-3.64 (m, 2H), 3.60 (s, 3H), 3.41 (s, 3H), 3.38 (s, 3H), 3.37 and 3.29 (2×d, J=4.7 Hz, 2H), 2.94-2.86 (m, 2H), 2.73-2.65 (m, 2H), 2.43 (s, 3H), 1.85-1.73 (m, 2H), 1.73-1.60 (m, 3H), 1.54-1.22 (m, 4H), 1.15-1.01 (m, 1H); a ~2:1 mixture of rotamers is observed.

Step ii) N-Cyclohexyl-3-(3-(1,2-dimethyl-1H-imidazol-4-yl)phenethoxy)-N-(2-(2-(5-hydroxy-3-oxo-3,4-dihydro-2H-benzo[b][1,4]oxazin-8-yl)ethylamino)ethyl)propanamide Trifluoroacetic Acid Salt

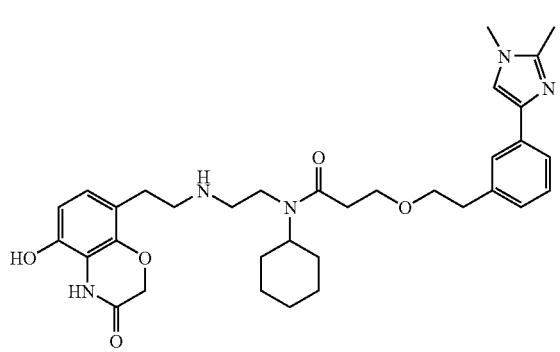

To N-cyclohexyl-N-(2,2-dimethoxyethyl)-3-(3-(1,2-dimethyl-1H-imidazol-4-yl)phenethoxy)propanamide [Example 35 Step i)] (250 mg) in DCM (3 mL) was added p-toluenesulfonic acid monohydrate (312 mg) and stirred for 1 h to form an aldehyde. 8-(2-Aminoethyl)-5-hydroxy-2H-benzo[b][1,4]oxazin-3(4H)-one hydrochloride (134 mg) and sodium bicarbonate (193 mg) was stirred in NMP (3 mL) and water (0.3 mL) was stirred for 60 min before being added to the aldehyde solution. The solution was stirred for 20 min before the addition of sodium triacetoxyborohydride (232 mg). The reaction mixture was stirred for 16 h. DCM was added and the mixture was washed with water and concentrated. The residue was purified by reverse phase prep HPLC—Sunfire column, 0.1% TFA aq/acetonitrile eluent to afford the titled compound (164 mg). MS [M+H]+=604.3 (calc=604.3499) (MultiMode+) ¹H NMR (400 MHz, CD₃OD) δ 7.74 (s, 1H), 7.53-7.51 (m, 1H), 7.49-7.45 (m, 1H), 7.40 (t, J=7.7 Hz, 1H), 7.34-7.31 (m, 1H), 6.70 (d, J=8.5 Hz, 1H), 6.47 (d, J=8.5 Hz, 1H), 4.60 (s, 2H), 3.82 (s, 3H), 3.75-3.68 (m, 5H), 3.54-3.50 (m, 2H), 3.17-3.11 (m, 2H), 3.09-3.05 (m, 2H), 2.94-2.84 (m, 4H), 2.68-2.63 (m, 2H), 2.65 (s, 3H), 1.84-1.77 (m, 2H), 1.74-1.61 (m, 3H), 1.50-1.26 (m, 4H), 1.19-1.06 (m, 1H).

Example 36

N-Cyclohexyl-N-(2-(2-(5-hydroxy-3-oxo-3,4-dihydro-2H-benzo[b][1,4]oxazin-8-yl)ethylamino)ethyl)-3-(3-(1-(2-methoxyethyl)-1H-pyrazol-4-yl)phenethoxy)propanamide Trifluoroacetic Acid Salt

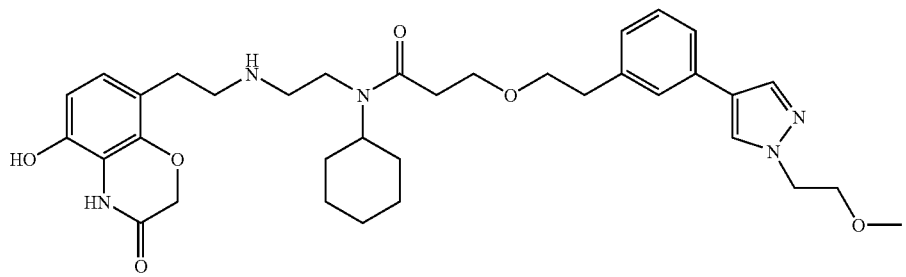

Step i) 1-(2-Methoxyethyl)-4-(4,4,5,5-tetramethyl-1,3,2-dioxaborolan-2-yl)-1H-pyrazole

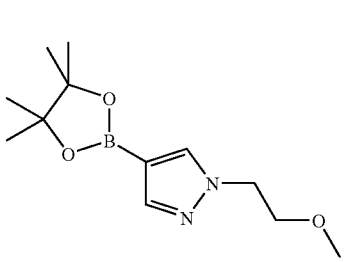

The subtitled compound (732 mg) was prepared from 1-bromo-2-methoxyethane using a similar method to that described in Example 20 Step i). MS [M+H]+=253 (MultiMode+) ¹H NMR (300 MHz, CDCl₃) δ 7.79 (s, 1H), 7.76 (s, 1H), 4.30 (t, J=5.4 Hz, 2H), 3.75 (t, J=5.4 Hz, 2H), 3.32 (s, 3H), 1.32 (d, J=4.0 Hz, 12H)

Step ii) tert-Butyl 3-(3-(1-(2-methoxyethyl)-1H-pyrazol-4-yl)phenethoxy)propanoate

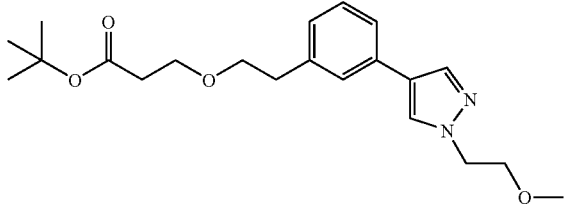

The subtitled compound (834 mg) was prepared from tert-butyl 3-(3-bromophenethoxy)propanoate [Preparation 3, Step i)] and 1-(2-methoxyethyl)-4-(4,4,5,5-tetramethyl-1,3,2-dioxaborolan-2-yl)-1H-pyrazole using a similar method to that described in Example 18, Step i). MS M+H-C4H8]+= 319 (MultiMode+) $^1$H NMR (300 MHz, CDCl$_3$) δ 7.78 (s, 1H), 7.72 (s, 1H), 7.37-7.22 (m, 3H), 7.07 (d, J=7.5 Hz, 1H), 4.32 (t, J=5.2 Hz, 2H), 3.78 (t, J=5.3 Hz, 2H), 3.70 (t, J=6.5 Hz, 2H), 3.68 (t, J=7.5 Hz, 2H), 3.35 (s, 3H), 2.89 (t, J=7.2 Hz, 2H), 2.49 (t, J=6.4 Hz, 2H), 1.47 (s, 9H)

Step iii) 3-(3-(1-(2-Methoxyethyl)-1H-pyrazol-4-yl)phenethoxy)propanoic acid

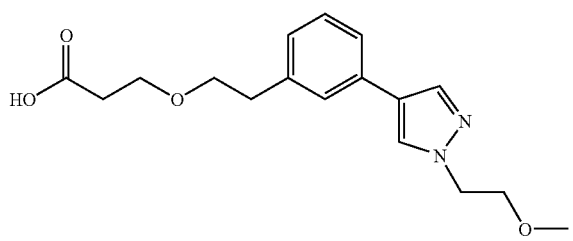

The subtitled compound (1.34 g) was prepared from tert-butyl 3-(3-(1-(2-methoxyethyl)-1H-pyrazol-4-yl)phenethoxy)propanoate [Example 36 Step ii)] using a similar method to that described in Example 4, Step iv). MS [M+H]+=319 (MultiMode+) $^1$H NMR (300 MHz, CDCl$_3$) δ 8.13 (s, 1H), 7.98 (s, 1H), 7.53 (s, 1H), 7.36-7.28 (m, 2H), 7.14-7.07 (m, 1H), 4.52 (t, J=4.8 Hz, 2H), 3.87-3.73 (m, 6H), 3.38 (s, 3H), 2.93 (t, J=5.9 Hz, 2H), 2.65 (t, J=5.5 Hz, 2H)

Step iv) N-Cyclohexyl-N-(2,2-dimethoxyethyl)-3-(3-(1-(2-methoxyethyl)-1H-pyrazol-4-yl)phenethoxy)propanamide

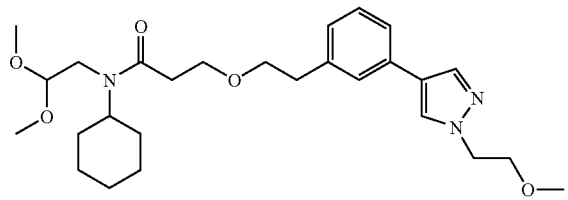

The subtitled compound (267 mg) was prepared from 3-(3-(1-(2-methoxyethyl)-1H-pyrazol-4-yl)phenethoxy)propanoic acid [Example 36 Step ii)] and N-(2,2-dimethoxyethyl)cyclohexanamine using a similar method to that described in Example 18, Step iii). MS [M+H-MeOH]+=456 (MultiMode+) $^1$H NMR (400 MHz, CD$_3$OD) δ 7.95 (s, 1H), 7.81 and 7.80 (2×s, 1H), 7.40-7.37 (m, 1H), 7.35 (d, J=7.7 Hz, 1H), 7.23 and 7.22 (2×t, J=7.7 Hz, 1H), 7.05 (d, J=7.9 Hz, 1H), 4.52 and 4.36 (2×t, J=5.3 Hz, 1H), 4.30 (t, J=5.2 Hz, 2H), 4.04-3.95 and 3.69-3.60 (2×m, 1H), 3.77-3.63 (m, 6H), 3.34 (s, 3H), 3.32 (s, 3H), 3.31 (s, 3H), 3.34 and 3.25 (2×d, J=5.1 Hz, 2H), 2.87-2.81 (m, 2H), 2.67-2.60 (m, 2H), 1.93-0.99 (m, 10H); a ~1:1 mixture of rotamers is observed.

Step v) N-Cyclohexyl-N-(2-(2-(5-hydroxy-3-oxo-3,4-dihydro-2H-benzo[b][1,4]oxazin-8-yl)ethylamino)ethyl)-3-(3-(1-(2-methoxyethyl)-1H-pyrazol-4-yl)phenethoxy)propanamide Trifluoroacetic Acid Salt

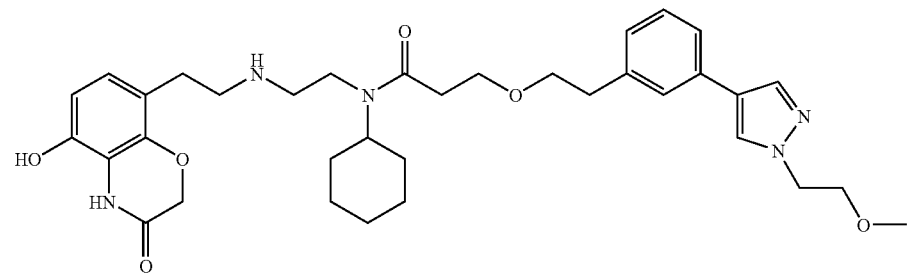

The titled compound (60 mg) was prepared from N-cyclohexyl-N-(2,2-dimethoxyethyl)-3-(3-(1-(2-methoxyethyl)-1H-pyrazol-4-yl)phenethoxy)propanamide [Example 36 Step iii)] using a similar method to that described in Example 20, Step v). MS [M+H]+=634.3 (calc=634.3604) (MultiMode+) ¹H NMR (400 MHz, CD₃OD) δ 7.93 (s, 1H), 7.79 (s, 1H), 7.40-7.38 (m, 1H), 7.36-7.32 (m, 1H), 7.23 (t, J=7.6 Hz, 1H), 7.05 (d, J=7.4 Hz, 1H), 6.69 (d, J=8.2 Hz, 1H), 6.47 (d, J=8.2 Hz, 1H), 4.60 (s, 2H), 4.29 (t, J=5.1 Hz, 2H), 3.77-3.64 (m, 7H), 3.48 (t, J=5.8 Hz, 2H), 3.31 (s, 3H), 3.09 (t, J=6.9 Hz, 2H), 3.01 (t, J=5.8 Hz, 2H), 2.89-2.82 (m, 4H), 2.62 (t, J=6.0 Hz, 2H), 1.83-1.58 (m, 5H), 1.48-1.22 (m, 4H), 1.19-1.04 (m, 1H)

Example 37

N-Cyclohexyl-3-(3-(1,5-dimethyl-1H-pyrazol-4-yl)phenethoxy)-N-(2-(2-(5-hydroxy-3-oxo-3,4-dihydro-2H-benzo[b][1,4]oxazin-8-yl)ethylamino)ethyl)propanamide Trifluoroacetic Acid Salt

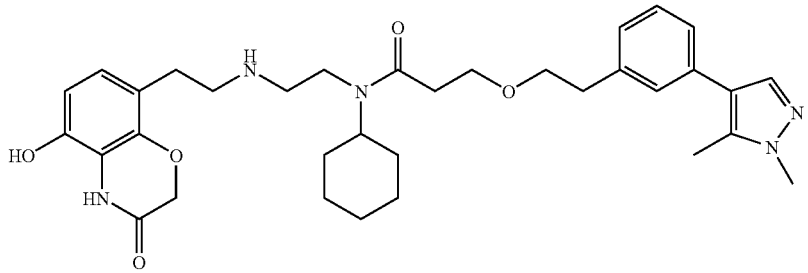

Step i) tert-Butyl 3-(3-(1,5-dimethyl-1H-pyrazol-4-yl)phenethoxy)propanoate

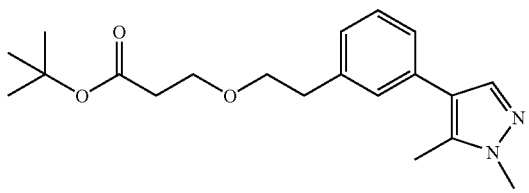

The subtitled compound (804 mg) was prepared from tert-butyl 3-(3-bromophenethoxy)propanoate [Preparation 3, Step i)] and 1 1,5-dimethyl-4-(4,4,5,5-tetramethyl-1,3,2-dioxaborolan-2-yl)-1H-pyrazole using a similar method to that described in Example 18, Step i). MS [M+H-C4H8]+=289 (MultiMode+) ¹H NMR (400 MHz, CDCl₃) δ 7.54 (s, 1H), 7.33-7.26 (m, 1H), 7.21-7.18 (m, 2H), 7.12 (d, 1H), 3.84 (s, 3H), 3.69 (q, 4H), 2.91 (t, 2H), 2.49 (t, 2H), 2.38 (s, 3H), 1.43 (s, 9H).

Step ii) 3-(3-(1,5-Dimethyl-1H-pyrazol-4-yl)phenethoxy)propanoic acid

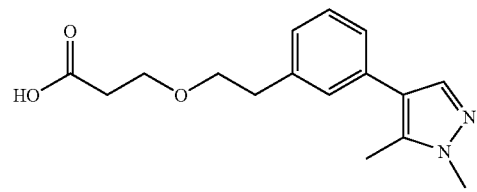

The subtitled compound (960 mg) was prepared from tert-butyl 3-(3-(1,5-dimethyl-1H-pyrazol-4-yl)phenethoxy)propanoate [Example 37 Step i)] using a similar method to that described in Example 4, Step iv). MS [M+H]+=289 (MultiMode+) ¹H NMR (400 MHz, CDCl₃) δ 7.98 (s, 1H), 7.36 (t, 1H), 7.30-7.28 (m, 1H), 7.24-7.15 (m, 2H), 4.01 (s, 3H), 3.74 (m, 4H), 2.93 (t, 2H), 2.62 (t, 2H), 2.46 (s, 3H)

Step iii) N-Cyclohexyl-N-(2,2-dimethoxyethyl)-3-(3-(1,5-dimethyl-1H-pyrazol-4-yl)phenethoxy)propanamide

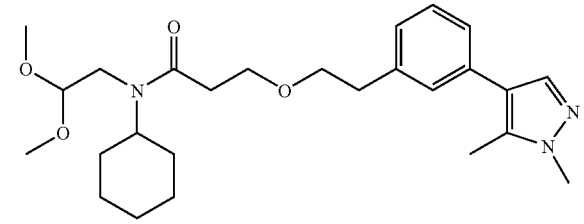

To a solution of 3-(3-(1,5-dimethyl-1H-pyrazol-4-yl)phenethoxy)propanoic acid [Example 37 Step ii)] (0.3 g) and DIPEA (0.545 mL) in DMF (4 mL) was added HATU (0.475 g) and the mixture was stirred at ambient temperature for 10 min. To this solution was added N-(2,2-dimethoxyethyl)cyclohexanamine (0.214 g) and the reaction mixture was stirred at ambient temperature for 2.5 h. The reaction mixture was poured onto water and extracted with ethyl acetate (2×100 mL). The organics were washed well with water, then brine and dried over anhydrous sodium sulfate, filtered and evaporated. The crude product was purified by flash silica chromatography, elution gradient 20-70% ethyl acetate in isohexane to afford the titled compound (0.185 g) as an oil. MS [M+H-MeOH]+=426 (MultiMode+) $^1$H NMR (400 MHz, CDCl$_3$) δ 7.54 (s, 1H), 7.33-7.27 (m, 1H), 7.22-7.17 (m, 2H), 7.12 (d, 1H), 3.84 (s, 3H), 3.79 (dt, 2H), 3.70 (dt, 2H), 3.40 (s, 6H), 3.37 (d, 1H), 3.30 (d, 1H), 2.94-2.88 (m, 2H), 2.74-2.65 (m, 2H), 2.38 (s, 3H), 1.86-1.73 (m, 2H), 1.73-1.59 (m, 3H), 1.53-1.19 (m, 5H), 1.14-1.02 (m, 1H).

Step iv) N-Cyclohexyl-3-(3-(1,5-dimethyl-1H-pyrazol-4-yl)phenethoxy)-N-(2-(2-(5-hydroxy-3-oxo-3,4-dihydro-2H-benzo[b][1,4]oxazin-8-yl)ethylamino)ethyl)propanamide Trifluoroacetic Acid Salt

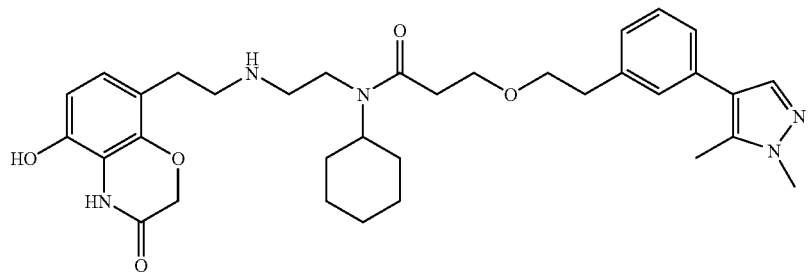

p-Toluenesulfonic acid monohydrate (0.308 g) was added in one portion to N-cyclohexyl-N-(2,2-dimethoxyethyl)-3-(3-(1,5-dimethyl-1H-pyrazol-4-yl)phenethoxy)propanamide [Example 37 Step iii)] (0.185 g) in DCM (10 mL) at 25° C. The resulting mixture was stirred at 25° C. for 30 min. To this mixture was added saturated sodium bicarbonate solution (3 mL) and the mixture stirred vigorously for 3.5 h and passed through a phase separation cartridge to remove the water. The filtrate was evaporated to dryness. The residue was dissolved in NMP (2 mL) and added to an ice cooled pre-prepared solution of 8-(2-aminoethyl)-5-hydroxy-2H-benzo[b][1,4]oxazin-3(4H)-one.hydrochloride (0.119 g), sodium bicarbonate (0.041 g) and water (0.5 mL) in NMP (5 mL) which had previously been stirred for 20 min. To this mixture was added sodium triacetoxyborohydride (0.129 g) and the resulting mixture was allowed to attain room temperature and was stirred at 25° C. for 17 h. The reaction mixture was poured onto saturated sodium bicarbonate solution (200 mL) and extracted into ethyl acetate. The organic phase was washed well with water before being dried (Na$_2$SO$_4$), filtered and concentrated. The crude product was purified by preparative HPLC on a Phenomenex Gemini column using a 65-30% gradient of aqueous 0.1% trifluoroacetic acid in methanol as eluent to afford the titled compound (38 mg). MS [M+H]+=604 (calc=604) (MultiMode+) $^1$H NMR (400 MHz, CD$_3$OD) δ 7.50 (s, 1H), 7.28 (t, J=7.6 Hz, 1H), 7.22 (s, 1H), 7.17 (d, J=6.1 Hz, 1H), 7.11 (d, J=7.4 Hz, 1H), 6.69 (d, J=8.4 Hz, 1H), 6.47 (d, J=8.3 Hz, 1H), 4.59 (s, 2H), 3.80 (s, 3H), 3.71 (d, J=5.6 Hz, 5H), 3.49 (t, J=5.6 Hz, 2H), 3.11 (t, J=7.2 Hz, 2H), 3.03 (t, J=5.6 Hz, 2H), 2.86 (t, J=6.8 Hz, 4H), 2.63 (t, J=6.0 Hz, 2H), 2.36 (s, 3H), 1.78 (d, J=13.1 Hz, 2H), 1.70-1.60 (m, 3H), 1.47-1.25 (m, 4H), 1.18-1.06 (m, 1H)

Biological Assays
Adrenergic β2 Mediated cAMP Production
Cell Preparation

H292 cells were grown in 225 cm2 flasks incubator at 37° C., 5% CO$_2$ in RPMI medium containing, 10% (v/v) FBS (foetal bovine serum) and 2 mM L-glutamine.

Experimental Method

Adherent H292 cells were removed from tissue culture flasks by treatment with Accutase™ cell detachment solution for 15 min. Flasks were incubated for 15 min in a humidified incubator at 37° C., 5% CO$_2$. Detached cells were re-suspended in RPMI media (containing 10% (v/v) FBS and 2 mM L-glutamine) at 1×10$^6$ cells per mL. 10000 cells in 100 μl were added to each well of a tissue-culture-treated 96-well plate and the cells incubated overnight in a humidified incubator at 37° C., 5% CO$_2$. The culture media was removed and cells were washed twice with 100 μl assay buffer and replaced with 50 μL assay buffer (HBSS solution containing 10 mM HEPES pH7.4 and 5 mM glucose). Cells were rested at room temperature for 20 min after which time 25 μl of rolipram (1.2 mM made up in assay buffer containing 2.4% (v/v) dimethylsulphoxide) was added. Cells were incubated with rolipram for 10 min after which time test compounds were added and the cells were incubated for 60 min at room temperature. The final rolipram concentration in the assay was 300 μM and final vehicle concentration was 1.6% (v/v) dimethylsulphoxide. The reaction was stopped by removing supernatants, washing once with 100 μL assay buffer and replacing with 50 μL lysis buffer. The cell monolayer was frozen at −80° C. for 30 min (or overnight).

AlphaScreen™ cAMP Detection

The concentration of cAMP (cyclic adenosine monophosphate) in the cell lysate was determined using AlphaScreen™ methodology. The frozen cell plate was thawed for 20 min on a plate shaker then 10 μl of the cell lysate was transferred to a 96-well white plate. 40 μL of mixed AlphaScreen™ detection beads pre-incubated with biotinylated cAMP, was added to each well and the plate incubated at room temperature for 10 h in the dark. The AlphaScreen™ signal was measured using an EnVision spectrophotometer (Perkin-Elmer Inc.) with the recommended manufacturer's settings. cAMP concentrations were determined by reference to a calibration curve determined in the same experiment using standard cAMP concentrations. Concentration response curves for agonists were constructed and data was fitted to a four parameter logistic equation to determine both the pEC$_{50}$ and Intrinsic Activity. Intrinsic Activity was expressed as a fraction relative to the maximum activity determined for formoterol in each experiment. Results for compounds of the invention are to be found in Table 1.

Selectivity Assays
Adrenergic α1D
Membrane Preparation

Membranes were prepared from human embryonic kidney 293 (HEK293) cells expressing recombinant human α1$_D$ receptor. These were diluted in Assay Buffer (50 mM HEPES, 1 mM EDTA, pH 7.4) to provide a final concentration of membranes that gave a clear window between maximum and minimum specific binding.
Experimental Method Assays were performed in U-bottomed 96-well polypropylene plates. 10 µl [$^3$H]-prazosin (0.3 nM final concentration) and 10 µl of test compound (10× final concentration) were added to each test well. For each assay plate 8 replicates were obtained for [$^3$H]-prazosin binding in the presence of 10 µl vehicle (10% (v/v) DMSO in Assay Buffer; defining maximum binding) or 10 µL BMY7378 (10 µM final concentration; defining non-specific binding (NSB)). Membranes were then added to achieve a final volume of 100 µL. The plates were incubated for 2 h at room temperature and then filtered onto PEI coated GF/B filter plates, pre-soaked for 1 h in Assay Buffer, using a 96-well plate Tomtec cell harvester. Five washes with 250 µl wash buffer (50 mM HEPES, 1 mM EDTA, pH 7.4) were performed at 4° C. to remove unbound radioactivity. The plates were dried then sealed from underneath using Packard plate sealers and MicroScint-O (50 µl) was added to each well. The plates were sealed (TopSeal A) and filter-bound radioactivity was measured with a scintillation counter (TopCount, Packard BioScience) using a 3-minute counting protocol.

Total specific binding ($B_0$) was determined by subtracting the mean NSB from the mean maximum binding. NSB values were also subtracted from values from all other wells. These data were expressed as percent of $B_0$. Compound concentration-effect curves (inhibition of [$^3$H]-prazosin binding) were determined using serial dilutions typically in the range 0.1 nM to 10 µM. Data was fitted to a four parameter logistic equation to determine the compound potency, which was expressed as pIC50 (negative log molar concentration inducing 50% inhibition of [$^3$H]-prazosin binding). Results are shown in Table 1 below.

Adrenergic β1
Membrane Preparation

Membranes containing recombinant human adrenergic beta 1 receptors were obtained from Euroscreen. These were diluted in Assay Buffer (50 mM HEPES, 1 mM EDTA, 120 mM NaCl, 0.1% gelatin, pH 7.4) to provide a final concentration of membranes that gave a clear window between maximum and minimum specific binding.
Experimental Method Assays were performed in U-bottomed 96-well polypropylene plates. 10 µL [$^{125}$I]-Iodocyanopindolol (0.036 nM final concentration) and 10 µL of test compound (10× final concentration) were added to each test well. For each assay plate 8 replicates were obtained for [$^{125}$I]-Iodocyanopindolol binding in the presence of 10 µl vehicle (10% (v/v) DMSO in Assay Buffer; defining maximum binding) or 10 µl Propranolol (10 µM final concentration; defining non-specific binding (NSB)). Membranes were then added to achieve a final volume of 100 µL. The plates were incubated for 2 h at room temperature and then filtered onto PEI coated GF/B filter plates, pre-soaked for 1 h in Assay Buffer, using a 96-well plate Tomtec cell harvester. Five washes with 250 µL wash buffer (50 mM HEPES, 1 mM EDTA, 120 mM NaCl, pH 7.4) were performed at 4° C. to remove unbound radioactivity. The plates were dried then sealed from underneath using Packard plate sealers and MicroScint-O (50 µl) was added to each well. The plates were sealed (TopSeal A) and filter-bound radioactivity was measured with a scintillation counter (TopCount, Packard BioScience) using a 3-minute counting protocol.

Total specific binding ($B_0$) was determined by subtracting the mean NSB from the mean maximum binding. NSB values were also subtracted from values from all other wells. These data were expressed as percent of $B_0$. Compound concentration-effect curves (inhibition of [$^{125}$I]-Iodocyanopindolol binding) were determined using serial dilutions typically in the range 0.1 nM to 10 µM. Data was fitted to a four parameter logistic equation to determine the compound potency, which was expressed as pIC$_{50}$ (negative log molar concentration inducing 50% inhibition of [$^{125}$I]-Iodocyanopindolol binding). Results are shown in Table 1 below.

Dopamine D2
Membrane Preparation

Membranes containing recombinant human Dopamine Subtype D2s receptors were obtained from Perkin Elmer. These were diluted in Assay Buffer (50 mM HEPES, 1 mM EDTA, 120 mM NaCl, 0.1% gelatin, pH 7.4) to provide a final concentration of membranes that gave a clear window between maximum and minimum specific binding.
Experimental Method Assays were performed in U-bottomed 96-well polypropylene plates. 30 µL [$^3$H]-spiperone (0.16 nM final concentration) and 30 µl of test compound (10× final concentration) were added to each test well. For each assay plate 8 replicates were obtained for [$^3$H]-spiperone binding in the presence of 30 µL vehicle (10% (v/v) DMSO in Assay Buffer; defining maximum binding) or 30 µl Haloperidol (10 µM final concentration; defining non-specific binding (NSB)). Membranes were then added to achieve a final volume of 300 µL. The plates were incubated for 2 h at room temperature and then filtered onto PEI coated GF/B filter plates, pre-soaked for 1 h in Assay Buffer, using a 96-well plate Tomtec cell harvester. Five washes with 250 µl wash buffer (50 mM HEPES, 1 mM EDTA, 120 mM NaCl, pH 7.4) were performed at 4° C. to remove unbound radioactivity. The plates were dried then sealed from underneath using Packard plate sealers and MicroScint-O (50 µl) was added to each well. The plates were sealed (TopSeal A) and filter-bound radioactivity was measured with a scintillation counter (TopCount, Packard BioScience) using a 3-minute counting protocol.

Total specific binding ($B_0$) was determined by subtracting the mean NSB from the mean maximum binding. NSB values were also subtracted from values from all other wells. These data were expressed as percent of $B_0$. Compound concentration-effect curves (inhibition of [$^3$H]-spiperone binding) were determined using serial dilutions typically in the range 0.1 nM to 10 µM. Data was fitted to a four parameter logistic equation to determine the compound potency, which was expressed as pIC$_{50}$ (negative log molar concentration inducing 50% inhibition of [$^3$H]-spiperone binding).

The results obtained for a representative selection of the compounds of the Examples are shown in Table 1 below.

TABLE 1

| Example No. | β2 pEC50 | β2 Int Act | α1 bind pIC50 | β1 bind p IC50 | D2 bind pIC50 |
|---|---|---|---|---|---|
| 01 and 02 | 8.2 | 0.96 | 6.0 | <5.1 | 5.3 |
| 03 | 8.0 | 0.81 | 5.7 | <5.0 | 5.6 |
| 04 | 7.9 | 0.96 | 5.7 | <5.0 | 5.2 |
| 05 | 8.1 | 0.87 | 5.7 | <5.1 | 5.5 |
| 06 | 7.9 | 0.95 | 5.8 | 5.1 | 5.7 |
| 07 | 7.8 | 0.92 | 6.0 | <5.0 | 5.2 |
| 08 | 7.8 | 0.92 | 5.4 | <5.0 | 5.5 |
| 09 | 8.1 | 0.92 | 6.0 | <5.0 | <5.0 |
| 10 | 8.0 | 0.88 | 6.5 | 5.2 | 6.0 |
| 11 | 8.0 | 0.85 | 6.2 | 5.1 | 5.4 |
| 12 | 7.7 | 0.91 | 5.8 | <5.0 | 5.4 |
| 13 | 8.0 | 0.85 | 6.2 | 5.2 | 5.5 |
| 14 | 8.1 | 0.95 | 6.0 | <5.0 | 5.6 |

TABLE 1-continued

| Example No. | β2 pEC50 | β2 Int Act | α1 bind pIC50 | β1 bind p IC50 | D2 bind pIC50 |
|---|---|---|---|---|---|
| 15 | 7.9 | 0.83 | <5.0 | <5.0 | <5.0 |
| 16 | 7.9 | 1.00 | 6.3 | 5.2 | 5.7 |
| 17 | 8.1 | 0.94 | 6.3 | 5.3 | 5.6 |
| 18 | 8.0 | 0.97 | 6.0 | <5.1 | 5.3 |
| 19 | 8.2 | 0.95 | 6.0 | 5.4 | 5.6 |
| 20 | 8.0 | 1.00 | 6.3 | <5.0 | 5.1 |
| 21 | 7.9 | 1.00 | 6.1 | 5.2 | 5.5 |
| 22 | 8.1 | 0.90 | 6.1 | 5.3 | 5.6 |
| 23 | 8.2 | 0.98 | 6.1 | <5.0 | 5.3 |
| 24 | 8.1 | 0.95 | 5.9 | 5.3 | 5.5 |
| 25 | 7.9 | 0.90 | 6.5 | <5.0 | 5.4 |
| 26 | 7.9 | 0.88 | 6.3 | <5.0 | 5.6 |
| 27 | 7.8 | 0.91 | 6.0 | <5.0 | <5.3 |
| 28 | 8.2 | 0.90 | 6.1 | <5.0 | <5.3 |
| 29 | 7.3 | 0.90 | 5.8 | <5.1 | 5.7 |
| 30 | 7.9 | 0.93 | 6.0 | 5.4 | 5.6 |
| 31 | 8.5 | 0.93 | 6.4 | 5.3 | 5.4 |
| 32 | 8.1 | 1.00 | 6.2 | 5.3 | 6.2 |
| 33 | 7.9 | 0.93 | 5.7 | <5.0 | 5.5 |
| 34 | 8.2 | 0.90 | 5.9 | <5.1 | 5.9 |
| 35 | 7.9 | 1.03 | 5.7 | <5.0 | 5.5 |
| 36 | 7.7 | 1.05 | 5.6 | <5.0 | <5.1 |
| 37 | 8.2 | 0.85 | 6.0 | <5.0 | 5.8 |

Inhibition of CYP 3A4 in Recombinant Human Enzyme

*E. coli* membranes co-expressing the P450 isozyme, CYP 3A4 and its corresponding reductase were purchased from CYPEX, Dundee, UK. Incubations were carried out in 0.1 M phosphate buffer (pH 7.4 at 37° C.) containing DMSO (1%), midazolam (2.5 mM), NADPH (1 mM), *E. coli* expressed 3A4 membranes (5 pmol/ml), and the test inhibitor ketoconazole. The assays were performed on a Tecan Genesis robotic sample processor in micro titre plates. The assay was started by the addition of NADPH, the reagents mixed and the plate pre-incubated. The plate was then incubated for 10 min at 37° C. The reaction was terminated with the addition of MeOH (1:1). The samples were centrifuged, transferred to a clean plate and analysed by LC MS/MS on a Quattro Ultima mass spectrometer. The formation of product (1'-hydroxymidazolam) was monitored. The concentrations used for test compounds were 50, 15, 5, 1.5, 0.5 and 0.15 mM. A 5 mM stock of test inhibitor in DMSO was used to achieve these concentrations. Ketoconazole was used as a standard inhibitor and was incubated at 0.1-0.0003 mM. Rates of reaction were calculated for each reaction by measuring MS/MS area units. Data analysis was performed by linearising the data using the pseudo Hill plot and utilizing an automated spreadsheet. The IC50 was estimated along with the IC50 for the standard inhibitor ketoconazole which is deemed to be acceptable if the IC50 value is in the range 0.0015 mM to 0.004 mM.

Onset Assay

Dunkin-Hartley guinea-pigs (between 200 g and 300 g on delivery) were supplied by a designated breeding establishment. The guinea-pigs were killed by cervical dislocation and the trachea removed. The adherent connective tissue was removed and each trachea cut into four rings. The tissue rings were then attached to an isometric transducer. The tissues were washed and a force of 1 g was applied to each ring. In all experiments a paired curve design was used. A priming dose of 1 μM methacholine was applied to the tissues. The tissues were then washed (three times, one minute between washes), the resting tension of 1 g was reapplied and the tissues were allowed to rest for 1 h to equilibrate. Tissues were then contracted with 1 μM methacholine and once a steady response was obtained a cumulative concentration response curve to isoprenaline ($10^{-9}$ M–$10^{-5}$ M) was constructed. The tissues were then washed (three times, one minute between washes) and left to rest for an h. At the end of the resting period the tissues were contracted with 1 μM methacholine and a $p[A]_{50}$ concentration of test compound added. Once the tissue had reached maximum relaxation, a 30×p[A]50 concentration of test compound was added. Once the tissue response had reached a plateau, 30 μM sotalol was added to the bath to confirm that the relaxation was β2 mediated.

Data were collected using the ADInstruments chart5 for windows software, which measured the maximum tension generated at each concentration of agonist.

For each concentration of the isoprenaline cumulative concentration curve, the response was calculated as % relaxation of the methacholine-induced contraction. A curve was plotted of $\log_{10}$[agonist] (M) versus percentage inhibition of the methacholine-induced contraction. These data were then fitted to a non-linear regression curve fit. For each experiment, E/[A] curve data were fitted using a 4-parameter logistic function of the form:

$$E = \beta + \frac{(\beta - \alpha) \cdot [A]^m}{[A]^m + [A]_{50}^m}$$

E and [A] are the pharmacological effect (% relaxation) and concentration of the agonist respectively; $\alpha$, $\beta$, $[A]_{50}$ and m are the asymptote, baseline, location and slope parameters, respectively. The $p[A]_{50}$ and IA of each isoprenaline curve was determined from this fit, to determine if the tissue was viable for generating an onset time for the test compounds.

For each $p[A]_{50}$ concentration of the test compound, the response was calculated as % relaxation of the methacholine-induced contraction. The results were plotted % relaxation against time and the time taken to reach a 90% relaxation value was calculated and recorded as the 'Onset time'.

The addition of a 30×$p[A]_{50}$ concentration enabled determination of the maximum compound effect within the individual tissue. Hence, the % of the maximum compound effect at the $p[A]_{50}$ concentration was calculated and recorded.

Data from the guinea pig $\beta_2$ onset time assay have shown that onset time is related to potency of the agonists such that higher potency leads to slower onset times. This observation is thought to be due to the compounds with high potency being dosed at very low concentrations where there is consequently a low concentration gradient for transport of such compounds through the tracheal tissue. An approximately linear relationship between Log(guinea pig onset time) and pEC50 in guinea pig tracheal tissue was found according to the equation below:

Log(Onset Time)=0.38pEC50−1.89

Since many compounds exhibit significant differences in human and guinea pig $\beta_2$ potency, it is expected that the potency difference will lead to a difference in onset time between the species. It is therefore important to consider this when making predictions of human onset time from the observed guinea pig onset time. This is achieved by using the following equation, which has been found to give good predictions of human onset time for a small set of compounds where potency and onset data are available in both guinea pig and human tissues.

Log(human onset time)=Log(guinea pig onset time)+
0.38(Human $\beta_2$ pEC50−GPT pEC50)

Evaluation of Lung Function in Anaesthetised Guinea-Pigs.

Male Dunkin-Hartley guinea-pigs (300-600 g) were weighed and dosed with either vehicle or compound in an appropriate vehicle according to the experimental protocol via the intratracheal route under recoverable gaseous anaesthesia (5% halothane in oxygen). Following dosing, the animals were administered supplemental oxygen and monitored until full recovery. Typically a dose volume of 0.5 mL/kg was used for the intratracheal route. In a dose response study, to generate an $ED_{80}$ (the dose of compound that gave 80% inhibition of the bronchoconstrictor effect of histamine) animals were dosed with compound or vehicle two hours prior to the administration of histamine. For a duration study the compound $ED_{80}$ dose or vehicle would be administered 2 hours to 72 hours prior to histamine challenge.

Test compound groups could either be the same compound at different doses or a single dose of several different compounds.

The guinea-pigs were anaesthetised with pentobarbitone (1 mL/kg of 60 mg/mL solution intraperitoneally) approximately 30 minutes prior to the first bronchoconstrictor administration. The trachea was cannulated (Portex intravenous cannula, 200/300/070 (orange) or 200/300/060 (yellow)) and the animal ventilated using a constant volume respiratory pump (Harvard Rodent Ventilator model 683) at a rate of 60 breath/min and a tidal volume of 5 ml/kg. A jugular vein was cannulated (Portex intravenous catheter 200/300/010 (green)) for the administration of histamine or maintenance anaesthetic (0.1 mL of pentobarbitone solution, 60 mg/mL, as required).

The animals were then transferred to a Flexivent System (SCIREQ, Montreal, Canada) in order to measure airway resistance. The animals were ventilated (quasi-sinusoidal ventilation pattern) at 60 breaths/min at a tidal volume of 5 mL/kg. A positive end expiratory pressure of 2-3 cmH$_2$O was applied. Respiratory resistance was measured using the Flexivent "snapshot" facility (1 second duration, 1 Hz frequency). Once stable baseline resistance value had been obtained the animals were given histamine dihydrochloride in ascending doses (Histamine; 0.5, 1, 2, 3 and 5 µg/kg, i.v) at approximately 4-minute intervals via the jugular catheter. After each administration of histamine the peak resistance value was recorded.

The mean of three baseline values for resistance was calculated immediately prior to each histamine administration. For each dose of histamine the maximum percentage change in airway resistance (cmH$_2$O.s/mL) from baseline was calculated.

$$\% \, changeR = \left(\frac{R_{maximum} - R_{baseline}}{R_{baseline}}\right) \times 100$$

The maximum percentage change in resistance at each dose of histamine was averaged across the treatment group.

Percentage bronchoprotection produced by a compound was calculated at each dose of histamine as follows:

$$\% \, bronchoprotection = \frac{\% \, changeR_{veh} - \% \, changeR_{cmpd}}{\% \, changeR_{veh}}$$

Where % change $R_{veh}$ is the mean of the maximum percentage change in airway resistance in the vehicle treated group.

For dose response studies, the concentration of compound that produced 80% bronchoprotection ($ED_{80}$ value) was calculated. The $ED_{80}$ value was determined as the dose of compound that produced 80% bronchoprotection 2 hours after dosing (usually at 5 µg/kg histamine dose level.) This value was calculated by fitting a 4-parameter logistic curve to the data (Meansys, AstraZeneca proprietary programme) and then using the curve parameters to calculate the $ED_{80}$ as follows:

$$ED = K\left(\frac{y - y_{min}}{y_{max} - y}\right)^{1/n}$$

where K is the concentration producing 50% bronchoprotection, $y_{max}$ and $y_{min}$ are the maximum and minimum values of the sigmoidal curve, and n is the Hill slope. These 4 parameters are calculated from the measured data by Meansys. ED is the dose required to produce y % bronchoprotection. To calculate $ED_{80}$, y is set to 80%.

All duration studies are conducted using the $ED_{80}$ dose so that equipotent doses of compound are administered. Compound was administered at various time points prior to histamine challenge. Guinea pigs were euthanised with approximately 1.0 mL pentobarbitone sodium (Euthatal) intravenously after the completion of the lung function measurements.

Pharmacokinetics in the Rat

A dose solution of the test compound was prepared using a suitable dose vehicle. The concentration of the compound in the dose solution was assayed by diluting an aliquot to a nominal concentration of 50 µg·ml$^{-1}$ and calibrating against duplicate injections of a standard solution and a QC standard at this concentration. Compounds were administered intravenously as a bolus into a caudal vein to groups of three 250-350 g rats (approximately 1 ml·kg$^{-1}$). For the oral dose, a separate group of 2 or 3 animals were dosed by oral gavage (3 ml·kg$^{-1}$). Delivered doses were estimated by weight loss. Food was not usually withdrawn from animals prior to dosing, although this effect was investigated if necessary.

Blood samples (0.25 ml) were taken into 1 ml syringes from the caudal vein, transferred to EDTA tubes and plasma was prepared by centrifugation (5 min at 13000 rpm) soon after sample collection, before storage at −20° C. Typical sampling times were 2, 4, 8, 15, 30, 60, 120, 180, 240, 300 (min) or until the terminal t1/2 was accurately described.

The concentration of the analyte(s) were determined in plasma by quantitative mass spectrometry. Standard and quality control stock solutions were prepared at a concentration 1 mg/ml in methanol. A range of standard and QC stocks produced by serial dilution were added to control rat plasma (50 µl). The range of concentrations covered the range of levels of analyte present in the rat samples. Standards, QCs and samples underwent liquid extraction using 50 µl of organic solvent and 100 µl of organic solvent containing an internal standard, chosen to closely resemble the analyte. The samples were then mixed by repeated inversion, stored at −20° C. for at least 1 h, and centrifuged at 3500 rpm in a centrifuge for 20 min. Aliquots (120 µl) of each sample were transferred for analysis using LC-MSMS. Standard and quality control samples covering the range of concentrations found in the test samples were within 25% of the nominal concentration.

Pharmacokinetic data analysis was achieved using WinNonlin. A standard non-compartmental analysis was used to estimate the parameters such as Tmax, Cmax, Lambda_z, t1/2_Lambda_z, AUCall, AUCINF(observed), Cl(observed), Vss(observed).

Measurement of Plasma Protein Binding

The extent of plasma protein binding was determined via equilibrium dialysis of a compound between human/animal plasma and aqueous buffer at 37° C., and determination of the concentrations of compound in the plasma and buffer by HPLC-MS/MS.

Method

Dialysis cells (molecular weight cut-off 5000) were prepared by rinsing with water followed by soaking in the dialysis buffer for a minimum of 1 h. The dialysis buffer was isotonic buffered saline pH 7.4. Stock solutions of compound in dimethylsulphoxide were prepared at a concentration of 0.5 mM.

The stock DMSO solution of compound was added to the plasma at a ratio of 10 µl of DMSO to each ml of plasma. This gave a 1% DMSO in plasma solution with each compound at a concentration of 5 µM. Dialysis cells were then prepared and one half of the cell filled with 750 µl of dialysis buffer and the other half of the cell with 750 µl of plasma solution of compound. Once prepared the cells were sealed and placed in an incubator box at 37° C. These cells were then rotated for a minimum of 4 h to equilibrate.

After equilibration 500 µl of the buffer samples were removed and added to HPLC vials along with 100 µl of plasma (sample in 6-fold diluted plasma), and 100 µl of the plasma samples were removed and added to HPLC vials along with 500 µl of dialysis buffer (sample in 6-fold diluted plasma).

The samples were then analysed using HPLC-MS/MS. A four point calibration curve was obtained by dilutions of the stock solutions with 6-fold diluted plasma at concentrations of 0.013 µM, 0.05 µM, 0.25 µM and 1.25 µM which were injected in this order followed by the buffer sample and then the plasma sample.

Calculation

The concentration of compound in the samples were determined using MassLynx version 4.1 software (produced by Waters/Micromass) that automatically calculated a calibration curve and interpolated the concentration of compound in the analytes. Plasma protein binding was determined from the measured concentration as the percentage of compound bound in plasma (% bound) using the following equation;

$$\% \text{ bound} = 100 - 100 \left( \frac{1.05(6*\text{plasma } conc - 1.2*\text{buffer } conc)}{1.05 \left( \begin{array}{c} 6*\text{plasma } conc - \\ 1.2*\text{buffer}.conc \end{array} \right) + 1.2*\text{buffer } conc} \right)$$

Routes A and B of Synthesis

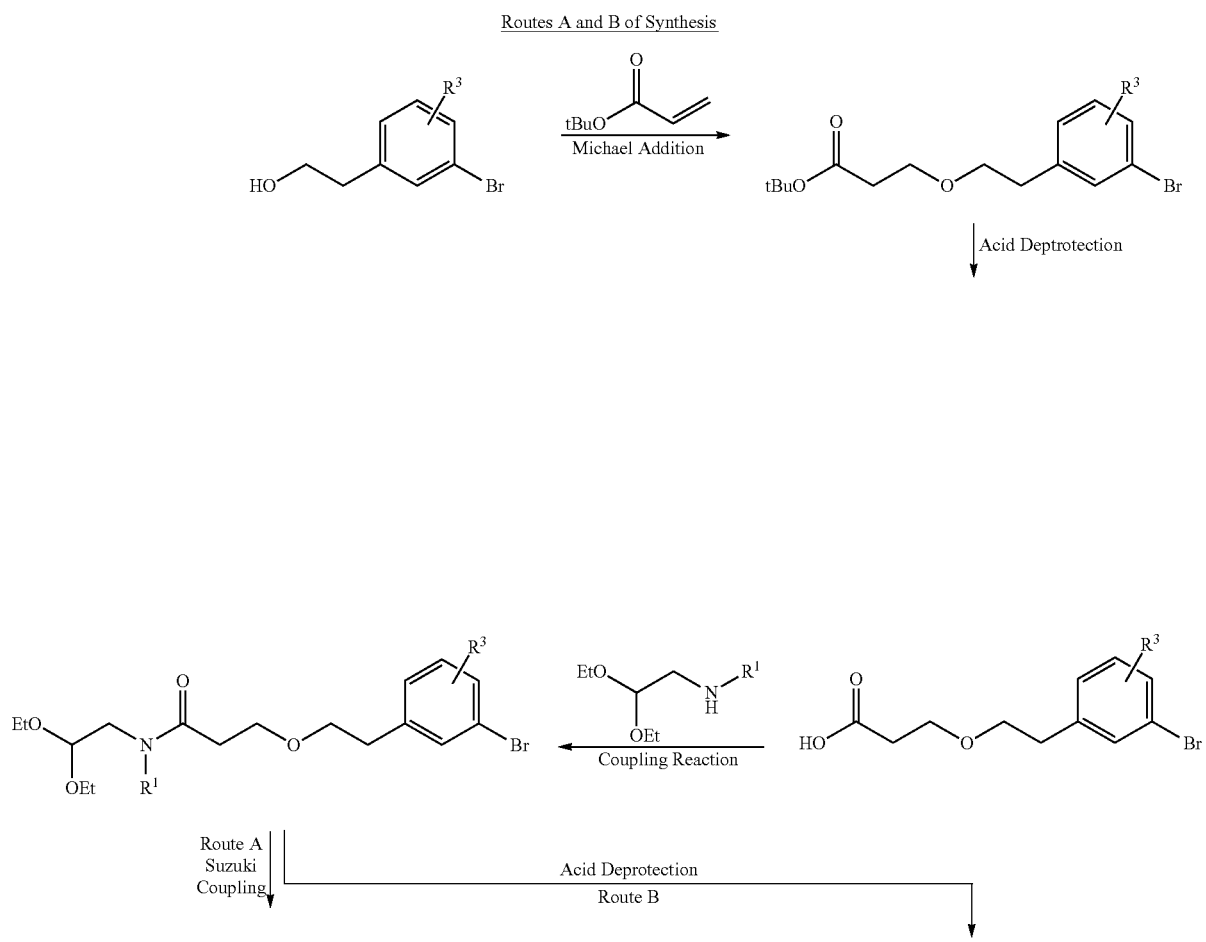

151
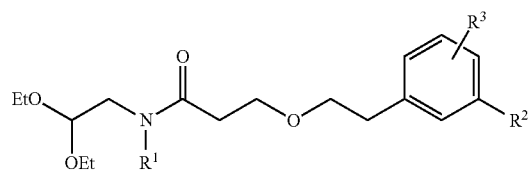
Acid Deprotection ↓
152
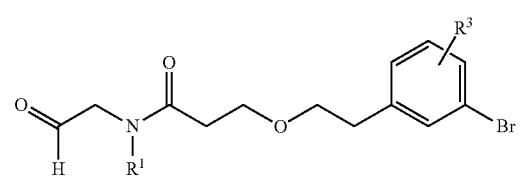
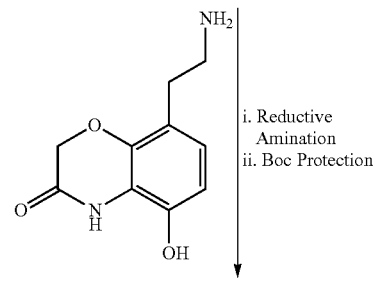
i. Reductive Amination
ii. Boc Protection ↓
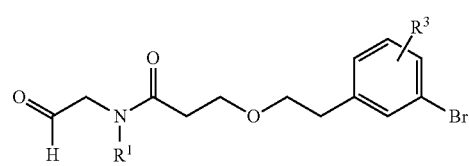
Reductive Amination ↓
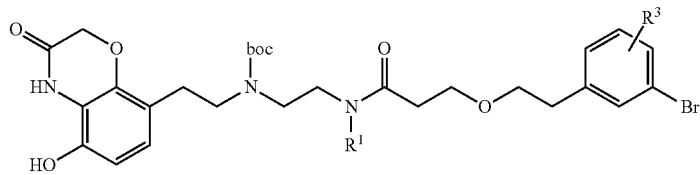
i. Suzuki Coupling
ii. Acid Deprotection ↓
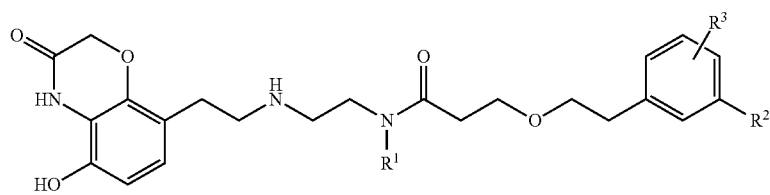
Route C of Synthesis (R is $C_{1-6}$ alkyl)

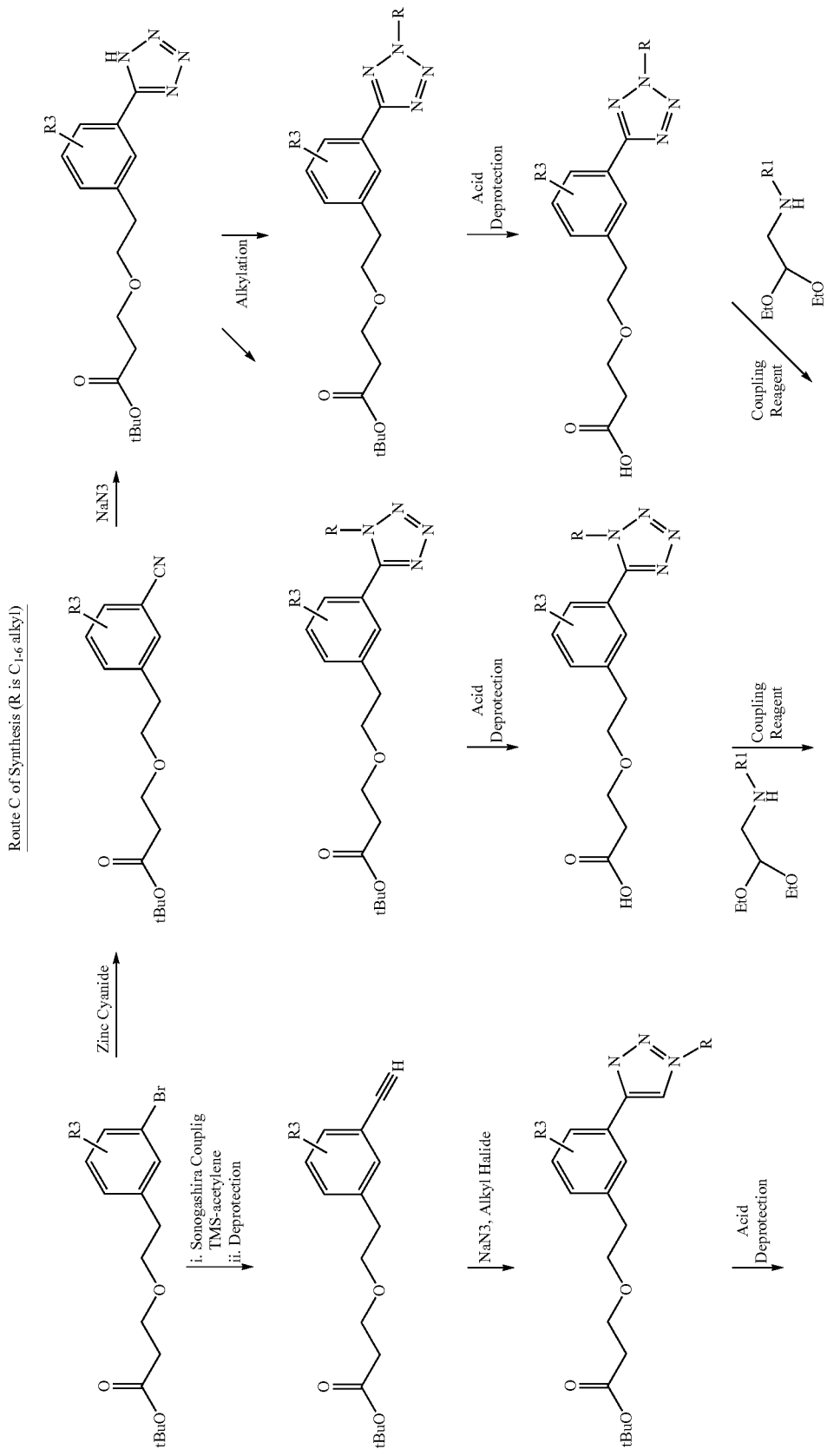

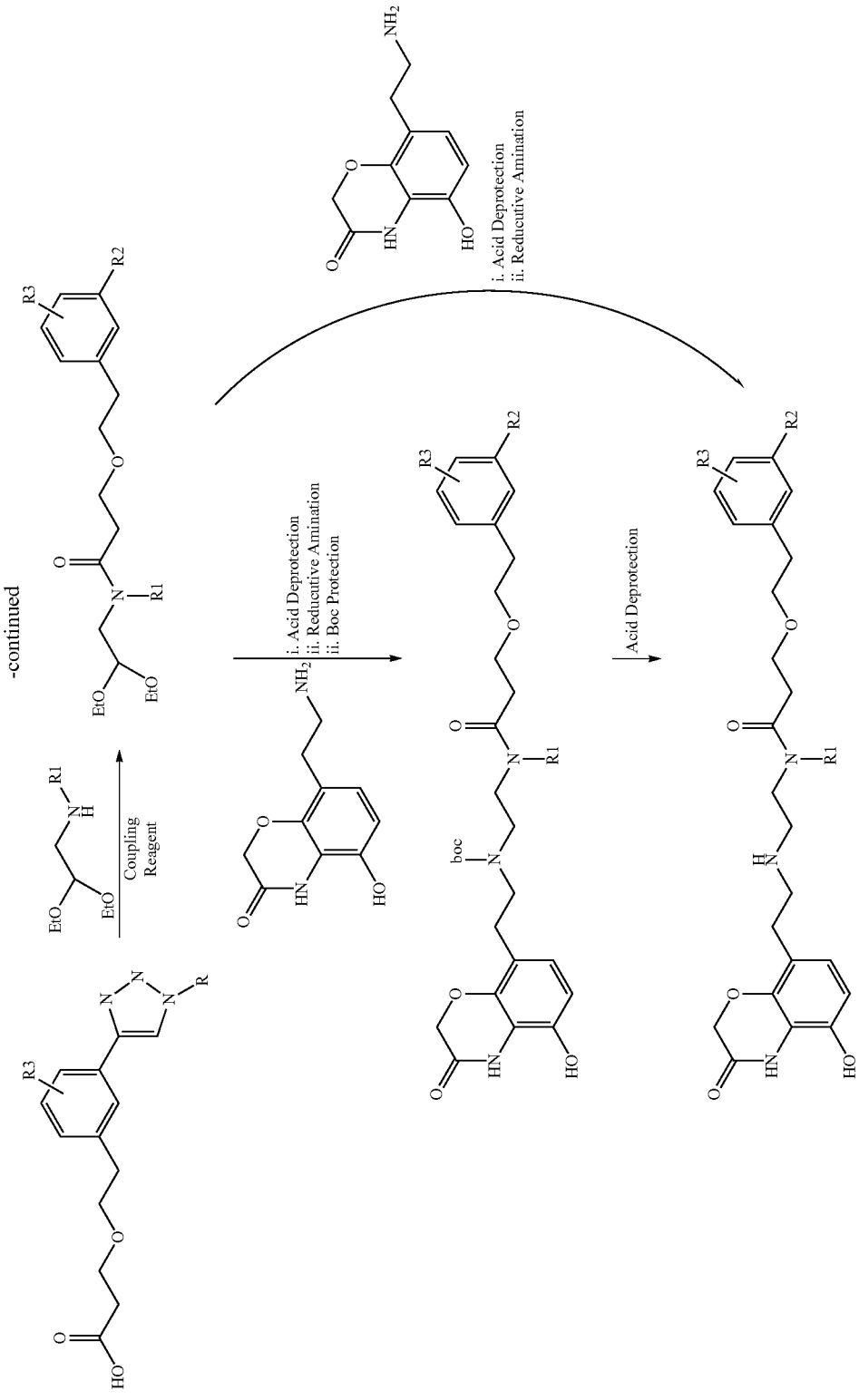

Route D of Synthesis

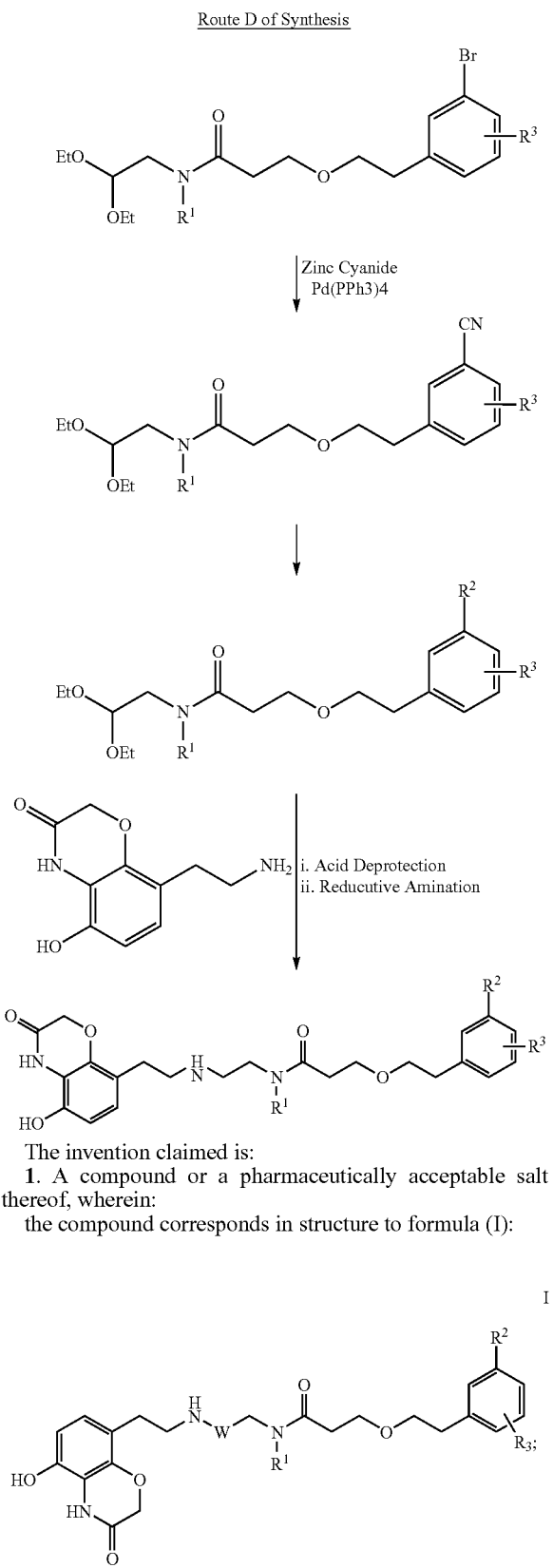

The invention claimed is:

1. A compound or a pharmaceutically acceptable salt thereof, wherein:
the compound corresponds in structure to formula (I):

I

W is $CH_2$ substituted by zero, 1, or 2 $CH_3$ groups;

$R^1$ is cyclopentyl, cyclohexyl, cycloheptyl, or $CH(CH_3)$ ($C_{1-6}$ alkyl);

$R^2$ is a 5-membered, nitrogen-containing heteroaryl that:
optionally has a ring oxygen atom, and
is optionally substituted by $C_{1-6}$ alkyl, wherein:
the $C_{1-6}$ alkyl is optionally substituted by $C_{1-6}$ alkoxy or $C_{3-6}$ cycloalkyl; and $R^3$ is hydrogen, halogen, $C_{1-4}$ alkyl, $CF_3$, $C_{1-4}$ alkoxy, or $OCF_3$.

2. A compound of formula (I) or a pharmaceutically acceptable salt thereof as claimed in claim 1, wherein $R^1$ is cyclohexyl.

3. A compound of formula (I) or a pharmaceutically acceptable salt thereof as claimed in claim 1 wherein $R^1$ is $CH(CH_3)CH(CH_3)_2$ or $CH(CH_3)(CH_2)_3CH_3$.

4. A compound of formula (I) or a pharmaceutically acceptable salt thereof as claimed in claim 1, wherein W is unsubstituted $CH_2$.

5. A compound of formula (I) or a pharmaceutically acceptable salt thereof as claimed in claim 1, wherein $R^3$ is hydrogen.

6. A compound or a pharmaceutically acceptable salt thereof as claimed in claim 1, wherein $R^2$ is C-linked imidazolyl, pyrazolyl, 1,2,3-triazolyl, 1,2,4-triazolyl, or tetrazolyl substituted with a $C_{1-6}$ alkyl group on a ring-nitrogen.

7. A compound of formula (I) or a pharmaceutically acceptable salt thereof as claimed in claim 1, wherein $R^2$ is C-linked pyrazolyl substituted with a methyl on a ring nitrogen.

8. A compound or a pharmaceutically acceptable salt thereof, wherein the compound is N-Cyclohexyl-N-(2-(2-(5-hydroxy-3-oxo-3,4-dihydro-2H-benzo[b] [1,4] oxazin-8-yl)ethylamino)ethyl)-3-(3-(1-methyl-1H-pyrazol-4-yl)phenethoxy)propanamide.

9. A pharmaceutical composition, wherein the composition comprises:
a compound of formula (I) or a pharmaceutically acceptable salt thereof as claimed in claim 1, and a pharmaceutically acceptable adjuvant, diluent, or carrier.

10. A method of treating, or reducing the risk of adult respiratory distress syndrome (ARDS), pulmonary emphysema, bronchitis, bronchiectasis, chronic obstructive pulmonary disease (COPD), asthma, or rhinitis, which comprises administering to a patient in need thereof a therapeutically effective amount of a compound of formula (I) or a pharmaceutically acceptable salt thereof as claimed in claim 1.

11. A compound or a pharmaceutically acceptable salt thereof as claimed in claim 8, wherein said pharmaceutically acceptable salt of said compound is N-Cyclohexyl-N-(2-(2-(5-hydroxy-3-oxo-3,4-dihydro-2H-benzo[b] [1,4] oxazin-8-yl)ethylamino)ethyl)-3-(3-(1-methyl-1H-pyrazol-4-yl)phenethoxy)propanamide Hemi-Fumaric Acid Salt.

12. A compound, wherein said compound is N-Cyclohexyl-N-(2-(2-(5-hydroxy-3-oxo-3,4-dihydro-2H-benzo[b] [1,4] oxazin-8-yl)ethylamino)ethyl)-3-(3-(1-methyl-1H-pyrazol-4-yl)phenethoxy)propanamide.

* * * * *